United States Patent

Narr et al.

Patent Number: 5,864,043
Date of Patent: Jan. 26, 1999

[54] BENZIMIDAZOLES, MEDICAMENTS CONTAINING THESE COMPOUNDS AND PROCESSES FOR THEIR PREPARATION

[75] Inventors: Berthold Narr, Biberach; Andres Bomhard, Dusseldorf; Norbert Hauel, Biberach; Jacques Van Meel, Mittelbiberach; Wolfgang Wienen; Michael Entzeroth, both of Apfingen, all of Germany

[73] Assignee: Karl Thomae GmbH, Biberach, Germany

[21] Appl. No.: 933,919

[22] Filed: Sep. 23, 1997

Related U.S. Application Data

[60] Continuation of Ser. No. 608,353, Feb. 28, 1996, abandoned, which is a division of Ser. No. 227,291, Apr. 13, 1994, Pat. No. 5,541,229, which is a continuation of Ser. No. 979,400, Nov. 19, 1992, abandoned, which is a continuation of Ser. No. 750,175, Aug. 26, 1991, abandoned, which is a continuation of Ser. No. 505,967, Apr. 6, 1990, abandoned.

[30] Foreign Application Priority Data

Apr. 8, 1989 [DE] Germany ............ 39 11 603.4
Aug. 25, 1989 [DE] Germany ............ 39 28 177.9

[51] Int. Cl.⁶ .................................... C07D 235/04
[52] U.S. Cl. .......................... 548/307.1; 548/306.4
[58] Field of Search ................ 548/306.4, 307.1

[56] References Cited

U.S. PATENT DOCUMENTS 4,880,804 11/1989 Carini .

FOREIGN PATENT DOCUMENTS 0132606 2/1985 Germany .
0142754 5/1985 Germany .
0253310 1/1988 Germany .
0291969 11/1988 Germany .

*Primary Examiner*—Robert Gerstl
*Attorney, Agent, or Firm*—Robert P. Raymond; Alan R. Stempel; Mary-Ellen Devlin

[57] ABSTRACT

The invention relates to benzimidazoles of the formula

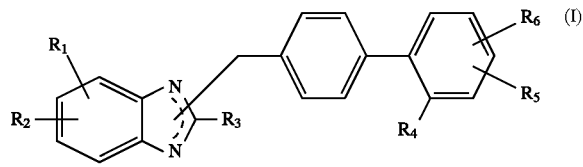

in which $R_1$ to $R_4$ are as defined in claim 1, 1 and 3 isomer mixtures thereof and addition salts thereof which have valuable properties.

In particular, the novel compounds are angiotensin II antagonists.

3 Claims, No Drawings

BENZIMIDAZOLES, MEDICAMENTS CONTAINING THESE COMPOUNDS AND PROCESSES FOR THEIR PREPARATION

This is a continuation of application Ser. No. 08/608,353, filed Feb. 28, 1996, now abandoned, which is a divisional of application U.S. Ser. No. 08/227,291, filed on Apr. 13, 1994, now U.S. Pat. No. 5,541,229 which is a continuation of application U.S. Ser. No. 07/979,400, filed on Nov. 19, 1992, now abandoned, which is a continuation of application U.S. Ser. No. 07/750,175, filed on Aug. 26, 1991, now abandoned, which is a continuation of application U.S. Ser. No. 07/505,967, filed on Apr. 6, 1990, now abandoned.

The present invention relates to 1 and 3 isomers of the benzimidazoles of the formula

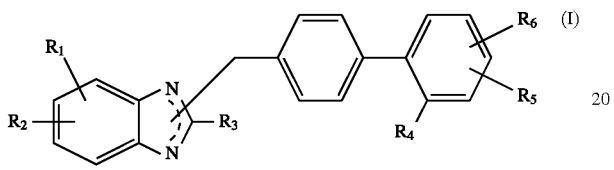

and, provided that $R_1$ and $R_2$ are not both a hydrogen atom at the same time or do not both have the same meanings in the 4 and 7 position or in the 5 and 6 position, the 1 and 3 isomer mixtures thereof and the addition salts thereof, in particular for the pharmaceutical use of their physiologically acceptable addition salts with inorganic or organic acids or bases.

In the above formula I $R_1$ denotes a hydrogen, fluorine, chlorine or bromine atom,
an alkyl group having 1 to 4 carbon atoms, which may be substituted by a hydroxy, alkoxy, amino, alkylamino, dialkylamino or acylamino group,
an alkoxy group having 1 to 4 carbon atoms, which may be substituted in the 2, 3 or 4 position by a hydroxy, alkoxy, amino, alkylamino, dialkylamino or imidazolyl group,
a hydroxy, phenylalkoxy, acyloxy, trifluoromethylsulphonyloxy, alkylaminocarbonyloxy, dialkylaminocarbonyloxy, cycloalkylaminocarbonyloxy, cycloalkylalkylaminocarbonyloxy, arylaminocarbonyloxy, aralkylaminocarbonyloxy, alkoxycarbonyloxy, cycloalkylalkoxycarbonyloxy, cycloalkylalkoxycarbonyloxy, aryloxycarbonyloxy, aralkoxycarbonyloxy, trifluoromethyl, cyano, nitro, alkylmercapto, alkylsulphinyl, alkylsulphonyl, aminosulphonyl, alkylaminosulphonyl, dialkylaminosulphonyl, arylaminosulphonyl, acylaminosulphonyl or acyl group,
an amino group, which may be monosubstituted by an imidazolylalkyl, dialkylaminoalkanoyl, acyl, cycloalkoxycarbonyl, cycloalkylalkoxycarbonyl, aryloxycarbonyl, aralkoxycarbonyl or trifluoroacetyl group, by a bicyclic or tricyclic alkyl group having 7 to 11 carbon atoms, by an alkylsulphonyl group having 1 to 4 carbon atoms, by an alkoxycarbonyl group having a total of 2 to 7 carbon atoms or by a thiazolidin-3-yl-carbonyl group substituted by an alkoxycarbonyl group,
an alkylamino group having 1 to 6 carbon atoms, which may be substituted at the nitrogen atom by an alkyl, alkylsulphonyl or acyl group, wherein, if the acyl group is an alkanoyl group, it may be additionally substituted by an alkoxy group, and the alkyl substituent may be substituted at position 2 by a hydroxy, alkoxy or arylamino group,
an amino group monosubstituted or disubstituted by a cycloalkyl, cycloalkylalkyl, phenylalkyl or phenyl group, wherein the substituents may be the same or different,
an N-alkyl-cycloalkylamino, N-alkyl-cycloalkylalkylamino, N-alkyl-phenylalkylamino or N-alkyl-phenylamino group,
a pyrrolidino, piperidino or hexamethyleneimino group optionally substituted by an alkyl, cycloalkyl or phenyl group,
an N-alkoxycarbonyl-alkylamino, N-cycloalkoxycarbonylalkylamino, N-cycloalkylalkoxycarbonyl-alkylamino, N-aryloxycarbonyl-alkylamino or N-aralkoxycarbonylalkylamino group, in which the alkyl group may contain 1 to 6 carbon atoms in each case, an alkoxycarbonylamino, cycloalkoxycarbonylamino, cycloalkylalkoxycarbonylamino, aryloxycarbonylamino, aralkoxycarbonylamino, acylamino or alkylsulphonylamino group substituted at the nitrogen atom by a cycloalkyl, cycloalkylalkyl or aralkyl group,
a carbonyl group, which is substituted by an alkyl group which is substituted in the 2 or 3 position by a hydroxy, alkanoyloxy or alkylamino group, by a hydroxycarbonylalkyl, hydroxy, alkoxy, amino, cycloalkylamino, cycloalkylalkylamino, arylamino or aralkylamino group, by an alkylamino group substituted in the 2 or 3 position by an arylamino group, or by an alkylamino group having 1 to 5 carbon atoms and optionally substituted by a carboxy group in the alkyl part, which may be substituted in each case additionally at the nitrogen atom by an alkyl group,
an aminoacetylamino group optionally substituted by an alkoxycarbonyl group having a total of 2 to 5 carbon atoms,
an aminocarbonylamino or aminothiocarbonylamino group, which may be monosubstituted, disubstituted or trisubstituted by an alkyl group having 1 to 20 carbon atoms, by an alkenyl or alkynyl group having 3 to 5 carbon atoms in each case, by a bicyclic or tricyclic alkyl group having 7 to 11 carbon atoms, by a cycloalkyl, cycloalkylalkyl, aralkyl or aryl group, wherein the substituents may be the same or different, and a methylene group in a cycloalkyl radical having 5 to 7 carbon atoms may be replaced by an oxygen atom, and an alkyl group may be substituted in the 4, 5 or 6 position by a hydroxy, alkanoyl or trifluoroacetyl group,
a cycloalkyleneiminocarbonylamino group having 4 to 6 carbon atoms in the cycloalkyleneimino moiety or a morpholinocarbonylamino group, which may both be substituted at the amino nitrogen by an alkyl group having 1 to 20 carbon atoms, or by a cycloalkyl, cycloalkylalkyl, aralkyl or aryl group,
a phthalimino, homophthalimino, 2-carboxyphenylcarbonylamino, 2-carboxyphenylmethylamino, 2-carboxyphenylmethylenecarbonylamino or 2-carboxymethylenephenylcarbonylamino group, whilst a carbonyl group in a phthalimino group may be replaced by a methylene group and a methylene group in a homophthalimino, 2-carboxyphenylmethylenecarbonylamino or 2-carboxymethylenephenylcarbonylamino group may be substituted by one or two alkyl groups, and additionally the above-mentioned phenyl nuclei may be mono- or disubstituted by alkyl or alkoxy groups, whilst the substituents may be identical or different, and at the same time they may be partially or wholly hydrogenated, a bicycloalkane-3-carboxylic acid amino or bicycloalkene-3-carboxylic acid amino group substituted by a carboxy group in the 2-position, a bicycloalkane- 2,3-dicarboxylic acid imino or bicycloalkene-2,3-dicarboxylic acid imino group, wherein the bicycloalkane and bicycloalkene parts each contain 9 or 10 carbon atoms, may be substituted by 1, 2 or 3 methyl groups and an endomethylene group may be replaced by an oxygen atom, a glutaric acid imino or 3-carboxy-n-propylene-carbonyl group wherein the n-propylene group may be perfluorinated, substituted by one or two alkyl groups or by a tetramethylene or pentamethylene group, or a 5,7-dioxa-1H,3H-imidazo[1,5-c]thiazolyl group, $R_2$ denotes the meanings for $R_1$ mentioned above, a 2-imidazolidon-1-yl or 3,4,5,6-tetrahydro-2-pyrimidon-1-yl group optionally substituted in the 3 position by an alkyl, cycloalkyl, cycloalkylalkyl or aralkyl group, or a tetrazolyl group or $R_1$ and $R_2$ together with 2 carbon atoms of the neighbouring phenyl ring denote a phenyl or 1-alkyl-3,3-dialkyl-2,3-dihydropyrrol-2-one group, $R_3$ denotes a hydrogen, fluorine, chlorine or bromine atom, an alkyl group having 1 to 6 carbon atoms, in which a methylene group may be replaced by an oxygen or sulphur atom, a sulphinyl, sulphonyl or alkylamino group, and a methyl group may be substituted by a hydroxy, alkoxy, amino, alkylamino or dialkylamino group, but wherein the methylene group next to the benzimidazole ring may not be replaced by a sulphinyl or sulphonyl group, and when a methylene group is replaced and a methyl group is substituted at the same time, they must be separated from one another by at least 2 carbon atoms, an alkenyl or alkynyl group each having 3 to 5 carbon atoms, a phenylalkyl group, a cycloalkyl or cycloalkylalkyl group, in which the cycloalkyl moiety may contain 5 to 7 carbon atoms in each case, an aryl, hydroxy or imidazolylalkylamino group, an alkylamino group having 1 to 4 carbon atoms, an aminocarbonyl group, which may be substituted by an alkyl or cycloalkyl group having 5 to 7 carbon atoms, a 5-membered heteroaromatic ring, which contains an NH group, an oxygen or sulphur atom, wherein this 5-membered heteroaromatic ring mentioned above may additionally contain a further 1 to 3N atoms, or a 6-membered heteroaromatic ring, which may contain 1 or 2 nitrogen atoms, wherein the 5-membered and 6-membered heteroaromatic rings mentioned above may be substituted by one or, with the exception of the tetrazolyl group, by two alkyl groups, $R_4$ denotes an amino, phthalimino, aminomethyl, cyano, tert.-butoxycarbonyl or 1-(triphenylmethyl)-tetrazolyl group, a group containing a Brönsted acid or a radical which can be converted in vivo to a group containing a Brönsted acid, $R_5$ denotes a hydrogen, fluorine, chlorine or bromine atom, $R_6$ denotes a hydrogen atom or $R_5$ and $R_6$ together with the two ortho position carbon atoms denote a phenyl group.

The term "a group containing a Brönsted acid" mentioned above especially means in this case a carboxy, aminoacetylamino, trifluoromethylcarbonylamino, trifluoromethylcarbonylaminomethyl, trifluoromethylsulphonylamino, trifluoromethylsulphonylaminomethyl or 1H-tetrazolyl group, an alkylcarbonylamino, alkylcarbonylaminomethyl, arylcarbonylamino, arylcarbonylaminomethyl, aralkylcarbonylamino, aralkylcarbonylaminomethyl, alkylsulphonylamino, alkylsulphonylaminomethyl, arylsulphonylamino, arylsulphonylaminomethyl, aralkylsulphonylamino, aralkylsulphonylaminomethyl, arylsulphonylaminocarbonyl or benzylsulphonylaminocarbonyl group, an alkylsulphonylaminocarbonyl or perfluoroalkylsulphonylaminocarbonyl group having in each case 1 to 6 carbon atoms in the alkyl moiety, "a radical which can be converted in vivo to a group containing a Brönsted acid", with the exception of the tert.-butoxycarbonyl group, especially means an alkoxycarbonyl group having a total of 2 to 7 carbon atoms, such as the methoxycarbonyl, ethoxycarbonyl, n-propoxycarbonyl, isopropoxycarbonyl, n-butoxycarbonyl, isobutoxycarbonyl, n-pentoxycarbonyl or n-hexoxycarbonyl group, an aralkoxycarbonyl group, such as the benzyloxycarbonyl, 1-phenylethoxycarbonyl, 2-phenylethoxycarbonyl or 3-phenylpropoxycarbonyl group or the pivaloyloxymethoxycarbonyl, phthalidylmethoxycarbonyl, ethoxycarbonyloxyethoxycarbonyl, methoxymethoxycarbonyl, cyclohexyloxycarbonylmethoxycarbonyl or (1,3-dioxa-2-oxo-4-methylcyclopenten-5-yl)-methoxycarbonyl group, "an acyl group" especially means an alkanoyl group having 1 to 7 carbon atoms, a cycloalkylcarbonyl group having a total of 4 to 8 carbon atoms, a cycloalkylalkanoyl group having a total of 5 to 10 carbonatoms, or an arylcarbonyl, aralkanoyl or phenylsulphonyl group optionally substituted by a fluorine, chlorine or bromine atom or by an alkyl or alkoxy group, "an aryl group" especially means a phenyl group optionally substituted by a fluorine, chlorine or bromine atom, or by a hydroxy, alkyl, alkoxy, phenylalkoxy or trifluoromethyl group, wherein the alkyl moiety may contain 1 to 4 carbon atoms in each case, or a naphthyl group, and "a cycloalkyl group" especially means a cycloalkyl group having 3 to 7 carbon atoms, which may be substituted by one or two alkyl groups, wherein, provided that nothing else has been mentioned, the alkyl and alkanoyl moieties mentioned in the definition of the radicals $R_1$ to $R_3$, and the alkyl moieties mentioned above may contain 1 to 3 carbon atoms in each case.

The novel compounds of the above formula I have valuable properties. Hence, the compounds of the formula I, in which $R_4$ denotes a group containing a Brönsted acid or a radical which can be converted in vivo to a group containing a Brönsted acid, have valuable pharmacological properties, in particular these compounds are angiotensin II antagonists.

The remaining compounds of the formula I are valuable intermediates as they can be converted chemically to one of the pharmacologically active compounds of the formula I mentioned above.

The present invention thus also relates to novel medicaments which contain one of the above-mentioned pharmacologically active compounds of the formula I or a corresponding physiologically acceptable addition salt, and are particularly suitable for the treatment of hypertonia and cardiac insufficiency, also for the treatment of ischaemic peripheral circulatory disorders, myocardial ischaemia (Angina), for the prevention of cardiac insufficiency progression after myocardial infarction, for the treatment of diabetic nephropathy, glaucoma, gastrointestinal illnesses and diseases of the bladder.

Suitable examples of the meanings mentioned in the definition of the radicals $R_1$, $R_2$, $R_3$ and $R_4$ are for $R_1$ the meaning hydrogen, fluorine, chlorine or bromine atom, methyl, ethyl, n-propyl, isopropyl, n-butyl, hydroxymethyl, 2-hydroxyethyl, 2-hydroxyisopropyl, 3-hydroxypropyl, methoxymethyl, 2-methoxyethyl, 2-ethoxyethyl, 2-methoxyisopropyl, 2-n-propoxyethyl, aminomethyl, 1-aminoethyl, 2-aminoethyl, 3-aminopropyl, methylaminomethyl, dimethylaminomethyl, ethylaminomethyl, diethylaminomethyl, N-methyl-isopropylaminomethyl, 2-methylaminoethyl, 2-dimethylaminoethyl, 2-isopropylaminoethyl, 2-diisopropylaminoethyl, 3-methylaminopropyl, 3-dimethylaminopropyl, acetaminomethyl, propionylaminomethyl, butanoylaminomethyl, pentanoylaminomethyl, benzoylaminomethyl, benzenesulphonylaminomethyl, 2-acetaminoethyl, 2-propionylaminoethyl, 2-butanoylaminoethyl, 2-benzoylaminoethyl, 3-acetaminopropyl, methoxy, ethoxy, n-propoxy, isopropoxy, n-butoxy, 2-hydroxyethoxy, 2-hydroxyisopropoxy, 3-hydroxypropoxy, 2-methoxyethoxy, 2-ethoxyethoxy, 2-methoxyisopropoxy, 3-methoxypropoxy, 3-n-propoxypropoxy, 2-aminoethoxy, 2-methylaminoethoxy, 2-dimethylaminoethoxy, 2-ethylaminoethoxy, 2-diethylaminoethoxy, 2-isopropylaminoethoxy, 3-aminopropoxy, 3-methylaminopropoxy, 3-dimethylaminopropoxy, 2-(imidazol- 1-yl)-ethoxy, 2-(imidazol-2-yl)-ethoxy, 2-(imidazol-4-yl)-ethoxy, 3-(imidazol-1-yl)-propoxy, 3-(imidazol-2-yl)-propoxy, 3-(imidazol-4-yl)-propoxy, hydroxy, benzyloxy, 2-phenylethoxy, 3-phenylpropoxy, acetoxy, propionyloxy, n-butanoyloxy, n-pentanoyloxy, trifluoromethylsulphonyloxy, methylaminocarbonyloxy, ethylaminocarbonyloxy, isopropylaminocarbonyloxy, dimethylaminocarbonyloxy, diethylaminocarbonyloxy, di-n-propylaminocarbonyloxy, N-methyl-ethylaminocarbony-loxy, cyclopropylaminocarbonyloxy, cyclobutylaminocarbonyloxy, cyclopentylaminocarbonyloxy, cyclohexylaminocarbonyloxy, cycloheptylaminocarbonyloxy, cyclopropylmethylaminocarbonyloxy, cyclobutylmethylaminocarbonyloxy, cyclopentylmethylaminocarbonyloxy, cyclohexylmethylaminocarbonyloxy, cycloheptylmethylaminocarbonyloxy, (2-cyclopropylethyl)-aminocarbonyloxy, (2-cyclobutylethyl)-aminocarbonyloxy, (2-cyclopentylethyl)-aminocarbonyloxy, (2-cyclohexylethyl)-aminocarbonyloxy, (2-cycloheptylethyl)-aminocarbonyloxy, (3-cyclopropylpropyl)-aminocarbonyloxy, (3-cyclobutylpropyl)-aminocarbonyloxy, (3-cyclopentylpropyl)-aminocarbonyloxy, (3-cyclohexylpropyl)-aminocarbonyloxy, (3-cycloheptylpropyl)-aminocarbonyloxy, methoxycarbonyloxy, ethoxycarbonyloxy, n-propoxycarbonyloxy, isopropoxycarbonyloxy, cyclopropoxycarbonyl-oxy, cyclobutoxycarbonyloxy, cyclopentoxycarbonyloxy, cyclohexoxycarbonyloxy, cycloheptoxycarbonyloxy, cyclopropylmethoxycarbonyloxy, cyclobutylmethoxycarbonyloxy, cyclopentylmethoxycarbonyloxy, cyclohexylmethoxycarbonyloxy, cycloheptylmethoxycarbonyloxy, (2-cyclopropylethoxy)-carbonyloxy, (2-cyclobutylethoxy)-carbonyloxy, (2-cyclopentylethoxy)-carbonyloxy, (2-cyclohexylethoxy)-carbonyloxy, (2-cycloheptylethoxy)-carbonyloxy, (3-cyclopropylpropoxy)-carbonyloxy, (3-cyclobutylpropoxy)-carbonyloxy, (3-cyclopentylpro-poxy)-carbonyloxy, (3-cyclohexylpropoxy)-carbonyloxy, (3cycloheptylpropoxy)-carbonyloxy, phenyloxycarbonyl-oxy, benzyloxycarbonyloxy, (2-phenylethoxy)-carbonyloxy, trifluoromethyl, phenylaminocarbonyloxy, benzylaminocarbonyloxy, (2-phenylethyl)-aminocarbonyloxy, cyano, nitro, methylmercapto, ethylmercapto, n-propylmercapto, isopropylmercapto, methylsulphinyl, ethylsulphinyl, n-propylsulphinyl, isopropylsulphinyl, methylsulphonyl, ethylsulphonyl, n-propylsulphonyl, isopropylsulphonyl, phenylsulphonyl, fluorophenylsulphonyl, chlorophenylsulphonyl, bromophenylsulphonyl, methylphenylsulphonyl, ethylphenylsulphonyl, isopropylphenylsulphonyl, methoxyphenylsulphonyl, ethoxyphenylsulphonyl, n-propoxyphenylsulphonyl, aminosulphonyl, methylaminosulphonyl, ethylaminosulphonyl, n-propylaminosulphonyl, isopropylaminosulphonyl, dimethylaminosulphonyl, diethylaminosulphonyl, di-n-propylaminosulphonyl, N-methylethylaminosulphonyl, phenylaminosulphonly, fluorophenylaminosulphonyl, chlorophenylaminosulphonyl, bromophenylaminosulphonyl, methylphenylaminosulphonyl, ethylphenylaminosulphonyl, isopropylphenylaminosulphonyl, methoxyphenylaminosulphonyl, ethoxyphenylaminosulphonyl, n-propoxyphenylaminosulphonyl, acetaminosulphonyl, propionylaminosulphonyl, n-butanoylaminosulphonyl, benzoylaminosulphonyl, fluorobenzoylaminosulphonyl, chlorobenzoylaminosulphonyl, bromobenzoylaminosulphonyl, methylbenzoylaminosulphonyl, methoxybenzoylaminosulphonyl, acetyl, propionyl, n-butanoyl, n-pentanoyl, n-hexanoyl, n-heptanoyl, phenylacetyl, 2-phenylpropionyl, cyclopropylcarbonyl, cyclobutylcarbonyl, cyclopentylcarbonyl, cyclohexylcarbonyl, cycloheptylcarbonyl, cyclopropylmethylcarbonyl, cyclobutylmethylcarbonyl, cyclopentylmethylcarbonyl, cyclohexylmethylcarbonyl, cycloheptylmethylcarbonyl, (2-cyclopropylethyl)-carbonyl, (2-cyclobutylethyl)-carbonyl, (2-cyclopentylethyl)-carbonyl, (2-cyclohexylethyl)-carbonyl, (2-cycloheptylethyl)-carbonyl, (3-cyclopropylpropyl)-carbonyl,(3-cyclobutylpropyl)-carbonyl, (3-cyclopentylpropyl)-carbonyl, (3-cyclohexylpropyl)-carbonyl, (3-cycloheptylpropyl)-carbonyl, benzoyl, fluorobenzoyl, chlorobenzoyl, bromobenzoyl, methylbenzoyl, methoxybenzoyl, phenylsulphonyl, fluorophenylsulphonyl, chlorophenylsulphonyl, bromophenylsulphonyl, methylphenylsulphonyl, methoxyphenylsulphonyl, amino, 2-(imidazol-1-yl)-ethylamino, 2-(imidazol-1-yl)-isopropylamino, 3-(imidazol-1-yl)-propylamino, (imidazol-4-yl)-methylamino, 2-(imidazol-4-yl)-ethylamino, 2-(imidazo-4-yl)-isopropylamino, 3-(imidazol-4-yl)-propylamino, acetylamino, propionylamino, n-butanoylamino, isobutanoylamino, n-pentanoylamino, n-hexanoylamino, n-heptanoylamino, cyclopropylcarbonylamino, cyclobutylcarbonylamino, cyclopentylcarbonylamino, cyclohexylcarbonylamino, cycloheptylcarbonylamino, cyclopropylmethylcarbonylamino, cyclobutylmethylcarbonylamino, cyclopentylmethylcarbonylamino, cyclohexylmethylcarbonylamino, cycloheptylmethylcarbonylamino, (2-cyclopropylethyl)-carbonylamino, (2-cyclobutylethyl)-carbonylamino, (2-cyclopentylethyl)-carbonylamino, (2-cyclohexylethyl)-carbonylamino, (2-cycloheptylethyl)-carbonylamino, (3-cyclopropylpropyl)-carbonylamino, (3-cyclobutylpropyl)-carbonylamino, (3-cyclopentylpropyl)-carbonylamino, (3-cyclohexylpropyl)-carbonylamino, (3-cycloheptylpropyl)-carbonylamino, benzoylamino, fluorobenzoylamino, chlorobenzoylamino, bromobenzoyl-amino, methylbenzoylamino, hydroxybenzoylamino, methoxybenzoylamino, phenylacetylamino, phenylpropionylamino, naphthylcarbonylamino, methoxycarbonylamino, ethoxycarbonylamino, n-propoxycarbonylamino, cyclopropyloxycarbonylamino, cyclobutyloxycarbonylamino, cyclopentoxycarbonylamino, cyclohexoxycarbonylamino, cycloheptoxycarbonylamino, cyclopropylmethoxycarbonylamino, cyclobutylmethoxycarbonylamino, cyclopentylmethoxycarbonylamino, cyclohexylmethoxycarbonylamino, cycloheptylmethoxycarbonylamino, (2-cyclopropylethoxy)-carbonylamino, (2-cyclobutylethoxy)-carbonylamino, (2-cyclopentylethoxy)-carbonylamino, (2-cyclohexylethoxy)-carbonylamino, (2-cycloheptylethoxy)-carbonylamino, (3-cyclopropylpropoxy)-carbonylamino, (3-cyclobutylpropoxy)-carbonylamino, (3-cyclopentylpropoxy)-carbonylamino, (3-cyclohexylpropoxy)-carbonylamino, (3-cycloheptylpropoxy)-carbonylamino, phenoxycarbonylamino, fluorophenoxycarbonylamino, chlorophenoxycarbonylamino, bromophenoxycarbonylamino, methylphenoxycarbonylamino, hydroxyphenoxycarbonylamino, methoxyphenoxycarbonylamino, benzyloxyphenoxycarbonylamino, benzyloxycarbonylamino, (2-phenylethoxy)-carbonylamino, trifluoroacetylamino, decalinylamino, adamantylamino, methylsulphonylamino, ethylsulphonylamino, n-propylsulphonylamino, n-butylsulphonylamino, methylamino, ethylamino, n-propylamino, isopropylamino, n-butylamino, isobutylamino, n-pentylamino, n-hexylamino, dimethylamino, diethylamino, di-n-propylamino, methyl-ethylamino, methyl-isopropylamino, methyl-n-butylamino, ethyl-n-propylamino, N-n-propylsulphonyl-methylamino, methyl-n-pentylamino, ethyl-n-hexylamino, N-methylsulphonyl-methylamino, N-ethylsulphonyl-methylamino, N-n-propylsulphonyl-methylamino, N-methylsulphonyl-ethylamino, N-ethylsulphonyl-ethylamino, N-n-propylsulphonyl-ethylamino, N-methylsulphonyl-n-propylamino, N-ethylsulphonyl-n-propylamino, N-n-propylsulphonyl-n-propylamino, N-methylsulphonyl-n-butylamino, N-ethylsulphonyl-n-pentylamino, N-n-propylsulphonyl-n-hexylamino, N-acetyl-methylamino, N-acetyl-ethylamino, N-acetyl-n-hexylamino, N-propionyl-methylamino, N-propionyl-ethyl-amino, N-propionyl-n-butylamino, N-n-butanoyl-methyl-amino, N-n-butanoyl-ethylamino, N-n-butanoyl-n-pentyl-amino, N-isobutanoyl-methylamino, N-isobutanoyl-ethyl-amino, N-isobutanoyl-isopropylamino, N-isobutanoyl-n-pentylamino, N-n-pentanoyl-methylamino, N-n-pentanoyl-ethylamino, N-n-pentanoyl-isopropylamino, N-n-pentanoyl-n-pentylamino, N-n-hexanoyl-methylamino, N-n-hexanoyl-ethylamino, N-n-hexanoyl-isopropylamino, N-n-hexanoyl-n-pentylamino, N-n-heptanoyl-methylamino, N-n-heptanoyl-ethylamino, N-n-heptanoyl-isopropylamino, N-n-heptanoyl-n-pentylamino, N-cyclopropylcarbonylmethyl-amino, N-cyclobutylcarbonyl-methylamino, N-cyclopentylcarbonyl-methylamino, N-cyclohexylcarbonyl-methylamino, N-cycloheptylcarbonyl-methylamino, N-cyclopropylmethylcarbonyl-methylamino, N-cyclobutylmethylcarbonyl-methylamino, N-cyclopentyl-methylcarbonyl-methylamino, N-cyclohexylmethylcarbonyl-methylamino, N-cycloheptylmethylcarbonyl-methylamino, N-(2-cyclopropylethylcarbonyl)-methylamino, N-(2-cyclobutylethylcarbonyl)-methylamino, N-(2-cyclopentylethylcarbonyl)-methylamino, N-(2-cyclohexylethylcarbonyl)-methylamino, N-(2-cycloheptylethylcarbonyl)-methylamino, N-(3-cyclopropylpropyl-carbonyl)-methylamino, N-(3-cyclobutylpropyl-carbonyl)-methylamino, N-(3-cyclopentylpropyl-carbonyl)-methylamino, N-(3-cyclohexylpropyl-carbonyl)-methylamino, N-(3-cycloheptylpropyl-carbonyl)-methylamino, N-benzoyl-methylamino, N-benzoyl-ethylamino, N-benzoyl-isopropylamino, N-benzoyl-n-butylamino, N-benzoyl-n-pentylamino, N-benzoyl-n-hexylamino, N-fluorobenzoyl-methylamino, N-methylbenzoyl-ethylamino, N-methoxybenzoyl-isopropylamino, N-chlorobenzoyl-n-butylamino, N-fluorobenzoyl-n-pentylamino, N-bromobenzoyl-n-hexylamino, N-phenylacetyl-methylamino, N-phenyl-sulphonyl-methylamino, N-(2-hydroxyethyl)-methyl-amino, N-(2-hydroxyethyl)-ethyl-amino, N-(2-methoxyethyl)-methylamino, N-(2-methoxy-ethyl)-ethylamino, N-hydroxy-acetyl-methylamino, N-hydroxyacetyl-ethylamino, N-methoxyacetyl-methylamino, N-methoxyacetyl-ethylamino, cyclopropylamino, cyclobutylamino, cyclopentylamino, cyclohexylamino, cycloheptylamino, cyclopropylmethylamino, cyclobutylmethyl-amino, cyclopentylmethylamino, cyclohexylmethylamino, cycloheptylmethylamino, (2-cyclopropylethyl)-amino, (2-cyclobutylethyl)-amino, (2-cyclopentylethyl)-amino, (2-cyclohexylethyl)-amino, (2-cycloheptylethyl)-amino, (3-cyclopropylpropyl)-amino, (3-cyclopentylpropyl)-amino, (3-cyclohexylpropyl)-amino, (3-cycloheptyl-propyl)-amino, benzylamino, 2-phenylethyl-amino, 3-phenylpropylamino, phenylamino, dicyclohexyl-amino, dicyclohexylmethylamino, dibenzylamino, N-methyl-cyclopropylamino, N-isopropyl-cyclopropylamino, N-ethyl-cyclobutylamino, N-methyl-cyclopentylamino, N-ethyl-cyclohexylamino, N-(n-propyl)-cycloheptylamino, N-methyl-cyclopropylmethylamino, N-isopropyl-cyclopropylmethylamino, N-ethyl-cyclobutylmethylamino, N-methyl-cyclopentylmethylamino, N-ethyl-cyclohexyl-methylamino, N-(n-propyl)-cycloheptylmethylamino, N-methyl-(2-cyclopropylethyl)-amino, N-isopropyl-(2-cyclopropylethyl)-amino, N-ethyl-(2-cyclobutylethyl)-amino, N-methyl-(2-cyclopentylethyl)-amino, N-ethyl-(2-cyclohexylethyl)-amino, N-(n-propyl-(2-cycloheptyl-ethyl)-amino, N-methyl-(3-cyclopropylpropyl)-amino, N-isopropyl-(3-cyclopropylpropyl)-amino, N-ethyl-(3-cyclobutylpropyl)-amino, N-methyl-(3-cyclopentylpropyl)-amino, N-ethyl-(3-cyclohexylpropyl)-amino, N-(n-propyl)-(3-cycloheptylpropyl)-amino, N-methyl-benzyl-amino, N-ethyl-benzylamino, N-isopropyl-benzylamino, N-methyl-(2-phenylethyl)-amino, N-methyl-phenylamino, N-(n-propyl)-phenylamino, pyrrolidino, methyl-pyrrolidino, ethylpyrrolidino, isopropylpyrrolidino, cyclopentylpyrrolidino, cyclohexylpyrrolidino, cycloheptylpyrrolidino, phenylpyrrolidino, piperidino, methylpiperidino, ethylpiperidino, isopropylpiperidino, cyclopentylpiperidino, cyclohexylpiperidino, cycloheptylpiperidino, phenylpiperidino, hexamethyleneimino, methylhexamethyleneimino, ethylhexamethyleneimino, isopropylhexamethyleneimino, cyclopentylhexamethyleneimino, cyclohexylhexamethyleneimino, cycloheptylhexamethyleneimino, phenylhexamethyleneimino, N-methoxycarbonyl-methylamino, N-methoxycarbonyl-N-ethylamino, N-methoxycarbonyl-n-pentylamino, N-methoxycarbonyl-n-hexylamino, N-ethoxycarbonyl-methylamino, N-ethoxycarbonyl-ethylamino, N-cyclopropyloxycarbonyl-methylamino, N-cyclopropyloxycarbonyl-ethylamino, N-cyclopropyloxycarbonyl-n-propylamino, N-cyclobutyloxycarbonyl-methylamino, N-cyclobutyloxycarbonyl-isopropylamino, N-cyclopentyloxycarbonyl-methylamino, N-cyclopentyloxycarbonyl-ethylamino, N-cyclohexyloxy-carbonyl-methylamino, N-cyclohexyloxycarbonyl-ethylamino, N-cycloheptyloxycarbonyl-methylamino, N-cyclopentylmethyloxycarbonyl-methylamino, N-cyclopentylmethyloxycarbonyl-ethylamino, N-cyclohexylmethyloxycarbonyl-methylamino, N-cyclohexylmethyloxycarbonyl-ethylamino, N-cycloheptylmethyloxycarbonyl-methylamino, N-cycloheptylmethyloxycarbonyl-ethylamino, N-(2-cyclopentylethyloxy)-carbonyl-methylamino, N-(2-cyclopentylethyloxy)-carbonyl-ethylamino, N-(2-cyclohexylethyloxy)-carbonyl-methylamino, N-(2-cyclohexylethyloxy)-carbonyl-ethylamino, N-(2-cycloheptylethyloxy)-carbonyl-methylamino, N-(2-cycloheptylethyloxy)-carbonyl-ethylamino, N-phenoxycarbonyl-methylamino, N-phenoxycarbonyl-ethylamino, N-phenoxycarbonyl-isopropylamino, N-benzyloxycarbonyl-methylamino, N-benzyloxycarbonyl-ethylamino, N-benzyloxycarbonyl-isopropylamino, N-(2-phenylethoxy)-carbonyl-methylamino, N-(2-phenylethoxy)-carbonyl-ethylamino, N-(2-phenylethoxy)-carbonyl-isopropylamino, N-(3-phenylpropoxy)-carbonyl-methylamino, N-(3-phenylpropoxy)-carbonyl-ethylamino, N-(3-phenylpropoxy)-carbonyl-isopropylamino, N-methoxycarbonyl-cyclopropylamino, N-methoxycarbonyl-cyclobutylamino, N-methoxycarbonyl, cyclopentylamino, N-methoxycarbonyl-cyclohexylamino, N-methoxycarbonyl-cycloheptylamino, N-ethoxycarbonyl-cyclopropylamino, N-ethoxycarbonyl-cyclobutylamino, N-ethoxycarbonyl-cyclopentylamino, N-ethoxycarbonyl-cyclohexylamino, N-ethoxycarbonyl-cycloheptylamino, N-methoxycarbonyl-cyclopropylmethylamino, N-methoxycarbonyl-cyclobutylmethylamino, N-methoxycarbonyl-cyclopentylmethylamino, N-methoxycarbonyl-cyclohexylmethylamino, N-methoxycarbonyl-cycloheptylmethylamino, N-ethoxycarbonyl-cyclopropylmethylamino, N-ethoxycarbonyl-cyclobutylmethylamino, N-ethoxycarbonyl-cyclopentylmethylamino, N-ethoxycarbonyl-cyclohexylmethylamino, N-ethoxycarbonyl-cycloheptylmethylamino, N-methoxycarbonyl-(2-cyclopropylethyl)-amino, N-methoxycarbonyl-(2-cyclobutylethyl)-amino, N-methoxycarbonyl-(2-cyclopentylethyl-amino, N-methoxycarbonyl-(2-cyclohexylethyl-amino, N-methoxycarbonyl-(2-cycloheptylethyl)-amino, N-ethoxycarbonyl-(2-cyclopropylethyl)-amino, N-ethoxycarbonyl-(2-cyclobutylethyl-amino, N-ethoxycarbonyl-2-cyclopentylethyl)-amino, N-ethoxycarbonyl-(2-cyclohexylethyl)-amino, N-ethoxycarbonyl-(2-cycloheptylethyl)-amino, N-methoxycarbonyl-(3-cyclopropylpropyl)-amino, N-methoxycarbonyl-(3-cyclobutylpropyl)-amino, N-methoxycarbonyl-(3-cyclopentylpropyl)-amino, N-methoxycarbonyl-(3-cyclohexylpropyl)-amino, N-methoxycarbonyl-(3-cycloheptylpropyl)-amino, N-ethoxycarbonyl-(3-cyclopropylpropyl)-amino, N-ethoxycarbonyl-(3-cyclobutylpropyl)-amino, N-ethoxycarbonyl-(3-cyclopentylpropyl)-amino, N-ethoxycarbonyl-(3-cyclohexylpropyl)-amino, N-ethoxycarbonyl-(3-cycloheptylpropyl)-amino, N-phenoxycarbonyl-cyclopropylamino, N-phenoxycarbonyl-cyclobutylamino, N-phenoxycarbonyl-cyclopentylamino, N-phenoxycarbonyl-cyclohexylamino, N-phenoxycarbonyl-cycloheptylamino, N-benzyloxycarbonyl-cyclopropylamino, N-benzyloxycarbonyl-cyclobutylamino, N-benzyloxycarbonyl-cyclopentylamino, N-benzyloxycarbonyl-cyclohexylamino, N-benzyloxycarbonyl-cycloheptylamino, N-(2-phenylethoxy)-carbonyl-cyclopropylamino, N-(2-phenylethoxy)-carbonyl-cyclobutylamino, N-(2-phenylethoxy)-carbonyl-cyclopentylamino, N-(2-phenylethoxy)-carbonyl-cyclohexylamino, N-(2-phenylethoxy)-carbonyl-cycloheptylamino, N-(3-phenylpropoxy)-carbonyl-cyclopropylamino, N-(3-phenylpropoxy)-carbonyl-cyclobutylamino, N-(3-phenylpropoxy)-carbonyl-cyclopentylamino, N-(3-phenylpropoxy)-carbonyl-cyclohexylamino, N-(3-phenylpropoxy)-carbonyl-cycloheptylamino, N-methylsulphonyl-cyclopropylamino, N-ethylsulphonyl-cyclobutylamino, N-n-propylsulphonyl-cyclopentylamino, N-ethylsulphonyl-cyclohexylamino, N-methylsulphonyl-cycloheptylamino, N-phenoxycarbonyl-cyclopropylmethylamino, N-phenoxycarbonyl-cyclobutylmethylamino, N-phenoxycarbonyl-cyclopentylmethylamino, N-phenoxycarbonyl-cyclohexylmethylamino, N-phenoxycarbonyl-cycloheptylmethylamino, N-benzyloxycarbonyl-cyclopropylmethylamino, N-benzyloxycarbonyl-cyclobutylmethylamino, N-benzyloxycarbonyl-cyclopentylmethylamino, N-benzyloxycarbonyl-cyclohexylmethylamino, N-benzyloxycarbonyl-cycloheptylmethylamino, N-(2-phenylethoxycarbonyl)-cyclopropylmethylamino, N-(2-phenylethoxycarbonyl)-cyclobutylmethylamino, N-(2-phenylethoxycarbonyl)-cyclopentylmethylamino, N-(2-phenylethoxycarbonyl-cyclohexylmethylamino, N-(2-phenylethoxycarbonyl-cycloheptylmethylamino, N-(3-phenylpropoxycarbonyl-cyclopropylmethylamino, N-(3-phenylpropoxycarbonyl)-cyclobutylmethylamino, N-(3-phenylpropoxycarbonyl)-cyclopentylmethylamino, N-(3-phenylpropoxycarbonyl)-cyclohexylmethylamino, N-(3-phenylpropoxycarbonyl)-cycloheptylmethylamino, N-methylsulphonyl-cyclopropylmethylamino, N-ethylsulphonyl-cyclobutylmethylamino, N-methylsulphonyl-cyclopentylmethylamino, N-ethylsulphonyl-cyclohexylmethylamino, N-ethylsulphonyl-cyclohexylmethylamino, N-isopropylsulphonyl-cycloheptylmethylamino, N-phenoxycarbonyl-(2-cyclopropylethyl)-amino, N-phenoxycarbonyl-(2-cyclobutylethyl)-amino, N-phenoxycarbonyl-(2-cyclopentylethyl)-amino, N-phenoxycarbonyl-(2-cyclohexylethyl)-amino, N-phenoxycarbonyl-(2-cycloheptylethyl)-amino, N-benzyloxycarbonyl-(2-cyclopropylethyl)-amino, N-benzyloxycarbonyl-(2-cyclobutylethyl)-amino, N-benzyloxycarbonyl-(2-cyclopentylethyl)-amino, N-benzyloxycarbonyl-(2-cyclohexylethyl)-amino, N-benzyloxycarbonyl-(2-cycloheptylethyl)-amino, N-(2-phenylethoxycarbonyl)-2-cyclopropylethyl)-amino, N-(2-phenylethoxycarbonyl)-(2-cyclobutylethyl)-amino, N-(2-phenylethoxycarbonyl)-(2-cyclopentylethyl)-amino, N-(2-phenylethoxycarbonyl)-2-cyclohexylethyl)-amino, N-(2-phenylethoxycarbonyl)-(2-cycloheptylethyl)-amino, N-(3-phenylpropoxycarbonyl)-(2-cyclopropylethyl)-amino, N-(3-phenylpropoxycarbonyl)-(2-cyclobutylethyl)-amino, N-(3-phenylpropoxycarbonyl)-2-cyclopentylethyl)-amino, N-(3-phenylpropoxycarbonyl)-(2-cyclohexylethyl)-amino, N-(3-phenylpropoxycarbonyl)-(2-cycloheptylethyl)-amino, N-methylsulphonyl-(2-cyclopropylethyl)-amino, N-ethylsulphonyl-(2-cyclobutylethyl)-amino, N-isopropylsulphonyl-(2-cyclopentylethyl)-amino, N-methylsulphonyl-(2-cyclohexylethyl)-amino, N-methylsulphonyl-(2-cycloheptylethyl)-amino, N-phenoxycarbonyl-(3-cyclopropylpropyl)-amino, N-phenoxycarbonyl-(3-cyclobutylpropyl)-amino, N-phenoxycarbonyl-(3-cyclopentylpropyl)-amino, N-phenoxycarbonyl-(3-cyclohexylpropyl)-amino, N-phenoxycarbonyl-(3-cycloheptylpropyl)-amino, N-benzyloxycarbonyl-(3-cyclopropylpropyl)-amino, N-benzyloxycarbonyl-(3-cyclobutylpropyl)-amino, N-benzyloxycarbonyl-(3-cyclopentylpropyl)-amino, N-benzyloxycarbonyl-(3-cyclohexylpropyl)-amino, N-benzyloxycarbonyl-(3-cycloheptylpropyl)-amino, N-(2-phenylethoxycarbonyl)-(3-cyclopropylpropyl)-amino, N-(2-phenylethoxycarbonyl)-(3-cyclobutylpropyl)-amino, N-(2-phenylethoxycarbonyl)-(3-cyclopentylpropyl)-amino, N-(2-phenylethoxycarbonyl)-(3-cyclohexylpropyl)-amino, N-(2-phenylethoxycarbonyl)-(3-cycloheptylpropyl)-amino, N-(3-phenylpropoxycarbonyl)-(3-cyclopropylpropyl)-amino, N-(3-phenylpropoxycarbonyl)-(3-cyclobutylpropyl)-amino, N-(3-phenylpropoxycarbonyl)-(3-cyclopentylpropyl)-amino, N-(3-phenylpropoxycarbonyl)-(3-cyclohexylpropyl)-amino, N-(3-phenylpropoxycarbonyl)-(3-cycloheptylpropyl)-amino, N-methylsulphonyl-(3-cyclopropylpropyl)-amino, N-ethylsulphonyl-(3-cyclobutylpropyl)-amino, N-isopropylsulphonyl-(3-cyclopentylpropyl)-amino, N-methylsulphonyl-(3-cyclohexylpropyl)-amino, N-methylsulphonyl-(3-cycloheptylpropyl)-amino, N-benzoyl-cyclopropylamino, N-benzoyl-cyclobutylamino, N-benzoyl-cyclopentylamino, N-benzoyl-cyclohexylamino, N-benzoyl-cycloheptylamino, N-phenylacetyl-cyclopropylamino, N-phenylacetyl-cyclobutylamino, N-phenylacetyl-cyclopentylamino, N-phenylacetyl-cyclohexylamino, N-phenylacetyl-cycloheptylamino, N-phenylsulphonyl-cyclopropylamino, N-phenylsulphonyl-cyclobutylamino, N-phenylsulphonyl-cyclopentylamino, N-phenylsulphonyl-cyclohexylamino, N-phenylsulphonyl-cycloheptylamino, N-benzoyl-cyclopropylmethylamino, N-benzoyl-cyclobutylmethylamino, N-benzoyl-cyclopentylmethylamino, N-benzoyl-cyclohexylmethylamino, N-phenylacetyl-cyclopropylmethylamino, N-phenylacetyl-cyclobutylmethylamino, N-phenylacetyl-cyclopentylmethylamino, N-phenylacetyl-cyclohexylmethylamino, N-phenylacetyl-cycloheptylmethylamino, N-phenylsulphonyl-cyclopropylmethylamino, N-phenylsulphonylcyclobutylmethylamino, N-phenylsulphonyl-cyclopentylmethylamino, N-phenyl-sulphonyl-cyclohexylmethylamino, N-phenylsulphonyl-cycloheptylmethylamino, N-benzoyl-(2-cyclopropyl-ethyl)-amino, N-benzoyl-(2-cyclobutylethyl)-amino, N-benzoyl-(2-cyclopentylethyl)-amino, N-benzoyl-(2-cyclohexylethyl)-amino, N-benzoyl-(2-cycloheptyl-ethyl)-amino, N-phenylacetyl-(2-cyclopropylethyl)-amino, N-phenylacetyl-(2-cyclobutylethyl)-amino, N-phenyl-acetyl-(2-cyclopentylethyl)-amino, N-phenylacetyl-(2-cyclohexylethyl)-amino, N-phenylacetyl-(2-cycloheptylethyl)-amino, N-phenylsulphonyl-(2-cyclopropylethyl)-amino, N-phenylsulphonyl-(2-cyclobutylethyl)-amino, N-phenylsulphonyl-(2-cyclopentylethyl)-amino, N-phenylsulphonyl-(2-cyclohexylethyl)-amino, N-phenylsulphonyl-(2-cycloheptylethyl)-amino, N-benzoyl-(3-cyclopropylpropyl)-amino, N-benzoyl-(3-cyclobutylpropyl)-amino, N-benzoyl-(3-cyclopentylpropyl)-amino, N-benzoyl-(3-cyclohexylpropyl)-amino, N-benzoyl-(3-cycloheptylpropyl)-amino, N-phenylacetyl-(3-cyclopropylpropyl)-amino, N-phenylacetyl-(3-cyclobutylpropyl)-amino, N-phenylacetyl-(3-cyclopentylpropyl)-amino, N-phenylacetyl-(3-cyclohexylpropyl)-amino, N-phenylacetyl-(3-cycloheptylpropyl)-amino, N-phenylsulphonyl-(3-cyclopropylpropyl)-amino, N-phenylsulphonyl-(3-cyclobutylpropyl)-amino, N-phenylsulphonyl-(3-cyclopentylpropyl)-amino, N-phenylsulphonyl-(3cyclohexylpropyl)-amino, N-phenylsulphonyl-(3-cycloheptylpropyl)-amino, N-acetyl-cyclopropylamino, N-acetyl-cyclobutylamino, N-acetyl-cyclopentylamino, N-acetyl-cyclohexylamino, N-acetyl-cycloheptylamino, N-acetyl-cyclopropylmethylamino, N-acetyl-cyclobutylmethylamino, N-acetyl-cyclopentylmethylamino, N-acetyl-cyclohexylmethylamino, N-acetyl-cycloheptylmethylamino, N-acetyl-(2-cyclopropylethyl)-amino, N-acetyl-(2-cyclobutylethyl)-amino, N-acetyl-(2-cyclopentylethyl)-amino, N-acetyl-(2-cyclohexylethyl)-amino, N-acetyl-(2-cycloheptylethyl)-amino, N-acetyl-(3-cyclopropylpropyl)-amino, N-acetyl-(3-cyclobutylpropyl)-amino, N-acetyl-(3-cyclopentylpropyl)-amino, N-acetyl-(3-cyclohexylpropyl)-amino, N-acetyl-(3-cycloheptylpropyl)-amino, N-acetyl-benzyl-amino, N-acetyl-(2-phenylethyl)-amino, N-acetyl-(3-phenylpropyl)-amino, N-benzoyl-benzylamino, N-benzoyl-(2-phenylethyl)-amino, N-benzoyl-(3-phenyl-propyl)-amino, N-methylsulphonyl-benzylamino, N-methyl-sulphonyl-(2-phenylethyl)-amino, N-methylsulphonyl-(3-phenylpropyl)-amino, carboxy, methoxycarbonyl, ethoxycarbonyl, n-propoxycarbonyl, aminocarbonyl, methylaminocarbonyl, ethylaminocarbonyl, n-propylaminocarbonyl, n-butylaminocarbonyl, n-pentylaminocarbonyl, dimethylaminocarbonyl, diethylaminocarbonyl, diisopropylaminocarbonyl, cyclopropylaminocarbonyl, cyclobutylaminocarbonyl, cyclopentylaminocarbonyl, cyclohexylaminocarbonyl, cycloheptylaminocarbonyl, cyclopentylmethylaminocarbonyl, cyclohexylmethylaminocarbonyl, cycloheptylmethylaminocarbonyl, 2-cyclohexylethyl-aminocarbonyl, phenylaminocarbonyl, fluorophenylaminocarbonyl, chlorophenylaminocarbonyl, bromophenylaminocarbonyl, methylphenylaminocarbonyl, ethylphenylaminocarbonyl, isopropylphenylaminocarbonyl, methoxyphenylaminocarbonyl, ethoxyphenylaminocarbonyl, isopropoxyphenylaminocarbonyl, n-butoxyphenylaminocarbonyl, benzylaminocarbonyl, (2-phenylethyl)-aminocarbonyl, dimethylaminocarbonyl, diethylaminocarbonyl, diisopropylaminocarbonyl, N-methylethylaminocarbonyl, N-methyl-n-propylaminocarbonyl, N-methyl-n-butylaminocarbonyl, aminoacetylamino, N-methoxycarbonyl-amino-acetylamino, N-ethoxycarbonyl-aminoacetylamino, N-isopropoxycarbonyl-aminoacetylamino, aminocarbonylamino, methylaminocarbonylamino, dimethylaminocarbonylamino, N-methylaminocarbonyl-methylamino, N-(dimethylaminocarbonyl)-methylamino, N-dimethylaminocarbonylethylamino, N-dimethylaminocarbonyl-isopropylamino, N-(dimethylaminocarbonyl)-n-pentylamino, N-methylaminocarbonyl-ethylamino, N-methylaminocarbonyl-n-pentylamino, N-methylaminocarbonyl-n-hexylamino, N-methylaminocarbonyl-n-octylamino, N-methylaminocarbonyl-n-dodecylamino, N-methylaminocarbonyl-cyclohexylamino, ethylaminocarbonylamino, N-ethylaminocarbonylmethylamino, N-ethylaminocarbonyl-ethylamino, N-ethylaminocarbonyl-n-hexylamino, N-ethylaminocarbonyl-n-octylamino, N-ethylaminocarbonyl-n-dodecylamino, N-ethylaminocarbonyl-cyclohexylamino, diethylaminocarbonylamino, N-(diethylaminocarbonyl)-methylamino, N-(diethylaminocarbonyl)-ethylamino, N-(diethylaminocarbonyl)-n-butylamino, N-(diethylaminocarbonyl)-n-hexylamino, N-(diethylaminocarbonyl)-n-octylamino, N-(diethylaminocarbonyl)-n-dodecylamino, isopropylaminocarbonylamino, N-isopropylaminocarbonyl-methylamino, n-butylaminocarbonylamino, N-(n-butylaminocarbonyl)-methylamino, N-(n-butylaminocarbonyl)-ethyl-amino, N-(n-butylaminocarbonyl)-isopropylamino, N-(n-butylaminocarbonyl)-n-butylamino, N-(n-butylaminocarbonyl)-n-hexylamino, N-(n-butylaminocarbonyl)-n-octylamino, N-(n-butylaminocarbonyl)-n-dodecylamino, N-(n-butylaminocarbonyl)-cyclohexylamino, N-(di-(n-butyl)-aminocarbonyl)-amino, N-(di-(n-butyl)-aminocarbonyl)-methylamino, N-(di-(n-butyl)-aminocarbonyl)-ethylamino, N-(di-(n-butyl)-aminocarbonyl)-n-butylamino, N-(di-(n-butyl)-aminocarbonyl)-n-hexylamino, N-(di-(n-butyl)-aminocarbonyl-n-octylamino, N-(di-(n-butyl)-aminocarbonyl)-n-dodecylamino, N-(n-pentylaminocarbonyl)-ethylamino, N-(n-hexylaminocarbonyl)-ethylamino, N-(n-octylaminocarbonyl)-ethylamino, N-(n- dodecylaminocarbonyl)-ethylamino, n-hexylaminocarbonylamino, n-octylaminocarbonylamino, n-dodecylaminocarbonylamino, N-(n-hexylaminocarbonyl)-n-butylamino, N-(n-hexylaminocarbonyl)-n-pentylamino, N-(n-hexylaminocarbonyl)-n-hexylamino, N-(n-hexylaminocarbonyl)-n-octylamino, N-(n-hexylaminocarbonyl)-n-dodecylamino, N-(n-octylaminocarbonyl)-n-butylamino, N-(n-octylaminocarbonyl)-n-pentylamino, N-(n-octylaminocarbonyl)-n-hexylamino, N-(n-octylaminocarbonyl)-n-octylamino, N-(n-octylaminocarbonyl)-n-dodecylamino, N-(n-dodecylaminocarbonyl)-n-butylamino, N-(n-dodecylaminocarbonyl)-n-pentylamino, N-(n-dodecylaminocarbonyl)-n-hexylamino, N-(n-dodecylaminocarbonyl)-n-octylamino, N-(n-dodecylaminocarbonyl)-n-dodecylamino, N-(n-hexylaminocarbonyl)-cyclohexylamino, N-(n-octylaminocarbonyl)-cyclohexylamino, N-(n-dodecylaminocarbonyl)-cyclohexylamino, di-(n-hexyl)-aminocarbonylamino, N-(di-(n-hexyl)-aminocarbonyl)-methylamino, N-(methyl-(n-hexyl)-aminocarbonyl)-amino, N-cyclohexylaminocarbonyl-n-pentylamino, N-cyclohexylaminocarbonyl-n-hexylamino, N-cyclohexylaminocarbonyl-n-octylamino, N-cyclohexylaminocarbonyl-n-dodecylamino, N-cyclohexylaminocarbonyl-cyclohexylamino, N-(ethyl-cyclohexylaminocarbonyl)-methylamino, N-(propyl-cyclohexylaminocarbonyl)-methylamino, N-(n-butyl-cyclohexylaminocarbonyl)-methylamino, adamant-1-yl-aminocarbonylamino, 4-hydroxybutylaminocarbonylamino, 5-hydroxypentylaminocarbonylamino, 6-hydroxyhexylaminocarbonylamino, allyl-aminocarbonylamino, but-2-enylaminocarbonylamino, pent-2-enylaminocarbonylamino, pent-3-enylaminocarbonylamino, crotylaminocarbonylamino, but-2-ynylaminocarbonylamino, pent-2-ynylaminocarbonylamino, pent-3-ynylaminocarbonylamino, tetrahydrofuran-2-yl-aminocarbonylamino, tetrahydropyran-2-yl-aminocarbonylamino, N-(ethyl-(n-pentyl)-aminocarbonyl)-ethylamino, N-(methyl-cyclopentylaminocarbonyl)-methylamino, N-(methyl-cyclohexylaminocarbonyl)-ethylamino, cyclopropylaminocarbonylamino, N-cyclopropylaminocarbonyl-methylamino, cyclobutylaminocarbonylamino, N-cyclobutylaminocarbonyl-methylamino, cyclopentylaminocarbonylamino, N-cyclopentylaminocarbonyl-methylamino, cyclohexylaminocarbonylamino, N-cyclohexylaminocarbonyl-methylamino, N-cyclohexylaminocarbonyl-ethylamino, N-cyclohexylaminocarbonyl-n-propylamino, N-cyclohexylaminocarbonyl-n-butylamino, N-cyclohexylaminocarbonyl-n-pentylamino, N-cyclohexylaminocarbonyl-n-hexylamino, N-cyclohexylaminocarbonyl-n-octylamino, N-cyclohexylaminocarbonyl-n-dodecylamino, cycloheptylaminocarbonylamino, N-cycloheptylaminocarbonyl-methylamino, cyclopentylmethylaminocarbonylamino, N-cyclopentylmethylamincarbonyl-methylamino, cyclohexylmethylaminocarbonylamino, N-cyclohexylmethylaminocarbonyl-methylamino, benzylaminocarbonylamino, (2-phenylethyl)-aminocarbonylamino, phenylaminocarbonylamino, fluorophenylaminocarbonylamino, chlorophenylaminocarbonylamino, bromophenylaminocarbonylamino, methylphenylaminocarbonylamino, ethylphenylaminocarbonylamino, isopropylphenylaminocarbonylamino, methoxyphenylaminocarbonylamino, ethoxyphenylaminocarbonylamino, isopropoxyphenylaminocarbonylamino, n-butoxyphenylaminocarbonylamino, aminothiocarbonylamino, methylaminothiocarbonylamino, N-methylaminocarbonylmethylamino, N-methylaminocarbonyl-ethylamino, ethylaminothiocarbonylamino, N-ethylaminothiocarbonylmethylamino, N-ethylaminothiocarbonyl-ethylamino, N-ethylaminothiocarbonyl-n-hexylamino, isopropylaminothiocarbonylamino, N-isopropylaminothiocarbonylmethylamino, allylaminothiocarbonylamino, but-2-enylaminothiocarbonylamino, pent-2-enylaminothiocarbonylamino, pent-3-enylaminothiocarbonylamino, crotylaminothiocarbonylamino, but-2-ynylaminothiocarbonylamino, pent-2-ynylaminothiocarbonylamino, pent-3-ynylaminothiocarbonylamino, tetrahydrofuran-2-yl-aminothiocarbonylamino, tetrahydropyran-2-yl-aminothiocarbonylamino, adamant-1-yl-aminothiocarbonylamino, cyclopropylaminothiocarbonylamino, N-cyclopropylaminothiocarbonylmethylamino, cyclobutylaminothiocarbonylamino, N-cyclobutylaminothiocarbonyl-methylamino, cyclopentylaminothiocarbonylamino, N-cyclopentylaminothiocarbonylmethylamino, cyclohexylaminothiocarbonylamino, N-cyclohexylaminothiocarbonyl-methylamino, cycloheptylaminothiocarbonylamino, N-cycloheptylaminothiocarbonylmethylamino, cyclopentylmethylaminothiocarbonylamino, N-cyclopentylmethylaminothiocarbonyl-methylamino, cyclohexylmethylaminothiocarbonylamino, N-cyclohexylmethylaminothiocarbonyl-methylamino, dimethylaminothiocarbonylamino, diethylaminothiocarbonylamino, N-((n-hexyl)-aminothiocarbonyl)amino, N-(methyl-(n-hexyl)-aminothiocarbonyl)amino, N-(dimethylamino-thiocarbonyl)-methylamino, N-(dimethylaminothiocarbonyl)-n-pentylamino, N-(diethylaminothiocarbonyl)-methylamino, N-(diethylaminothiocarbonyl)-ethylamino, N-(di-(n-hexyl)-aminothiocarbonyl)-methylamino, N-(di-(n-butyl)-aminothiocarbonyl)-n-butylamino, N-(methyl-(n-hexyl)-aminothiocarbonyl)-methylamino, N(ethyl-(n-pentyl)-aminothiocarbonyl)-ethylamino, N-(methylcyclopentylaminothiocarbonyl)-methylamino, N-(methylcyclohexylaminothiocarbonyl)-ethylamino, benzylaminothiocarbonylamino, phenylaminothiocarbonylamino, fluorophenylaminothiocarbonylamino, chlorophenylaminothiocarbonylamino, bromophenylaminothiocarbonylamino, methylphenylaminothiocarbonylamino,
ethylphenylaminothiocarbonylamino,
isopropylphenylaminothiocarbonylamino,
methoxyphenylaminothiocarbonylamino,
ethoxyphenylaminothiocarbonylamino,
isopropoxyphenylaminothiocarbonylamino,
n-butoxyphenylaminothiocarbonylamino,
pyrrolidinocarbonylamino, piperidinocarbonylamino,
hexamethyleneiminocarbonylamino,
N-pyrrolidinocarbonyl-methylamino,
N-pyrrolidinocarbonyl-ethylamino,
N-pyrrolidinocarbonyl-isopropylamino,
N-pyrrolidinocarbonyl-n-butylamino,
N-pyrrolidinocarbonyl-n-pentylamino,
N-pyrrolidinocarbonyl-n-hexylamino,
N-pyrrolidinocarbonyl-n-octylamino,
N-pyrrolidinocarbonyl-n-dodecylamino,
N-pyrrolidinocarbonyl-cyclopropylamino,
N-pyrrolidinocarbonyl-cyclobutylamino,
N-pyrrolidinocarbonyl-cyclopentylamino,
N-pyrrolidinocarbonyl-cyclohexylamino,
N-pyrrolidinocarbonyl-cycloheptylamino,
N-pyrrolidinocarbonyl-cyclopropylmethylamino,
N-pyrrolidinocarbonyl-cyclobutylmethylamino,
N-pyrrolidinocarbonyl-cyclopentylmethylamino,
N-pyrrolidinocarbonyl-cyclohexylmethylamino,
N-pyrrolidinocarbonyl-cycloheptylmethylamino,
N-pyrrolidinocarbonyl-(2-cyclopropylethyl)-amino,
N-pyrrolidinocarbonyl-(2-cyclobutylethyl)-amino,
N-pyrrolidinocarbonyl-(2-cyclopentylethyl)-amino,
N-pyrrolidinocarbonyl-(2-cyclohexylethyl)-amino,
N-pyrrolidinocarbonyl-(2-cycloheptylethyl)-amino,
N-pyrrolidinocarbonyl-(3-cyclopropylpropyl)-amino,
N-pyrrolidinocarbonyl-(3-cyclobutylpropyl)-amino,
N-pyrrolidinocarbonyl-(3-cyclopentylpropyl)-amino,
N-pyrrolidinocarbonyl-(3-cyclohexylpropyl)-amino,
N-pyrrolidinocarbonyl-(3-cycloheptylpropyl)-amino,
N-pyrrolidinocarbonyl-phenylamino,
N-pyrrolidinocarbonyl-benzylamino,
N-piperidinocarbonyl-methylamino,
N-piperidinocarbonyl-ethylamino,
N-piperidinocarbonyl-isopropylamino,
N-piperidinocarbonyl-n-butylamino,
N-piperidinocarbonyl-n-pentylamino,
N-piperidinocarbonyl-n-hexylamino,
N-piperidinocarbonyl-n-octylamino,
N-piperidinocarbonyl-n-dodecylamino,
N-piperidinocarbonyl-cyclopropylamino,
N-piperidinocarbonyl-cyclobutylamino,
N-piperidinocarbonyl-cyclopentylamino,
N-piperidinocarbonyl-cyclohexylamino,
N-piperidinocarbonyl-cycloheptylamino,
N-piperidinocarbonyl-cyclopropylmethylamino,
N-piperidinocarbonyl-cyclobutylmethylamino,
N-piperidinocarbonyl-cyclopentylmethylamino,
N-piperidinocarbonyl-cyclohexylmethylamino,
N-piperidinocarbonyl-cycloheptylmethylamino,
N-piperidinocarbonyl-(2-cyclopropylethyl)-amino,
N-piperidinocarbonyl-(2-cyclobutylethyl)-amino,
N-piperidinocarbonyl-(2-cyclopentylethyl)-amino,
N-piperidinocarbonyl-(2-cyclohexylethyl)-amino,
N-piperidinocarbonyl-(2-cycloheptylethyl)-amino,
N-piperidinocarbonyl-(3-cyclopropylpropyl)-amino,
N-piperidinocarbonyl-(3-cyclobutylpropyl)-amino,
N-piperidinocarbonyl-(3-cyclopentylpropyl)-amino,
N-piperidinocarbonyl-(3-cyclohexylpropyl)-amino,
N-piperidinocarbonyl-(3-cycloheptylpropyl)-amino,
N-piperidinocarbonyl-phenylamino,
N-piperidinocarbonyl-benzylamino,
N-hexamethyleneiminocarbonyl-methylamino,
N-hexamethyleneiminocarbonyl-ethylamino,
N-hexamethyleneiminocarbonyl-isopropylamino,
N-hexamethyleneiminocarbonyl-n-butylamino,
N-hexamethyleneiminocarbonyl-n-pentylamino,
N-hexamethyleneiminocarbonyl-n-hexylamino,
N-hexamethyleneiminocarbonyl-n-octylamino,
N-hexamethyleneiminocarbonyl-n-dodecylamino,
N-hexamethyleneiminocarbonyl-cyclopropylamino,
N-hexamethyleneiminocarbonyl-cyclobutylamino,
N-hexamethyleneiminocarbonyl-cyclopentylamino,
N-hexamethyleneiminocarbonyl-cyclohexylamino,
N-hexamethyleneiminocarbonyl-cycloheptylamino,
N-hexamethyleneiminocarbonyl-cyclopropylmethylamino,
N-hexamethyleneiminocarbonyl-cyclobutylmethylamino,
N-hexamethyleneiminocarbonyl-cyclopentylmethylamino,
N-hexamethyleneiminocarbonyl-cyclohexylmethylamino,
N-hexamethyleneiminocarbonyl-cycloheptylmethylamino,
N-hexamethyleneiminocarbonyl-(2-cyclopropylethyl)-amino
N-hexamethyleneiminocarbonyl-(2-cyclobutylethyl)-amino,
N-hexamethyleneiminocarbonyl-(2-cyclopentylethyl)-amino
N-hexamethyleneiminocarbonyl-(2-cyclohexylethyl)-amino
N-hexamethyleneiminocarbonyl-(2-cycloheptylethyl)-amino
N-hexamethyleneiminocarbonyl-(3-cyclopropylpropyl)-amino
N-hexamethyleneiminocarbonyl-(3-cyclobutylpropyl)-amino
N-hexamethyleneiminocarbonyl-(3-cyclopentylpropyl)-amino
N-hexamethyleneiminocarbonyl-(3-cyclohexylpropyl)-amino
N-hexamethyleneiminocarbonyl-(3-cycloheptylpropyl)-amino
N-hexamethyleneiminocarbonyl-phenylamino,
N-hexamethyleneiminocarbonyl-benzylamino,
N-morpholinocarbonyl-methylamino,
N-morpholinocarbonyl-ethylamino,
N-morpholinocarbonyl-isopropylamino,
N-morpholinocarbonyl-n-butylamino,
N-morpholinocarbonyl-n-pentylamino,
N-morpholinocarbonyl-n-hexylamino,
N-morpholinocarbonyl-n-octylamino,
N-morpholinocarbonyl-n-dodecylamino,
N-morpholinocarbonyl-cyclopropylamino,
N-morpholinocarbonyl-cyclobutylamino,
N-morpholinocarbonyl-cyclopentylamino,
N-morpholinocarbonyl-cyclohexylamino,
N-morpholinocarbonyl-cycloheptylamino,
N-morpholinocarbonyl-cyclopropylmethylamino,
N-morpholinocarbonyl-cyclobutylmethylamino,
N-morpholinocarbonyl-cyclopentylmethylamino,
N-morpholinocarbonyl-cyclohexylmethylamino,
N-morpholinocarbonyl-cycloheptylmethylamino,
N-morpholinocarbonyl-(2-cyclopropylethyl)-amino,
N-morpholinocarbonyl-(2-cyclobutylethyl)-amino,
N-morpholinocarbonyl-(2-cyclopentylethyl)-amino,
N-morpholinocarbonyl-(2-cyclohexylethyl)-amino,
N-morpholinocarbonyl-(2-cycloheptylethyl)-amino,
N-morpholinocarbonyl-(3-cyclopropylpropyl)-amino,
N-morpholinocarbonyl-(3-cyclobutylpropyl)-amino, N-morpholinocarbonyl-(3-cyclopentylpropyl)-amino, N-morpholinocarbonyl-(3-cyclohexylpropyl)-amino, N-morpholinocarbonyl-(3-cycloheptylpropyl)-amino, N-morpholinocarbonyl-phenylamino, N-morpholinocarbonyl-benzylamino, phthalimino, 5-methoxy-phthalimino, 5,6-dimethoxy-phthalimino, 6-methoxy-phthalimino, homophthalimino, 4,4-dimethyl-homophthalimino, 7-methoxy-homophthalimino, 6,7-dimethoxy-homophthalimino, 7-methoxy-4,4-diethyl-homophthalimino, 6,7-dimethoxy-4,4-dimethyl-homophthalimino, 1,2,3,6-tetrahydrophthalimino, hexahydrophthalimino, 1-oxo-isoindolin-2-yl, 3,4-dimethyl-phthalimino, 4,5-dimethyl-1,2,3,6-tetrahydrophthalimino, 4,5-dimethyl-hexahydrophthalimino, 4,5-dimethyl-1-oxo-isoindolin-2-yl, 3,4-dimethoxy-phthalimino, 4,5-dimethoxy-1,2,3,6-tetrahydrophthalimino, 4,5-dimethoxy-hexahydrophthalimino, 4,5dimethoxy-1-oxo-isoindolin-2-yl, glutarimino, 3,3-tetramethylene-glutarimino, 3,3-pentamethylene-glutarimino, 2,2-dimethyl-glutarimino, 3-methyl-glutarimino, 3,3dimethyl-glutarimino, 3-ethyl-glutarimino, hexafluoro-glutarimino, 3-ethyl-3-methyl-glutarimino, 1,3-cyclopentanedicarbonylimino, 2,4-dimethyl-glutarimino, 1,3-cyclopentanedicarbonylimino, 2,4-dimethyl-glutarimino, 2,4-di-n-propyl-glutarimino, endo-bicyclo[2,2,2]oct-5-ene-2,3-dicarboxylic acid-imino, methyl-5-norbornene-2,3-di-carboxylic acid-imino, 3,6-endoxo-1,2,3,6-tetrahydrophthalimino or 5-norbornene-endo-2,3-dicarboxylic acid-imino group, for $R_2$ the meanings mentioned above for $R_1$ or 1H-tetrazol-5-yl, 2-imidazolidon-1-yl, 3-methyl-2-imidazolidon-1-yl, 3-ethyl-2-imidazolidon-1-yl, 3-n-propyl-2-imidazolidon-1-yl, 3-isopropyl-2-imidazolidon-1-yl, 3-cyclopropyl-2-imidazolidon-1-yl, 3-cyclobutyl-2-imidazolidon-1-yl, 3-cyclopentyl-2-imidazolidon-1-yl, 3-cyclohexyl-2-imidazolidon-1-yl, 3-cycloheptyl-2imidazolidon-1-yl, 3-cyclopropylmethyl-2-imidazolidon-1-yl, 3-cyclobutylmethyl-2-imidazolidon-1-yl, 3-cyclopentylmethyl-2-imidazolidon-1-yl, 3-cyclohexylmethyl-2imidazolidon-1-yl, 3-cycloheptylmethyl-2-imidazolidon-1-yl, 3-(2-cyclopropylethyl)-2-imidazolidon-1-yl, 3-(2-cyclobutylethyl)-2-imidazolidon-1-yl, 3-(2-cyclopentylethyl)-2-imidazolidon-1-yl, 3-(2-cyclohexylethyl)-2-imidazolidon-1-yl, 3-(2-cycloheptylethyl)-2-imidazolidon-1-yl, 3-(3-cyclopropylpropyl)-2-imidazolidon-1-yl, 3-(3-cyclobutylpropyl)-2-imidazolidon-1-yl, 3-(3-cyclopentylpropyl)-2-imidazolidon-1-yl, 3-(3-cyclohexylpropyl)-2-imidazolidon-1-yl, 3-(3-cycloheptylpropyl)-2-imidazolidon-1-yl, 3-benzyl-2-imidazolidon-1-yl, 3-(2-phenylethyl)-2-imidazolidon-1-yl, 3-(3-phenylpropyl)-2-imidazolidon-1-yl, 3,4,5,6-tetrahydro-2-pyrimidon-1-yl, 3-methyl-3,4,5,6-tetrahydro-2-pyrimidon-1-yl, 3-ethyl-3,4,5,6-tetrahydro-2-pyrimidon-1-yl, 3-n-propyl-3,4,5,6-tetrahydro-2pyrimidon-1-yl, 3-isopropyl-3,4,5,6-tetrahydro-2pyrimidon-1-yl, 3-cyclopropyl-3,4,5,6-tetrahydro-2-pyrimidon-1-yl, 3-cyclobutyl-3,4,5,6-tetrahydro-2-pyrimidon-1-yl, 3-cyclopentyl-3,4,5,6-tetrahydro-2-pyrimidon-1-yl, 3-cyclohexyl-3,4,5,6-tetrahydro-2-pyrimidon-1-yl, 3-cycloheptyl-3,4,5,6-tetrahydro-2-pyrimidon-1-yl, 3-cyclopropylmethyl-3,4,5,6-tetrahydro-2-pyrimidon-1-yl, 3-cyclobutylmethyl-3,4,5,6-tetrahydro-2-pyrimidon-1-yl, 3-cyclopentylmethyl-3,4,5,6-tetrahydro-2-pyrimidon-1-yl, 3-cyclohexylmethyl-3,4,5,6-tetrahydro-2-pyrimidon-1-yl, 3-cycloheptylmethyl-3,4,5,6-tetrahydro-2-pyrimidon-1-yl, 3-(2-cyclopropylethyl)-3,4,5,6-tetrahydro-2-pyrimidon-1-yl, 3-(2-cyclobutylethyl)-3,4,5,6-tetrahydro-2-pyrimidon-1-yl, 3-(2-cyclopentylethyl)-3,4,5,6-tetrahydro-2-pyrimidon-1-yl, 3-(2-cyclohexylethyl)-3,4,5,6-tetrahydro-2-pyrimidon-1-yl, 3-(2-cycloheptylethyl)-3,4,5,6-tetrahydro-2-pyrimidon-1-yl, 3-(3-cyclopropyl-propyl)-3,4,5,6-tetrahydro-2-pyrimidon-1-yl, 3-(3-cyclobutylpropyl)-3,4,5,6-tetrahydro-2-pyrimidon-1-yl, 3-(3-cyclopentylpropyl)-3,4,5,6-tetrahydro-2-pyrimidon-1-yl, 3-(3-cyclohexylpropyl)-3,4,5,6-tetrahydro-2-pyrimidon-1-yl, 3-(3-cycloheptylpropyl)-3,4,5,6-tetrahydro-2-pyrimidon-1-yl, 3-benzyl-3,4,5,6-tetrahydro-2-pyrimidon-1-yl, 3-(2-phenylethyl)-3,4,5,6-tetrahydro-2-pyrimidon-1-yl or 3-(3-phenylpropyl)-3,4,5,6-tetrahydro-2-pyrimidon-1-yl group, for $R_3$ those of hydrogen, fluorine, chlorine or bromine atom, methyl, ethyl, n-propyl, isopropyl, n-butyl, isobutyl, tert.butyl, n-pentyl, n-hexyl, 1-methylpropyl, 1-methylbutyl, 2-methylbutyl, 3-methylbutyl, 1-methylpentyl, 2-methylpentyl, 3-methylpentyl, 4-methylpentyl, 1-ethylpropyl, 1,1-diethylethyl, methoxymethyl, ethoxymethol, (2-hydroxyethoxy)-methyl, 2-methoxyethyl, 2-ethoxyethyl, 3-methoxypropyl, methylmercaptomethyl, 2-methylmercapto-ethyl, 3-methylmercapto-propyl, 4methylmercapto-butyl, methylsulphinyl-methyl, 2-methylsulphinyl-ethyl, 3-methylsulphinyl-propyl, 4-methylsulphinyl-butyl, methylsulphonyl-methyl, 2-methylsulphonyl-ethyl, 3-methylsulphonyl-propyl, 4-methylsulphonyl-butyl, 2-methylamino-ethyl, 3-methylamino-propyl, 4-methylamino-butyl, 2-dimethylamino-ethyl, 3-dimethylamino-propyl, 4-dimethylamino-butyl, 5-dimethylamino-pentyl, 2-diethylamino-ethyl, 2-di-n-propylamino-ethyl, 2-(2-hydroxyethoxy)-ethyl, 3-(2-hydroxyethoxy)-propyl, 2-(2-methoxyethoxy)-ethyl, 2-(2-methoxyethoxy)-isopropyl, 3-(2-methoxyethoxy)-propyl, 2-(2-ethoxyethoxy)-ethyl, 2-(2-ethoxyethoxy)-isopropyl, 3-(2-ethoxyethoxy)-propyl, 2-(2-isopropoxyethoxy)-ethyl, methoxy, ethoxy, n-propoxy, isopropoxy, n-butoxy, 2-hydroxyethoxy, 3-hydroxypropoxy, 2-methoxyethoxy, 2-ethoxyethoxy, 2-isopropoxyethoxy, 3-methoxypropoxy, 3-isopropoxypropoxy, mercapto, methylmercapto, ethylmercapto, n-propylmercapto, isopropylmercapto, n-butylmercapto, benzyl, 2-phenylethyl, 3-phenylpropyl, allyl, n-but-2-enyl, n-pent-2-enyl, n-prop-1-enyl, n-but-1-enyl, n-pent-1-enyl, n-but-3-enyl, n-pent-3-enyl, n-pent-4-enyl, propargyl, n-but-3-ynyl, n-pent-3-ynyl, n-pent-4ynyl, cyclopentyl, cyclohexyl, cycloheptyl, cyclopentylmethyl, cyclohexylmethyl, cycloheptylmethyl, 2-cyclopentylethyl, 2-cyclohexyl-ethyl, 2-cycloheptylethyl, 3-cyclopentylpropyl, 3-cyclohexylpropyl, phenyl, hydroxyphenyl, fluorophenyl, chlorophenyl, bromophenyl, methylphenyl, ethylphenyl, isopropylphenyl, methoxyphenyl, ethoxyphenyl, n-propoxyphenyl, n-butoxyphenyl, hydroxy, (imidazol-4-yl)methylamino, 2-(imidazol-4-yl)ethylamino, 3-(imidazol-4-yl)propylamino, methylamino, ethylamino, n-propylamino, isopropylamino, n-butylamino, isobutylamino, aminocarbonyl, methylaminocarbonyl, ethylaminocarbonyl, isopropylaminocarbonyl, n-butylaminocarbonyl, cyclopentylaminocarbonyl, cyclohexylaminocarbonyl, cycloheptylaminocarbonyl, naphthyl, pyridyl, pyrimidyl, pyridazinyl, pyrazinyl, pyrazolyl, 1,3-dimethylpyrazolyl, pyrrolyl, imidazolyl, oxazolyl, thiazolyl, triazolyl or tetrazolyl group, and for $R_4$ those of carboxy, methoxycarbonyl, ethoxycarbonyl, n-propoxycarbonyl, isopropoxycarbonyl, n-butoxycarbonyl, isobutoxycarbonyl, tert.butoxycarbonyl, n-pentoxycarbonyl, n-hexoxycarbonyl, benzyloxycarbonyl, 1-phenylethoxycarbonyl, 2-phenyl-ethoxycarbonyl, 3-phenylpropoxycarbonyl, pivaloyloxymethoxycarbonyl, phthalidyloxycarbonyl, ethoxycarbonyloxyethoxycarbonyl, methoxymethoxycarbonyl, cyclohexyloxycarbonylmethoxycarbonyl, (1,3-dioxa-2-oxo-4-methyl-cyclopentan-5-yl)-methoxycarbonyl, amino, phthalimido, aminoacetylamino, methoxycarbonylaminoacetylamino, ethoxycarbonylaminoacetylamino, isopropoxycarbonylaminoacetylamino, n-butoxycarbonylaminoacetylamino, methylcarbonylamino, trifluoromethylcarbonylamino, ethylcarbonylamino, n-propylcarbonylamino, isopropylcarbonylamino, cyclopentylcarbonylamino, cyclohexylcarbonylamino, cycloheptylcarbonylamino, phenylcarbonylamino, fluorophenylcarbonylamino, chlorophenylcarbonylamino, bromophenylcarbonylamino, methylphenylcarbonylamino, ethylphenylcarbonylamino, isopropylphenylcarbonylamino, methoxyphenylcarbonylamino, ethoxyphenylcarbonylamino, n-propoxyphenylcarbonylamino, benzylcarbonylamino, 2-phenylethylcarbonylamino, methylsulphonylamino, trifluoromethylsulphonylamino, ethylsulphonylamino, n-propylsulphonylamino, isopropylsulphonylamino, phenylsulphonylamino, fluorophenylsulphonylamino, chlorophenylsulphonylamino, bromophenylsulphonylamino, methylphenylsulphonylamino, ethylphenylsulphonylamino, isopropylphenylsulphonylamino, methoxyphenylsulphonylamino, ethoxyphenylsulphonylamino, benzylsulphonylamino, cyano, aminomethyl, methylsulphonylaminomethyl, ethylsulphonylaminomethyl, n-propylsulphonylaminomethyl, phenylsulphonylaminomethyl, methylphenylsulphonylaminomethyl, trifluoromethylsulphonylaminomethyl, methylsulphonylaminocarbonyl, ethylsulphonylaminocarbonyl, n-propylsulphonylaminocarbonyl, isopropylsulphonylaminocarbonyl, n-butylsulphonylaminocarbonyl, trifluoromethylsulphonylaminocarbonyl, perfluoro-n-butylsulphonylaminocarbonyl, phenylsulphonylaminocarbonyl, benzylsulphonylaminocarbonyl, 4-methylphenylsulphonylaminocarbonyl, 4-chlorophenylsulphonylaminocarbonyl, trifluoroacetylaminomethyl, 1H-tetrazolyl or 1-(triphenylmethyl)-tetrazolyl group.

Preferred compounds of the general formula I are those in which $R_1$ denotes a hydrogen, fluorine or chlorine atom, a trifluoromethyl, hydroxy, benzyloxy, carboxy, cyano, amino, nitro, aminosulphonyl, methylaminosulphonyl, dimethylaminosulphonyl, trifluoromethylsulphonyloxy or tetrazolyl group, an alkyl group having 1 to 4 carbon atoms, wherein the methyl group may be additionally substituted by a hydroxy or alkylamino group having 1 to 4 carbon atoms, an alkoxy group having 1 to 4 carbon atoms, which may be substituted in the 2, 3 or 4 position by a hydroxy, alkoxy, alkylamino, dialkylamino or imidazolyl group and the alkyl substituent may contain 1 to 3 carbon atoms in each case, an alkanoyloxy group having 1 to 4 carbon atoms or a cycloalkylaminocarbonyloxy group having 5 to 7 carbon atoms in the cycloalkyl moiety, an amino group, which is substituted by a benzyl, Decalin, trifluoromethylcarbonyl, benzylcarbonyl, benzyloxycarbonyl, 2-ethyl-5-methylcyclohexyloxy or tert.butoxycarbonylaminoacetyl group, by an alkyl group having 1 to 5 carbon atoms, by a cycloalkyl, cycloalkylalkyl, cycloalkoxycarbonyl, cycloalkylcarbonyl or cycloalkylalkanoyl group, wherein the cycloalkyl moiety may contain 5 to 7 carbon atoms, the alkyl moiety may contain 1 to 3 carbon atoms and the alkanoyl moiety may contain 1 to 3 carbon atoms, by an alkanoyl group having 1 to 6 carbon atoms, by an aminoalkanoyl or dialkylaminoalkanoyl group, in which the alkyl moiety and the alkanoyl moiety may each contain 1 to 3 carbon atoms by an alkoxycarbonyl group having a total of 2 to 7 carbon atoms, by an alkylsulphonyl group having 1 to 4 carbon atoms or by a thiazolidin-3-ylcarbonyl group substituted by an alkoxycarbonyl group having a total of 2 to 4 carbon atoms, a benzylamino or alkylamino group having 1 to 5 carbon atoms, which is substituted at the nitrogen atom additionally by a benzyl or cyclohexyl group, by an alkyl group having 1 to 3 carbon atoms, which may be substituted in the 2 or 3 position by an alkoxy group having 1 to 3 carbon atoms or by a phenylamino group, by an alkanoyl group having 1 to 5 carbon atoms, which may be substituted by an alkoxy group having 1 to 3 carbon atoms, by a cycloalkylcarbonyl group having a total of 6 to 8 carbon atoms or by an alkoxycarbonyl group having a total of 2 to 4 carbon atoms, a carbonyl group, which is substituted by an alkyl group which may be substituted in the 2- or 3-position by a hydroxy, alkoxycarbonyl or alkylamino group, by an alkylamino group with 1 to 5 carbon atoms which may be substituted by a carboxy group in the alkyl moiety, by an alkylamino group substituted by a phenylamino group in the 2- or 3-position, by a phenyl, alkoxy, amino, benzylamino, phenylethylamino, cycloalkylamino or cycloalkylalkylamino, in which the alkyl moiety may contain 1 to 3 carbon atoms and the cycloalkyl moiety may contain 5 to 7 carbon atoms, and additionally a $C_{1-5}$ alkylamino group may be substituted at the nitrogen atom by an alkyl group having 1 to 4 carbon atoms, an aminocarbonylamino or aminothiocarbonylamino group, which may be monosubstituted, disubstituted or trisubstituted by an alkyl group having 1 to 12 carbon atoms, by an alkenyl or alkynyl group having 3 to carbon atoms in each case, by a bicyclic or tricyclic alkyl group having 7 to 11 carbon atoms, by a cycloalkyl, cycloalkylalkyl or phenylalkyl group, wherein the substituents may be the same or different, and the alkyl moiety may contain 1 to 3 carbon atoms and the cycloalkyl moiety may contain 5 to 7 carbon atoms, and a methylene group in a cycloalkyl radical having 5 to 7 carbon atoms may be replaced by an oxygen atom, and an alkyl group may be substituted in the 4, 5 or 6 position by a hydroxy or trifluoroacetyl group, a cycloalkyleneiminocarbonylamino group having 4 to 6 carbon atoms in the cycloalkyleneimino moiety or a morpholinocarbonylamino group, which may both be substituted at the amino nitrogen by an alkyl group having 1 to 12 carbon atoms, by a cycloalkyl, cycloalkylalkyl or phenylalkyl group, in which the alkyl moiety may contain 1 to 3 carbon atoms and the cycloalkyl moiety may contain 5 to 7 carbon atoms, a phthalimino, homophthalimino, 2-carboxyphenylcarbonylamino, 2-carboxyphenylmethylamino, 2-carboxyphenylmethylenecarbonylamino or 2-carboxymethylenephenylcarbonylamino group, whilst a carbonyl group in a phthalimino group may be replaced by a methylene group and a methylene group in a homophthalimino, 2-carboxyphenylmethylenecarbonylamino or 2-carboxymethylenephenylcarbonylamino group may be substituted by one or two alkyl groups, and additionally the above-mentioned phenyl nuclei may be mono- or disubstituted by alkyl or alkoxy groups, whilst the substituents may be identical or different, and at the same time they may be partially or wholly hydrogenated, a bicycloalkane-3-carboxylic acid amino or bicycloalkene-3-carboxylic acid amino group substituted by a carboxy group in the 2-position, a bicycloalkane-2,3-dicarboxylic acid imino or bicycloalkene-2,3-dicarboxylic acid imino group, wherein the bicycloalkane and bicycloalkene parts each contain 9 or 10 carbon atoms, may be substituted by 1, 2 or 3 methyl groups and an endomethylene group may be replaced by an oxygen atom, a glutaric acid imino or 3-carboxy-n-propylene-carbonyl group wherein the n-propylene group may be perfluorinated, substituted by one or two alkyl groups or by a tetramethylene or pentamethylene group, or a 5,7-dioxa-1H,3H-imidazo [1,5-c]thiazolyl group, a 2-imidazolidon-1-yl group optionally substituted in the 3 position by an alkyl group having 1 to 3 carbon atoms, or a 3,4,5,6-tetrahydro-2-pyrimidon-1-yl group, $R_2$ denotes a hydrogen, fluorine or chlorine, a methyl, hydroxy or methoxy group, or $R_1$ and $R_2$ together with the two ortho position carbon atoms of the neighbouring phenyl ring denote a phenyl or 1-alkyl-3,3-dialkyl-2,3-dihydro-pyrrol-2-one group, in which the alkyl moiety may contain 1 to 3 carbon atoms in each case, $R_3$ denotes a hydrogen, fluorine or chlorine atom, a hydroxy, benzyl or aminocarbonyl group, an alkyl group having 1 to 5 carbon atoms, wherein the methyl group may be additionally substituted by a hydroxy group, by an alkoxy, alkylsulphenyl, alkylsulphinyl or alkylsulphonyl group each having 1 to 3 carbon atoms, a cycloalkyl or cycloalkylalkyl group, in which the cycloalkyl moiety may contain 5 to 7 carbon atoms and the alkyl moiety may contain 1 to 3 carbon atoms, an alkenyl or alkynyl group each having 3 to 5 carbon atoms, a phenylalkyl group having 1 to 3 carbon atoms, an alkylamino group having 1 to 4 carbon atoms, a pyridyl, furyl, thiazolyl or pyrazolyl group, which may be substituted by one or two methyl groups, $R_4$ denotes an alkoxycarbonyl having a total of 1 to 5 carbon atoms, an amino, phthalimino, aminomethyl, carboxy, cyano, methylsulphonylaminocarbonyl, trifluoromethylsulphonylaminocarbonyl, benzenesulphonylaminocarbonyl, trifluorocarbonylaminomethyl, trifluoromethylaminomethyl, tetrazolyl or 1-(triphenylmethyl)tetrazolyl group, $R_5$ denotes a hydrogen, fluorine, chlorine or bromine atom, $R_6$ denotes a hydrogen atom or $R_5$ and $R_4$ together with the two ortho position carbon atoms denote a phenyl group, and 1 and 3 isomer mixtures thereof and the addition salts thereof, in particular for pharmaceutical application their physiologically acceptable addition salts with inorganic or organic acids.

However, particularly preferred compounds of the general formula I are those in which $R_1$ denotes an amino group, which is substituted by a benzyl, Decalin, trifluoromethylcarbonyl, benzylcarbonyl, benzyloxycarbonyl, 2-ethyl-5-methylcyclohexyloxy or tert-butoxycarbonylaminoacetyl group, by an alkyl group having 1 to 5 carbon atoms, by acycloalkyl, cycloalkylalkyl, cycloalkoxycarbonyl, cycloalkylcarbonyl or cycloalkylalkanoyl group, wherein the cycloalkyl moiety may contain 5 to 7 carbon atoms, the alkyl moiety may contain 1 to 3 carbon atoms and the alkanoyl moiety may contain 1 to 3 carbon atoms, by an alkanoyl group having 1 to 6 carbon atoms, by an aminoalkanoyl or dialkylaminoalkanoyl group, in which the alkyl moiety and the alkanoyl moiety may each contain 1 to 3 carbon atoms, by an alkoxycarbonyl group having a total of 2 to 7 carbon atoms, by an alkylsulphonyl group having 1 to 4 carbon atoms or by a thiazolidin-3-ylcarbonyl group substituted by an alkoxycarbonyl group having a total of 2 to 4 carbon atoms, a benzylamino or alkylamino group having 1 to 5 carbon atoms, which is additionally substituted at the nitrogen atom by a benzyl or cyclohexyl group, by an alkyl group having 1 to 3 carbon atoms, which may be substituted in the 2 or 3 position by an alkoxy group having 1 to 3 carbon atoms or by a phenylamino group, by an alkanoyl group having 1 to 5 carbon atoms, which may be substituted by an alkoxy group having 1 to 3 carbon atoms, by a cycloalkylcarbonyl group having a total of 6 to 8 carbon atoms or by an alkoxycarbonyl group having a total of 2 to 4 carbon atoms, an aminocarbonylamino or aminothiocarbonylamino group, which may be monosubstituted, disubstituted or trisubstituted by an alkyl group having 1 to 12 carbon atoms, by an alkenyl or alkynyl group each having 3 to 5 carbon atoms, by a bicyclic or tricyclic alkyl group having 7 to 11 carbon atoms, by a cycloalkyl, cycloalkylalkyl or phenylalkyl group, wherein the substituents may be the same or different, and the alkyl moiety may contain 1 to 3 carbon atoms and the cycloalkyl moiety may contain 5 to 7 carbon atoms, and a methylene group in a cycloalkyl radical having 5 to 7 carbon atoms may be replaced by an oxygen atom, and an alkyl group may be substituted in the 4, 5 or 6 position by a hydroxy or trifluoroacetyl group, a cycloalkyleneiminocarbonylamino group having 4 to 6 carbon atoms in the cycloalkyleneimino moiety or a morpholinocarbonylamino group, which may both be substituted at the amino nitrogen by an alkyl group having 1 to 12 carbon atoms, by a cycloalkyl, cycloalkylalkyl or phenylalkyl group, in which the alkyl moiety may contain 1 to 3 carbon atoms and the cycloalkyl moiety may contain 5 to 7 carbon atoms, a phthalimino, homophthalimino, 2-carboxyphenylcarbonylamino, 2-carboxyphenylmethylamino, 2-carboxyphenylmethylenecarbonylamino or 2-carboxymethylenephenylcarbonylamino group, whilst a carbonyl group in a phthalimino group may be replaced by a methylene group and a methylene group in a homophthalimino, 2-carboxyphenylmethylenecarbonylamino or 2-carboxymethylenephenylcarbonylamino group may be substituted by one or two alkyl groups, and additionally the above-mentioned phenyl nuclei may be mono- or disubstituted by alkyl or alkoxy groups, whilst the substituents may be identical or different, and at the same time they may be partially or wholly hydrogenated, a bicycloalkane-3-carboxylic acid amino or bicycloalkene-3-carboxylic acid amino group substituted by a carboxy group in the 2-position, a bicycloalkane-2,3-dicarboxylic acid imino or bicycloalkene-2,3dicarboxylic acid imino group, wherein the bicycloalkane and bicycloalkene parts each contain 9 or 10 carbon atoms, may be substituted by 1, 2 or 3 methyl groups and an endomethylene group may be replaced by an oxygen atom, a glutaric acid imino or 3-carboxy-n-propylene-carbonyl group wherein the n-propylene group may be perfluorinated, substituted by one or two alkyl groups or by a tetramethylene or pentamethylene group, or a 5,7-dioxa-1H,3H-imidazo[1,5-c]thiazolyl group, $R_2$ denotes a hydrogen atom, a methyl or hydroxy group, or $R_1$ and $R_2$ together with the two ortho position carbon atoms of the neighbouring phenyl ring denote a phenyl group, $R_3$ denotes an alkyl group having 3 to 5 carbon atoms, an alkenyl or alkynyl group each having 3 to 5 carbon atoms, $R_4$ denotes a carboxy, methylsulphonylaminocarbonyl, trifluoromethylsulphonylaminocarbonyl, benzenesulphonylaminocarbonyl, trifluorocarbonylaminomethyl, trifluoromethylaminomethyl or tetrazolyl group, $R_5$ denotes a hydrogen atom, $R_6$ denotes a hydrogen atom or $R_5$ and $R_6$ together with the two ortho position carbon atoms denote a phenyl group, in particular those compounds of the general formula I in which $R_1$ denotes an amino group, which is substituted by an alkanoyl group having 1 to 6 carbon atoms, by an aminoalkanoyl or dialkylaminoalkanoyl group, in which the alkyl moiety and the alkanoyl moiety may each contain 1 to 3 carbon atoms, by an alkoxycarbonyl group having a total of 2 to 7 carbon atoms or by a thiazolidin-3-ylcarbonyl group substituted by an alkoxycarbonyl group having a total of 2 to 4 carbon atoms, a benzylamino or alkylamino group having 1 to 5 carbon atoms, which is substituted at the nitrogen atom by an alkanoyl group having 1 to 5 carbon atoms, which may be substituted by an alkoxy group having 1 to 3 carbon atoms, by a cycloalkylcarbonyl group having a total of 6 to 8 carbon atoms or by an alkoxycarbonyl group having a total of 2 to 4 carbon atoms, an aminocarbonylamino or aminothiocarbonylamino group, which may be monosubstituted, disubstituted or trisubstituted by an alkyl group having 1 to 8 carbon atoms, by an alkenyl or alkynyl group each having 3 to 5 carbon atoms, by a bicyclic or tricyclic alkyl group having 7 to 11 carbon atoms, by a cycloalkyl, cycloalkylalkyl or phenylalkyl group, wherein the substituents may be the same or different, and the alkyl moiety may contain 1 to 3 carbon atoms and the cycloalkyl moiety may contain 5 to 7 carbon atoms, and a methylene group in a cycloalkyl radical having 5 to 7 carbon atoms may be replaced by an oxygen atom, and an alkyl group may be substituted in the 4, 5 or 6 position by a hydroxy or trifluoroacetyl group, a cycloalkyleneiminocarbonylamino group having 4 to 6 carbon atoms in the cycloalkyleneimino moiety or a morpholinocarbonylamino group, which may both be substituted at the amino nitrogen by an alkyl group having 1 to 8 carbon atoms, by a cycloalkyl, cycloalkylalkyl or phenylalkyl group, in which the alkyl moiety may contain 1 to 3 carbon atoms and the cycloalkyl moiety may contain 5 to 7 carbon atoms, a phthalimino, homophthalimino, 2-carboxyphenylcarbonylamino, 2-carboxyphenylmethylamino, 2-carboxyphenylmethylenecarbonylamino or 2-carboxymethylenephenylcarbonylamino group, whilst a carbonyl group in a phthalimino group may be replaced by a methylene group and a methylene group in a homophthalimino, 2-carboxyphenylmethylenecarbonylamino or 2-carboxymethylenephenylcarbonylamino group may be substituted by one or two alkyl groups, and additionally the above-mentioned phenyl nuclei may be mono- or disubstituted by alkyl or alkoxy groups, whilst the substituents may be identical or different, and at the same time they may be partially or wholly hydrogenated, a bicycloalkane-3-carboxylic acid amino or bicycloalkene-3-carboxylic acid amino group substituted by a carboxy group in the 2-position, a bicycloalkane-2,3-dicarboxylic acid imino or bicycloalkene-2,3-dicarboxylic acid imino group, wherein the bicycloalkane and bicycloalkane parts each contain 9 or 10 carbon atoms, may be substituted by 1, 2 or 3 methyl groups and an endomethylene group may be replaced by an oxygen atom, a glutaric acid imino or 3-carboxy-n-propylene-carbonyl group wherein the n-propylene group may be perfluorinated, substituted by one or two alkyl groups or by a tetramethylene or pentamethylene group, or a 5,7-dioxa-1H,3H-imidazo[1,5-c]thiazolyl group, $R_2$ denotes a hydrogen atom, or $R_1$ and $R_2$ together with the two ortho position carbon atoms of the neighbouring phenyl ring denote a phenyl group, $R_3$ denotes an alkyl group having 3 to 5 carbon atoms, an alkenyl or alkynyl group each having 3 to 5 carbon atoms, $R_4$ denotes a carboxy or tetrazolyl group, $R_5$ denotes a hydrogen atom, $R_6$ denotes a hydrogen atom or $R_5$ and $R_6$ together with the two ortho position carbon atoms denote a phenyl group, 1-isomer and 3-isomer mixtures thereof and addition salts thereof, in particular for pharmaceutical application their physiologically acceptable addition salts with inorganic or organic acids.

The novel compounds of the formula I are obtained in accordance with the invention by the following processes:

a) cyclisation of a compound of the formula

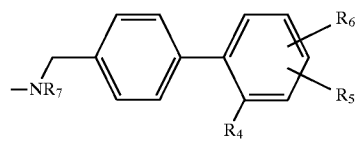

(II)

in which $R_1$ and $R_2$ are as hereinbefore defined, one of the radicals $X_1$ or $Y_1$ is a group of the formula

and the other of the radicals $X_1$ or $Y_1$ is a group of the formula

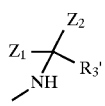

wherein $R_3'$ as hereinbefore defined for $R_3$, with the exception of the fluorine, chlorine or bromine atom, the hydroxy, mercapto or aminocarbonyl group, wherein the latter may be substituted by an alkyl group having 1 to 3 carbon atoms or by a cycloalkyl group having 5 to 7 carbon atoms, $R_4$ to $R_6$ are as hereinbefore defined, $R_7$ denotes a hydrogen atom, a hydroxy group or an $R_3'CO$ group, wherein $R_3'$ is defined as above, $Z_1$ and $Z_2$, which may be the same or different, denote optionally substituted amino groups or hydroxy or mercapto groups optionally substituted by lower alkyl groups, or $Z_1$ and $Z_2$, together denote an oxygen or sulphur atom, an imino group optionally substituted by an alkyl group having 1 to 3 carbon atoms, an alkylenedioxy or alkylenedithio group each having 2 or 3 carbon atoms, but wherein one of the radicals $X_1$ or $Y_1$ must be a group of the formula

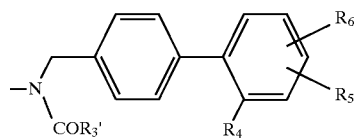

or

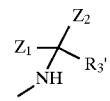

The cyclisation is advantageously carried out in a solvent or solvent mixture, such as ethanol, isopropanol, glacial acetic acid, benzene, chlorobenzene, toluene, xylene, glycol, glycolmonomethylether, diethyleneglycoldimethylether, sulpholane, dimethylformamide, Tetralin or in an excess of the acylating agent used for the preparation of the compound of the general formula II, for example in the corresponding nitrile, anhydride, acid halide, ester or amide, for example at temperatures between 0° and 250° C., but preferably at the boiling temperature of the reaction mixture, optionally in the presence of a condensation agent, such as phosphorusoxychloride, thionylchloride, sulphurylchloride, sulphuric acid, p-toluenesulphonic acid, methanesulphonic acid, hydrochloric acid, phosphoric acid, polyphosphoric acid, acetic anhydride, or optionally also in the presence of a base, such as potassium ethoxide or potassium tert.butoxide. However, cyclisation may also be carried out without a solvent and/or condensing agent.

However, the reaction is particularly advantageously carried out by preparing a compound of the formula II in the reaction mixture by reducing a corresponding o-nitroamino compound, optionally in the presence of a carboxylic acid of the formula $R_3'COOH$, or by acylation of a corresponding o-diamino compound. When the reduction of the nitro group is terminated at the hydroxylamine step, the N oxide of a compound of the formula I is obtained in the subsequent cyclisation. The N oxide thus obtained is then converted to a corresponding compound of the formula I by means of reduction.

The subsequent reduction of the N oxide of formula I obtained is preferably carried out in a solvent, such as water, water/ethanol, methanol, glacial acetic acid, ethyl acetate or dimethylformamide, with hydrogen in the presence of a hydrogenation catalyst, such as Raney nickel, platinum or palladium/carbon, with metals, such as iron, tin or zinc in the presence of an acid such as acetic acid, hydrochloric acid or sulphuric acid, with salts, such as iron (II) sulphate, tin (II) chloride or sodium dithionite, or with hydrazine in the presence of Raney nickel, at temperatures between 0° and 50° C., but preferably at ambient temperature.

A 2-alkoxy compound of formula I optionally thus obtained, can then be converted to a corresponding 2-hydroxy compound of formula I, optionally by means of hydrolysis, preferably in the presence of an acid, such as hydrochloric acid, hydrobromic acid, sulphuric acid, phosphoric acid or trichloroacetic acid, in a suitable solvent, such as water, water/methanol, ethanol, water/ethanol, water/isopropanol or water/dioxane, at temperatures between –10° and 120° C., for example at temperatures between 20° C. and the boiling temperature of the reaction mixture.

b) For the preparation of the compounds of formula I, in which $R_3$ represents the aromatic or heteroaromatic radicals mentioned hereinbefore for $R_3$:

Reaction of phenylenediamine of the formula

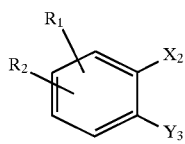

(III)

(in which

R$_1$ and R$_2$ are as hereinbefore defined, one of the radicals X$_2$ or Y$_2$ denotes a group of the formula

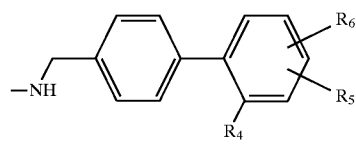

in which

R$_4$ to R$_6$ are as hereinbefore defined, and the other of the radicals X$_2$ or Y$_2$ denotes an amino group) with an aldehyde of the formula

OCH—R$_3$"  (IV)

in which

R$_3$" denotes an aromatic or heteroaromatic radical as hereinbefore defined for R$_3$.

The reaction is preferably carried out in a suitable solvent, such as benzene, toluene, xylene, mesitylene or dimethylacetamide, in the presence of a oxidising agent, such as sulphur or air oxygen, at temperatures between 80° and 250° C., preferably at the boiling temperature of the reaction mixture.

A 2-alkoxy compound of formula I optionally thus obtained can then be converted to a corresponding 2-hydroxy compound of formula I, optionally by means of hydrolysis, preferably in the presence of an acid, such as hydrochloric acid, hydrobromic acid, sulphuric acid, phosphoric acid or trichloroacetic acid, in a suitable solvent, such as water, water/methanol, ethanol, water/ethanol, water/isopropanol or water/dioxane, at temperatures between −10° and 120° C., for example at temperatures between 20° C. and the boiling temperature of the reaction mixture.

c) For the preparation of compounds of the formula I, in which at least one of the radicals R$_1$, R$_2$ and/or R$_3$ is one of the radicals containing a sulphinyl or sulphonyl group as hereinbefore defined for R$_1$, R$_2$ and/or R$_3$, and the remainder of the radicals R$_1$, R$_2$ and/or R$_3$ are as hereinbefore defined:

Oxidation of a compound of the formula

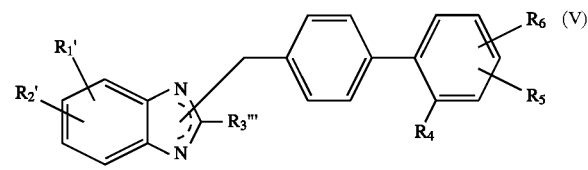

(V)

in which

R$_4$ to R$_6$ are as hereinbefore defined, at least one of the radicals R$_1$', R$_2$' and/or R$_3$'" is one of the radicals containing a sulphur atom or a sulphinyl group as hereinbefore defined for R$_1$, R$_2$ and/or R$_3$, and the remainder of the radicals R$_1$', R$_2$' and/or R$_3$'" have the meanings hereinbefore defined for R$_1$, R$_2$ and/or R$_3$.

The oxidation is preferably carried out in a solvent or solvent mixture, for example in water, water/pyridine, acetone, glacial acetic acid, dilute sulphuric acid or trifluoroacetic acid, advantageously at temperatures between −80° and 100° C., depending on the oxidising agent used.

For the preparation of a sulphinyl compound of the formula I, the oxidation is advantageously carried out using one equivalent of the oxidising agent used, for example using hydrogen peroxide in glacial acetic acid, trifluoroacetic acid or formic acid at 0° to 20° C. or in acetone at 0° to 60° C. using a peracid, such as performic acid in glacial acetic acid or trifluoroacetic acid at 0° to 50° C., or using m-chloroperbenzoic acid in methylene chloride or chloroform at −20° to 60° C., using sodium metaperiodate in aqueous methanol or ethanol at −15° to 25° C., using bromine in glacial acetic acid or aqueous acetic acid, using N-bromosuccinimide in ethanol, using tert.butyl hypochlorite in methanol at −80° to −30° C., using iodobenzodichloride in aqueous pyridine at 0° to 50° C., using nitric acid in glacial acetic acid at 0° to 20° C., using chromic acid in glacial acetic acid or in acetone at 0° to 20° C., and using sulphuryl chloride in methylene chloride at −70° C., the thioether-chlorine complex thus obtained is advantageously hydrolysed using aqueous ethanol.

For the preparation of a sulphonyl compound of the formula I, the oxidation is advantageously carried out using one or using two or more equivalents of the oxidising agent used, for example using hydrogen peroxide in glacial acetic acid, trifluoroacetic acid or in formic acid at 20° to 100° C., or in acetone at 0° to 60° C., using a peracid, such as performic acid or m-chloroperbenzoic acid in glacial acetic acid, trifluoroacetic acid, methylene chloride or chloroform at temperatures between 0° and 60° C., using nitric acid in glacial acetic acid at 0° to 20° C., using chromic acid or potassium permanganate in glacial acetic acid, water/sulphuric acid or in acetone at 0° to 20° C.

d) For the preparation of a compound of the formula I, in which R$_4$ is a carboxy or amino group:

Conversion of a compound of the formula

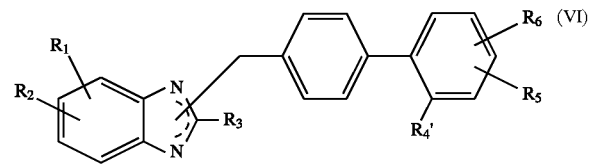

(VI)

in which

R$_1$ to R$_2$, R$_3$ and R$_4$ are as hereinbefore defined, and R$_4$' is a group which can be converted to a carboxy group by means of hydrolysis, thermolysis or hydrogenolysis, or a group which can be converted to an amino group by means of hydrolysis, hydrogenolysis or transamidation.

For example, functional derivatives of the carboxy group, such as its unsubstituted or substituted amides, esters, thiolesters, orthoesters, iminoethers, amidines or anhydrides, the nitrile group or the tetrazolyl group, can be converted to a carboxy group by means of hydrolysis, esters of tertiary alcohols, for example tert.butylester, can be converted to a carboxy group by means of thermolysis, esters of aralkanols, for example benzyl ester, can be converted to a carboxy group by means of hydrogenolysis, acylamino groups, for example the benzoylamino or phthalimido group, can be converted to an amino group by means of hydrolysis and imino groups, for example the phthalimino group, can be converted to an amino group by means of transamidation.

The hydrolysis is advantageously carried out either in the presence of an acid, such as hydrochloric acid, sulphuric acid, phosphoric acid, trichloroacetic acid or trifluoroacetic acid, in the presence of a base, such as sodium hydroxide or potassium hydroxide, in a suitable solvent, such as water, water/methanol, ethanol water/ethanol, water/isopropanol or water/dioxane, at temperatures between −10° C. and 120° C., for example at temperatures between ambient temperature and the boiling temperature of the reaction mixture. During hydrolysis in the presence of an organic acid, such as trichloroacetic acid or trifluoroacetic acid, alcohol hydroxy groups, which are optionally present, may also be converted to a corresponding acyloxy group, such as the trifluoroacetoxy group.

If $R_4'$ in a compound of formula VI denotes a cyano or aminocarbonyl group, these groups may also be converted to the carboxy group using a nitrite, for example sodium nitrite, in the presence of an acid, such as sulphuric acid, this advantageously being used at the same time as solvent, at temperatures between 0° and 50° C.

If $R_4'$ in a compound of formula VI denotes, for example the tert.butyloxycarbonyl group, the tert.butyl group may also be cleaved thermally, optionally in a inert solvent, such as methylene chloride, chloroform, benzene, toluene, tetrahydrofuran or dioxane, and preferably in the presence of a catalytic amount of an acid, such as p-toluenesulphonic acid, sulphuric acid, phosphoric acid or polyphosphoric acid, preferably at the boiling temperature of the solvent used, for example at temperatures between 40° C. and 100° C.

If $R_4'$ in a compound of formula VI denotes, for example the benzyloxycarbonyl group, the benzyl group may also be cleaved hydrogenolytically in the presence of a hydrogenation catalyst, such as palladium/carbon, in a suitable solvent, such as methanol, ethanol, ethanol/water, glacial acetic acid, ethyl acetate, dioxane or dimethylformamide, preferably at temperatures between 0° and 50° C., for example at ambient temperature, and a hydrogen pressure of 1 to 5 bar. During the hydrogenolysis, other radicals may also be reduced at the same time, for example a nitro group to the amino group, a benzyloxy group to the hydroxy group, a vinylidene group to the corresponding alkylidene group or a cinnamic acid group to the corresponding phenylpropionic acid group, or may be replaced by hydrogen atoms, for example a halogen atom may be replaced by a hydrogen atom.

If $R_4'$ denotes a phthalimino group, this group may be converted particularly advantageously to an amino group, in the presence of a primary organic base, such as methylamine, ethylamine or propylamine, in a suitable solvent, such as methanol, ethanol, isopropanol, dimethylformamide, methanol/dimethylformamide or methanol/water, by transamidation at temperatures between 0° and 50° C., but preferably at ambient temperature. If $R_1$ and/or $R_2$ denote here one of the imino radicals mentioned hereinbefore, they are similarly converted to a corresponding amino group.

If $R_1$ and/or $R_2$ in a compound of formula VI represents one of the above-mentioned imino groups, this may also be partially hydrolysed during the reaction, for example into a 2-carboxyphenylcarbonylamino, 2 0 carboxyphenylmethylamino, 2-carboxyphenylmethylenecarbonylamino or 2-carboxymethylenephenylcarbonylamino group, whilst a methylene group in a 2-carboxyphenylmethylenecarbonylamino or 2-carboxymethylenephenylcarbonylamino group may be substituted by one or two alkyl groups, and additionally the above-mentioned phenyl nuclei may be mono- or disubstituted by alkyl or alkoxy groups, the substituents being identical or different, and at the same time they may be wholly or partially hydrogenated, a bicycloalkane-3-carboxylic acid amino or bicycloalkene-3-carboxylic acid amino group substituted by a carboxy group in the 2-position, wherein the bicycloalkane and bicycloalkene moieties each contain 9 or 10 carbon atoms, may be substituted by 1, 2 or 3 methyl groups and an endomethylene group may be replaced by an oxygen atom, a 3-carboxy-n-propylenecarbonyl group wherein the n-propylene group may be perfluorinated, substituted by one or two alkyl groups or substituted by a tetramethylene or pentamethylene group.

e) Reaction of a benzimidazole of the formula

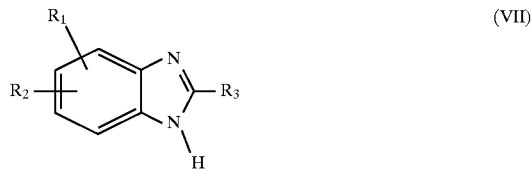

in which
$R_1$ to $R_3$ are as hereinbefore defined, with a biphenyl compound of the formula

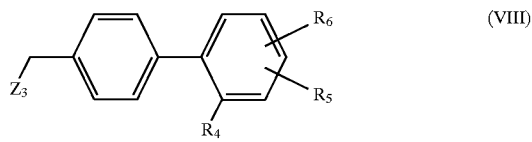

in which
$R_4$ to $R_6$ are as hereinbefore defined, and
$Z_3$ is a nucleophilic leaving group, such as a halogen atom, for example a chlorine, bromine or iodine atom, or a substituted sulphonyloxy group, for example a methanesulphonyloxy, phenylsulphonyloxy or p-toluenesulphonyloxy group.

The reaction is advantageously carried out in a solvent or solvent mixture, such as methylene chloride, diethylether, tetrahydrofuran, dioxane, dimethylsulphoxide or benzene, optionally in the presence of an acid-binding agent, such as sodium carbonate, potassium carbonate, sodium hydroxide, potassium tert.butoxide, triethylamine or pyridine, wherein the two latter agents may also be used at the same time as solvent, preferably at temperatures between 0° and 100° C., for example at temperatures between ambient temperature and 50° C.

During the reaction, a mixture of the 1-isomer and 3-isomer is preferably obtained.

f) For the preparation of a compound of the formula I, in which $R_4$ is a 1-H-tetrazolyl group:

Cleaving a protective radical from a compound of the formula

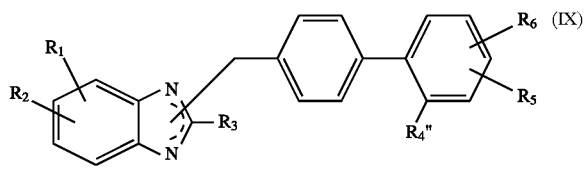

in which
$R_1$ to $R_3$, $R_3$ and $R_4$ are as hereinbefore defined, and $R_4''$ is a 1H-tetrazolyl group protected in the 1 position by a protective radical.

Suitable examples of a protective radical are the triphenylmethyl, tributyltin or triphenyltin group.

Cleaving a protective radical used is preferably carried out in the presence of a hydrogen halide, preferably in the presence of hydrogen chloride, in the presence of a base, such as sodium hydroxide or alcoholic ammonia, in a suitable solvent, such as methylene chloride, methanol, methanol/ammonia, ethanol or isopropanol, at temperatures between 0° and 100° C., but preferably at ambient temperature, or even at elevated temperatures, if the reaction is carried out in the presence of alcoholic ammonia, for example at temperatures between 100° and 150° C., preferably at temperatures between 120° and 140° C.

g) For the preparation of a compound of formula I, in which $R_4$ is a 1H-tetrazolyl group:

Reaction of a compound of the formula

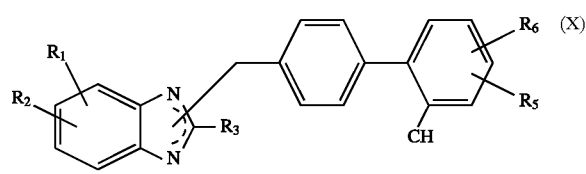 (X)

(in which $R_1$ to $R_3$, $R_3$ and $R_4$ are hereinbefore as defined with hydrazoic acid.

The reaction is preferably carried out in a solvent, such as benzene, toluene or dimethylformamide, at temperatures between 80° and 130° C., preferably at 125° C. The hydrazoic acid is thus particularly advantageously released during the reaction from an alkali azide, for example from sodium azide, in the presence of a weak acid, such as ammonium chloride.

h) For the preparation of a compound of formula I, in which $R_1$ and/or $R_2$ is an aminocarbonylamino group, which may be monosubstituted, disubstituted or trisubstituted by a bicyclic or tricyclic alkyl group or by an alkyl, alkenyl, alkynyl, cycloalkyl, cycloalkylalkyl, aralkyl or aryl group, wherein a methylene group in a cycloalkyl radical having 4 to 7 carbon atoms may be replaced by an oxygen atom:

Reaction of a compound of the formula

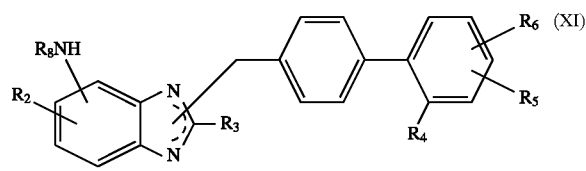 (XI)

(in which $R_2$ to $R_4$ are as hereinbefore defined, and $R_6$ denotes a hydrogen atom, an alkyl group having 1 to 20 carbon atoms, an alkenyl or alkynyl group each having 3 to 5 carbon atoms, a cycloalkyl group having 3 to 7 carbon atoms, a cycloalkylalkyl group, in which the cycloalkyl moiety may contain 3 to 7 carbon atoms, the alkyl moiety may contain 1 to 3 carbon atoms and in a cycloalkyl moiety having 4 to 7 carbon atoms a methylene group may be replaced by an oxygen atom, a bicyclic or tricyclic alkyl group having 7 to 10 carbon atoms, an aryl or aralkyl group having 1 to 3 carbon atoms in the alkyl moiety, wherein the aryl group may be a phenyl group optionally substituted by a fluorine, chlorine or bromine atom a hydroxy, alkyl or alkoxy group each having 1 to 4 carbon atoms) with a compound of the formula

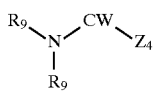 (XII)

in which $R_9$, which may be the same or different, have the meanings mentioned above for $R_9$, W is an oxygen or sulphur atom, $Z_4$ is a nucleophilic leaving group, such as a chlorine or bromine atom, or also if at least one of the radicals $R_1$ is a hydrogen atom, $Z_4$ and $R_4$ together are a nitrogen-carbon bond or a cycloalkyleneimino group having 4 to 6 carbon atoms, or a morpholino group.

The reaction is preferably carried out in a solvent, such as tetrahydrofuran, dioxane, ethylene chloride or benzene, optionally in the presence of an acid-binding agent, such as triethylamine or pyridine, advantageously at temperatures between 0° and 100° C., preferably at temperatures between 20° and 80° C.

i) For the preparation of a compound of the formula I, in which $R_4$ is a trifluoromethylcarbonylamino, trifluoromethylcarbonylaminomethyl, trifluoroethylsulphonylamino, trifluoromethylsulphonylaminomethyl or 1H-tetrazolyl group, an alkylcarbonylamino, alkylcarbonylaminomethyl, arylcarbonylamino, arylcarbonylaminomethyl, aralkylcarbonylamino, aralkylcarbonylaminomethyl, alkylsulphonylamino, alkylsulphonylaminomethyl, arylsulphonylamino, arylsulphonylaminomethyl, aralkylsulphonylamino or aralkylsulphonylaminomethyl group, in which the alkyl moiety may contain 1 to 3 carbon atoms in each case:

Acylation of a compound of the formula

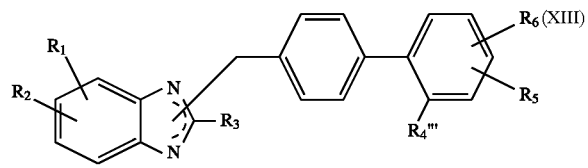 (XIII)

(in which $R_1$ to $R_3$, $R_5$ ad $R_6$ are as hereinbefore defined, and $R_4'''$ is an amino or aminomethyl group) using a compound of the formula

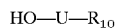 (XIV)

in which $R_{10}$ denotes a trifluoromethyl group, an alkyl, aryl or aralkyl group, wherein the alkyl moiety may contain 1 to 3 carbon atoms in each case, and U denotes a carbonyl or sulphonyl group, or using reactive derivatives thereof, such as acid halides, acid esters or acid anhydrides.

Suitable examples of reactive derivatives of a compound of the formula XIV are esters thereof, such as methyl, ethyl or benzyl esters, thioesters thereof, such as methylthio or ethylthio ester, halides thereof, such as the acid chlorides, anhydrides or imidazolides thereof.

The reaction is advantageously carried out in a solvent or solvent mixture, such as water, methylene chloride, chloroform, ether, tetrahydrofuran, dioxane or dimethylformamide, using a corresponding carboxylic acid in the presence an acid activating or a dehydrating agent, such as thionyl chloride, using anhydrides thereof, such as acetic anhydride, using esters thereof, such as ethyl acetate, using halides thereof, such as acetyl chloride or methanesulphonyl chloride, optionally in the presence of an inorganic or tertiary organic base, such as sodium hydroxide, potassium carbonate, triethylamine or pyridine, wherein the two latter bases may also serve as solvent at the same time, at temperatures between −25° and 100° C., but preferably at temperatures between −10° and 80° C.

k) For the preparation of a compound of the formula I, in which $R_4$ is an alkylsulphonylaminocarbonyl or perfluoroalkylsulphonylamino group each having 1 to 4 carbon atoms in the alkyl moiety, or is a benzylsulphonylaminocarbonyl group:

Reaction of a reactive derivative of a carboxylic acid of the formula

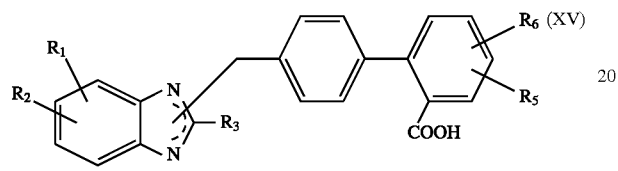

in which $R_1$ to $R_3$, $R_5$ and $R_6$ are as hereinbefore defined, with a sulphonamide of the formula

in which $R_{11}$ is an alkyl or perfluoroalkyl group each having 1 to 4 carbon atoms, or is a benzyl group, or with alkali metal salt thereof.

Suitable reactive derivatives of a carboxylic acid of the formula XV, which may be prepared in the reaction mixture, are halides thereof, such as the chloride or bromide, or carbonate derivatives thereof, such as the imidazolcarbonyloxy or diphenylcarbamoyloxy derivative.

The reaction is advantageously carried out in a suitable solvent, such as methylene chloride, tetrahydrofuran, dioxane or dimethylsulphoxide, at temperatures between 0° and 180° C., preferably between ambient temperature and 150° C. However, the reaction may also be carried out in a melt.

l) For the preparation of a compound of the formula I, in which $R_2$ is a 2-imidazolidon-1-yl or 3,4,5,6-tetrahydro-2-pyrimidon-1-yl group optionally substituted in the 3 position by an alkyl, cycloalkyl, cycloalkylalkyl or aralkyl group:

Cyclisation of a compound of the formula

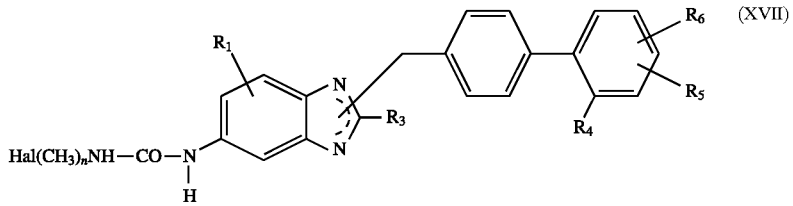

(in which $R_1$, $R_3$ and $R_4$ to $R_6$ are as hereinbefore defined, Hal is a chlorine, bromine or iodine atom, and n is the number 2 or 3) and, if required, subsequent reaction with a compound of the formula

in which $R_{12}$ is an alkyl, cycloalkyl, cycloalkylalkyl or aralkyl group, and Hal is a chlorine, bromine or iodine atom.

Cyclisation and, if required, the subsequent alkylation, is advantageously carried out in a solvent, such as methanol, ethanol, benzene or dimethylsulphoxide, optionally in the presence of a phase transfer catalyst, such as benzyltriethylammonium bromide, in the presence of an acid-binding agent, such as sodium hydroxide, sodium methoxide, sodium ethoxide, sodium hydride or potassium tert.butoxide, at temperatures between 20° and 100° C., preferably at temperatures between 30° and 70° C.

m) For the preparation of compounds of the general formula I, in which $R_1$ denotes an amino group, which is monosubstituted by a dialkylaminoalkanoyl, acyl, cycloalkoxycarbonyl, cycloalkylalkoxycarbonyl, aryloxycarbonyl, aralkoxycarbonyl or trifluoroacetyl group, by an alkylsulphonyl group having 1 to 4 carbon atoms, by an alkoxycarbonyl group having a total of 2 to 7 carbon atoms, or by a thiazolidin-3-ylcarbonyl group substituted by an alkoxycarbonyl group, an alkylamino group having 1 to 6 carbon atoms, which may be substituted at the nitrogen atom by an alkylsulphonyl or acyl group, wherein, if the acyl group is an alkanoyl group, it may additionally be substituted by an alkoxy group, and the alkyl substituent may be substituted at position 2 by a hydroxy, alkoxy or arylamino group, an N-alkoxycarbonyl-alkylamino, N-cycloalkoxycarbonylalkylamino, N-cycloalkylalkoxycarbonyl-alkylamino, N-aryloxycarbonyl-alkylamino or N-aralkoxycarbonyl-alkylamino group, in which the alkyl group may contain 1 to 6 carbon atoms in each case, an alkoxycarbonylamino, cycloalkoxycarbonylamino, cycloalkylalkoxycarbonylamino, aryloxycarbonylamino, aralkoxycarbonylamino, acylamino or alkylsulphonylamino group substituted at the nitrogen atom by a cycloalkyl, cycloalkylalkyl or aralkyl group, or a phthalimino, homophthalimino, 2-carboxyphenylcarbonylamino, 2-carboxyphenylmethylamino, 2-carboxyphenylmethylenecarbonylamino or 2-carboxymethylenephenylcarbonylamino group, whilst a carbonyl group in a phthalimino group may be replaced by a methylene group and a methylene group in a homophthalimino, 2-carboxyphenylmethylenecarbonylamino or 2-carboxymethylenephenylcarbonylamino group may be substituted b one or two alkyl groups, and additionally the above-mentioned phenyl nuclei may be mono- or disubstituted by alkyl or alkoxy groups, whilst the substituents may be identical or different, and at the same time they may be partially or wholly hydrogenated, a bicycloalkane-3-carboxylic acid amino or bicycloalkene-3-carboxylic acid amino group substituted by a carboxy group in the 2-position, a bicycloalkane-2,3-dicarboxylic acid imino or bicycloalkane-2,3-dicarboxylic acid imino group, wherein the bicycloalkane and bicycloalkene parts each contain 9 or 10 carbon atoms, may be substituted by 1, 2 or 3 methyl groups and an endomethylene group may be replaced by an oxygen atom, a glutaric acid imino or 3-carboxy-n-propylene-carbonyl group wherein the n-propylene group may be perfluorinated, substituted by one or two alkyl groups or by a tetramethylene or pentamethylene group, and $R_4$ has the meanings mentioned hereinbefore for $R_4$, with the exception of the amino group:

Acylation of a compound of the general formula

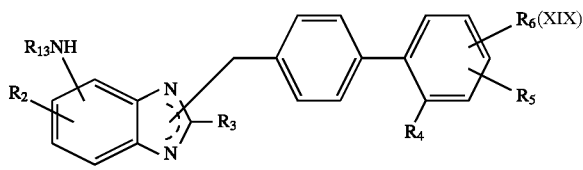

(in which
$R_2$, $R_4$, $R_5$ and $R_6$ are as hereinbefore defined,
$R_4$ is as hereinbefore defined, with the exception of the amino group, and
$R_{13}$ denotes a hydrogen atom, an alkyl group having 1 to 6 carbon atoms, which may be substituted at position 2 by a hydroxy, alkoxy or arylamino group, a cycloalkyl, cycloalkylalkyl or aralkyl group) using a compound of the formula

(in which
$R_{14}$ denotes a dialkylaminoalkanoyl, cycloalkoxycarbonyl, cycloalkylalkoxycarbonyl, aryloxycarbonyl, aralkoxycarbonyl or trifluoroacetyl group, an alkylsulphonyl group having 1 to 4 carbon atoms, an alkoxycarbonyl group having a total of 2 to 7 carbon atoms, a thiazolidin-3-ylcarbonyl group substituted by an alkoxycarbonyl group, or an acyl group, in which, if the acyl group is an alkanoyl group, it may additionally be substituted by an alkoxy group, or a 2-carboxyphenylcarbonyl, 2-carboxyphenylmethyl, 2-carboxyphenylmethylenecarbonyl or 2-carboxymethylenephenylcarbonyl group, whilst a methylene group in a 2-carboxyphenylmethylenecarbonyl or 2-carboxymethylenephenylcarbonyl group may be substituted by one or two alkyl groups, and in addition the above-mentioned phenyl nuclei may be mono- or disubstituted by alkyl or alkoxy groups, the substituent being identical or different, and at the same time they may be wholly or partially hydrogenated, a bicycloalkane-3-carbonyl or bicycloalkene-3-carbonyl groups substituted in the 2-position by a carboxy group, wherein the bicycloalkane and bicycloalkene moieties each contain 9 or 10 carbon atoms, may be substituted by 1, 2 or 3 methyl groups and an endomethylene group may be replaced by an oxygen atom, a 3-carboxy-n-propylenecarbonyl group wherein the n-propylene group may be perfluorinated, substituted by one or two alkyl groups or by a tetramethylene or pentamethylene group, and $Z_5$ denotes a nucleophilic leaving group) or reactive derivatives thereof, such as acid halides, acid esters or acid anhydrides.

Suitable examples of reactive derivatives of a compound of the formula XIX are esters thereof, such as methyl, ethyl or benzyl esters; thioesters thereof, such as methylthio or ethylthio esters; halides thereof, such as acid chlorides, anhydrides or imidazolides thereof.

The reaction is advantageously carried out in a solvent or solvent mixture, such as water, methylene chloride, chloroform, ether, tetrahydrofuran, dioxane or dimethylformamide, using a corresponding carboxylic acid in the presence of an acid activating or dehydrating agent, such as thionyl chloride, using anhydrides thereof, such as acetic anhydride, using esters thereof, such as ethyl acetate, using halides thereof, such as acetyl chloride or methanesulphonyl chloride, optionally in the presence of an inorganic or tertiary organic base, such as sodium hydroxide, potassium carbonate, triethylamine or pyridine, wherein the two latter bases may also serve as solvent at the same time, at temperatures between −25° and 100° C., but preferably at temperatures between −10° and 80° C.

n) In order to prepare compounds of general formula I wherein at least one of the groups $R_1$ or $R_2$ represents a 2-carboxyphenylcarbonylamino, 2-carboxyphenylmethylamino, 2-carboxyphenylmethylenecarbonylamino or 2-carboxymethylenephenylcarbonylamino group, where a methylene groups in a 2-carboxyphenylmethylenecarbonylamino or 2-carboxymethylenephenylcarbonylamino group may be substituted by one or two alkyl groups, and in addition the above-mentioned phenyl nuclei may be mono- or disubstituted by alkyl or alkoxy groups, whilst the substituents may be identical or different, and at the same time may be wholly or partially hydrogenated, a bicycloalkane-3-carboxylic acid amino or bicycloalkene-3-carboxylic acid amino group substituted by a carboxy group in the 2-position, wherein the bicycloalkane and bicycloalkene moieties each contain 9 or 10 carbon atoms, may be substituted by 1, 2 or 3 methyl groups and an endomethylene group may be replaced by an oxygen atom, a 3-carboxy-n-propylenecarbonyl group wherein the n-propylene group may be perfluorinated, substituted by one or two alkyl groups or by a tetramethylene or pentamethylene group:

Partial hydrolysis of a compound of general formula

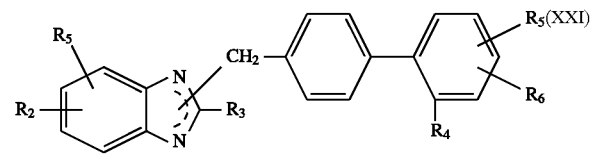

wherein
$R_2$ to $R_6$ are defined as hereinbefore and
$R_{15}$ represents a phthalimino or homophthalimino group, whilst a carbonyl group in a phthalimino group may be replaced by a methylene group and a methylene group in a homophthalimino group may be substituted by one or two alkyl groups, and in addition the above-mentioned phenyl nuclei may be mono- or disubstituted by alkyl or alkoxy groups, the substituents being identical or different, and at the same time may be wholly or partially hydrogenated, a bicycloalkane-2,3-dicarboxylic acid imino or bicycloalkene-2,3-dicarboxylic acid imino group wherein the bicycloalkane and bicycloalkane moieties each contain 9 or 10 carbon atoms, may be substituted by 1, 2 or 3 methyl groups and an endomethylene group may be replaced by an oxygen atom, a glutaric acid imino group wherein the n-propylene group may be perfluorinated, substituted by one or two alkyl groups or by a tetramethylene or pentamethylene group.

Partial hydrolysis is expediently carried out either in the presence of an acid such as hydrochloric, sulphuric, phosphoric, trichloroacetic or trifluoroacetic acid or in the presence of a base such as sodium hydroxide or potassium hydroxide in a suitable solvent such as water, water/methanol, ethanol, water/ethanol, water/isopropanol or water/dioxan at temperatures between −10° C. and 120° C., e.g. at temperatures between ambient temperature and the boiling temperature of the reaction mixture. However, it is particularly advantageous to carry out the partial hydrolysis in the presence of one equivalent of an inorganic base at ambient temperature.

In the reactions described above, optionally present reactive groups, such as hydroxy, amino or alkylamino groups may be protected during the reaction by conventional protective groups, which are cleaved again after the reaction.

Suitable examples of a protective radical for a hydroxy group are the trimethylsilyl, acetyl, benzoyl, methyl, ethyl, tert.butyl, benzyl or tetrahydropyranyl group, and of protective radicals for an amino, alkylamino or imino group are acetyl, benzoyl, ethoxycarbonyl or benzyl groups.

The optional subsequent cleaving of a protective group used is preferably carried out hydrolytically in an aqueous solvent, for example in water, isopropanol/water, tetrahydrofuran/water or dioxane/water, in the presence of an acid, such as hydrochloric acid or sulphuric acid, or in the presence of an alkali metal base, such as sodium hydroxide or potassium hydroxide, at temperatures between 0° and 100° C., preferably at the boiling temperature of the reaction mixture. However, cleaving a benzyl radical is preferably carried out hydrogenolytically, for example with hydrogen in the presence of a catalyst, such as palladium/carbon, in a solvent, such as methanol, ethanol, ethyl acetate or glacial acetic acid, optionally with addition of an acid, such as hydrochloric acid, at temperatures between 0° and 50° C., but preferably at ambient temperature, and a hydrogen pressure of 1 to 7 bar, but preferably 3 to 5 bar.

If a compound of the formula I in which $R_1$ and/or $R_2$ is a nitro group is obtained in accordance with the invention, it may be converted to a corresponding amino compound of the formula I by means of reduction, or if a compound of the formula I in which $R_1$ and/or $R_2$ is a hydroxy, amino, alkylamino, phenylalkylamino, alkylsulphonylamino or acylamino group is obtained in accordance with the invention, it may be converted to a corresponding alkylated compound of the formula I by means of alkylation, or if a compound of the formula I in which $R_1$ and/or $R_2$ is a benzyloxy group is obtained in accordance with the invention, it may be converted to a corresponding compound of the formula I, in which $R_1$ and/or $R_2$ is a hydroxy group, by means of debenzylation, or if a compound of the formula I in which $R_1$ and/or $R_2$ is a carboxy group is obtained in accordance with the invention, it may be converted to a corresponding compound of the formula I, in which $R_1$ and/or $R_2$ is an aminocarbonyl group optionally substituted by one or two alkyl groups each having 1 to 3 carbon atoms, by means of amidation, or if a compound of the formula I in which $R_1$ and/or $R_2$ is a carboxy group and/or $R_4$ is a cyano group is obtained in accordance with the invention, it may be converted to a corresponding compound of the formula I, in which $R_1$ and/or $R_2$ is a hydroxymethyl group and/or $R_4$ is an aminomethyl group, by means of reduction, or if a compound of the formula I in which $R_1$ and/or $R_2$ is an alkoxycarbonyl group is obtained in accordance with the invention, it may be converted in accordance with the invention to a corresponding compound of the formula I, in which $R_1$ and/or $R_2$ is a carboxy group, by means of hydrolysis, or if a compound of the formula I in which $R_1$ and/or $R_2$ is an alkoxy or phenylalkoxy group is obtained in accordance with the invention, it may be converted to a corresponding compound of the formula I, in which $R_1$ and/or $R_2$ is a hydroxy group, by means of ether cleaving, or if a compound of the formula I, in which $R_1$ and/or $R_2$ is an aminocarbonylamino or aminothiocarbonyl group, which is substituted by a cycloalkyl group having 5 to 10 carbon atoms, in which a methylene group is replaced in the 2 position by an oxygen atom, and which may be additionally monosubstituted or disubstituted by an alkyl group having 1 to 20 carbon atoms, by an alkenyl or alkynyl group each having 3 to 5 carbon atoms, by a bicyclic or tricyclic alkyl group having 7 to 11 carbon atoms, by a cycloalkyl, cycloalkylalkyl, aralkyl or aryl group, is obtained in accordance with the invention, it may be converted to a corresponding compound of the formula I, in which $R_1$ and/or $R_2$ is an aminocarbonylamino or aminothiocarbonyl group, which is substituted by a 4-hydroxy-n-butyl, 5-hydroxy-n-pentyl or 6-hydroxy-n-hexyl group and may additionally be monosubstituted or disubstituted by an alkyl group having 1 to 20 carbon atoms, by an alkenyl or alkynyl group each having 3 to 5 carbon atoms, by a bicyclic or tricyclic alkyl group having 7 to 11 carbon atoms, by a cycloalkyl, cycloalkylalkyl, aralkyl or aryl group, by means of reduction, or if a compound of the formula I, in which $R_1$ and/or $R_2$ is a phthalimino group, which may be monosubstituted or disubstituted by an alkyl or alkoxy group, wherein the substituents may be the same or different, is obtained in accordance with the invention, it may be converted to a corresponding compound of the formula I, in which $R_1$ and/or $R_2$ is a 1-oxo-isoindolin-2-yl group, which may be monosubstituted or disubstituted by an alkyl or alkoxy group, wherein the substituents may be the same or different, by means of reduction, or a resulting 1 and 3 isomer mixture of a compound of the formula I may be separated into its 1 isomer and 3 isomer by means of isomer separation.

The subsequent reduction of the nitro group is preferably carried out in a solvent, such as water, water/ethanol, methanol, glacial acetic acid, ethyl acetate or dimethylformamide, advantageously using hydrogen in the presence of a hydrogenation catalyst, such as Raney nickel, platinum or palladium/carbon, using metals, such as iron, tin or zinc, in the presence of an acid, using salts, such as iron (II) sulphate, tin (II) chloride, sodium sulphide, sodium hydrogen sulphite or sodium dithionite, or using hydrazine in the presence of Raney nickel, at temperatures between 0° and 80° C., but preferably at temperatures between 20° and 40° C.

The subsequent alkylation is preferably carried out in a solvent or solvent mixture, such as methylformamide, dimethylformamide, dimethylsulphoxide, benzene, chlorobenzene, tetrahydrofuran, benzene/tetrahydrofuran or dioxane, in the presence of an alkylating agent, such as methyliodide, methylbromide, ethylbromide, dimethylsulphate, benzylchloride or diazomethane, optionally preferably in the presence of an acid-binding agent, for example an alkoxide such as potassium tert.butoxide, an alkali metal hydroxide, such as sodium hydroxide or potassium hydroxide, an alkali metal carbonate, such as potassium carbonate, an alkali metal amide, such as sodium amide, or an alkali metal hydride, such as sodium hydride, advantageously at temperatures between 0° and 150° C., preferably at temperatures between 0° and 50° C.

The subsequent reductive amination of an amino group is carried out in a suitable solvent, such as methanol, ethanol, tetrahydrofuran, dioxane or acetonitrile, in the presence of a suitable reducing agent, such as a suitable complex metal hydride, but preferably in the presence of sodium cyanoborohydride, at a pH of 5 to 7, at temperatures between 0° and 50° C., but preferably at ambient temperature.

The subsequent cleaving of a benzyl radical is preferably carried out hydrogenolytically, for example using hydrogen in the presence of a catalyst, such as palladium/carbon, in a solvent, such as methanol, ethanol, ethyl acetate or glacial acetic acid, optionally with addition of an acid, such as hydrochloric acid, at temperatures between 0° and 50° C., but preferably at ambient temperature, and a hydrogen pressure of 1 to 7 bar, but preferably 3 to 5 bar.

The subsequent amidation is advantageously carried out in a solvent, such as methylene chloride, chloroform, carbon tetrachloride, ether, tetrahydrofuran, dioxane, benzene, toluene, acetonitrile or dimethylformamide, but particularly advantageously in an excess of the amine used, for example in methanol, ethanol, n-propanol, isopropanol, ammonia, methylamine, ethylamine, dimethylamine or diethylamine, optionally in the presence of an acid activating agent or a dehydrating agent, for example in the presence of ethyl chloroformate, thionyl chloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole or triphenylphosphine/carbon tetrachloride, or an agent activating the amino group, for example phosphorus trichloride, and optionally in the presence of an inorganic base, such as sodium carbonate, or a tertiary organic base, such as triethylamine or pyridine, which may serve as solvent at the same time, at temperatures between −25° C. and 250° C., but preferably at temperatures between −10° C. and the boiling temperature of the solvent used.

The subsequent reduction of the carboxy group is carried out in a suitable solvent, such as methanol, ethanol ether, tetrahydrofuran, dioxane or glacial acetic acid, in the presence of catalytically activated hydrogen, for example hydrogen in the presence of platinum or palladium/carbon, and optionally in the presence of an acid, such as hydrochloric acid or perchloric acid, or in the presence of a metal hydride, such as sodium borohydride, lithium borohydride or lithium aluminium hydride, at temperatures between 0° and 100° C., preferably at temperatures between 20° and 80° C.

The subsequent hydrolysis is preferably carried out hydrolytically in an aqueous solvent, for example in water, isopropanol/water, tetrahydrofuran/water or dioxane/water, in the presence of an acid, such as hydrochloric acid or sulphuric acid, or in the presence of an alkali metal base, such as sodium hydroxide or potassium hydroxide, at temperatures between 0° and 100° C., preferably at the boiling temperature of the reaction mixture.

The subsequent ether cleaving is carried out in the presence of an acid, such as hydrogen chloride, hydrogen bromide, sulphuric acid, boron trichloride, boron tribromide or aluminium chloride, in a suitable solvent, such as methanol, ethanol, water/isopropanol, methylene chloride, chloroform or carbon tetrachloride, at temperatures between −30° C. and the boiling temperature of the reaction mixture.

The subsequent reduction if preferably carried out in a solvent, such as water, water/ethanol, methanol, glacial acetic acid, ethyl acetate or dimethylformamide, advantageously using hydrogen in the presence of a hydrogenation catalyst, such as Raney nickel, platinum or palladium/carbon, or using hydrazine in the presence of Raney nickel, at temperatures between 0° and 50° C., but preferably at ambient temperature.

The subsequent reduction of a phthalimino group is preferably carried out in a solvent, such as glacial acetic acid using nascent hydrogen, for example using zinc/glacial acetic acid, at temperatures between 80° and 120° C., preferably at the boiling temperature of the reaction mixture.

The subsequent isomer separation is preferably carried out chromatographically using a carrier, such as silica gel or aluminium oxide.

Furthermore, the compounds of the formula X obtained may be converted to their acid addition salts, in particular for the pharmaceutical application, to their physiologically acceptable salts, using inorganic or organic acids. Examples of acids suitable for this purpose are hydrochloric acid, hydrobromic acid, sulphuric acid, phosphoric acid, fumaric acid, succinic acid, lactic acid, citric acid, tartaric acid or maleic acid.

In addition, the novel compounds of the formula I thus obtained, if they contain a carboxy group, can then be converted, if desired to their addition salts using inorganic or organic bases, in particular for the pharmaceutical application, to their physiologically acceptable addition salts. Examples of bases suitable for this purpose are sodium hydroxide, potassium hydroxide, cyclohexylamine, ethanolamine, diethanolamine and triethanolamine.

Some of the compounds of the formulae II to XXI used as starting materials are known in the literature or they are obtained by processes known in the literature.

Thus for example a compound of the formula II or III is obtained by alkylating a corresponding o-amino-nitro compound and subsequently reducing the nitro group.

A compound of the formulae V, VI, VII, IX, X, XI, XIII, XV, XVII, XIX or XXI used as starting material is obtained by alkylating a corresponding o-phenylenediamine or a corresponding o-amino-nitro compound and subsequently reducing the nitro group and subsequently cyclising an o-diaminophenyl compound thus obtained, or by NH-alkylating a corresponding 1H-benzimidazole, wherein the isomer mixture thus obtained may then be separated by means of conventional methods, for example by means of chromatography.

The novel compounds of the formula I and their physiologically acceptable addition salts have valuable pharmacological properties. In particular, they are angiotensin II antagonists.

By way of example, the compounds

A=4'-[(2-n-butyl-6-(N-(n-hexylaminocarbonyl)-benzylamino)-benzimidazol-1-yl)-methyl]biphenyl-2-carboxylic acid B=4'-[(2-n-butyl-6-(N-cyclohexylaminocarbonyl-n-butylamino)-benzimidazol-1-yl)-methyl]biphenyl-2-carboxylic acid, C=4'-[(2-n-butyl-6-(N-cyclohexylaminocarbonyl-ethylamino)-benzimidazol-1-yl)-methyl]biphenyl-2-carboxylic acid, D=4'-[(2-n-butyl-6-(N-cyclohexylaminocarbonyl-n-propyl-amino)-benzimidazol-1-yl)-methyl]biphenyl-2-carboxylic acid, E=4'-[(2-n-butyl-6-(N-cyclohexylaminocarbonyl-methylamino)-benzimidazol-1-yl)-methyl]biphenyl-2-carboxylic acid, F=4'-[(2-n-butyl-6-cyclohexylaminocarbonylamino-benzimidazol-1-yl)-methyl]biphenyl-2-carboxylic acid trifluoroacetate, G=4'-[(2-n-butyl-6-(N-cyclohexylaminocarbonyl-n-pentyl-amino)-benzimidazol-1-yl)-methyl]biphenyl-2-carboxylic acid, H=4'-[(2-n-butyl-6-(N-methylaminocarbonyl-benzylamino)-benzimidazol-1-yl)-methyl]biphenyl-2-carboxylic acid, I=4'-[(2-n-butyl-6-(1-oxo-isoindolin-2-yl)-benzimidazol-1-yl)-methyl]biphenyl-2-carboxylic acid trifluoroacetate, J=4'-[(2-n-butyl-6-(N-cyclohexylaminocarbonyl-benzylamino)-benzimidazol-1-yl)-methyl]biphenyl-2-carboxylic acid, K=4'-[(2-n-butyl-6-n-pentanoylamino-benzimidazol-1-yl)-methyl]biphenyl-2-carboxylic acid, L=4'-[(2-n-butyl-6-propionylamino-benzimidazol-1-yl)-methyl]biphenyl-2-carboxylic acid, M=4'-[(2-n-butyl-6-isopropylcarbonylamino-benzimidazol-1-yl)-methyl]biphenyl-2-carboxylic acid, N=4'-[(2-n-butyl-6-(tetrahydropyran-2-yl-aminocarbonylamino)-benzimidazol-1-yl)-methyl]biphenyl-2-carboxylic acid, O=4'-[(2-n-butyl-6-(n-butylaminocarbonylamino)-benzimidazol-1-yl)-methyl]biphenyl-2-carboxylic acid, P=4'-[(6-n-butanoylamino-2-n-butyl-benzimidazol-1-yl)-methyl]biphenyl-2-carboxylic acid, Q=4'-[(2-n-butyl-6-(N-ethoxycarbonyl-benzylamino)-benzimidazol-1-yl)-methyl]biphenyl-2-carboxylic acid, R=4'-[(2-n-butyl-6-(N-(dimethylaminocarbonyl)-amino)-benzimidazol-1-yl)-methyl]biphenyl-2-carboxylic acid trifluoroacetate, S=4'-[(2-n-butyl-6-(N-cyclohexylaminocarbonyl-n-hexylamino)-benzimidazol-1-yl)-methyl]biphenyl-2-carboxylic acid T=4'-[(2-n-butyl-6-((5-hydroxy-n-pentyl)-aminocarbonylamino)-benzimidazol-1-yl)-methyl]biphenyl-2-carboxylic acid monohydrate, U=4'-[(2-n-butyl-6-(N-methylaminocarbonyl-n-pentylamino)-benzimidazol-1-yl)-methyl]biphenyl-2-carboxylic acid, V=4'-[(2-n-butyl-6-cyclohexylcarbonylamino-benzimidazol-1-yl)-methyl]biphenyl-2-carboxylic acid, W=4'-[(2-n-butyl-6-(N-(n-butylaminocarbonyl)-methylamino)-benzimidazol-1-yl)-methyl]biphenyl-2-carboxylic acid, X=4'-[(2-n-butyl-7-hydroxy-4-methyl-benzimidazol-1-yl)-methyl]-2-(1H-tetrazol-5-yl)-biphenyl hydrate, Y=4'-[(2-n-butyl-6-(cis-hexahydrophthalimino)-benzimidazol-1-yl)-methyl]biphenyl-2-carboxylic acid trifluoroacetate, Z=4'-[(2-n-butyl-6-(N-(dimethylaminocarbonyl)-benzylamino)-benzimidazol-1-yl)-methyl]-biphenyl-2-carboxylic acid, AA=4'-[(2-n-butyl-6-(N-(n-hexylaminocarbonyl)-N-(2-phenylethyl)-amino)-benzimidazol-1-yl)-methyl]biphenyl-2-carboxylic acid BB=4'-[(2-n-butyl-6-cyclopentylcarbonylamino-benzimidazol-1-yl)-methyl]biphenyl-2-carboxylic acid semihydrate CC=4'-[(2-n-butyl-6-(cis-hexahydrophthalimino)-benzimidazol-1-yl)-methyl]-2-(1H-tetrazol-5-yl)-biphenyl were investigated for their biological effects as follows:

a) rats (male, 180–220 g) are anaesthetised using sodium hexobarbital (150 mg/kg i.p.). After the anaesthetic has taken effect, a tracheal cannula is inserted, the spine is destroyed in the animals and then they are immediately respirated artifically using a respiratory pump. The arterial blood pressure is recorded via a cannula in the carotid artery by means of a Bell & Howell pressure sensor. Substances are administered via a cannula in the jugular vein.

Test substances are administered in three doses (10, 20 and 30 mg/kg i.v.), wherein one dose of substance is tested per animal. Three minutes after intravenous administration of the test substance, angiotensin II is administered intravenously in increasing doses, and hence a cumulative dose-effect relationship is established for angiotensin II in the presence of the test substances. The measured parameter is the increase in the arterial blood pressure.

These dose-effect graphs are compared with standard graphs for angiotensin II without test substances. A computer program determines the displacements to the right of the dose-effect graphs for angiotensin II as a result of test substances, and calculates corresponding $pA_2$ values for the test substances.

The following table shows the average $pA_2$ values of the substances investigated:

| Substances | $pA_2$ values |
|---|---|
| A | 7, 23 |
| B | 6, 63 |
| C | 6, 36 |
| D | 6, 59 |
| E | 7, 34 |
| F | 7, 56 |
| G | 6, 89 |
| H | 6, 48 |
| I | 6, 12 |
| J | 7, 38 |
| K | 6, 38 |
| L | 6, 04 |
| M | 6, 87 |
| N | 7, 02 |
| O | 6, 46 |
| P | 6, 46 |
| Q | 6, 83 |
| R | 7, 16 |
| S | 6, 69 |
| T | 7, 20 |
| U | 7, 26 |
| V | 7, 26 |
| W | 6, 28 |
| X | 6, 57 |
| Y | 6, 97 |
| Z | 7, 15 |
| AA | — |
| BB | — |
| CC | 8, 54 | b) The inhibiting effect of the novel compounds on the bonding of angiotensin II to bovine adrenal gland receptor preparations was tested analogously to the method of Glossmann et al. (J. Biol. Chem. 249, 825–834 (1974). The incubation batch contained aliquots of a membrane preparation of bovine adrenal cortex in tris buffer, increasing concentrations of the possible antagonists and 50 pM $^{125}$I-angiotensin II. After 45 minutes the incubation was stopped by rapid filtration through glass fibre filters. The radioactivity associated with the filter was determined in a γ-counter at a counting efficiency of 80%.

The following table shows the inhibitor concentration of the antagonists which effected 50% inhibition of the specific $^{125}$I-angiotensin II bonding:

| Substances | IC$_{50}$ [nM/l] |
|---|---|
| A | 29 |
| B | 29 |
| C | 31 |
| D | 44 |
| E | 46 |
| F | 47 |
| G | 46 |
| H | 51 |
| I | 51 |
| J | 54 |
| K | 57 |
| L | 58 |
| M | 61 |
| N | 65 |
| O | 65 |
| P | 67 |
| Q | 68 |
| R | 72 |
| S | 72 |
| T | 76 |
| U | 79 |
| V | 84 |
| W | 86 |
| X | 99 |
| Y | 150 |
| Z | 133 |
| AA | 100 |
| BB | 46 |
| CC | 1000 |

Furthermore, no toxic side effects could be observed for the administration of the above compounds up to a dose of 30 mg/kg i.v., for example no negative inotropic effect and no cardiac rythmn disorders. Accordingly, the compounds are well tolerated.

The novel compounds and their physiologically acceptable addition salts due to their pharmacological properties, are suitable for the treatment of hypertonia and cardiac insufficiency, also for the treatment of ischaemic peripheral circulatory disorders, myocardial ischaemia (Angina), for the prevention of cardiac insufficiency progression after myocardial infarction, for the treatment of diabetic nephropathy, glaucoma, gastrointestinal illnesses and diseases of the bladder.

The dosage required to achieve a corresponding effect is conveniently 20 to 100 mg for intravenous administration, preferably 30 to 70 mg, and 50 to 200 mg for oral administration, preferably 75 to 150 mg, 1 to 3×daily in each case. The compounds of the formula I prepared in accordance with the invention can be formulated for this purpose, optionally in combination with other active ingredients, together with one or more inert conventional excipients and/or diluents, for example with corn starch, lactose, cane sugar, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fat-containing substances, such as hard fat or suitable mixtures thereof, in conventional galenic preparations, such as tablets, coated tablets, capsules, powders, suspensions or suppositories.

The following Examples should illustrate the invention in more detail:

EXAMPLE A

Tert.butyl 4'[N-(5-benzylamino-2-nitrophenyl)-pentanoylaminomethyl]biphenyl-2-carboxylate 3.9 g (7.5 mmol) of tert.butyl 4'-[N-(5-chloro-2-nitrophenyl)-pentanoylaminomethyl]biphenyl-2-carboxylate are stirred together with 3.9 ml of benzylamine for 3 hours in an oil bath heated at 150°–160° C. After cooling the reaction mixture, the residue is dissolved in about 25 ml of methylene chloride and the substance is purified over a silica gel column (grain size: 0.063–0.2 mm, eluting agent: cyclohexane/5–10% ethyl acetate). The appropriate fractions are evaporated on a rotary evaporator.

Yield: 2.9 g (65.5% of theoretical),

Oil, R$_f$ value: 0.55 (Silica gel: cyclohexane/ethyl acetate= 2:1).

The following compounds are obtained in analogous manner:

tert.butyl 4'-[N-(5-(N-benzyl-methylamino)-2-nitrophenyl)-pentanoylaminomethyl]biphenyl-2-carboxylate oil, R$_f$ value: 0.40 (Silica gel: cyclohexane/ethyl acetate=4:1).

tert.butyl 4'-[N-(5-dimethylamino-2-nitrophenyl)-pentanoylaminomethyl]biphenyl-2-carboxylate oil, R$_f$ value: 0.35 (Silica gel: hexane/ethyl acetate=4:1).

EXAMPLE 1

Tert.butyl 4'-[(benzimidazol-1-yl)-methyl]biphenyl-2-carboxylate 0.95 g (8 mmol) of benzimidazole are dissolved in 50 ml of dimethylsulphoxide and treated with 1.0 g (9 mmol) of potassium tert.butoxide. To form the salt, the mixture is then stirred for 30 minutes at ambient temperature and 2.8 g (8 mmol) of tert.butyl 4'-bromomethyl-biphenyl-2-carboxylate are then added. The reaction is completed after stirring for 2 hours at ambient temperature. The mixture is diluted to 500 ml using water and extracted 3 times using about 100 ml of ethyl acetate. The combined organic phases are dried using magnesium sulphate and evaporated to dryness. The oily residue is purified over a silica gel column (grain size: 0.063–0.2 mm), methylene chloride with 1% ethanol being used as eluting agent. The homogeneous fractions are evaporated to dryness. The residue is an oil.

Yield: 2.8 g (90.8% of theoretical),

R$_f$ value: 0.35 (Silica gel: methylene chloride/ethanol= 19:1)

Calculated: C 78.10 H 6.29 N 7.29 Found: 78.18 6.34 7.19

The following compounds are obtained in analogous manner:

tert.butyl 4'-[(2-hydroxy-benzimidazol-1-yl)-methyl]biphenyl-2-carboxylate oil, R$_f$ value: 0.15 (Silica gel: methylene chloride/ethanol=49:1)

tert.butyl 4'-[(2-n-butyl-7-(2-diethylamino-ethoxy)-4-methyl-benzimidazol-1-yl)-methyl]biphenyl-2-carboxylate oil, R$_f$ value: 0.55 (Silica gel: methylene chloride/ethanol=9:1)

tert.butyl 4'-[(2-ethylthio-benzimidazol-1-yl)-methyl]-biphenyl-2-carboxylate oil, R$_f$ value: 0.45 (Silica gel: methylene chloride/ethanol=49:1)

tert.butyl 4'-[(2-n-propylthiomethyl-benzimidazol-1-yl)-methyl]biphenyl-2-carboxylate oil, R$_f$ value: 0.55 (Silica gel: methylene chloride/ethanol=19:1)

tert.butyl 4'-[(2-methyl-benzimidazol-1-yl)-methyl]-biphenyl-2-carboxylate oil, R$_f$ value: 0.60 (Silica gel: methylene chloride/ethanol=19:1)

tert.butyl 4'-[(2-methylmercapto-benzimidazol-1-yl)-methyl]biphenyl-2-carboxylate oil, R$_f$ value: 0.55 (Silica gel: methylene chloride/ethanol=19:1)

tert.butyl 4'-[(2-methyl-5- and 6-nitro-benzimidazol-1-yl)-methyl]biphenyl-2-carboxylate oil, R$_f$ value: 0.50 (Silica gel: methylene chloride/ethanol=19:1)

tert.butyl 4'-[(2-methyl-5- and 6-butanoylamino-benzimidazol-1-yl)-methyl]biphenyl-2-carboxylate oil, $R_f$ value: 0.60 (Silica gel: methylene chloride/ethanol=9:1)

tert.butyl 4'-[(2-(2-methylpropyl)-benzimidazol-1-yl)-methyl]biphenyl-2-carboxylate oil, $R_f$ value: 0.50 (Silica gel: methylethylketone/xylene=1.1)

tert.butyl 4'-[(2-methoxymethyl-benzimidazol-1-yl)-methyl]biphenyl-2-carboxylate oil, $R_f$ value: 0.50 (Silica gel: methylethylketone/xylene=1:1)

tert.butyl 4'-[(2-(pyrid-2-yl)-benzimidazol-1-yl)-methyl]biphenyl-2-carboxylate oil, $R_f$ value: 0.40 (Silica gel: methylene chloride/ethanol=19:1)

tert.butyl 4'-[(5- and 6-methyl-benzimidazol-1-yl)-methyl]biphenyl-2-carboxylate oil, $R_f$ value: 0.25 (Silica gel: methylene chloride/ethanol=19:1)

tert.butyl 4'-[(2-phenyl-benzimidazol-1-yl)-methyl]-biphenyl-2-carboxylate oil, $R_f$ value: 0.45 (Silica gel: methylene chloride/ethanol=19:1)

tert.butyl 4'-[(2-(thiazol-4-yl)-benzimidazol-1-yl)-methyl]biphenyl-2-carboxylate oil, $R_f$ value: 0.30 (Silica gel: methylene chloride/ethanol=49:1)

tert.butyl 4'-[(2-(3,5-dimethyl-pyrazol-1-yl)-benzimidazol-1-yl)-methyl]biphenyl-2-carboxylate oil, $R_f$ value: 0.35 (Silica gel: methylene chloride/ethanol=19:1)

tert.butyl 4'-[(2-(fur-2-yl)-benzimidazol-1-yl)-methyl]-biphenyl-2-carboxylate oil, $R_f$ value: 0.40 (Silica gel: methylene chloride/ethanol=19:1)

tert.butyl 4'-[(2-aminocarbonylamino-benzimidazol-1-yl)-methyl]biphenyl-2-carboxylate oil, $R_f$ value: 0.50 (Silica gel: methylene chloride/ethanol=19:1)

tert.butyl 4'-[(2-isopropyl-benzimidazol-1-yl)-methyl]-biphenyl-2-carboxylate oil, $R_f$ value: 0.50 (Silica gel: methylethylketone/xylene=1:1)

tert.butyl 4'-[(2-hydroxymethyl-benzimidazol-1-yl)-methyl]biphenyl-2-carboxylate oil, $R_f$ value: 0.35 (Silica gel: methylene chloride/ethanol=19:1)

tert.butyl 4'-[(2-(3-hydroxypropyl)-benzimidazol-1-yl)-methyl]biphenyl-2-carboxylate oil, $R_f$ value: 0.40 (Silica gel: methylene chloride/ethanol=19:1)

tert.butyl 4'-[(2-methyl-5- and 6-(N-(methoxyacetyl)-n-butylamino)-benzimidazol-1-yl)-methyl]biphenyl-2-carboxylate oil, $R_f$ value: 0.20 (Silica gel: methylene chloride/ethanol=19:1)

tert.butyl 4'-[(2-(1-methylpropyl)-benzimidazol-1-yl)-methyl]biphenyl-2-carboxylate oil, $R_f$ value: 0.80 (Silica gel: methylethylketone/xylene=1:1)

tert.butyl 4'-[(2-(2-methylbutyl)-benzimidazol-1-yl)-methyl]biphenyl-2-carboxylate oil, $R_f$ value: 0.60 (Silica gel: methylethylketone/xylene=1:1)

tert.butyl 4'-[(2-methyl-5- and 6-(N-(2-methoxyethyl)-n-butylamino)-benzimidazol-1-yl)-methyl]biphenyl-2-carboxylate oil, $R_f$ value: 0.25 (Silica gel: methylene chloride/ethanol=19:1)

tert.butyl 4'-[(2-n-pentyl-benzimidazol-1-yl)-methyl]-biphenyl-2-carboxylate oil, $R_f$ value: 0.50 (Silica gel: methylethylketone/xylene=1:1)

tert.butyl 4'-[(2-n-butyl-7-methoxy-4-methyl-benzimidazol-1-yl)-methyl]biphenyl-2-carboxylate oil, $R_f$ value: 0.50 (Silica gel: methylene chloride/ethanol=19:1)

tert.butyl 4'-[(2-n-propyl-benzimidazol-1-yl)-methyl]-biphenyl-2-carboxylate melting point: 140°–141° C.

tert.butyl 4'-[(2-ethyl-benzimidazol-1-yl)-methyl]-biphenyl-2-carboxylate melting point: 129°–130° C.

tert.butyl 4'-[(2-ethylthiomethyl-benzimidazol-1-yl)-methyl]biphenyl-2-carboxylate oil, $R_f$ value: 0.50 (Silica gel: methylene chloride/ethanol=19:1)

tert.butyl 4'-[(2-methylthiomethyl-benzimidazol-1-yl)-methyl]biphenyl-2-carboxylate oil, $R_f$ value: 0.45 (Silica gel: methylene chloride/ethanol=19:1)

tert.butyl 4'-[(2-chloro-benzimidazol-1-yl)-methyl]-biphenyl-2-carboxylate oil, $R_f$ value: 0.55 (Silica gel: methylene chloride/ethanol=19:1)

tert.butyl 4'-[(2-n-butylthio-benzimidazol-1-yl)-methyl]biphenyl-2-carboxylate oil, $R_f$ value: 0.55 (Silica gel: methylene chloride/ethanol=49:1)

tert.butyl 4'-[(2-(4-methoxyphenyl)-benzimidazol-1-yl)-methyl]biphenyl-2-carboxylate oil, $R_f$ value: 0.80 (Silica gel: methylethylketone/xylene=1:1)

tert.butyl 4'-[(2-n-propylthio-benzimidazol-1-yl)-methyl]biphenyl-2-carboxylate oil, $R_f$ value: 0.50 (Silica gel: methylene chloride/ethanol=49:1)

tert.butyl 4'-[(2-n-butylamino-benzimidazol-1-yl)-methyl]biphenyl-2-carboxylate oil, $R_f$ value: 0.45 (Silica gel: methylene chloride/ethanol=19:1)

tert.butyl 4'-[(2-(4-methoxyphenyl)-5- and 6-chloro-benzimidazol-1-yl)-methyl]biphenyl-2-carboxylate oil, $R_f$ value: 0.50 (Silica gel: methylethylketone/xylene=1:1)

tert.butyl 4'-[(2-n-butyl-5- and 6-acetamino-benzimidazol-1-yl)-methyl]biphenyl-2-carboxylate oil, $R_f$ value: 0.60 (Silica gel: ethyl acetate/ethanol/ammonia=90:10:1)

tert.butyl 4'-[(2-n-butyl-5- and 6-butanoylamino-benzimidazol-1-yl)-methyl]biphenyl-2-carboxylate oil, $R_f$ value: 0.80 (Silica gel: ethyl acetate/ethanol/ammonia=90:10:1)

tert.butyl 4'-[(2-n-butyl-5- and 6-methoxy-benzimid-azol-1-yl)-methyl]biphenyl-2-carboxylate oil, $R_f$ value: 0.70 (Silica gel: methylethylketone/xylene=1:1)

tert.butyl 4'-[(7-n-butoxy-2-n-butyl-4-methyl-benzimidazol-1-yl)-methyl]biphenyl-2-carboxylate oil, $R_f$ value: 0.55 (Silica gel: methylene chloride/ethanol=19:1)

tert.butyl 4'-[(2-(4-hydroxyphenyl)-benzimidazol-1-yl)-methyl]biphenyl-2-carboxylate melting point: 258°–260° C.

tert.butyl 4'-[(2-(4-n-butoxyphenyl)-benzimidazol-1-yl)-methyl]biphenyl-2-carboxylate oil, $R_f$ value: 0.70 (Silica gel: methylethylketone/xylene=1:1)

tert.butyl 4'-[(2-n-butyl-4-nitro-benzimidazol-1-yl)-methyl]biphenyl-2-carboxylate oil, $R_f$ value: 0.45 (Silica gel: methylene chloride/ethanol=19:1)

tert.butyl 4'-[(2-(3-pyridyl)-benzimidazol-1-yl)-methyl]biphenyl-2-carboxylate oil, $R_f$ value: 0.40 (Silica gel: methylethylketone/xylene=5:2)

tert.butyl 4'-[(2-(4-benzyloxyphenyl)-benzimidazol-1-yl)-methyl]biphenyl-2-carboxylate oil, $R_f$ value: 0.75 (Silica gel: methylethylketone/xylene=1:1)

tert.butyl 4'-[(2-n-butyl-5,6-dimethyl-benzimidazol-1-yl)-methyl]biphenyl-2-carboxylate oil, $R_f$ value: 0.50 (Silica gel: methylene chloride/ethanol=19:1)

tert.butyl 4'-[(2-(2,2-dimethylpropyl)-5,6-dimethyl-benzimidazol-1-yl)-methyl]biphenyl-2-carboxylate oil, $R_f$ value: 0.48 (Silica gel: methylene chloride/ethanol=19:1)

tert.butyl 4'-[(2-benzyl-5,6-dimethyl-benzimidazol-1-yl)-methyl]biphenyl-2-carboxylate oil, $R_f$ value: 0.52 (Silica gel: methylene chloride/ethanol=19:1)

tert.butyl 4'-[(2-(2-methylbutyl)-5,6-dimethyl-benzimidazol-1-yl)-methyl]biphenyl-2-carboxylate oil, $R_f$ value: 0.50 (Silica gel: methylene chloride/ethanol=19:1)

tert.butyl 4'-[(2-cyclohexylmethyl-5,6-dimethyl-benzimidazol-1-yl)-methyl]biphenyl-2-carboxylate oil, $R_f$ value: 0.52 (Silica gel: methylene chloride/ethanol=19:1)

tert.butyl 4'-[(2-cyclohexylmethyl-5,6-dichloro-benzimidazol-1-yl)-methyl]biphenyl-2-carboxylate oil, $R_f$ value: 0.46 (Silica gel: methylene chloride/ethanol= 19:1)

tert.butyl 4'-[(2-(2-methylbutyl)-naphtho[2,3-d]imidazol-1-yl)-methyl]biphenyl-2-carboxylate oil, $R_f$ value: 0.57 (Silica gel: methylene chloride/ethanol=19:1)

tert.butyl 4'-[(2-n-propyl-naphtho[2,3-d]imidazol-1-yl)-methyl]biphenyl-2-carboxylate oil, $R_f$ value: 0.57 (Silica gel: methylene chloride/ethanol=19:1)

tert.butyl 4'-[(2-n-butyl-5,6-dichloro-benzimidazol-1-yl)-methyl]biphenyl-2-carboxylate oil, $R_f$ value: 0.45 (Silica gel: methylene chloride/ethanol=19:1)

tert.butyl 4'-[(2-cyclohexylmethyl-5,6-dimethoxy-benzimidazol-1-yl)-methyl]biphenyl-2-carboxylate oil, $R_f$ value: 0.47 (Silica gel: methylene chloride/ethanol= 19:1)

tert.butyl 4'-[(2-n-butyl-5,6-dimethoxy-benzimidazol-1-yl)-methyl]biphenyl-2-carboxylate oil, $R_f$ value: 0.46 (Silica gel: methylene chloride/ethanol=19:1)

tert.butyl 4'-[(2-cyclopentylmethyl-5,6-dimethoxy-benzimidazol-1-yl)-methyl]biphenyl-2-carboxylate oil, $R_f$ value: 0.47 (Silica gel: methylene chloride/ethanol= 19:1)

tert.butyl 4'-[(2-(3-methylbutyl)-5,6-dimethoxy-benzimidazol-1-yl)-methyl]biphenyl-2-carboxylate oil, $R_f$ value: 0.47 (Silica gel: methylene chloride/ethanol= 19:1)

tert.butyl 4'-[(2-cyclohexyl-5,6-dimethyl-benzimidazol-1-yl)-methyl]biphenyl-2-carboxylate oil, $R_f$ value: 0.50 (Silica gel: methylene chloride/ethanol=19:1)

tert.butyl 4'-[(2-(1-butyn-4-yl)-benzimidazol-1-yl)-methyl]biphenyl-2-carboxylate oil, $R_f$ value: 0.49 (Silica gel: methylene chloride/ethanol=19:1)

tert.butyl 4'-[(2-n-butyl-6-ethoxycarbonyl-benzimidazol-1-yl)-methyl]biphenyl-2-carboxylate oil, $R_f$ value: 0.60 (Silica gel: petroleum ether/ethyl acetate=1:1+1% glacial acetic acid)

tert.butyl 4'-[(2-cyclopentyl-5,6-dimethyl-benzimidazol-1-yl)-methyl]biphenyl-2-carboxylate oil, $R_f$ value: 0.50 (Silica gel: methylene chloride/ethanol=19:1)

tert.butyl 4'-[(2-n-butyl-5- and 6-fluoro-benzimidazol-1-yl)-methyl]biphenyl-2-carboxylate oil, $R_f$ value: 0.25 (Silica gel: methylene chloride/ethanol=50:1)

tert.butyl 4'-[(2-n-butyl-5- and 6-benzoyl-benzimidazol-1-yl)-methyl]biphenyl-2-carboxylate oil, $R_f$ value: 0.28 (Silica gel: methylene chloride/ethanol=50:1)

tert.butyl 4'-[(2-n-butyl-5- and 6-trifluoromethyl-benzimidazol-1-yl)-methyl]biphenyl-2-carboxylate oil, $R_f$ value: 0.33 (Silica gel: methylene chloride/ethanol= 50:1)

tert.butyl 4'-[(2-n-butyl-4-cyano-benzimidazol-1-yl)-methyl]biphenyl-2-carboxylate oil, $R_f$ value: 0.50 (Silica gel: methylene chloride/ethanol=19:1)

tert.butyl 4'-[(2-n-butyl-5- and 6-n-butylaminocarbonyl-benzimidazol-1-yl)-methyl]biphenyl-2-carboxylate oil, $R_f$ value: 0.30 (Silica gel: methylene chloride/methanol/acetic acid=19:0.8:0.2)

tert.butyl 4'-[(2-n-butyl-6-carboxy-benzimidazol-1-yl)-methyl]biphenyl-2-carboxylate oil, $R_f$ value: 0.90 (Silica gel: methylene chloride/methanol/acetic acid=9:0.8:0.2)

tert.butyl 4'-[(2-n-butyl-5-carboxy-benzimidazol-1-yl)-methyl]biphenyl-2-carboxylate melting point: 224°–225° C.

tert.butyl 4'-[(2-n-butyl-6-aminocarbonyl-benzimidazol-1-yl)-methyl]biphenyl-2-carboxylate melting point: 159°–160° C.

tert.butyl 4'-[(2-n-butyl-5-aminocarbonyl-benzimidazol-1-yl)-methyl]biphenyl-2-carboxylate melting point: 135°–138° C. (decomposition)

tert.butyl 4'-[(2-n-butyl-5- and 6-cyano-benzimidazol-1-yl)-methyl]biphenyl-2-carboxylate oil, $R_f$ value: 0.50 (Silica gel: methylene chloride/ethanol=100:1)

tert.butyl 4'-[(2-n-butyl-6-(1H-tetrazol-5-yl)-benzimidazol-1-yl)-methyl]biphenyl-2-carboxylate melting point: from 115° C. (decomposition)

tert.butyl 4'-[(2-n-butyl-5- and 6-(1H-tetrazol-5-yl)-benzimidazol-1-yl)-methyl]biphenyl-2-carboxylate melting point: from 92° C. (decomposition)

4'-[(2-n-butyl-6-(cis-hexahydrophthalinino)-benzimidazol-1-yl)-methyl]-1-cyano-2-phenylnaphthalene tert.butyl 4'-[(2-n-butyl-benzimidazol-1-yl)-methyl]-2-phenylnaphthalene-1-carboxylate oil, $R_f$ value: 0.25 (Silica gel: methylene chloride/ethanol=50:1)

tert.butyl 4'-[(2-n-butyl-6-(cis-hexahydrophthalimino)-benzimidazol-1-yl)-methyl]-2-phenylnaphthalene-1-carboxylate tert.butyl 4'-[(2-n-butyl-6-(cis-hexahydrophthalimino)-benzimidazol-1-yl)-methyl]-4-bromo-biphenyl-2-carboxylate oil, $R_f$ value: 0.43 (Silica gel: ethyl acetate/petroleum ether=2:1)

tert.butyl 4'-[(2-n-butyl-benzimidazol-1-yl)-methyl]-4-bromo-biphenyl-2-carboxylate oil, $R_f$ value: 0.35 (Silica gel: methylene chloride/ethanol=50:1)

4'-[(2-n-butyl-6-(cis-hexahydrophthalimino)-benzimidazol-1-yl)-methyl]-4-chloro-2-cyano-biphenyl oil, $R_f$ value: 0.90 (Silica gel: methylene chloride/ethanol=9:1)

EXAMPLE 2

Tert.butyl 4'-[(2-n-butyl-5- and 6-nitro-benzimidazol-1-yl)-methyl]biphenyl-2-carboxylate a) 2-n-butyl-6-nitro-benzimidazole 11.5 g (0.075 mol) of 4-nitro-o-phenylenediamine are introduced in portions at ambient temperature into a mixture of 8.66 g (0.085 mol) of valeric acid and 120 ml of phosphorus oxychloride. The mixture is then heated for 3 hours under reflux. The reaction mixture is separated in 1.5 kg of iced water, rendered alkaline using concentrated ammonia and extracted three times using 500 ml of ethyl acetate. The organic phase is separated off, dried using magnesium sulphate and rotary evaporated. The oily residue is purified over a silica gel column (grain size: 0.063–0.2 mm, eluting agent: methylene chloride/0–2% ethanol). The homogeneous fractions are evaporated to dryness.

Yield: 10.2 g (62.2% of theoretical),

Melting point: 139°–141° C.

Calculated: C 60.27 H 5.98 N 19.17 Found: 60.30 6.00 19.42 b) 9.5 g (43 mmol) of 2-n-butyl-6-nitro-benzimidazole are dissolved in 100 ml of dimethylsulphoxide and treated with 5.3 g (47.6 mmol) of potassium tert.butoxide. The mixture is stirred for 30 minutes and 16.6 g (47.6 mmol) of tert.butyl 4'-bromomethyl-biphenyl-2-carboxylate are added. After 2 hours, about 600 ml of water are added to the reaction mixture and it is extracted 3 times using about 200 ml of ethyl acetate. The organic phase is dried using magnesium sulphate and rotary evaporated. The crude product thus obtained is purified over a silica gel column (grain size: 0.063–0.2 mm, eluting agent: methylene chloride/0–1% ethanol). The homogeneous fractions are evaporated to dryness.

Yield: 19.9 g (95.2% of theoretical),

Oil, $R_f$ value: 0.50 (Silica gel: methylene chloride+5% ethanol)

Calculated: C 71.73 H 6.43 N 8.65 Found: 72.00 6.66 8.80

The following compounds are obtained in analogous manner:

tert.butyl 4'-[(2-n-butyl-4- and 7-nitro-benzimid-azol-1-yl)-methyl]biphenyl-2-carboxylate oil, $R_f$ value: 0.45 and 0.47 (Silica gel: methylene chloride/ethanol=19:1)

tert.butyl 4'-[(2-n-butyl-5- and 6-methoxy-benzimid-azol-1-yl)-methyl]biphenyl-2-carboxylate oil, $R_f$ value: 0.55 (Silica gel: methylethylketone/xylene=1:1)

tert.butyl 4'-[(2-n-butyl-5- and 6-nitro-benzimidazol-1-yl)-methyl]biphenyl-2-carboxylate oil, $R_f$ value: 0.60 (Silica gel: methylethylketone/xylene=1:1)

tert.butyl 4'-[(2-n-butyl-5- and 6-chloro-benzimidazol-1-yl)-methyl]biphenyl-2-carboxylate oil, $R_f$ value: 0.55 (Silica gel: methylethylketone/xylene=1:1)

tert.butyl 4'-[(2-n-butyl-5- and 6-acetamino-benzimidazol-1-yl)-methyl]biphenyl-2-carboxylate oil, $R_f$ value: 0.20 (Silica gel: methylethylketone/xylene=1:1)

tert.butyl 4'-[(2-n-butyl-5- and 6-butanoylamino-benzimidazol-1-yl)-methyl]biphenyl-2-carboxylate oil, $R_f$ value: 0.80 (Silica gel: ethyl acetate/ethanol/ammonia=90:10:1)

EXAMPLE 3

Tert.butyl 4'-[(5- and 6-amino-2-n-butyl-benzimidazol-1-yl)-methyl]biphenyl-2-carboxylate 18.3 g (37.7 mmol) of tert.butyl 4'-[(5- and 6-nitro-2-n-butyl-benzimidazol-1-yl)-methyl]biphenyl-2-carboxylate are dissolved in 200 ml of ethanol, 10 g of Raney nickel are added, and the mixture is hydrogenated for 3 hours at 50° C. and 5 bar hydrogen pressure. When the uptake of hydrogen is completed, the catalyst is filtered off under suction and the filtrate is rotary evaporated.

Yield: 17.1 g (100% of theoretical),

Oil, $R_f$ value: 0.1 and 0.2 (Silica gel: methylene chloride/ethanol=95:5)

The following compound is prepared in analogous manner:

tert.butyl 4'-[(4- and 7-amino-2-n-butyl-benzimidazol-1-yl)-methyl]biphenyl-2-carboxylate oil, $R_f$ value: 0.20 and 0.22 (Silica gel: methylene chloride/ethanol=50:1)

EXAMPLE 4

Tert.butyl 4'-[(6-amino-2-n-butyl-benzimidazol-1-yl)-methyl]biphenyl-2-carboxylate (I) and tert.butyl 4'-[(5-amino-2-n-butyl-benzimidazol-1-yl)-methyl]biphenyl-2-carboxylate (II)

The isomer mixture of I and II (17.1 g) obtained in Example 3 is separated over a chromatography column filled with 1,700 ml of silica gel (grain size: 0.063–0.2 mm), I being initially removed by elution using methylene chloride/ethanol=98:2.

Yield: 7.32 g (42.8% of theoretical),

Oil, $R_f$ value: 0.2 (Silica gel: methylene chloride/ethanol=95:5)

II is then eluted using methylene chloride/ethanol=96:4.

Yield: 9.28 g (54.3% of theoretical),

Oil, $R_f$ value: 0.1 (Silica gel: methylene chloride/ethanol=95:5)

The following pure compounds were isolated from the corresponding isomer mixtures in analogous manner:

tert.butyl 4'-[(4-amino-2-n-butyl-benzimidazol-1-yl)-methyl]biphenyl-2-carboxylate Yield: 86.1% of theoretical, Oil, $R_f$ value: 0.25 (Silica gel: methylene chloride/ethanol=99:1)

and tert.butyl 4'-[(7-amino-2-n-butyl-benzimidazol-1-yl)-methyl]biphenyl-2-carboxylate Yield: 5.0% of theoretical, Oil, $R_f$ value: 0.30 (Silica gel: methylene chloride/ethanol=99:1)

tert.butyl 4'-[(7-benzyloxy-2-n-butyl-4-methyl-benzimidazol-1-yl)-methyl]biphenyl-2-carboxylate Yield: 90.5% of theoretical, Melting point: 100°–102° C.

and tert.butyl 4'-[(4-benzyloxy-2-n-butyl-7-methyl-benzimidazol-1-yl)-methyl]biphenyl-2-carboxylate Yield: 1.9% of theoretical, Oil, $R_f$ value: 0.20 (Aluminum oxide: cyclohexane/ethyl acetate=4:1)

EXAMPLE 5

Tert.butyl 4'-[(2-n-butyl-6-methyl-benzimidazol-1-yl)-methyl]biphenyl-2-carboxylate a) 2-Pentanoylamido-5-methyl-nitro-benzene 6 g (0.04 mol) of 2-nitro-6-methyl-aniline are dissolved in 50 ml of pyridine, cooled to 0° C. and treated with 5.3 g (0.04 mol+10%) of valeryl chloride while stirring. After stirring for 1 hour at ambient temperature, the mixture is poured into iced water and the crystals are filtered off under suction and dried.

Yield: 9 g (96.7% of theoretical),

Melting point: 69°–71° C.

Calculated: C 61.00 H 6.83 N 11.86 Found: 61.21 6.79 11.72 b) 2-Pentanoylamido-5-methyl-aniline 8.5 g (0.035 mol) of 2-pentanoylamino-5-methyl-nitrobenzene are dissolved in 100 ml of methyl alcohol and hydrogenated at ambient temperature and 5 bar using 2 g of 10% palladium/carbon. When the reaction is completed, the catalyst is filtered off under suction and evaporated in vacuum.

Yield: 7.1 g (94.7% of theoretical),

Melting point: 132°–134° C. (methanol)

Calculated: C 69.87 N 8.80 N 13.58 Found: 69.28 8.74 13.31 c) N-(2-Pentanoylamino-5-methyl-phenyl)-2-tert.butoxycarbonyl-biphenyl-4'-yl-methylamine 2.1 g (0.01 mol) of 2-pentanoylamino-5-methyl-aniline are dissolved in 10 ml of dimethylformamide and 5 ml of N,N-diisopropylethylamine, treated with 3.5 g (0.01 mol) of tert.butyl 4'-bromomethyl-biphenyl-2-carboxylate and heated at 120° C. with stirring. The reaction is complete after 2 hours and the solvent is distilled off in vacuum. The oily residue obtained is dissolved in ethyl acetate, washed with water and evaporated in vacuum after drying over sodium sulphate. A yellowish oil is obtained after column chromatography over silica gel (grain size: 0.06–0.2 mm, eluting agent: methylene chloride).

Yield: 3.8 g (80.0% theoretical),

Oil, $R_f$ value: 0.75 (Silica gel: methylethylketone/xylene=1:1)

Calculated: C 76.24 H 7.68 N 5.93 Found: 76.16 7.85 5.87 d) Tert.butyl 4'-[(2-n-butyl-6-methyl-benzimidazol-1-yl)-methyl]biphenyl-2-carboxylate 3.6 g (0.076 mol) of N-(2-pentanoylamino-5-methylphenyl)-2-tert.butoxycarbonyl-biphenyl-4'-yl-methylamine are taken up in 5 ml of diglyme and heated to reflux. The reaction is completed after 2 hours, the reaction product is dissolved in ethyl acetate, washed with water and evaporated in vacuum after drying over sodium sulphate. A yellowish oil is obtained after column chromatography over silica gel (grain size: 0.06–0.2 mm, eluting agent: methylene chloride+1% ethanol).

Yield: 2.1 g (61.7% of theoretical),

Oil, $R_f$ value: 0.6 (Silica gel: methylethylketone/xylene=1:2)

Calculated: C 79.26 H 7.54 N 6.16 Found: 79.12 7.46 6.09

The following compounds are obtained in analogous manner:

tert.butyl 4'-[(2-n-butyl-6-chloro-benzimidazol-1-yl)-methyl]biphenyl-2-carboxylate oil, $R_f$ value: 0.6 (Silica gel: methylethylketone/xylene=1:2)

tert.butyl 4'-[(2-n-butyl-6-methoxy-benzimidazol-1-yl)-methyl]biphenyl-2-carboxylate oil, $R_f$ value: 0.65 (Silica gel: methylethylketone/xylene=1:2)

EXAMPLE 6

Tert.butyl 4'-[(2-n-butyl-5-methoxy-benzimidazol-1-yl)-methyl]biphenyl-2-carboxylate a) 2-Pentanoylamino-5-methoxy-nitrobenzene 4.2 g (0.025 mol) of 2-nitro-4-methoxy-aniline are dissolved in 30 ml of pyridine, cooled to 0° C. and treated with 3.3 g (0.0275 mol) of valeryl chloride with stirring. After stirring for 1 hour at ambient temperature, the mixture is poured into iced water, the crystals are filtered off under suction and dried.

Yield: 6 g (95.2% of theoretical),

Melting point: 74°–75° C.

$C_{19}N_{10}N_8O_6$ (252.27)

Calculated: C 57.13 H 6.39 N 11.11 Found: 57.43 6.45 10.97 b) N-(2-Nitro-4-methoxy-phenyl)-N-pentanoyl-(2-tert.butoxycarbonyl-biphenyl-4'-yl)-methylamine 2.5 g (0.01 mol) of 2-pentanoylamino-5-methoxy-nitrobenzene are dissolved in 30 ml of dimethylformamide, treated with 550 mg (0.11 mol) of sodium hydride (50% in oil) and stirred for 30 minutes at 80° C. 3.5 g (0.01 mol) of tert.butyl 4'-bromomethyl-biphenyl-2-carboxylate are then added and stirred for a further 2 hours at 80° C. The solvent is distilled off in vacuum, the oily residue obtained is dissolved in ethyl acetate, washed with water and evaporated in vacuum after drying over sodium sulphate. A yellowish oil is obtained after column chromatography (silica gel: 0.06–0.2 mm, eluting agent: methylene chloride).

Yield: 4.0 g (78.4% of theoretical),

Oil, $R_f$ value: 0.8 (Silica gel: methylethylketone/xylene=1:2)

$C_{30}H_{34}N_2O_6$ (518.61)

Calculated: C 69.48 H 6.61 N 5.40 Found: 69.31 6.53 5.39 c) N-(2-Amino-4-methoxy-phenyl)-N-pentanoyl-(2-tert.butoxycarbonyl-biphenyl-4'-yl)-methylamine 3.8 g (0.007 mol) of N-(2-nitro-4-methoxy-phenyl)-N-pentanoyl-(2-tert.butoxycarbonyl-biphenyl-4'-yl)-methylamine are dissolved in 100 ml of methanol and hydrogenated at ambient temperature and 5 bar in the presence of 1 g of 70% palladium/carbon. After the reaction is completed, the catalyst is filtered off under suction and evaporated in vacuum.

Yield: 3.2 g (93.6% of theoretical),

Oil, $R_f$ value: 0.5 (Silica gel: methylethylketone/xylene=1:2)

$C_{30}H_{36}N_2O_4$ (488.63)

Calculated: C 73.74 H 7.43 N 5.73 Found: 73.59 7.40 5.72 d) Tert.butyl 4'-[(2-n-butyl-5-methoxy-benzimidazol-1-yl)-methyl]biphenyl-2-carboxylate 3 g (0.006 mol) of N-(2-amino-4-methoxy-phenyl)-N-pentanoyl-(2-tert.butoxycarbonyl-biphenyl-4'-yl)-methylamine are dissolved in 100 ml of glacial acetic acid and heated to reflux with stirring. After one hour the solvent is distilled off and the resulting oil is chromatographed for further purification over silica gel (grain size: 0.06–0.2 mm, eluting agent: methylene chloride/ethanol=19:1).

Yield: 2.3 g (82.1% of theoretical),

Oil, $R_f$ value: 0.7 (Silica gel: ethyl acetate/ethanol/ammonia=90:10:1)

$C_{30}H_{34}N_2O_3$ (470.61)

Calculated: C 76.56 H 7.28 N 5.95 Found: 76.36 7.31 5.79

The following compounds are obtained in analogous manner:

tert.butyl 4'-[(2-n-butyl-5-chloro-benzimidazol-1-yl)-methyl]biphenyl-2-carboxylate oil, $R_f$ value: 0.7 (Silica gel: ethyl acetate/ethanol/ammonia=90:10:1)

tert.butyl 4'-[(5-amino-2-n-butyl-benzimidazol-1-yl)-methyl]biphenyl-2-carboxylate oil, $R_f$ value: 0.5 (Silica gel: ethyl acetate/ethanol/ammonia=90:10:1)

tert.butyl 4'-[(2-n-butyl-5-methyl-benzimidazol-1-yl)-methyl]biphenyl-2-carboxylate oil, $R_f$ value: 0.8 (Silica gel: ethyl acetate/ethanol/ammonia=90:10:1)

tert.butyl 4'-[(2-n-butyl-7-cyano-benzimidazol-1-yl)-methyl]biphenyl-2-carboxylate oil, $R_f$ value: 0.49 (Silica gel: methylene chloride/ethanol=19:1)

tert.butyl 4'-[(2-n-butyl-5,7-difluoro-benzimidazol-1-yl)-methyl]biphenyl-2-carboxylate oil, $R_f$ value: 0.27 (Silica gel: methylene chloride/ethanol=50:1)

tert.butyl 4'-[(2-n-butyl-5-acetyl-benzimidazol-1-yl)-methyl]biphenyl-2-carboxylate oil, $R_f$ value: 0.30 (Silica gel: methylene chloride/ethanol=50:1)

tert.butyl 4'-[(2-n-butyl-6-dimethylamino-benzimidazol-1-yl)-methyl]biphenyl-2-carboxylate oil, $R_f$ value: 0.60 (Silica gel: methylene chloride/ethanol=19:1)

tert.butyl 4'-[(7-amino-2-n-butyl-benzimidazol-1-yl)-methyl]biphenyl-2-carboxylate oil, $R_f$ value: 0.30 (Aluminium oxide: methylene chloride/ethanol=99:1)

tert.butyl 4'-[(6-N-benzyl-methylamino)-2-n-butyl-benzimidazol-1-yl)-methyl]biphenyl-2-carboxylate oil, $R_f$ value: 0.40 (Silica gel: methylene chloride/ethanol=19:1)

tert.butyl 4'-[(2-n-butyl-5-dimethylamino-sulphonyl-3-N-oxido-benzimidazol-1-yl)-methyl]biphenyl-2-carboxylate (prepared by incomplete reduction of the nitro group and subsequent cyclisation) melting point: 59°–62° C.

tert.butyl 4'-[(7-benzyloxy-2-n-butyl-benzimidazol-1-yl)-methyl]biphenyl-2-carboxylate oil, $R_f$ value: 0.50 (Silica gel: methylethylketone/xylene=1:1)

tert.butyl 4'-[(4-benzyloxy-2-n-butyl-benzimidazol-1-yl)-methyl]biphenyl-2-carboxylate oil, $R_f$ value: 0.65 (Silica gel: methylethylketone/xylene=1:4)

tert.butyl 4'-[(2-n-butyl-7-methoxy-benzimidazol-1-yl)-methyl]biphenyl-2-carboxylate oil, $R_f$ value: 0.80 (Silica gel: methylethylketone/xylene=1:1)

tert.butyl 4'-[(2-n-butyl-4-methoxy-benzimidazol-1-yl)-methyl]biphenyl-2-carboxylate oil, $R_f$ value: 0.70 (Silica gel: methylethylketone/xylene=1:2)

tert.butyl 4'-[(2,5-di-n-butyl-benzimidazol-1-yl)-methyl]biphenyl-2-carboxylate tert.butyl 4'-[(2,6-di-n-butyl-benzimidazol-1-yl)-methyl]biphenyl-2-carboxylate tert.butyl 4'-[(6-benzyloxy-2-n-butyl-benzimidazol-1-yl)-methyl]biphenyl-2-carboxylate oil, $R_f$ value: 0.40 (Silica gel: methylethylketone/xylene=1:2)

tert.butyl 4'-[(2-n-butyl-6-methylamino-benzimidazol-1-yl)-methyl]biphenyl-2-carboxylate oil, $R_f$ value: 0.10 (Silica gel: methylene chloride/ethanol=50:1)

tert.butyl 4'-[(2-n-butyl-6-cyclohexylamino-benzimidazol-1-yl)-methyl]biphenyl-2-carboxylate oil, $R_f$ value: 0.20 (Silica gel: ethyl acetate/petroleum ether=60:40)

tert.butyl 4'-[(2-n-butyl-6-(3-cyclohexyl-piperidino)-benzimidazol-1-yl)-methyl]biphenyl-2-carboxylate oil, $R_f$ value: 0.65 (Silica gel: methylene chloride/ethanol=9:1)

tert.butyl 4'-[(2-n-butyl-6-phthalimino-benzimidazol-1-yl)-methyl]biphenyl-2-carboxylate melting point: 182°–184° C.

tert.butyl 4'-[(2-n-butyl-6-(n-pentylamino)-benzimidazol-1-yl)-methyl]biphenyl-2-carboxylate oil, $R_f$ value: 0.70 (Silica gel: methylethylketone/xylene=1:1)

tert.butyl 4'-[(2,5-di-n-butyl-benzimidazol-1-yl)-methyl]biphenyl-2-carboxylate oil, $R_f$ value: 0.30 (Silica gel: methylethylketone/xylene=1:4)

tert.butyl 4'-[(2,6-di-n-butyl-benzimidazol-1-yl)-methyl]biphenyl-2-carboxylate oil, $R_f$ value: 0.50 (Silica gel: methylethylketone/xylene=1:4)

EXAMPLE 7 tert.butyl 4'-[(2-n-butyl-5-(n-butylaminocarbonylamino)-benzimidazol-1-yl)-methyl]biphenyl-2-carboxylate 2.09 g (4.4 mmol) of tert.butyl 4'-[(5-amino-2-n-butyl-benzimidazol-1-yl)-methyl]biphenyl-2-carboxylate are dissolved in 50 ml of tetrahydrofuran and treated with 2.0 ml of triethylamine and 2.0 ml of n-butylisocyanate. The reaction mixture is heated at reflux for 4 hours, rotary evaporated, and the residue is purified over a silica gel column (grain size: 0.063 mm–0.2 mm, eluting agent: methylene chloride/0–2% ethanol). The homogeneous fractions are evaporated to dryness.

Yield: 2.1 g (86.4% of theoretical),

Oil, $R_f$ value: 0.45 (Silica gel: methylene chloride/ethanol=19:1).

The following compounds are obtained in analogous manner:

tert.butyl 4'-[(2-n-butyl-6-phenylaminocarbonylamino-benzimidazol-1-yl)-methyl]biphenyl-2-carboxylate amorphous substance, $R_f$ value: 0.30 (Silica gel: methylene chloride/ethanol=19:1)

tert.butyl 4'-[(2-n-butyl-6-cyclohexylaminocarbonylamino-benzimidazol-1-yl)-methyl]biphenyl-2-carboxylate amorphous substance, $R_f$ value: 0.25 (Silica gel: methylene chloride/ethanol=19:1)

tert.butyl 4'-[(2-n-butyl-4-ethylaminocarbonylamino-benzimidazol-1-yl)-methyl]biphenyl-2-carboxylate amorphous substance, $R_f$ value: 0.50 (Silica gel: methylene chloride/ethanol=19:1)

tert.butyl 4'-[(6-aminocarbonylamino-2-n-butyl-benzimidazol-1-yl)-methyl]biphenyl-2-carboxylate melting point: 210°–211° C.

tert.butyl 4'-[(2-n-butyl-6-(n-hexylaminocarbonylamino)-benzimidazol-1-yl)-methyl]biphenyl-2-carboxylate melting point: 142°–143° C.

tert.butyl 4'-[(2-n-butyl-4-cyclohexylaminocarbonylamino-benzimidazol-1-yl)-methyl]biphenyl-2-carboxylate melting point: 104°–106° C. (amorphous)

tert.butyl 4'-[(2-n-butyl-5-cyclohexylaminocarbonylamino-benzimidazol-1-yl)-methyl]biphenyl-2-carboxylate melting point: 118°–120° C. (amorphous)

ethyl 4'-[(2-n-butyl-7-cyclohexylaminocarbonylamino-benzimidazol-1-yl)-methyl]biphenyl-2-carboxylate melting point: 152°–154° C.

tert.butyl 4'-[(6-aminothiocarbonylamino-2-n-butyl-benzimidazol-1-yl)-methyl]biphenyl-2-carboxylate melting point: 175°–176° C.

tert.butyl 4'-[(2-n-butyl-6-cyclohexylaminothiocarbonylamino-benzimidazol-1-yl)-methyl]biphenyl-2-carboxylate melting point: 91°–93° C. (amorphous)

tert.butyl 4'-[(5-aminothiocarbonylamino-2-n-butyl-benzimidazol-1-yl)-methyl]biphenyl-2-carboxylate melting point: 196°–197° C.

tert.butyl 4'-[(2-n-butyl-6-benzylaminocarbonylamino-benzimidazol-1-yl)-methyl]biphenyl-2-carboxylate melting point: 163°–165° C.

tert.butyl 4'-[(6-allylaminocarbonylamino-2-n-butyl-benzimidazol-1-yl)-methyl]biphenyl-2-carboxylate oil, $R_f$ value: 0.10 (Silica gel: methylene chloride/ethanol=19:1)

ethyl 4'-[(2-n-butyl-6-(tetrahydropyran-2-yl-aminocarbonylamino)-benzimidazol-1-yl)-methyl]biphenyl-2-carboxylate melting point: 86°–88° C. (amorphous)

tert.butyl 4'-[(2-n-butyl-6-(tetrahydropyran-2-yl-aminocarbonylamino)-benzimidazol-1-yl)-methyl]biphenyl-2-carboxylate oil, $R_f$ value: 0.20 (Silica gel: methylene chloride/ethanol=19:1)

tert.butyl 4'-[(2-n-butyl-6-(N-methylaminocarbonyl-n-pentylamino)-benzimidazol-1-yl)-methyl]biphenyl-2-carboxylate oil, $R_f$ value: 0.30 (Silica gel: methylethylketone/xylene=5:2)

4'-[(2-n-butyl-6-cyclohexylaminocarbonylamino-benzimidazol-1-yl)-methyl]-2-phthalimino-biphenyl oil, $R_f$ value: 0.45 (Silica gel: methylene chloride/ethanol=9:1)

4'-[(6-adamant-1-yl-aminocarbonylamino)-2-n-butyl-benzimidazol-1-yl)-methyl]biphenyl-3-carboxylic acid melting point: 251°–253° C.

tert.butyl 4'-[(6-(adamant-1-yl-aminocarbonylamino)-2-n-butyl-benzimidazol-1-yl)-methyl]biphenyl-2-carboxylate melting point: 196°–198° C.

tert.butyl 4'-[(2-n-butyl-6-(N-methylaminocarbonylmethylamino)-benzimidazol-1-yl)-methyl]biphenyl-2-carboxylate oil, $R_f$ value: 0.30 (Silica gel: methylethylketone/xylene=5:2)

tert.butyl 4'-[(2-n-butyl-6-(N-(n-butylaminocarbonyl)-methylamino)-benzimidazol-1-yl)-methyl]biphenyl-2-carboxylate oil, $R_f$ value: 0.70 (Silica gel: methylethylketone/xylene=5:2)

tert.butyl 4'-[(2-n-butyl-5-(N-methylaminocarbonyl-n-pentylamino)-benzimidazol-1-yl)-methyl]biphenyl-2-carboxylate oil, $R_f$ value: 0.45 (Silica gel: methylethylketone/xylene=1:2)

tert.butyl 4'-[(6-(n-butylaminocarbonylamino)-2-n-butyl-benzimidazol-1-yl)-methyl]biphenyl-2-carboxylate oil, $R_f$ value: 0.7 (Silica gel: ethyl acetate/ethanol/ammonia=90:10:1)

tert.butyl 4'-[(2-n-butyl-6-(N-cyclohexylaminocarbonyl-methylamino)-benzimidazol-1-yl)-methyl]biphenyl-2-carboxylate oil, $R_f$ value: 0.7 (Silica gel: methylethylketone/xylene=5:2)

tert.butyl 4'-[(2-n-butyl-6-(N-(n-butylaminocarbonyl)-methylamino)-benzimidazol-1-yl)-methyl]biphenyl-2-carboxylate oil, $R_f$ value: 0.55 (Silica gel: methylethylketone=5:2)

tert.butyl 4'-[(2-n-butyl-6-(N-cyclohexylaminocarbonyl-n-pentylamino)-benzimidazol-1-yl)-methyl]biphenyl-2-carboxylate oil, $R_f$ value: 0.8 (Silica gel: methylethylketone=5:2)

tert.butyl 4'-[(2-n-butyl-6-(N-(n-hexylaminocarbonyl)-cyclohexylamino)-benzimidazol-1-yl)-methyl]biphenyl-2-carboxylate oil, $R_f$ value: 0.40 (Aluminium oxideplate-:ethyl acetate/petroleum ether=3:7)

tert.butyl 4'-[(2-n-butyl-6-(N-cyclohexylaminocarbonyl-cyclohexylamino)-benzimidazol-1-yl)-methyl]biphenyl-2-carboxylate oil, $R_f$ value: 0.40 (Aluminium oxide: ethyl acetate/petroleum ether=4:1)

tert.butyl 4'-[(2-n-butyl-6-(N-(n-butylaminocarbonyl)-cyclohexylamino)-benzimidazol-1-yl)-methyl]biphenyl-2-carboxylate oil, $R_f$ value: 0.35 (Silica gel: ethyl acetate/petroleum ether=4:1)

tert.butyl 4'-[(2-n-butyl-6-(N-methylaminocarbonyl-cyclohexylamino)-benzimidazol-1-yl)-methyl]biphenyl-2-carboxylate oil, $R_f$ value: 0.45 (Aluminium oxide: ethyl acetate/petroleum ether=7:3)

tert.butyl 4'-[(2-n-butyl-6-(N-methylaminocarbonyl-benzylamino)-benzimidazol-1-yl)-methyl]biphenyl-2-carboxylate oil, $R_f$ value: 0.45 (Aluminium oxide: ethyl acetate/petroleum ether=6:4)

tert.butyl 4'-[(2-n-butyl-6-(N-(n-hexylaminocarbonyl)-benzylamino)-benzimidazol-1-yl)-methyl]biphenyl-2-carboxylate oil, $R_f$ value: 0.50 (Aluminium oxide: ethyl acetate/petroleum ether=4:6)

tert.butyl 4'-[(2-n-butyl-6-(N-cyclohexylaminocarbonyl-n-butylamino)-benzimidazol-1-yl)-methyl]biphenyl-2-carboxylate melting point: 106°–108° C. (amorphous)

tert.butyl 4'-[(2-n-butyl-6-(N-cyclohexylaminocarbonyl-benzylamino)-benzimidazol-1-yl)-methyl]biphenyl-2-carboxylate oil, $R_f$ value: 0.60 (Silica gel: ethyl acetate/petroleum ether=6:4)

tert.butyl 4'-[(2-n-butyl-6-(N-(2-trifluoromethylphenyl-aminocarbonyl)-methylamino)-benzimidazol-1-yl)-methyl]-biphenyl-2-carboxylate oil, $R_f$ value: 0.90 (Silica gel: methylethylketone/xylene=5:2)

tert.butyl 4'-[(2-n-butyl-6-(N-cyclohexylaminocarbonyl-n-hexylamino)-benzimidazol-1-yl)-methyl]biphenyl-2-carboxylate oil, $R_f$ value: 0.70 (Silica gel: ethyl acetate/petroleum ether=6:4)

tert.butyl 4'-[(2-n-butyl-6-(N-cyclohexylaminocarbonyl-n-propylamino)-benzimidazol-1-yl)-methyl]biphenyl-2-carboxylate oil, $R_f$ value: 0.50 (Silica gel: ethyl acetate/petroleum ether=6:4)

tert.butyl 4'-[(2-n-butyl-6-(N-cyclohexylaminocarbonyl-ethylamino)-benzimidazol-1-yl)-methyl]biphenyl-2-carboxylate oil, $R_f$ value: 0.20 (Silica gel: ethyl acetate/petroleum ether=6:4)

tert.butyl 4'-[(2-n-butyl-6-(N-cyclohexylaminocarbonyl-N-(2-phenylethyl)-amino)-benzimidazol-1-yl)-methyl]biphenyl-2-carboxylate oil, $R_f$ value: 0.55 (Silica gel: ethyl acetate/petroleum ether=6:4)

tert.butyl 4'-[(2-n-butyl-6-(N-(n-hexylaminocarbonyl)-N-(2-phenylethyl)-amino)-benzimidazol-1-yl)-methyl]biphenyl-2-carboxylate oil, $R_f$ value: 0.20 (Silica gel: ethyl acetate/petroleum ether=7:3)

tert.butyl 4'-[(2-(1-trans-butenyl)-6-cyclohexylamino-carbonylamino-benzimidazol-1-yl)-methyl]biphenyl-2-carboxylate oil, $R_f$ value: 0.20 (Aluminium oxide: methylene chloride/ethanol=50:1)

tert.butyl 4'-[(2-n-butyl-6-(N-(dimethylaminocarbonyl)-n-pentylamino)-benzimidazol-1-yl)-methyl]biphenyl-2-carboxylate oil, $R_f$ value: 0.50 (Silica gel: methylethylketone/xylene=1:1)

4'-[(2-n-butyl-6-cyclohexylaminocarbonylamino-benzimidazol-1-yl)-methyl]-2-(1H-triphenyl-methyl-tetrazol-5-yl)-biphenyl melting point: 183°–187° C.

4'-[(2-n-butyl-6-(N-cyclohexylaminocarbonylmethylamino)-benzimidazol-1-yl)-methyl]-2-(1H-tetrazol-5-yl)-biphenyl melting point: 185°–186° C.

tert.butyl 4'-[(2-n-butyl-6-cyclohexylaminocarbonyloxy-benzimidazol-1-yl)-methyl]biphenyl-2-carboxylate melting point: 76°–78° C. (amorphous)

tert.butyl 4'-[(2-n-butyl-6-(N-methylaminocarbonyl-N-(3-cyclohexyl-n-propyl)-amino)-benzimidazol-1-yl)-methyl]biphenyl-2-carboxylate oil, $R_f$ value: 0.15 (aluminium oxide: petroleum ether/ethyl acetate=2:3)

4'-[(2-n-butyl-6-(N-cyclohexylaminocarbonyl-methylamino)-benzimidazol-1-yl)-methyl]-1-cyano-2-phenyl-naphthalene tert.butyl 4'-[(2-n-butyl-6-(N-cyclohexylaminocarbonyl-methylamino)-benzimidazol-1-yl)-methyl]-2-phenyl-napthalene-1-carboxylate 4'-[(2-n-butyl-6-(N-cyclohexylaminocarbonyl-methylamino)-benzimidazol-1-yl)-methyl]-4-chloro-2-cyano-biphenyl tert.butyl 4'-[(2-n-butyl-6-(N-(n-dodecylaminocarbonyl)-methylamino)-benzimidazol-1-yl)-methyl]biphenyl-2-carboxylate oil, $R_f$ value: 0.40 (aluminium oxide: petroleum ether/ethyl acetate=3:7)

tert.butyl 4'-[(2-n-butyl-6-(N-(cyclohexylaminocarbonyl)-n-octylamino)-benzimidazol-1-yl)-methyl]biphenyl-2-carboxylate oil, $R_f$ value: 0.35 (aluminium oxide: petroleum ether/ethyl acetate=3:2)

tert.butyl 4'-[(2-n-butyl-6-(N-(n-dodecylaminocarbonyl)-methylamino)-benzimidazol-1-yl)-methyl]biphenyl-2-carboxylate oil, $R_f$ value: 0.35 (aluminium oxide: petroleum ether/ethyl acetate=2:3)

EXAMPLE 8

Tert.butyl 4'-[(2-n-butyl-4-butanoylamino-benzimidazol-1-yl)-methyl]biphenyl-2-carboxylate 1.6 g (3.5 mmol) of tert.butyl 4'-[(4-amino-2-n-butyl-benzimidazol-1-yl)-methyl]biphenyl-2-carboxylate are dissolved in 30 ml of pyridine and 0.52 ml (5.0 mmol) of butyryl chloride is added dropwise at ambient temperature with stirring. After one hour the solvent is distilled off and the residue is mixed with about 20 ml of diethylether. The precipitate is filtered off under suction and dried at 50° C. in vacuum.

Yield: 1.75 g (94.6% of theoretical),

Melting point: 167°–168° C.

The following compounds are obtained in analogous manner:

tert.butyl 4'-[(2-n-butyl-5-acetamino-benzimidazol-1-yl)-methyl]biphenyl-2-carboxylate oil, $R_f$ value: 0.70 (Silica gel: methylene chloride/ethanol=9:1)

tert.butyl 4'-[(2-n-butyl-5-butanoylamino-benzimidazol-1-yl)-methyl]biphenyl-2-carboxylate oil, $R_f$ value: 0.80 (Silica gel: ethyl acetate/ethanol/ammonia=90:10:1)

tert.butyl 4'-[(2-n-butyl-5-methanesulphonamino-benzimidazol-1-yl)-methyl]biphenyl-2-carboxylate oil, $R_f$ value: 0.75 (Silica gel: ethyl acetate/ethanol/ammonia=90:10:1)

tert.butyl 4'-[(2-n-butyl-6-isopropylsulphonamino-benzimidazol-1-yl)-methyl]biphenyl-2-carboxylate amorphous substance, $R_f$ value: 0.55 (Silica gel: methylene chloride/ethanol=19:1)

tert.butyl 4'-[(2-n-butyl-6-ethoxycarbonylamino-benzimidazol-1-yl)-methyl]biphenyl-2-carboxylate amorphous substance, $R_f$ value: 0.30 (Silica gel: methylene chloride/ethanol=19:1)

tert.butyl 4'-[(2-n-butyl-5-(tert.butoxycarbonylaminoacetamino)-benzimidazol-1-yl)-methyl]biphenyl-2-carboxylate melting point: 101°–103° C. (amorphous)

tert.butyl 4'-[(2-n-butyl-6-(N-butanoyl-methylamino)-benzimidazol-1-yl)-methyl]biphenyl-2-carboxylate oil, $R_f$ value: 0.70 (Silica gel: methylene chloride/ethanol=19:1)

ethyl 4'-[(2-n-butyl-7-butanesulphonylamino-benzimidazol-1-yl)-methyl]biphenyl-2-carboxylate oil, $R_f$ value: 0.50 (Silica gel: methylene chloride/ethanol=19:1)

ethyl 4'-[(2-n-butyl-5-propanoylamino-benzimidazol-1-yl)-methyl]biphenyl-2-carboxylate melting point: 221°–223° C.

tert.butyl 4'-[(6-acetamino-2-n-butyl-benzimidazol-1-yl)-methyl]biphenyl-2-carboxylate melting point: 192°–194° C.

tert.butyl 4'-[(2-n-butyl-6-propanoylamino-benzimidazol-1-yl)-methyl]biphenyl-2-carboxylate melting point: 133°–135° C.

tert.butyl 4'-[(6-butanoylamino-2-n-butyl-benzimid-azol-1-yl)-methyl]biphenyl-2-carboxylate melting point: 127°–129° C.

tert.butyl 4'-[(2-n-butyl-6-n-pentanoylamino-benzimidazol-1-yl)-methyl]biphenyl-2-carboxylate oil, $R_f$ value: 0.6 (Silica gel: methylene chloride/ethanol=19:1)

tert.butyl 4'-[(2-n-butyl-6-dimethylaminocarbonylamino-benzimidazol-1-yl)-methyl]biphenyl-2-carboxylate oil, $R_f$ value: 0.4 (Silica gel: methylethylketone/xylene=5:2)

tert.butyl 4'-[(2-n-butyl-6-(N-(dimethylaminocarbonyl)-methylamino)-benzimidazol-1-yl)-methyl]biphenyl-2-carboxylate oil, $R_f$ value: 0.45 (Silica gel: methylene chloride/ethanol=19:1)

tert.butyl 4'-[(2-n-butyl-6-phenylacetamino-benzimidazol-1-yl)-methyl]biphenyl-2-carboxylate $R_f$ value: 0.30 (Silica gel: methylene chloride/ethanol=50:1) melting point: 178°–180° C.

tert.butyl 4'-[(2-n-butyl-6-cyclohexylacetamino-benzimidazol-1-yl)-methyl]biphenyl-2-carboxylate $R_f$ value: 0.30 (Silica gel: ethyl acetate/petroleum ether=4:1) melting point: 64°–66° C. (amorphous)

tert.butyl 4'-[(2-n-butyl-6-cyclohexylcarbonylamino-benzimidazol-1-yl)-methyl]biphenyl-2-carboxylate $R_f$ value: 0.70 (Silica gel: ethyl acetate/petroleum ether=9:1) melting point: 72°–76° C. (amorphous)

tert.butyl 4'-[(6-benzyloxycarbonylamino-2-n-butyl-benzimidazol-1-yl)-methyl]biphenyl-2-carboxylate $R_f$ value: 0.80 (Silica gel: ethyl acetate/petroleum ether=9:1) melting point: 84°–86° C.

tert.butyl 4'-[(2-n-butyl-6-cyclohexylmethylaminocarbonyl-benzimidazol-1-yl)-methyl]biphenyl-2-carboxylate oil, $R_f$ value: 0.45 (Silica gel: petroleum ether/ethyl acetate/ethanol=2.5:2.5:0.5)

tert.butyl 4'-[(2-n-butyl-6-cyclohexylaminocarbonyl-benzimidazol-1-yl)-methyl]biphenyl-2-carboxylate oil, $R_f$ value: 0.50 (Silica gel: petroleum ether/ethyl acetate/ethanol=2.5:2.5:0.5)

tert.butyl 4'-[(2-n-butyl-6-(N-methyl-n-butyl-aminocarbonyl)-benzimidazol-1-yl)-methyl]biphenyl-2-carboxylate oil, $R_f$ value: 0.40 (Silica gel: petroleum ether/ethyl acetate/ethanol=6:3:1+1% glacial acetic acid)

tert.butyl 4'-[(2-n-butyl-5-(n-butylaminocarbonyl)-benzimidazol-1-yl)-methyl]biphenyl-2-carboxylate oil, $R_f$ value: 0.75 (Silica gel: petroleum ether/ethyl acetate=1:2+1% glacial acetic acid)

tert.butyl 4'-[(2-n-butyl-6-(2-isopropyl-5-methyl-cyclohexyloxycarbonylamino)-benzimidazol-1-yl)-methyl]biphenyl-2-carboxylate oil, $R_f$ value: 0.45 (Silica gel: ethyl acetate/petroleum ether=60:40)

tert.butyl 4'-[(2-n-butyl-6-(N-ethoxycarbonyl-cyclohexylamino)-benzimidazol-1-yl)-methyl]biphenyl-2-carboxylate oil, $R_f$ value: 0.65 (Silica gel: ethyl acetate/petroleum ether=6:4)

tert.butyl 4'-[(2-n-butyl-6-cyclohexylacetamino-benzimidazol-1-yl)-methyl]biphenyl-2-carboxylate melting point: 65°–66° C. (amorphous)

tert.butyl 4'-[(2-n-butyl-6-(N-ethoxycarbonyl-benzylamino)-benzimidazol-1-yl)-methyl]biphenyl-2-carboxylate oil, $R_f$ value: 0.60 (Silica gel: ethyl acetate/petroleum ether=7:3)

tert.butyl 4'-[(2-n-butyl-6-(n-hexyloxycarbonylamino)-benzimidazol-1-yl)-methyl]biphenyl-2-carboxylate oil, $R_f$ value: 0.55 (Silica gel: ethyl acetate/petroleum ether=6:4)

tert.butyl 4'-[(2-n-butyl-6-(5,7-dioxo-1H,3H-imidazo[1,5-c]thiazol-6-yl)-benzimidazol-1-yl)-methyl]biphenyl-2-carboxylate oil, $R_f$ value: 0.55 (Aluminium oxide: ethyl acetate/petroleum ether=7:3)

tert.butyl 4'-[(2-n-butyl-6-(N-(n-butanoyl)-n-butylamino)-benzimidazol-1-yl)-methyl]biphenyl-2-carboxylate oil, $R_f$ value: 0.60 (Silica gel: ethyl acetate/petroleum ether=6:4)

tert.butyl 4'-[(2-n-butyl-6-(N-(4-methoxycarbonyl-thiazolidin-3-ylcarbonyl)-n-butylamino)-benzimidazol-1-yl)-methyl]biphenyl-2-carboxylate oil, $R_f$ value: 0.55 (Silica gel: ethyl acetate/petroleum ether=6:4)

tert.butyl 4'-[(2-n-butyl-6-(N-cyclohexylcarbonyl-n-hexylamino)-benzimidazol-1-yl)-methyl]biphenyl-2-carboxylate oil, $R_f$ value: 0.55 (Silica gel: ethyl acetate/petroleum ether=6:4)

tert.butyl 4'-[(2-n-butyl-6-(N-cyclohexylcarbonyl-methylamino)-benzimidazol-1-yl)-methyl]biphenyl-2-carboxylate oil, $R_f$ value: 0.70 (Silica gel: ethyl acetate/petroleum ether=6:4)

tert.butyl 4'-[(2-n-butyl-6-(N-(n-butanoyl)-n-pentylamino)-benzimidazol-1-yl)-methyl]biphenyl-2-carboxylate oil, $R_f$ value: 0.60 (Silica gel: methylethylketone/xylene=1:1)

tert.butyl 4'-[(2-n-butyl-6-isopropylcarbonylamino-benzimidazol-1-yl)-methyl]biphenyl-2-carboxylate oil, $R_f$ value: 0.15 (Silica gel: ethyl acetate/petroleum ether=7:3)

tert.butyl 4'-[(2-n-butyl-6-(N-ethoxycarbonyl-methylamino)-benzimidazol-1-yl)-methyl]biphenyl-2-carboxylate oil, $R_f$ value: 0.35 (Silica gel: ethyl acetate/petroleum ether=6:4)

tert.butyl 4'-[(2-n-butyl-6-(N-ethoxycarbonyl-n-pentylamino)-benzimidazol-1-yl)-methyl]biphenyl-2-carboxylate oil, $R_f$ value: 0.70 (Silica gel: methylethylketone/xylene=1:1)

tert.butyl 4'-[(2-n-butyl-6-(N-(dimethylaminocarbonyl)-benzylamino)-benzimidazol-1-yl)-methyl]biphenyl-2-carboxylate oil, $R_f$ value: 0.45 (Silica gel: ethyl acetate/petroleum ether=4:1)

tert.butyl 4'-[(2-n-butyl-6-diethylaminocarbonylamino-benzimidazol-1-yl)-methyl]biphenyl-2-carboxylate oil, $R_f$ value: 0.20 (Silica gel: ethyl acetate/petroleum ether= 9:1)

tert.butyl 4'-[(2-n-butyl-6-(dimethylaminoacetamino)-benzimidazol-1-yl)-methyl]biphenyl-2-carboxylate oil, $R_f$ value: 0.40 (Silica gel: methylethylketone/xylene=5:2)

tert.butyl 4'-[(2-n-butyl-6-(2,2-dimethylpropionylamino)-benzimidazol-1-yl)-methyl]biphenyl-2-carboxylate oil, $R_f$ value: 0.60 (Silica gel: ethyl acetate/petroleum ether= 9:1)

tert.butyl 4'-[(2-n-butyl-6-cyclopentylcarbonylamino-benzimidazol-1-yl)-methyl]biphenyl-2-carboxylate oil, $R_f$ value: 0.35 (Silica gel: ethyl acetate/petroleum ether= 7:3)

tert.butyl 4'-[(2-n-butyl-6-cyclopropylcarbonylamino-benzimidazol-1-yl)-methyl]biphenyl-2-carboxylate melting point: 175°–177° C.

tert.butyl 4'-[(2-n-butyl-6-cyclohexyloxycarbonylamino-benzimidazol-1-yl)-methyl]biphenyl-2-carboxylate melting point: 68°–70° C. (amorphous)

4'-[(2-n-butyl-6-dimethylaminocarbonylamino-benzimidazol-1-yl)-methyl]-2-(1-triphenylmethyl-tetrazol-5-yl)-biphenyl oil, $R_f$ value: 0.75 (Silica gel: ethyl acetate/ethanol/ammonia=90:10:1)

tert.butyl 4'-[(2-n-butyl-6-morpholinocarbonylamino-benzimidazol-1-yl)-methyl]biphenyl-2-carboxylate melting point: 74°–76° C.

tert.butyl 4'-[(2-n-butyl-6-pyrrolidinocarbonylamino-benzimidazol-1-yl)-methyl]biphenyl-2-carboxylate

EXAMPLE 9

4'-[(2-Hydroxybenzimidazol-1-yl)-methyl]biphenyl-2-carboxylic acid 0.9 g (2.25 mmol) of tert.butyl 4'-[(2-hydroxybenzimidazol-1-yl)-methyl]biphenyl-2-carboxylate are dissolved in 10 ml of methylene chloride and treated with 10 ml of trifluoroacetic acid. The solution is stirred for 2 hours at ambient temperature and then evaporated to dryness on a rotary evaporator. The oily residue is dissolved in 50 ml of methylene chloride and extracted by shaking twice using water. The organic phase is dried using magnesium sulphate and evaporated to dryness. The crystalline residue thus obtained is mixed with a small amount of diethylether, filtered under suction and dried in vacuum at 50° C.

Yield: 0.75 g (97.4% of theoretical),
Melting point: 303°–304° C.
$C_{21}H_{16}N_2O_3$ (344.37)
Calculated: C 73.24 H 4.68 N 8.13 Found: 73.07 4.81 7.95

The following compounds are obtained in analogous manner:

4'-[(2,5-di-n-butylbenzimidazol-1-yl)-methyl]biphenyl-2-carboxylic acid M.p.: 199°–201° C.

4'-[(2,6-di-n-butylbenzimidazol-1-yl)-methyl]biphenyl-2-carboxylic acid M.p.: 188°–190° C.

EXAMPLE 10

4'-[(2-n-Butyl-6-methoxybenzimidazol-1-yl)-methyl]biphenyl-2-carboxylic acid

Prepared in analogous manner to Example 9 from tert. butyl 4'-[(2-n-butyl-6-methoxybenzimidazol-1-yl)-methyl]biphenyl-2-carboxylate and trifluoroacetic acid.

Yield: 73.9% of theoretical,
Oil, $R_f$ value: 0.6 (Silica gel: ethyl acetate/ethanol/ammonia=50:45:5)
$C_{28}H_{26}N_2O_3$ (414.51)
Calculated: C 75.34 H 6.23 N 6.76 Found: 75.27 6.03 6.52

EXAMPLE 11

4'-[(2-n-Butyl-4-methyl-7-(2-diethylamino-ethoxy)-benzimidazol-1-yl)-methyl]biphenyl-2-carboxylic acid dihydrate Prepared in analogous manner to Example 9 from tert. butyl 4'-[(2-n-butyl-4-methyl-7-(2-diethylamino-ethoxy)-benzimidazol-1-yl)-methyl]biphenyl-2-carboxylate and trifluoroacetic acid.

Yield: 94.2% of theoretical,
Melting point: 94°–96° C.
$C_{23}H_{33}N_3O_3 \times 2\ H_2O$ (549.72)
Calculated: C 69.92 H 7.88 N 7.64 Found: 69.62 7.60 7.40

Example 12

4'-[(2-Ethylthio-benzimidazol-1-yl)-methyl]biphenyl-2-carboxylic acid

Prepared in analogous manner to Example 9 from tert. butyl 4'-[(2-ethylthio-benzimidazol-1-yl)-methyl]biphenyl-2-carboxylate and trifluoroacetic acid.

Yield: 92.9% of theoretical,
Melting point: 197°–198° C.
$C_{23}H_{30}N_2O_2S$ (388.48), Calculated: C, 71.11; H, 5.19; N, 7.21; S, 8.25. Found: C, 71.12; H, 5.13; N, 7.23; S, 8.31.

Example 13

4'-[(2-n-Propylthiomethyl-benzimidazol-1-yl)-methyl]biphenyl-2-carboxylic acid

Prepared in analogous manner to Example 9 from tert. butyl 4'-[(2-n-propylthiomethyl-benzimidazol-1-yl)-methyl]biphenyl-2-carboxylate and trifluoroacetic acid.

Yield: 96.8% of theoretical,
Melting point: 139°–141° C.
$C_{25}H_{24}N_2O_2S$ (416.54), Calculated: C, 72.09; H, 5.81; N, 6.73; S, 7.70. Found: C, 71.82; H, 5.83; N, 6.57; S, 7.43.

Example 14

4'-[(2-Methyl-benzimidazol-1-yl)-methyl]biphenyl-2-carboxylic acid×0.33 HCl

Prepared in analogous manner to Example 9 from tert. butyl 4'-[(2-methyl-benzimidazol-1-yl)-methyl]biphenyl-2-carboxylate and trifluoroacetic acid.

Yield: 93.2% of theoretical,
Melting point: 255°–256° C.
$C_{22}H_{18}N_2O_2 \times 0.33\ HCl$ (354.54), Calculated: C, 74.53; H, 5.21; N, 7.90; Cl, 3.32. Found: C, 74.60; H, 5.14; N, 8.16; Cl, 3.49.

Example 15

4'-[(2-Methylmercapto-benzimidazol-1-yl)-methyl]biphenyl-2-carboxylic acid

Prepared in analogous manner to Example 9 from tert. butyl 4'-[(2-methylmercapto-benzimidazol-1-yl)-methyl]biphenyl-2-carboxylate and trifluoroacetic acid.

Yield: 88.2% of theoretical,
Melting point: 197°–199° C.

$C_{22}H_{10}N_2O_2S$ (374.46), Calculated: C, 70.57; H, 4.84; N, 7.48; S, 8.56. Found: C, 70.30; H, 4.87; N, 7.25; S, 8.25.

Example 16

4'-[(2-Methyl-5- and 6-nitro-benzimidazol-1-yl)-methyl]biphenyl-2-carboxylic acid Prepared in analogous manner to Example 9 from tert. butyl 4'-[(2-methyl-5- and 6-nitro-benzimidazol-1-yl)-methyl]biphenyl-2-carboxylate and trifluoroacetic acid.

Yield: 71.1% of theoretical,
Melting point: 285°–288° C.

$C_{23}H_{17}N_3O_4$ (387.39), Calculated: C, 68.21; H, 4.42; N, 10.85. Found: C, 67.96; H, 4.40; N, 10.83.

Example 17

4'-[(2-Methyl-5-and 6-butanoylamino-benzimidazol-1-yl)-methyl]biphenyl-2-carboxylic acid Prepared in analogous manner to Example 9 from tert. butyl 4'-[(2-methyl-5- and 6-butanoylamino-benzimidazol-1-yl)-methyl]biphenyl-2-carboxylate and trifluoroacetic acid.

Yield: 79.5% of theoretical,
Melting point: 261°–262° C.

$C_{26}H_{25}N_3O_3$ (427.50), Calculated: C, 73.05; H, 5.89; N, 9.83. Found: C, 72.85; H, 5.90; N, 9.80.

Example 18

4'-[(2-(2-Methylpropyl)-benzimidazol-1-yl)-methyl]biphenyl-2-carboxylic acid

Prepared in analogous manner to Example 9 from tert. butyl 4'-[(2-methylpropyl)-benzimidazol-1-yl)-methyl]biphenyl-2-carboxylate and trifluoroacetic acid.

Yield: 71.9% of theoretical,
Melting point: 211°–212° C.

$C_{25}H_{24}N_2O_2$ (384.48), Calculated: C, 78.10; H, 6.29; N, 7.29. Found: C, 77.95; H, 6.22; N, 7.15.

Example 19

4'-[(2-Methoxymethyl-benzimidazol-1-yl)-methyl]biphenyl-2-carboxylic acid

Prepared in analogous manner to Example 9 from tert. butyl 4'-[(2-methoxymethyl-benzimidazol-1-yl)-methyl]biphenyl-2-carboxylate and trifluoroacetic acid.

Yield: 80.3% of theoretical,
Melting point: 195°–197° C.

$C_{23}H_{20}N_2O_3$ (372.43), Calculated: C, 74.18; H, 5.41; N, 7.52. Found: C, 73.99; H, 5.39; N, 7.43.

Example 20

4'-[(2-Pyridyl)-benzimidazol-1-yl)-methyl]biphenyl-2-carboxylic acid

Prepared in analogous manner to Example 9 from tert. butyl 4'-[(2-pyridyl)-benzimidazol-1-yl)-methyl]biphenyl-2-carboxylate and trifluoroacetic acid.

Yield: 50.0% of theoretical,
Melting point: 262°–264° C.

$C_{20}H_{18}N_3O_3$ (405.45), Calculated: C, 77.02; H, 4.72; N, 10.36. Found: C, 77.21; H, 4.58; N, 10.20.

Example 21

4'-[(5- and 6-Methyl-benzimidazol-1-yl)-methyl]biphenyl-2-carboxylic acid

Prepared in analogous manner to Example 9 from tert. butyl 4'-[(5- and 6-methyl-benzimidazol-1-yl)-methyl]biphenyl-2-carboxylate and trifluoroacetic acid.

Yield: 92.0% of theoretical,
Melting point: 228°–230° C.

$C_{23}H_{18}N_2O_2$ (342.396), Calculated: C, 77.17; H, 5.30; N, 8.18. Found: C, 76.94; H, 5.23; N, 7.93.

Example 22

4'-[(2-Phenyl-benzimidazol-1-yl)-methyl]biphenyl-2-carboxylic acid

Prepared in analogous manner to Example 9 from tert. butyl 4'-[(2-phenyl-benzimidazol-1-yl)-methyl]biphenyl-2-carboxylate and trifluoroacetic acid.

Yield: 56.8% of theoretical,
Melting point: 275°–277° C.

$C_{27}H_{20}N_2O_2$ (404.47), Calculated: C, 80.18; H, 4.98; N, 6.93. Found: C, 79.90; H, 5.05; N, 6.92.

Example 23

4'-[(2-Thiazol-4-yl)-benzimidazol-1-yl)-methyl]biphenyl-2-carboxylic acid

Prepared in analogous manner to Example 9 from tert. butyl 4'-[(2-(thiazol-4-yl)-benzimidazol-1-yl)-methyl]biphenyl-2-carboxylate and trifluoroacetic acid.

Yield: 94.6% of theoretical,
Melting point: 284°–286° C.

$C_{24}H_{17}N_3O_2S$ (411.48), Calculated: C, 70.06; H, 4.16; N, 10.21; S, 7.79. Found: C, 69.90; H, 4.29; N, 9.97; S, 7.59.

Example 24

4'-[(2-(3,5-Dimethyl-pyrazol-1-yl)-benzimidazol-1-yl)-methyl]biphenyl-2-carboxylic acid Prepared in analogous manner to Example 9 from tert. butyl 4'-[(2-(3,5-dimethyl-pyrazol-1-yl)-benzimidazol-1-yl)-methyl]biphenyl-2-carboxylate and trifluoroacetic acid.

Yield: 87.2% of theoretical,
Melting point: 185°–187° C.

$C_{26}H_{22}N_4O_2$ (422.49), Calculated: C, 73.92; H, 5.25; N, 13.26. Found: C, 73.86; H, 5.37; N, 13.27.

Example 25

4'-[(Fur-2-yl)-benzimidazol-1-yl)-methyl]biphenyl-2-carboxylic acid

Prepared in analogous manner to Example 9 from tert. butyl 4'-[(2-(fur-2-yl)-benzimidazol-1-yl)-methyl]biphenyl-2-carboxylate and trifluoroacetic acid.

Yield: 78.4% of theoretical,
Melting point: 263°–265° C.

$C_{25}H_{18}N_2O_3$ (394.43), Calculated: C, 76.13; H, 4.60; N, 7.10. Found: C, 75.94; H, 4.64; N, 6.83.

Example 26

4'-[(2-Aminocarbonylamino-benzimidazol-1-yl)-methyl]biphenyl-2-carboxylic acid

Prepared in analogous manner to Example 9 from tert. butyl 4'-[(2-aminocarbonylamino-benzimidazol-1-yl)-methyl]biphenyl-2-carboxylate and trifluoroacetic acid.

Yield: 53.3% of theoretical,

Melting point: 214°–216° C.

$C_{22}H_{18}N_4O_3 \times H_2O$ (404.42), Calculated: C, 65.34; H, 4.98; N, 13.85. Found: C, 65.18; H, 5.05; N, 13.61.

Example 27

4'-[(2-Isopropyl-benzimidazol-1-yl)-methyl]biphenyl-2-carboxylic acid

Prepared in analogous manner to Example 9 from tert. butyl 4'-[(2-isopropyl-benzimidazol-1-yl)-methyl]biphenyl-2-carboxylate and trifluoroacetic acid.

Yield: 80% of theoretical,

Melting point: 206°–208° C.

$C_{24}H_{22}N_2O_2$ (370.46), Calculated: C, 77.81; H, 5.99; N, 7.56. Found: C, 77.55; H, 5.97; N, 7.43.

Example 28

4'-[(7-Benzyloxy-2-n-butyl-4-methyl-benzimidazol-1-yl)-methyl]biphenyl-2-carboxylic acid Prepared in analogous manner to Example 9 from tert. butyl 4'-[(7-benzyloxy-2-n-butyl-4-methyl-benzimidazol-1-yl)-methyl]biphenyl-2-carboxylate and trifluoroacetic acid.

Yield: 85.5% of theoretical,

Melting point: 217°–219° C.

$C_{33}H_{32}N_2O_3 \times CF_3COOH$ (618.66), Calculated: C, 67.95; H, 5.37; N, 4.52. Found: C, 68.19; H, 5.56; N, 4.74.

Example 29

4'-[(2-Hydroxymethyl-benzimidazol-1-yl)-methyl]biphenyl-2-carboxylic acid

Prepared in analogous manner to Example 9 from tert. butyl 4'-[(2-hydroxymethyl-benzimidazol-1-yl)-methyl]biphenyl-2-carboxylate and trifluoroacetic acid.

Yield: 81.9% of theoretical,

Melting point: 188°–190° C.

$C_{22}H_{18}N_2O_3 \times CF_3COOH$ (472.42), Calculated: C, 61.02; H, 4.05; N, 5.93. Found: C, 61.23; H, 4.08; N, 5.91.

Example 30

4'-[(2-(3-Hydroxypropyl-benzimidazol-1-yl)-methyl]biphenyl-2-carboxylic acid

Prepared in analogous manner to Example 9 from tert. butyl 4'-[(2-(3-hydroxypropyl-benzimidazol-1-yl)-methyl]biphenyl-2-carboxylate and trifluoroacetic acid.

Yield: 58.8% of theoretical,

Melting point: 150°–152° C.

$C_{24}H_{22}N_2O_3 \times CH_3COOH$ (500.47), Calculated: C, 62.40; H, 4.63; N, 5.60. Found: C, 62.13; H, 4.70; N, 5.83.

Example 31

4'-[(2-Methyl-5- and 6-(N-(2-methoxyacetyl)-n-butylamino)-benzimidazol-1-yl)-methyl]biphenyl-2-carboxylic acid Prepared in analogous manner to Example 9 from tert. butyl 4'-[(2-methyl-5- and 6-(N-(2-methoxyacetyl)-n-butylamino)-benzimidazol-1-yl)-methyl]biphenyl-2-carboxylate and trifluoroacetic acid.

Yield: 84.8% of theoretical,

Melting point: 186°–188° C.

$C_{29}H_{31}N_3O_6$ (485.58), Calculated: C, 71.73; H, 6.43; N, 8.65. Found: C, 72.67; H, 6.68; N, 8.74.

Example 32

4'-[(2-(1-Methylpropyl)-benzimidazol-1-yl)-methyl]biphenyl-2-carboxylic acid

Prepared in analogous manner to Example 9 from tert. butyl 4'-[(2-(1-methylpropyl)-benzimidazol-1-yl)-methyl]biphenyl-2-carboxylate and trifluoroacetic acid.

Yield: 80% of theoretical,

Melting point: 147°–148° C.

$C_{25}H_{24}N_2O_2$ (384.48), Calculated: C, 78.10; H, 6.29; N, 7.29. Found: C, 77.91; H, 6.23; N, 7.37.

Example 33

4'-[(2-Methylbutyl)-benzimidazol-1-yl)-methyl]biphenyl-2-carboxylic acid

Prepared in analogous manner to Example 9 from tert. butyl 4'-[(2-(2-methylbutyl)-benzimidazol-1-yl)-methyl]biphenyl-2-carboxylate and trifluoroacetic acid.

Yield: 60% of theoretical,

Melting point: 209°–210° C.

$C_{26}H_{28}N_2O_2$ (398.51), Calculated: C, 78.36; H, 6.58; N, 7.03. Found: C, 78.27; H, 6.51; N, 6.99.

Example 34

4'-[(2-Methyl-4- and 6-(N-(2-methoxyethyl)-n-butylamino)-benzimidazol-1-yl)-methyl]biphenyl-2-carboxylic acid Prepared in analogous manner to Example 9 from tert. butyl 4'-[(2-methyl-5- and 6-(N-(2-methoxyethyl)-n-butylamino)-benzimidazol-1-yl)-methyl]biphenyl-2-carboxylate and trifluoroacetic acid.

Yield: 46.5% of theoretical,

Melting point: 102°–106° C.

$C_{29}H_{33}N_3O_3$ (471.598), Calculated: C, 73.86; H, 7.05; N, 8.91. Found: C, 73.60; H, 7.13; N, 8.85.

Example 35

4'-[(2-n-Pentyl-benzimidazol-1-yl)-methyl]biphenyl-2-carboxylic acid

Prepared in analogous manner to Example 9 from tert. butyl 4'-[(2-n-pentyl-benzimidazol-1-yl)-methyl]biphenyl-2-carboxylate and trifluoroacetic acid.

Yield: 87% of theoretical,

Melting point: 181°–183° C.

$C_{25}H_{26}N_2O_2$ (387.51), Calculated: C, 78.36; H, 6.58; N, 7.03. Found: C, 78.12; H, 6.42; N, 7.09.

Example 36

4'-[(Benzimidazol-1-yl)-methyl]biphenyl-2-carboxylic acid

Prepared in analogous manner to Example 9 from tert. butyl 4'-[(benzimidazol-1-yl)-methyl]biphenyl-2-carboxylate and trifluoroacetic acid.

Yield: 90.9% of theoretical,
Melting point: 217°–219° C.
$C_{31}H_{18}N_2O_2$ (328.37), Calculated: C, 76.81; H, 4.91; N, 8.53. Found: C, 77.03; H, 5.00; N, 8.42.

Example 37

4'-[(2-n-Butyl-4-methyl-7-methoxy-benzimidazol-1-yl)-methyl]biphenyl-2-carboxylic acid Prepared in analogous manner to Example 9 from tert. butyl 4'-[(2-n-butyl-4-methyl-7-methoxy-benzimidazol-1-yl)-methyl]biphenyl-2-carboxylate and trifluoroacetic acid in methylene chloride.

Yield: 86.6% of theoretical,
Melting point: 216°–218° C.
$C_{27}H_{26}N_2O_3$ (428.54), Calculated: C, 75.68; H, 6.59; N, 6.54. Found: C, 75.48; H, 6.59; N, 6.45.

Example 38

4'-[(2-n-Propyl-benzimidazol-1-yl)-methyl]biphenyl-2-carboxylic acid

Prepared in analogous manner to Example 9 from tert. butyl 4'-[(2-n-propyl-benzimidazol-1-yl)-methyl]biphenyl-2-carboxylate and trifluoroacetic acid.

Yield: 85.2% of theoretical,
Melting point: 237°–238° C.
$C_{24}H_{23}N_2O_2$ (370.45), Calculated: C, 77.81; H, 5.99; N, 7.56. Found: C, 78.08; H, 5.74; N, 7.37.

Example 39

4'-[(2-Ethyl-benzimidazol-1-yl)-methyl]biphenyl-2-carboxylic acid

Prepared in analogous manner to Example 9 from tert. butyl 4'-[(2-ethyl-benzimidazol-1-yl)-methyl]biphenyl-2-carboxylate and trifluoroacetic acid.

Yield: 81.6% of theoretical,
Melting point: 251°–253° C.
$C_{23}H_{20}N_2O_2$ (356.42), Calculated: C, 77.51; H, 5.66; N, 7.86. Found: C, 77.72; H, 5.64; N, 7.59.

Example 40

4'-[(2-Ethylthiomethyl-benzimidazol-1-yl)-methyl] biphenyl-2-carboxylic acid semi-trifluoroacetate Prepared in analogous manner to Example 9 from tert. butyl 4'-[(2-ethylthiomethyl-benzimidazol-1-yl)-methyl] biphenyl-2-carboxylate and trifluoroacetic acid.

Yield: 96.1% of theoretical,
Melting point: 139°–141° C.
$C_{24}H_{22}N_2O_2S \times \frac{1}{2}CF_3COOH$ (459.52), Calculated: C, 65.35; H, 4.94; N, 6.10; S, 6.98. Found: C, 65.24; H, 5.00; N, 6.18; S, 6.98.

Example 41

4'-[(2-Methylthiomethyl-benzimidazol-1-yl)-methyl] biphenyl-2-carboxylic acid semi-trifluoroacetate Prepared in analogous manner to Example 9 from tert. butyl 4'-[(2-methylthiomethyl-benzimidazol-1-yl)-methyl] biphenyl-2-carboxylate and trifluoroacetic acid.

Yield: 98.6% of theoretical,
Melting point: 147°–149° C.
$C_{23}H_{20}N_2O_2S \times \frac{1}{2}CF_3COOH$ (445.495), Calculated: C, 64.71; H, 4.64; N, 6.29; S, 7.30. Found: C, 64.70; H, 5.04; N, 6.51; S, 6.91.

Example 42

4'-[(2-Chloro-benzimidazol-1-yl)-methyl]biphenyl-2-carboxylic acid

Prepared in analogous manner to Example 9 from tert. butyl 4'-[(2-chloro-benzimidazol-1-yl)-methyl]biphenyl-2-carboxylate and trifluoroacetic acid.

Yield: 84.0% of theoretical,
Melting point: 169°–171° C.
$C_{21}H_{15}ClN_2O_2$ (362.815), Calculated: C, 69.52; H, 4.17; N, 7.72; Cl, 9.77. Found: C, 69.39; H, 4.13; N, 7.66; Cl, 9.72.

Example 43

4'-[(2-n-Butylthio-benzimidazol-1-yl)-methyl] biphenyl-2-carboxylic acid

Prepared in analogous manner to Example 9 from tert. butyl 4'-[(2-n-butylthio-benzimidazol-1-yl)-methyl] biphenyl-2-carboxylate and trifluoroacetic acid.

Yield: 88.0% of theoretical,
Melting point: 160°–162° C.
$C_{23}H_{24}N_2O_2S$ (416.54), Calculated: C, 72.09; H, 5.81; N, 6.73; S, 7.70. Found: C, 71.93; H, 5.75; N, 6.74; S, 7.71.

Example 44

4'-[(2-n-Butyl-5-acetamino-benzimidazol-1-yl)-methyl]biphenyl-2-carboxylicacid hydrate Prepared in analogous manner to Example 9 from tert. butyl 4'-[(2-n-butyl-5-acetamino-benzimidazol-1-yl)-methyl]biphenyl-2-carboxylate and trifluoroacetic acid.

Yield: 71.3% of theoretical,
Melting point: 187°–189° C.
$C_{27}H_{27}N_3O_3 \times H_2O$ (459.54), Calculated: C, 70.56; H, 6.36; N, 9.14. Found: C, 70.40; H, 6.22; N, 9.08.

Example 45

4'-[(2-(4-Methoxyphenyl)-benzimidazol-1-yl)-methyl]biphenyl-2-carboxylic acid

Prepared in analogous manner to Example 9 from tert. butyl 4'-[(2-(4-methoxyphenyl)-benzimidazol-1-yl)-methyl] biphenyl-2-carboxylate and trifluoroacetic acid.

Yield: 87.5% of theoretical,
Melting point: 283°–286° C.
$C_{28}H_{23}N_2O_3$ (434.50), Calculated: C, 77.40; H, 5.10; N, 6.45. Found: C, 77.45; H, 5.20; N, 6.44.

Example 46

4'-[(2-n-Propylthio-benzimidazol-1-yl)-methyl] biphenyl-2-carboxylic acid

Prepared in analogous manner to Example 9 from tert. butyl 4'-[(2-n-propylthio-benzimidazol-1-yl)-methyl] biphenyl-2-carboxylate and trifluoroacetic acid.

Yield: 90.5% of theoretical,
Melting point: 219°–220° C.

Example 47

4'-[(2-n-Butylamino-benzimidazol-1-yl)-methyl]biphenyl-2-carboxylic acid semi-trifluoroacetate

Prepared in analogous manner to Example 9 from tert. butyl 4'-[(2-n-butylamino-benzimidazol-1-yl)-methyl]biphenyl-2-carboxylate and trifluoroacetic acid.

Yield: 80.0% of theoretical,
Melting point: 247°–249° C.
$C_{23}H_{23}N_3O_2 \times \frac{1}{2}CF_3COOH$ (456.50), Calculated: C, 68.41; H, 5.63; N, 9.20. Found: C, 68.56; H, 5.84; N, 9.07.

Example 48

4'-[(2-(4-Methoxyphenyl)-5- and 6-chloro-benzimidazol-1-yl)-methyl]biphenyl-2-carboxylic acid

Prepared in analogous manner to Example 9 from tert. butyl 4'-[(2-(4-methoxyphenyl)-5- and 6-chloro-benzimidazol-1-yl)-methyl]biphenyl-2-carboxylate and trifluoroacetic acid.

Yield: 76.3% of theoretical,
Melting point: 234°–236° C.
$C_{20}H_{21}ClN_2O_3$ (468.95), Calculated: C, 71.71; H, 4.51; N, 5.97; Cl, 7.56. Found: C, 71.57; H, 4.39; N, 5.85; Cl, 7.79.

Example 49

4'-[(2-n-Butyl-5-methoxy-benzimidazol-1-yl)-methyl]biphenyl-2-carboxylic acid

Prepared in analogous manner to Example 9 from tert. butyl 4'-[(2-n-butyl-5-methoxy-benzimidazol-1-yl)-methyl]biphenyl-2-carboxylate and trifluoroacetic acid.

Yield: 66.2% of theoretical,
Melting point: 203°–205° C.
$C_{26}H_{26}N_2O_3$ (414.51), Calculated: C, 75.34; H, 6.323; N, 6.76. Found: C, 75.19; H, 6.31; N, 6.61.

Example 50

4'-[(2-n-Butyl-5- and 6-acetamino-benzimidazol-1-yl)-methyl]biphenyl-2-carboxylic acid

Prepared in analogous manner to Example 9 from tert. butyl 4'-[(2-n-butyl-5- and 6-acetamino-benzimidazol-1-yl)-methyl]biphenyl-2-carboxylate and trifluoroacetic acid.

Yield: 83.7% of theoretical,
Melting point: 117°–119° C.
$C_{27}H_{27}N_3O_3$ (441.54), Calculated: C, 73.45; H, 6.16; N, 9.52. Found: C, 73.25; H, 6.23; N, 9.47.

Example 51

4'-[(2-n-Butyl-5- and 6-butanoylamino-benzimidazol-1-yl)-methyl]biphenyl-2-carboxylic acid

Prepared in analogous manner to Example 9 from tert. butyl 4'-[(2-n-butyl-5- and 6-butanoylamino-benzimidazol-1-yl)-methyl]biphenyl-2-carboxylate and trifluoroacetic acid.

Yield: 80.0% of theoretical,
Melting point: 123°–127° C.
$C_{29}H_{31}N_3O_3$ (469.59), Calculated: C, 74.18; H, 6.65; N, 8.95. Found: C, 73.96; H, 6.19; N, 8.99.

Example 52

4'-[(6-(N-Benzyl-methylamino)-2-n-butyl-benzimidazol-1-yl)-methyl]biphenyl-2-carboxylic acid

Prepared in analogous manner to Example 9 from tert. butyl 4'-[(6-(N-benzyl-methylamino)-2-n-butyl-benzimidazol-1-yl)-methyl]biphenyl-2-carboxylate and trifluoroacetic acid.

Yield: 82.0% of theoretical,
Melting point: 237°–238° C.
$C_{23}H_{33}N_3O_2$ (503.64), Calculated: C, 78.70; H, 6.60; N, 8.34. Found: C, 78.68; H, 6.71; N, 8.44.

Example 53

4'-[(2-n-Butyl-5-chloro-benzimidazol-1-yl)-methyl]biphenyl-2-carboxylic acid

Prepared in analogous manner to Example 9 from tert. butyl 4'-[(2-n-butyl-5-chloro-benzimidazol-1-yl)-methyl]biphenyl-2-carboxylate and trifluoroacetic acid.

Yield: 70.6% of theoretical,
Melting point: 191°–193° C.
$C_{23}H_{23}ClN_2O_2$ (418.92), Calculated: C, 71.68; H, 5.53; N, 6.69; Cl, 8.46. Found: C, 71.48; H, 5.40; N, 6.53; S, 8.43.

Example 54

4'-[(2-n-Butyl-5- and 6-methoxy-benzimidazol-1-yl)-methyl]biphenyl-2-carboxylic acid

Prepared in analogous manner to Example 9 from tert. butyl 4'-[(2-n-butyl-5- and 6-methoxy-benzimid-azol-1-yl)-methyl]biphenyl-2-carboxylate and trifluoroacetic acid.

Yield: 84.1% of theoretical,
Melting point: 128°–133° C.
$C_{23}H_{23}N_2O_3$ (414.51), Calculated: C, 75.34; H, 6.32; N, 6.76. Found: C, 75.32; H, 6.14; N, 6.75.

Example 55

4'-[(2-n-Butyl-7-n-butoxy-4-methyl-benzimidazol-1-yl)-methyl]biphenyl-2-carboxylicacid trifluoroacetate

Prepared in analogous manner to Example 9 from tert. butyl 4'-[(2-n-butyl-7-n-butoxy-4-methyl-benzimidazol-1-yl)-methyl]biphenyl-2-carboxylate in methylene chloride.

Yield: 63.3% of theoretical,
Melting point: 172°–173° C.
$C_{26}H_{24}N_2O_3 \times CF_3COOH$ (584.65), Calculated: C, 65.74; H, 6.03; N, 4.73. Found: C, 66.52; H, 6.15; N, 4.95.

Example 56

2-n-Butyl-1-[(2-carboxy-biphenyl-4'-yl)methyl]-6,7-dihydro-7,7-dimethyl-5-ethyl-5H-pyrrolo[2,3-f]benzimidazol-6-one semi-hydrate

5 g (10.3 mmol) of 6-amino-5-[(2-tert.butoxycarbonyl-biphenyl-4'-yl)-methyl]-amino-3,4-dimethyl-1-ethyl-indol- 2-one and 5 ml of valeric acid are heated at reflux for 4 hours. After cooling, the mixture is stirred into 50 ml of saturated aqueous sodium carbonate solution. It is extracted by shaking 3 times using 30 ml of methylene chloride each time. The methylene chloride phase is dried using sodium sulphate and evaporated in vacuum. The crude product is purified using a silica gel column (eluting agent: ethyl acetate/ethanol/ammonia=90:10:1).

Yield: 1.55 g (30.3% of theoretical),

Melting point: 185°–187° C.

$C_{31}H_{23}N_3O_3 \times \frac{1}{2}H_2O$ (504.64), Calculated: C, 73.81; H, 6.79; N, 8.33, Found: C, 73.91; H, 6.86; N, 7.25; S, 8.36.

Example 57

4'-[(2-n-Butyl-7-hydroxy-4-methyl-benzimidazol-1-yl)-methyl]-2-(1H-tetrazol-5-yl)-biphenyl hydrate 0.9 g (1.7 mmol) of 4'-[(2-n-butyl-7-benzyloxy-4-methyl-benzimidazol-1-yl)-methyl]-2-(1H-tetrazol-5-yl)-biphenyl, dissolved in 100 ml of methanol, are hydrogenated at ambient temperature at 5 bar hydrogen pressure in the presence of 0.9 g of 20% palladium hydroxide on carbon. The catalyst is then filtered off under suction and the filtrate is evaporated to dryness in vacuum. The crude product is recrystallised from acetone/ether and dried at 50° C. in vacuum.

Yield: 0.72 g (97.3% of theoretical),

Melting point: 331°–333° C.

$C_{25}H_{26}N_6O \times H_2O$ (456.56), Calculated: C, 68.40; H, 6.18; N, 18.40. Found: C, 68.64; H, 6.18; N, 18.55.

The following compounds are obtained in analogous manner:

4'-[2-n-butyl-7-hydroxy-4-methyl-benzimidazol-1-yl)-methyl]-2-trifluoroacetamino-biphenyl
melting point: 243°–245° C.

4'-[2-n-butyl-7-hydroxy-4-methyl-benzimidazol-1-yl)-methyl]-2-trifluoromethanesulphonamino-biphenyl
melting point: 160°–162° C.

tert.butyl 4'-[2-n-butyl-7-hydroxy-benzimidazol-1-yl)-methyl]biphenyl-2-carboxylate
oil, $R_f$ value: 0.60 (silica gel: methylethylketone/xylene=1:1)

tert.butyl 4'-[2-n-butyl-6-hydroxy-benzimidazol-1-yl)-methyl]biphenyl-2-carboxylate
oil, $R_f$ value: 0.55 (silica gel: methylethylketone/xylene=1:1)

tert.butyl 4'-[2-n-butyl-4-hydroxy-benzimidazol-1-yl)-methyl]biphenyl-2-carboxylate
melting point: 91°–93° C.

tert.butyl 4'-[2-n-butyl-5-hydroxy-benzimidazol-1-yl)-methyl]biphenyl-2-carboxylate
oil, $R_f$ value: 0.60 (silica gel: methylethylketone/xylene=1:2)

4'-[2-n-butyl-7-hydroxy-4-methyl-benzimidazol-1-yl)-methyl]-2-phthalimino-biphenyl
melting point: 224°–226° C.

Example 58

4'-[(2-n-Butyl-benzimidazol-1-yl)-methyl]-2-(1H-tetrazol-5-yl)-biphenyl a) 4'-[(2-n-Butyl-benzimidazol-1-yl)-methyl]-2-(1-triphenylmethyltetrazol-5-yl)-biphenyl 0.87 g (5 mmol) of 2-n-butyl-benzimidazole is dissolved in 20 ml of dimethylsulphoxide and 0.61 g (5.5 mmol) of potassium tert.butoxide is added with stirring. After ½ hour, 4'-bromomethyl-2-(1-triphenylmethyl-1H-tetrazol-5-yl)-biphenyl is added and the mixture is stirred for 3 hours at ambient temperature. It is poured into about 50 ml of iced water and extracted by shaking 3 times using 30 ml of ethyl acetate each time. The ethyl acetate phase is extracted by shaking using 30 ml of water, dried over sodium sulphate and evaporated to dryness. The crude product is purified over a silica gel column (grain size: 0.063–0.2 mm, eluting agent: methylene chloride/ethanol=100:1).

Yield: 2.1 g (64.6% of theoretical),

Melting point: 85°–87° C.

$C_{44}H_{36}N_6$ (650.84), Calculated: C, 81.20; H, 5.88; N, 12.91. Found: C, 80.97; H, 5.90; N, 12.66.

b) 4'-[(2-n-Butyl-benzimidazol-1-yl)-methyl]-2-(1H-tetrazol-5-yl)-biphenyl 2 g (3 mmol) of 4'-[(2-n-butyl-benzimidazol-1-yl)-methyl]-2-(1-triphenylmethyl-tetrazol-5-yl)-biphenyl are dissolved in a mixture of 10 ml of methylene chloride and 10 ml of methanol, treated with 10 ml of etherified hydrochloric acid and stirred at ambient temperature for 3 hours. The mixture is rotary evaporated to dryness in vacuum. The residue is dissolved in methanol, rendered alkaline using ammonia and rotary evaporated once again. The crude product is purified over a silica gel column (grain size: 0.063–0.2 mm, eluting agent: methylene chloride/ethanol/ammonia=19:1:0.1). The product is crystallised from ether and dried at 50° C. in vacuum.

Yield: 1.02 g (81.6% of theoretical),

Melting point: 241°–243° C.

$C_{25}H_{24}N_6$ (408.52), Calculated: C, 73.50; H, 5.92; N, 20.57. Found: C, 73.34; H, 5.92; N, 20.47.

Example 59

4'-[(2-n-Butyl-7-benzyloxy-4-methyl-benzimidazol-1-yl)-methyl]-2-(1H-tetrazol-5-yl)-biphenyl semihydrate A mixture of 3.8 g (7.1 mmol) of ammonium chloride, 4.5 g (69 mmol) of sodium azide, 20 ml of dimethylformamide and 2.2 g (4.53 mmol) of 4'-[(2-n-butyl-7-benzyloxy-4-methyl-benzimidazol-1-yl)-methyl]-2-cyano-biphenyl is heated at 120° C. internal temperature for 36 hours with stirring. The sodium chloride formed is filtered off and the filtrate is rotary evaporated in vacuum. 50 ml of water are added to the oily residue and the solution is adjusted to pH 2 using concentrated hydrochloric acid with cooling. The oily crude product is filtered off, taken up in 50 ml of methylene chloride and dried over sodium sulphate. It is then purified over a silica gel column (grain size 0.063–0.2 mm, eluting agent: methylene chloride/ethanol=19:1). The homogeneous fractions are evaporated to dryness in vacuum and the residue is dried at 50° C.

Yield: 1.6 g (68% of theoretical),

Melting point: 112°–116° C.

$C_{33}H_{32}N_6O \times \frac{1}{2}H_2O$ (537.66), Calculated: C, 73.73; H, 6.18; N, 15.63. Found: C. 73.55; H, 6.33; N, 15.91.

Example 60

4'-[(7-Acetoxy-2-n-butyl-4-methyl-benzimidazol-1-yl)-methyl]biphenyl-2-carboxylic acid 0.55 g (1 mmol) of 4'-[(2-n-butyl-7-hydroxy-4-methyl-benzimidazol-1-yl)-methyl]biphenyl-2-carboxylic acid trifluoroacetate is dissolved in 20 ml of pyridine. 0.5 ml (7 mmol) of acetyl chloride is added dropwise to the mixture at 5° C. with stirring. The mixture is stirred for 1 hour at 5° C. and then for 2 hours at ambient temperature. The pyridine is distilled off in vacuum on a rotary evaporator. The residue is mixed with water and filtered under suction. After washing with water, it is dried at 50° C. in vacuum.

Yield: 0.43 g (94% of theoretical),

Melting point: 242°–244° C.

$C_{20}N_{23}N_2O_4$ (456.55), Calculated: C, 73.66; H, 6.18; N, 6.14. Found: C, 73.50; H, 6.20; N, 6.36.

Example 61

4'-[(7-n-Butoxy-2-n-butyl-4-methyl-benzimidazol-1-yl)-methyl]biphenyl-2-carboxylic acid trifluoroacetate a) Tert.butyl 4'-[(7-n-butoxy-2-n-butyl-4-methylbenzimidazol-1-yl)-methyl]biphenyl-2-carboxylate A mixture of 0.94 g (2 mmol) of tert.butyl 4'-[(2-n-butyl-7-hydroxy-4-methyl-benzimidazol-1-yl)-methyl]biphenyl-2-carboxylate, 36 ml of dimethylformamide, 4 ml of water, 1.4 g (10 mmol) of potassium carbonate and 0.9 g (6.6 mmol) of n-butylbromide is stirred for 16 hours at ambient temperature. The mixture is poured onto 200 ml of iced water and the oily precipitate obtained is taken up in methylene chloride after being decanted off. The methylene chloride solution is dried over sodium sulphate and evaporated in vacuum. The crude product is purified over a silica gel column (grain size: 0.065–0.2 mm, eluting agent: methylene chloride/ethanol=50:1).

Yield: 0.8 g (76.2% of theoretical),

Oil, $R_f$ value: 0.6 (silica gel: methylene chloride/ethanol= 19:1)

$C_{24}H_{42}N_2O_3$ (526.7), Calculated: C, 77.53; H, 8.04; N, 5.32. Found: C, 77.53; H, 7.87; N, 5.31.

The following compounds are obtained in analogous manner:

tert.butyl 4'[(2-n-butyl-7-methoxy-benzimidazol-1-yl)-methyl]biphenyl-2-carboxylate oil, $R_f$ value: 0.70 (silica gel: methylethylketone/xylene= 1:1)

tert.butyl 4'-[(2-n-butyl-7-(2-methoxyethoxy)-4-methyl-benzimidazol-1-yl)-methyl]biphenyl-2-carboxylate oil, $R_f$ value: 0.35 (Aluminium oxide plate: methylene chloride/ethanol=99:1)

b) 4'-[(7-n-Butoxy-2-n-butyl-4-methyl-benzimidazol-1-yl)-methyl]biphenyl-2-carboxylic acid trifluoroacetate 0.8 g (1.5 mmol) of tert.butyl 4'-[(7-n-butoxy-2-n-butyl-4-methyl-benzimidazol-1-yl)-methyl]biphenyl-2-carboxylate are dissolved in 15 ml of methylene chloride, 5 ml of trifluoroacetic acid are added and the mixture is stirred for 2 hours at ambient temperature. The product is rotary evaporated to dryness in vacuum and the residue is recrystallised from acetone. The crystals are dried at 50° C. in vacuum.

Yield: 0.45 g (51.3% of theoretical),

Melting point: 172°–174° C.

$C_{26}H_{34}N_2O_3 \times CF_3COOH$ (584.65), Calculated: C, 65.74; H, 6.03; N, 4.73. Found: C, 65.62; H, 6.15; N, 4.95.

The following compounds are obtained in analogous manner:

4'-[(2-n-butyl-7-(2-(1-imidazolyl)-ethoxy)-4-methyl-benzimidazol-1-yl)-methyl]biphenyl-2-carboxylic acid bis-trifluoroacetate melting point: 229°–231° C.

4'-[(2-n-butyl-7-(2-hydroxyethoxy)-4-methyl-benzimidazol-1-yl)-methyl]biphenyl-2-carboxylic acid melting point: 216° C.

Example 62

4'-[(2-n-Butyl-4-hydroxy-7-methyl-benzimidazol-1-yl)-methyl]biphenyl-2-carboxylic acid Prepared in analogous manner to Example 57 from 4-'-[(4-benzyloxy-2-n-butyl-7-methyl-benzimidazol-1-yl)-methyl]biphenyl-2-carboxylic acid and hydrogen in methanol/dimethylformamide in the presence of 20% palladium hydroxide on carbon.

Yield: 64.4% of theoretical,

Melting point: 291°–294° C.

$C_{26}H_{26}N_2O_3$ (414.51), Calculated: C, 75.34; H, 6.32; N, 6.76. Found: C, 75.22; H, 6.40; N, 6.64.

Example 63

4'-[(2-Ethylsulphinylmethyl-benzimidazol-1-yl)-methyl]biphenyl-2-carboxylic acid 2.01 g (5.0 mmol) of 4'-[(2-ethylthiomethyl-benzimidazol-1-yl)-methyl]biphenyl-2-carboxylic acid are dissolved in 25 ml of glacial acetic acid and treated with 0.51 ml of 30% strength hydrogen peroxide. The solution is allowed to stand for 24 hours at ambient temperature and is then evaporated to dryness. The residue is purified over a silica gel column (grain size: 40–63 μm, eluting agent: methylene chloride/ethanol/glacial acetic acid=50/1/0.15). The homogeneous fractions are combined, the solvents are distilled off, the residue is dissolved in methylene chloride and washed three times using water. The organic phase is dried using magnesium sulphate and evaporated to dryness. The crystalline residue is mixed with diethylether, the mixture is filtered under suction and the crystals are dried at 75° C. in vacuum.

Yield: 1.90 g (90.9% of theoretical), Melting point: 161°–163° C.

$C_{24}H_{22}N_2O_3S$ (418.51), Calculated: C, 68.88; H, 5.30; N, 6.69; S, 7.66. Found: C, 68.65; H, 5.40; N, 6.72; S, 7.64.

Example 64

4'-[(2-n-Propylsulphinylmethyl-benzimidazol-1-yl)-methyl]biphenyl-2-carboxylic acid Prepared in analogous manner to Example 63 from 4'-[(2-n-propylthiomethyl-benzimidazol-1-yl)-methyl]-biphenyl-2-carboxylic acid and hydrogen peroxide in glacial acetic acid.

Yield: 78.7% of theoretical,

Melting point: 128°–130° C.

$C_{23}H_{24}N_2O_3S$ (432.54), Calculated: C, 69.42; H, 5.59; N, 6.48; S, 7.41. Found: C, 69.57; H, 5.46; N, 6.04; S, 7.28.

Example 65

4'-[(2-Hydroxy-benzimidazol-1-yl)-methyl]biphenyl-2-carboxylic acid 3-N-oxide

Prepared in analogous manner to Example 63 from 4'-[(2-methylmercapto-benzimidazol-1-yl)-methyl]biphenyl-2-carboxylic acid and hydrogen peroxide in glacial acetic acid.

Yield: 35.9% of theoretical,

Melting point: 272°–274° C.

$C_{21}H_{16}N_2O_4$ (360.37), Calculated: C, 69.99; H, 4.47; N, 7.77. Found: C, 70.00; H, 4.85; N, 7.51.

Example 66

4'-[(2-Methylsulphinylmethyl-benzimidazol-1-yl)-methyl]biphenyl-2-carboxylic acid Prepared in analogous manner to Example 63 from 4'-[(2-methylthiomethyl-benzimidazol-1-yl)-methyl]biphenyl-2-carboxylic acid and hydrogen peroxide/acetic acid.

Yield: 79.2% of theoretical,

Melting point: 232°–234° C.

$C_{23}H_{20}N_2O_3S$ (404.48), Calculated: C, 68.30; H, 4.98; N, 6.93; S, 7.93. Found: C, 68.17; H, 4.86; N, 7.04; S, 7.89.

Example 67

4'-[(2-Ethylsulphonylmethyl-benzimidazol-1-yl)-methyl]biphenyl-2-carboxylic acid 2.01 g (5.0 mmol) of 4'-[(2-ethylthiomethyl-benzimidazol-1-yl)-methyl]biphenyl-2-carboxylic acid are dissolved in 25 ml of formic acid and 1.02 ml (10 mmol) of 30% strength hydrogen peroxide are added. The solution is allowed to stand at ambient temperature for 24 hours and is then evaporated to dryness. The residue is purified over a silica gel column (grain size: 40–63 μm, eluting agent: methylene chloride/ethanol/glacial acetic acid=100/1/0.15 to 50/1/0.15. The homogeneous fractions are combined and evaporated to dryness. The residue is dissolved in methylene chloride, washed three times using water, the organic phase is dried using magnesium sulphate and evaporated to dryness. The crystalline residue is mixed with diethylether, filtered under suction and dried at 75° C. in vacuum.

Yield: 1.80 g (82.9% of theoretical),

Melting point: 158°–160° C.

$C_{24}H_{22}N_2O_4S$ (434.51), Calculated: C, 66.34; H, 5.10; N, 6.45; S, 7.38. Found: C, 66.32; H, 5.05; N, 6.54; S, 7.27.

The following compounds are obtained in analogous manner:

4'-[(2-n-butyl-6-methylsulphonyl-benzimidazol-1-yl)-methyl]biphenyl-2-carboxylic acid 4'-[(2-n-butyl-6-ethylsulphonyl-benzimidazol-1-yl)-methyl]biphenyl-2-carboxylic acid 4'-[(2-n-butyl-6-butylsulphonyl-benzimidazol-1-yl)-methyl]biphenyl-2-carboxylic acid

Example 68

4'-[(2-n-Propylsulphonylmethyl-benzimidazol-1-yl)-methyl]biphenyl-2-carboxylic acid Prepared in analogous manner to Example 67 from 4'-[(2-n-propylthiomethyl-benzimidazol-1-yl)-methyl]biphenyl-2-carboxylic acid and hydrogen peroxide in formic acid.

Yield: 78.1% of theoretical,

Melting point: 135°–137° C.

$C_{23}H_{24}N_3O_4S$ (448.54), Calculated: C, 66.95; H, 5.39; N, 6.25; S, 7.15. Found: C, 66.83; H, 5.46; N, 6.03; S, 7.06.

Example 69

4'-[(2-Methylsulphonylmethyl-benzimidazol-1-yl)-methyl]biphenyl-2-carboxylic acid Prepared in analogous manner to Example 67 from 4'-[(2-methylthiomethyl-benzimidazol-1-yl)-methyl]biphenyl-2-carboxylic acid and hydrogen peroxide.

Yield: 80.0% of theoretical,

Melting point: 290°–292° C.

$C_{23}H_{20}N_2O_4S$ (420.43), Calculated: C, 65.70; H, 4.79; N, 6.66; S, 7.62. Found: C, 65.67; H, 4.64; N, 6.88; S, 7.72.

Example 70

Ethyl 4'-[(2-n-butyl-benzimidazol-1-yl)-methyl]biphenyl-2-carboxylate 1.2 g (7 mmol) of 2-n-butyl-benzimidazole are dissolved in 25 ml of dimethylsulphoxide, treated with 0.8 g (7 mmol) of potassium tert.butoxide and the mixture is stirred for 20 minutes at ambient temperature. 2.25 g (7 mmol) of 2-carbethoxy-biphenyl-4'-yl-methylbromide are then added and the mixture is stirred at ambient temperature until conversion is quantitative (about 1 hour). After pouring into 100 ml of iced water, the product is extracted 2 times using ethyl acetate, the combined organic extracts are dried over sodium sulphate and evaporated. The crude product obtained is purified over a silica gel column (grain size: 0.04–0.2 mm, eluting agent: methylene chloride/ethanol= 24.1).

Yield: 2.3 g (79.3% of theoretical),

Oil, $R_f$ value: 0.6 (Silica gel: methylethylketone/xylene= 1:1)

$C_{27}H_{33}H_2O_2$ (412.53), Calculated: C, 78.41; H, 6.84; N, 6.79. Found: C, 78.43; H, 6.76; N, 7.01.

The following compound is obtained in analogous manner:

ethyl 4'-[(2-n-butyl-7-n-butylsulphonamino-benzimidazol-1-yl)-methyl]biphenyl-2-carboxylate oil, $R_f$ value: 0.50 (Silica gel: methylene chloride/ethanol=10:1)

Example 71

4'-[(2-n-Butyl-benzimidazol-1-yl)-methyl]biphenyl-2-carboxylic acid

Prepared in analogous manner to Example 9 from tert. butyl 4'-[(2-n-butyl-benzimidazol-1-yl)-methyl]biphenyl-2-carboxylate and trifluoroacetic acid in methylene chloride.

Yield: 62.3% of theoretical,

Melting point: 214°–215° C.

$C_{23}H_{24}N_3O_2$ (384.48), Calculated: C, 78.10; H, 6.29; N, 7.29. Found: C, 77.93; H, 6.21; N, 7.39.

Example 72

4'-[(6-Benzylamino-2-n-butyl-benzimidazol-1-yl)-methyl]biphenyl-2-carboxylic acid 1.30 g (2.5 mmol) of ethyl 4'-[(6-benzylamino-2-n-butylbenzimidazol-1-yl)-methyl]biphenyl-2-carboxylate are dissolved in 20 ml of ethanol, treated with 20 ml of 2N sodium hydroxide and heated at reflux for 2 hours. After cooling to ambient temperature, the solution is diluted to 500 ml using water and acidified to pH 5 using glacial acetic acid. The precipitate thus obtained is filtered off once again under suction, suspended in acetone, filtered off once again under suction and dried at 90° C. in vacuum.

Yield: 1.10 g (89.4% of theoretical),

Melting point: 250°–251° C.

$C_{23}H_{21}H_3O_2$ (489.62), Calculated: C, 78.50; H, 6.38; N, 8.56. Found: C, 78.30; H, 6.49; N, 8.71.

The following compound is obtained in analogous manner:

4'-[(2-n-butyl-7-cyclohexylaminocarbonylamino-benzimidazol-1-yl)-methyl]biphenyl-2-carboxylic acid Melting point: 278°–279° C. (decomposition)

Example 73

4'-[(2-n-Butyl-4-methyl-7-hydroxy-benzimidazol-1-yl)-methyl]biphenyl-2-carboxylic acid hydrate Prepared in analogous manner to Example 72 from methyl 4'-[(2-n-butyl-4-methyl-7-hydroxy-benzimidazol-1-yl)-methyl]biphenyl-2-carboxylate and 2N sodium hydroxide in ethanol.

Yield: 55.1% of theoretical,

Melting point: 313°–315° C.

$C_{29}H_{30}N_2O_3 \times H_2O$ (432.52), Calculated: C, 72.20; H, 6.83; N, 6.43. Found: C, 72.43; H, 6.30; N, 6.34.

Example 74

Tert.butyl 4'-[(2-n-butyl-4-methyl-7-hydroxy-benzimidazol-1-yl)-methyl]biphenyl-2-carboxylate Prepared in analogous manner to Example 57 from tert. butyl 4'-[(2-n-butyl-4-methyl-7-benzyloxy-benzimidazol-1-yl)-methyl]biphenyl-2-carboxylate and hydrogen in the presence of palladium hydroxide on carbon in methanol.

Yield: 80.0% of theoretical,

Melting point: 214°–216° C.

$C_{33}H_{34}N_2O_3$ (470.62), Calculated: C, 76.57; H, 7.28; N, 5.95. Found: C, 76.83; H, 7.12; N, 6.00.

Example 75

Tert.butyl 4'-[(2-n-Butyl-7-methyl-benzimidazol-1-yl)-methyl]biphenyl-2-carboxylic acid hydrate Prepared in analogous manner to Example 56 from 3-amino-2-[(2-tert.butoxycarbonyl-biphenyl-4'yl)-methyl]aminotoluene and valeric acid Yield: 28.6% of theoretical, Melting point: 231°–233° C.

$C_{29}H_{29}N_2O_2 \times H_2O$ (416.52), Calculated: C, 74.98; H, 6.78; N, 6.73. Found: C, 74.89; H, 6.52; N, 6.85.

Example 76

4'-[(6-Amino2-n-butyl-benzimidazol-1-yl)-methyl]biphenyl-2-carboxylate acid ditrifluoroacetate Prepared in analogous manner to Example 9 from tert. butyl 4'-[(6-amino-2-n-butyl-benzyloxy-benzimidazol-1-yl)-methyl]biphenyl-2-carboxylate and trifluoroacetic acid.

Yield: 72.5% of theoretical,

Melting point: 72°–74° C.

$C_{29}H_{28}N_3O_2 \times 2CF_3COOH$ (627.54), Calculated: C, 55.51; H, 4.34; N, 6.70. Found: C, 55.70; H, 4.61; N, 6.55.

Example 77

4'-[(5-Amino-2-n-butyl-benzimidazol-1-yl)-methyl]biphenyl-2-carboxylate acid ditrifluoroacetate Prepared in analogous manner to Example 9 from tert. butyl 4'-[(5-amino-2-n-butyl-benzyloxy-benzimidazol-1-yl)-methyl]biphenyl-2-carboxylate and trifluoroacetic acid.

Yield: 45.9% of theoretical,

Melting point: 64°–66° C.

$C_{29}H_{28}N_3O_2 \times 2CF_3COOH$ (627.54), Calculated: C, 55.51; H, 4.34; N, 6.70. Found: C, 55.66; H, 4.42; N, 6.54.

Example 78

4'-[(2-n-Butyl-5-(n-butylaminocarbonylamino)-benzimidazol-1-yl)-methyl]biphenyl-2-carboxylate acid semitrifluoroacetate Prepared in analogous manner to Example 9 from tert. butyl 4'-[(2-n-butyl-5-(n-butylaminocarbonylamino)-benzyloxy-benzimidazol-1-yl)-methyl]biphenyl-2-carboxylate and trifluoroacetic acid.

Yield: 84.2% of theoretical,

Melting point: 165°–167° C.

$C_{30}H_{34}N_4O_3 \times \frac{1}{2}CF_3COOH$ (555.64), Calculated: C, 67.01; H, 6.26; N, 10.08. Found: C, 66.88; H, 6.51; N, 9.89.

Example 79

4'-[(2-n-Butyl-6-phenylaminocarbonylamino-benzimidazol-1-yl)-methyl]biphenyl-2-carboxylic acid Prepared in analogous manner to Example 9 from tert. butyl 4'-[(2-n-butyl-6-phenylaminocarbonylamino)-benzyloxy-benzimidazol-1-yl)-methyl]biphenyl-2-carboxylate and trifluoroacetic acid.

Yield: 92.6% of theoretical,

Melting point: 281°–283° C.

$C_{32}H_{30}N_4O_3$ (518.61), Calculated: C, 74.11; H, 5.83; N, 10.80. Found: C, 73.93; H, 5.83; N, 10.58.

Example 80

4'-[(2-n-Butyl-6-cyclohexylaminocarbonylamino)-benzimidazol-1-yl)-methyl]biphenyl-2-carboxylic acid trifluoroacetate Prepared in analogous manner to Example 9 from tert. butyl 4'-[(2-n-butyl-6-cyclohexylaminocarbonylamino)-benzyloxy-benzimidazol-1-yl)-methyl]biphenyl-2-carboxylate and trifluoroacetic acid.

Yield: 86.5% of theoretical,

Melting point: 199°–200° C.

$C_{33}H_{30}N_4O_3 \times CF_3COOH$ (638.68), Calculated: C, 63.94; H, 5.84; N, 8.77. Found: C, 64.12; H, 6.15; N, 9.01.

Example 81

4'-[(2-n-Butyl-5-butanoylamino-benzimidazol-1-yl)-methyl]biphenyl-2-carboxylic acid Prepared in analogous manner to Example 9 from tert. butyl 4'-[(2-n-butyl-5-butanoylamino-benzimidazol-1-yl)-methyl]biphenyl-2-carboxylate and trifluoroacetic acid.

Yield: 93% of theoretical,

Melting point: 163°–165° C.

$C_{33}H_{32}N_3O_2$ (469.59), Calculated: C, 74.18; H, 6.65; N, 8.95. Found: C, 74.13; H, 6.67; N, 8.74.

Example 82

4'-[(2-(4-Hydroxyphenyl)-benzimidazol-1-yl)-methyl]biphenyl-2-carboxylic acid

Prepared in analogous manner to Example 9 from tert. butyl 4'-[(2-(4-hydroxyphenyl)-benzimidazol-1-yl)-methyl]biphenyl-2-carboxylate and trifluoroacetic acid/methylene chloride.

Yield: 87.3% of theoretical,
Melting point: 251°–253° C.
$C_{27}H_{20}N_2O_3$ (420.47), Calculated: C, 77.13; H, 4.79; N, 6.66. Found: C, 76.98; H, 4.83; N, 6.62.

Example 83

4'-[(2-(4-n-Butoxyphenyl)-benzimidazol-1-yl)-methyl]biphenyl-2-carboxylic acid

Prepared in analogous manner to Example 9 from tert. butyl 4'-[(2-(4-n-butoxyphenyl)-benzimidazol-1-yl)-methyl]biphenyl-2-carboxylate and trifluoroacetic acid/methylene chloride.

Yield: 85.2% of theoretical,
Melting point: 246°–248° C.
$C_{31}H_{26}N_2O_3$ (476.58), Calculated: C, 78.13; H, 5.92; N, 5.88. Found: C, 78.33; H, 5.76; N, 5.67.

Example 84

4'-[(2-n-Butyl-6-chloro-benzimidazol-1-yl)-methyl]biphenyl-2-carboxylic acid

Prepared in analogous manner to Example 9 from tert. butyl 4'-[(2-n-butyl-6-chloro-benzimidazol-1-yl)-methyl]biphenyl-2-carboxylate and trifluoroacetic acid/methylene chloride.

Yield: 63.6% of theoretical,
Melting point: 220°–222° C.
$C_{25}H_{23}ClN_2O_2$ (418.92), Calculated: C, 71.68; H, 5.53; N, 6.69; Cl, 8.46. Found: C, 71.81; H, 5.64; N, 6.69; Cl, 8.39.

Example 85

4'-[(2-n-Butyl-6-methyl-benzimidazol-1-yl)-methyl]biphenyl-2-carboxylic acid

Prepared in analogous manner to Example 9 from tert. butyl 4'-[(2-n-butyl-6-methyl-benzimidazol-1-yl)-methyl]biphenyl-2-carboxylate and trifluoroacetic acid/methylene chloride.

Yield: 70.6% of theoretical,
Melting point: 219°–221° C.
$C_{26}H_{28}N_2O_2$ (398.51), Calculated: C, 78.36; H, 6.58; N, 7.03. Found: C, 78.49; H, 6.53; N, 6.98.

Example 86

4'-[(2-n-Butyl-5-methanesulphonamino-benzimidazol-1-yl)-methyl]biphenyl-2-carboxylic acid Prepared in analogous manner to Example 9 from tert. butyl 4'-[(2-n-butyl-5-methanesulphonamino-benzimidazol-1-yl)-methyl]biphenyl-2-carboxylate and trifluoroacetic acid/methylene chloride Yield: 75.7% of theoretical,
Melting point: 242°–244° C.
$C_{30}H_{27}N_2O_4S$ (477.59), Calculated: C, 65.39; H, 5.70; N, 8.80; S, 6.71. Found: C, 65.52; H, 5.65; N, 8.55; S, 6.51.

Example 87

4'-[(7-n-Butanoyloxy-2-n-butyl-4-methyl-benzimidazol-1-yl)-methyl]biphenyl-2-carboxylic acid Prepared in analogous manner to Example 60 from 4'-[(2-n-butyl-7-hydroxy-4-methyl-benzimidazol-1-yl)-methyl]biphenyl-2-carboxylate and butyric acid chloride in pyridine.

Yield: 29.1% of theoretical,
Melting point: 240°–242° C.
$C_{30}H_{32}N_2O_4$ (484.60), Calculated: C, 74.63; H, 6.66; N, 5.78. Found: C, 74.20; H, 6.76; N, 5.87.

Example 88

4'-[(2-n-Butyl-6-ethoxycarbonylamino-benzimidazol-1-yl)-methyl]biphenyl-2-carboxylic acid Prepared in analogous manner to Example 9 from tert. butyl 4'-[(2-n-butyl-6-ethoxycarbonylamino-benzimidazol-1-yl)-methyl]biphenyl-2-carboxylate and trifluoroacetic acid/methylene chloride.

Yield: 85.2% of theoretical,
Melting point: 240°–242° C.
$C_{25}H_{23}N_3O_3$ (471.55), Calculated: C, 71.32; H, 6.20; N, 8.91. Found: C, 71.06; H, 6.36; N, 9.04.

Example 89

4'-[(2-n-Butyl-6-isopropylsulphonamino-benzimidazol-1-yl)-methyl]biphenyl-2-carboxylic acid Prepared in analogous manner to Example 9 from tert. butyl 4'-[(2-n-butyl-6-isopropylsulphonamino-benzimidazol-1-yl)-methyl]biphenyl-2-carboxylate and trifluoroacetic acid/methylene chloride.

Yield: 91.5% of theoretical,
Melting point: 155°–157° C.
$C_{29}H_{31}N_3O_4S$ (505.63), Calculated: C, 66.51; H, 6.18; N, 8.31; S, 6.34. Found: C, 66.26; H, 6.33; N, 8.34; S, 6.43.

Example 90

4'-[(2-n-Butyl-4-nitrobenzimidazol-1-yl)-methyl]biphenyl-2-carboxylic acid

Prepared in analogous manner to Example 9 from tert. butyl 4'-[(2-n-butyl-4-nitrobenzimidazol-1-yl)-methyl]biphenyl-2-carboxylate and trifluoroacetic acid/methylene chloride.

Yield: 84.6% of theoretical,
Melting point: 238°–240° C.
$C_{25}H_{23}N_3O_4$ (429.48), Calculated: C, 69.92; H, 5.40; N, 9.78. Found: C, 69.85; H, 5.43; N, 9.67.

Example 91

4'-[(2-n-Butyl-4-butanoylamino-benzimidazol-1-yl)-methyl]biphenyl-2-carboxylic acid Prepared in analogous manner to Example 9 from tert. butyl 4'-[(2-n-butyl-4-butanoylamino-benzimidazol-1-yl)-methyl]biphenyl-2-carboxylate and trifluoroacetic acid/methylene chloride.

Yield: 96.1% of theoretical,
Melting point: 270°–271° C.
$C_{29}H_{31}N_3O_2$ (469.58), Calculated: C, 74.18; H, 6.65; N, 8.95. Found: C, 74.02; H, 6.74; N, 8.90.

Example 92

4'-[(2-n-Butyl-4-ethylaminocarbonylamino-benzimidazol-1-yl)-methyl]biphenyl-2-carboxylic acid Prepared in analogous manner to Example 9 from tert. butyl 4'-[(2-n-butyl-4-ethylamino-carbonylaminobenzimidazol-1-yl)-methyl]biphenyl-2-carboxylate and trifluoroacetic acid/methylene chloride.

Yield: 87.5% of theoretical,

Melting point: 344°–346° C.

$C_{26}H_{28}N_4O_3$ (470.57), Calculated: C, 71.47; H, 6.43; N, 11.91. Found: C, 71.51; H, 6.29; N, 11.48.

Example 93

4'-[(2-(3-Pyridyl)-benzimidazol-1-yl)-methyl] biphenyl-2-carboxylic acid

Prepared in analogous manner to Example 9 from tert. butyl 4'-[(2-(3-pyridyl)-benzimidazol-1-yl)-methyl] biphenyl-2-carboxylate and trifluoroacetic acid/methylene chloride.

Yield: 73.3% of theoretical,

Melting point: 249°–251° C.

$C_{26}H_{18}N_3O_2$ (405.46), Calculated: C, 77.02; H, 4.72; N, 10.36. Found: C, 76.85; H, 4.72; N, 10.15.

Example 94

4'-[(2-n-Butyl-5-methyl-benzimidazol-1-yl)-methyl] biphenyl-2-carboxylic acid

Prepared in analogous manner to Example 9 from tert. butyl 4'-[(2-n-butyl-5-methyl-benzimidazol-1-yl)-methyl] biphenyl-2-carboxylate and trifluoroacetic acid/methylene chloride.

Yield: 58.7% of theoretical,

Melting point: 188°–190° C.

$C_{28}H_{26}N_2O_2$ (398.51), Calculated: C, 78.36; H, 6.58; N, 7.03. Found: C, 78.21; H, 6.62; N, 6.98.

Example 95

4'-[(2-n-Butyl-6-dimethylamino-benzimidazol-1-yl)-methyl]biphenyl-2-carboxylic acid trifluoroacetate Prepared in analogous manner to Example 9 from tert. butyl 4'-[(2-n-butyl-6-dimethylamino-benzimidazol-1-yl)-methyl]biphenyl-2-carboxylate and trifluoroacetic acid in methylene chloride.

Yield: 65.4% of theoretical, $C_{27}H_{29}N_3O_5 \times CF_3COOH$ (541.58), Calculated: C, 64.31; H, 5.59; N, 7.76. Found: C, 64.53; H, 5.66; N, 7.09.

Example 96

4'-[(2-n-Butyl-5-(tert.butoxycarbonylaminoacetamino)-benzimidazol-1-yl)-methyl]biphenyl-2-carboxylic acid Prepared in analogous manner to Example 72 from ethyl 4'-[(2-n-butyl-5-(tert.butoxycarbonylaminoacetamino)-benzimidazol-1-yl)-methyl]biphenyl-2-carboxylate and 2N sodium hydroxide.

Yield: 16.7% of theoretical,

Melting point: 149°–151° C.

$C_{23}H_{30}N_4O_3$ (556.66), Calculated: C, 69.05; H, 6.52; N, 10.06. Found: C, 69.12; H, 6.32; N, 9.87.

Example 97

4'-[(2-n-Butyl-5,6-dimethyl-benzimidazol-1-yl)-methyl]biphenyl-2-carboxylic acid Prepared in analogous manner to Example 9 from tert. butyl 4'-[(2-n-butyl-5,6-dimethyl-benzimidazol-1-yl)-methyl]biphenyl-2-carboxylate and trifluoroacetic acid in methylene chloride.

Yield: 17.5% of theoretical,

Melting point: 222°–225° C.

$C_{27}H_{23}N_2O_2$ (412.50), Calculated: C, 78.62; H, 6.84; N, 6.79. Found: C, 78.36; H, 6.90; N, 6.83.

Example 98

4'-[(2-(2,2-Dimethylpropyl)-5,6-dimethyl-benzimidazol-1-yl)-methyl]biphenyl-2-carboxylic acid Prepared in analogous manner to Example 9 from tert. butyl 4'-[(2-(2,2-dimethylpropyl)-5,6-dimethyl-benzimidazol-1-yl)-methyl]biphenyl-2-carboxylate and trifluoroacetic acid in methylene chloride.

Yield: 45% of theoretical,

Melting point: from 115° C. (amorphous)

$C_{29}H_{33}N_2O_2$ (426.60), Calculated: C, 78.83; H, 7.09; N, 6.57. Found: C, 78.64; H, 7.11; N, 6.89.

Example 99

4'-[(2-n-Benzyl-5,6-dimethyl-benzimidazol-1-yl)-methyl]biphenyl-2-carboxylic acid Prepared in analogous manner to Example 9 from tert. butyl 4'-[(2-benzyl-5,6-dimethyl-benzimidazol-1-yl)-methyl]biphenyl-2-carboxylate and trifluoroacetic acid in methylene chloride.

Yield: 68% of theoretical,

Melting point: 252°–255° C.

$C_{30}H_{26}N_2O_3$ (446.60), Calculated: C, 80.69; H, 5.87; N, 6.27. Found: C, 80.94; H, 5.76; N, 5.97.

Example 100

4'-[(2-(2-Methylbutyl))-5,6-dimethyl-benzimidazol-1-yl)-methyl]biphenyl-2-carboxylic acid Prepared in analogous manner to Example 9 from tert. butyl 4'-[(2-(2-methylbutyl)-5,6-dimethyl-benzimidazol-1-yl)-methyl]biphenyl-2-carboxylate and trifluoroacetic acid in methylene chloride.

Yield: 57% of theoretical,

Melting point: 211°–215° C.

$C_{28}H_{25}N_2O_2$ (426.60), Calculated: C, 78.84; H, 7.09; N, 6.57. Found: C, 78.67; H, 7.24; N, 6.43.

Example 101

4'-[(2-(Cyclohexylmethyl-5,6-dimethyl-benzimidazol-1-yl)-methyl]biphenyl-2-carboxylic acid Prepared in analogous manner to Example 9 from tert. butyl 4'-[(2-(cyclohexylmethyl-5,6-dimethyl-benzimidazol-1-yl)-methyl]biphenyl-2-carboxylate and trifluoroacetic acid in methylene chloride.

Yield: 31% of theoretical,

Melting point: 199°–201° C.

$C_{30}H_{28}N_2O_2$ (452.60), Calculated: C, 79.61; H, 7.13; N, 6.19. Found: C, 79.45; H, 7.17; N, 6.06.

Example 102

4'-[(2-(Cyclohexylmethyl-5,6-dichloro-benzimidazol-1-yl)-methyl]biphenyl-2-carboxylic acid Prepared in analogous manner to Example 9 from tert. butyl 4'-[(2-cyclohexylmethyl-5,6-dimethyl-benzimidazol- 1-yl)-methyl]biphenyl-2-carboxylate and trifluoroacetic acid in methylene chloride.

Yield: 39% of theoretical,

Melting point: 219°–222° C.

$C_{28}H_{26}Cl_2N_2O_2$ (493.40), Calculated: C, 68.16; H, 5.31; N, 5.68; Cl, 14.37. Found: C, 67.97; H, 5.29; N, 5.52; Cl, 14.12.

Example 103

4'-[(2-(2-Methylbutyl)-naphtho[2,3-d]imidazol-1-yl)-methyl]biphenyl-2-carboxylic acid Prepared in analogous manner to Example 9 from tert. butyl 4'-[(2-(2-methylbutyl)-naphtho[2,3-d]imidazol-1-yl)-methyl]biphenyl-2-carboxylate and trifluoroacetic acid in methylene chloride.

Yield: 64% of theoretical,

Melting point: 206°–208° C.

$C_{30}H_{26}N_2O_2$ (448.60), Calculated: C, 80.33; H, 6.29; N, 6.25. Found: C, 80.20; H, 6.36; N, 6.24.

Example 104

4'-[(2-n-Propyl-naphtho[2,3-d]imidazol-1-yl)-methyl]biphenyl-2-carboxylic acid

Prepared in analogous manner to Example 9 from tert. butyl 4'-[(2-n-propyl-naphtho[2,3-d]imidazol-1-yl)-methyl]biphenyl-2-carboxylate and trifluoroacetic acid in methylene chloride.

Yield: 85% of theoretical,

Melting point: 269°–272° C.

$C_{26}H_{24}N_2O_2$ (420.50), Calculated: C, 79.98; H, 5.75; N, 6.66. Found: C, 79.87; H, 5.48; N, 6.48.

Example 105

4'-[(2-n-Butyl-5,6-dichloro-benzimidazol-1-yl)-methyl]biphenyl-2-carboxylic acid Prepared in analogous manner to Example 9 from tert. butyl 4'-[(2-n-butyl-5,6-dichloro-benzimidazol-1-yl)-methyl]biphenyl-2-carboxylate and trifluoroacetic acid in methylene chloride.

Yield: 50% of theoretical,

Melting point: 237°–239° C.

$C_{23}H_{22}Cl_2N_2O_2$ (453.40), Calculated: C, 66.23; H, 4.89; N, 6.18; Cl, 15.64. Found: C, 66.10; H, 4.82; N, 6.05; Cl, 15.42.

Example 106

4'-[(2-Cyclohexylmethyl-5,6-dimethoxy-benzimidazol-1-yl)-methyl]biphenyl-2-carboxylic acid Prepared in analogous manner to Example 9 from tert. butyl 4'-[(2-cyclohexylmethyl-5,6-dimethoxy-benzimidazol-1-yl)-methyl]biphenyl-2-carboxylate and trifluoroacetic acid in methylene chloride.

Yield: 45% of theoretical,

Melting point: 245°–247° C.

$C_{30}H_{22}N_2O_4$ (484.60), Calculated: C, 74.36; H, 6.66; N, 5.78. Found: C, 74.11; H, 6.58; N, 6.02.

Example 107

4'-[(2-n-Butyl-5,6-dimethoxy-benzimidazol-1-yl)-methyl]biphenyl-2-carboxylic acid Prepared in analogous manner to Example 9 from tert. butyl 4'-[(2-n-butyl-5,6-dimethoxy-benzimidazol-1-yl)-methyl]biphenyl-2-carboxylate and trifluoroacetic acid in methylene chloride.

Yield: 52% of theoretical,

Melting point: 257°–259° C.

$C_{27}H_{26}N_2O_4$ (444.50), Calculated: C, 72.95; H, 6.35; N, 6.30. Found: C, 72.77; H, 6.26; N, 6.49.

Example 108

4'-[(2-Cyclopentylmethyl-5,6-dimethoxy-benzimidazol-1-yl)-methyl]biphenyl-2-carboxylic acid Prepared in analogous manner to Example 9 from tert. butyl 4'-[(2-cyclopentylmethyl-5,6-dimethoxy-benzimidazol-1-yl)-methyl]biphenyl-2-carboxylate and trifluoroacetic acid in methylene chloride.

Yield: 47% of theoretical,

Melting point: 233°–234° C.

$C_{26}H_{20}N_2O_4$ (470.60), Calculated: C, 74.02; H, 6.43; N, 5.95. Found: C, 73.96; H, 6.56; N, 6.18.

Example 109

4'-[(2-(3-Methylbutyl)-5,6-dimethoxy-benzimidazol-1-yl)-methyl]biphenyl-2-carboxylic acid Prepared in analogous manner to Example 9 from tert. butyl 4'-[(2-(3-methylbutyl)-5,6-dimethoxy-benzimidazol-1-yl)-methyl]biphenyl-2-carboxylate and trifluoroacetic acid in methylene chloride.

Yield: 39% of theoretical,

Melting point: 237°–239° C.

$C_{28}H_{24}N_3O_4$ (458.60), Calculated: C, 73.34; H, 6.59; N, 6.11. Found: C, 73.50; H, 6.48; N, 6.02.

Example 110

4'-[(2-Cyclohexyl-5,6-dimethyl-benzimidazol-1-yl)-methyl]biphenyl-2-carboxylic acid Prepared in analogous manner to Example 9 from tert. butyl 4'-[(2-cyclohexyl-5,6-dimethyl-benzimidazol-1-yl)-methyl]biphenyl-2-carboxylate and trifluoroacetic acid in methylene chloride.

Yield: 27% of theoretical,

Melting point: 240°–242° C.

$C_{28}H_{26}N_2O_2$ (438.60), Calculated: C, 79.42; H, 6.89; N, 6.39. Found: C, 79.30; H, 7.02; N, 6.39.

Example 111

4'-[(2-(1-Butyn-4-yl)-benzimidazol-1-yl)-methyl]biphenyl-2-carboxylic acid

Prepared in analogous manner to Example 9 from tert. butyl 4'-[(2-(1-butyn-4-yl)-benzimidazol-1-yl)-methyl]biphenyl-2-carboxylate and trifluoroacetic acid in methylene chloride.

Yield: 55% of theoretical,

Melting point: 218°–221° C.

$C_{23}H_{20}N_2O_2$ (380.50), Calculated: C, 78.93; H, 5.30; N, 7.36. Found: C, 78.97; H, 5.24; N, 7.31.

Example 112

4'-[(2-Cyclopentyl-5,6-dimethyl-benzimidazol-1-yl)-methyl]biphenyl-2-carboxylic acid Prepared in analogous manner to Example 9 from tert. butyl 4'-[(2-cyclopentyl-5,6-dimethyl-benzimidazol-1-yl)- methyl]biphenyl-2-carboxylate and trifluoroacetic acid in methylene chloride.

Yield: 75% of theoretical,

Melting point: 262°–265° C.

$C_{25}H_{20}N_2O_2$ (424.50), Calculated: C, 79.22; H, 6.65; N, 6.60. Found: C, 78.99; H, 6.54; N, 6.67.

Example 113

4'-[(2-n-Butyl-5- and 6-fluoro-benzimidazol-1-yl)-methyl]biphenyl-2-carboxylic acid Prepared in analogous manner to Example 9 from tert. butyl 4'-[(2-n-butyl-5- and 6-fluoro-benzimidazol-1-yl)-methyl]biphenyl-2-carboxylate and trifluoroacetic acid in methylene chloride.

Yield: 80% of theoretical,

Melting point: 167°–169° C.

$C_{23}H_{22}FN_2O_2$ (402.50), Calculated: C, 74.61; H, 5.76; N, 6.56. Found: C, 74.57; H, 5.77; N, 7.05.

Example 114

4'-[(2-n-Butyl-5- and 6-benzoyl-benzimidazol-1-yl)-methyl]biphenyl-2-carboxylic acid Prepared in analogous manner to Example 9 from tert. butyl 4'-[(2-n-butyl-5-benzoyl-and 6-benzoyl-benzimidazol-1-yl)-methyl]biphenyl-2-carboxylate and trifluoroacetic acid in methylene chloride.

Yield: 58.5% of theoretical,

Melting point: 180°–182° C.

$C_{32}H_{28}N_2O_3$ (488.50)

Calculated: C 78.67 H 5.78 N 5.73

Found: C 78.75 H 5.74 N 5.63

EXAMPLE 115

4'-[(2-n-Butyl-5-and 6-trifluoromethyl-benzimidazol-1-yl)-methyl]biphenyl-2-carboxylic acid Prepared in analogous manner to Example 9 from tert. butyl 4'-[(2-n-butyl-5-and 6-trifluoromethyl-benzimidazol-1-yl)-methyl]biphenyl-2-carboxylate and trifluoroacetic acid in methylene chloride.

Yield: 65% of theoretical,

Melting point: 172°–174° C.

$C_{20}H_{23}F_3N_2O_3$ (452.50)

Calculated: C 69.01 H 5.12 N 6.19

Found: C 69.10 H 5.24 N 6.11

EXAMPLE 116

4'-[(2-n-Butyl-4-cyano-benzimidazol-1-yl)-methyl]biphenyl-2-carboxylic acid

Prepared in analogous manner to Example 9 from tert. butyl 4'-[(2-n-butyl-4-cyano-benzimidazol-1-yl)-methyl]biphenyl-2-carboxylate and trifluoroacetic acid in methylene chloride.

Yield: 72% of theoretical,

Melting point: 190°–192° C.

$C_{26}H_{23}N_3O_2$ (409.49)

Calculated: C 76.26 H 5.66 N 10.62

Found: C 76.01 H 5.72 N 10.51

EXAMPLE 117

4'-[(2-n-Butyl-5-and 6-n-butylaminocarbonyl-benzimidazol-1-yl)-methyl]biphenyl-2-carboxylic acid Prepared in analogous manner to Example 9 from tert. butyl 4'-[(2-n-butyl-5-and 6-n-butylamino-carbonyl-benzimidazol-1-yl)-methyl]biphenyl-2-carboxylate and trifluoroacetic acid in methylene chloride.

Yield: 69% of theoretical,

Melting point: 88° C. (decomposition)

$C_{20}H_{23}N_2O_3 \times \frac{1}{2}$ $CF_3COOH$ (483.60)

Calculated: C 68.88 H 6.25 N 7.77

Found: C 68.65 H 6.32 N 7.71

EXAMPLE 118

4'-[(2-n-Butyl-6-carboxy-benzimidazol-1-yl)-methyl]biphenyl-2-carboxylic acid

Prepared in analogous manner to Example 9 from tert. butyl 4'-[(2-n-butyl-6-carboxy-benzimidazol-1-yl)-methyl]biphenyl-2-carboxylate and trifluoroacetic acid in methylene chloride.

Yield: 91% of theoretical,

Melting point: 315°–320° C. (decomposition)

$C_{20}H_{24}N_2O_4$ (428.50)

Calculated: C 72.88 H 5.65 N 6.54

Found: C 72.74 H 5.66 N 6.58

EXAMPLE 119

4'-[(2-n-Butyl-5-carboxy-benzimidazol-1-yl)-methyl]biphenyl-2-carboxylic acid

Prepared in analogous manner to Example 9 from tert. butyl 4'-[(2-n-butyl-5-carboxy-benzimidazol-1-yl)-methyl]biphenyl-2-carboxylate and trifluoroacetic acid in methylene chloride.

Yield: 63% of theoretical,

Melting point: 247°–248° C.

$C_{28}H_{24}N_2O_4$ (428.50)

Calculated: C 72.88 H 5.65 N 6.54

Found: C 72.76 H 5.52 N 6.52

EXAMPLE 120

4'-[(2-n-Butyl-6-aminocarbonyl-benzimidazol-1-yl)-methyl]biphenyl-2-carboxylic acid Prepared in analogous manner to Example 9 from tert. butyl 4'-[(2-n-butyl-6-aminocarbonyl-benzimidazol-1-yl)-methyl]biphenyl-2-carboxylate and trifluoroacetic acid in methylene chloride.

Yield: 45% of theoretical,

Melting point: 243°–244° C.

$C_{26}H_{25}N_3O_3 \times \frac{1}{2}$ $H_2O$ (436.51)

Calculated: C 71.54 H 6.00 N 9.63

Found: C 71.34 H 6.16 N 9.45

EXAMPLE 121

4'-[(2-n-Butyl-5-aminocarbonyl-benzimidazol-1-yl)-methyl]biphenyl-2-carboxylic acid Prepared in analogous manner to Example 9 from tert. butyl 4'-[(2-n-butyl-5-aminocarbonyl-benzimidazol-1-yl)- methyl]biphenyl-2-carboxylate and trifluoroacetic acid in methylene chloride.

Yield: 55% of theoretical,
Melting point: 227°–228° C.
$C_{26}H_{25}N_3O_3 \times \frac{1}{2} H_2O$ (436.51)
Calculated: C 71.54 H 6.00 N 9.63
Found: C 71.42 H 5.94 N 9.46

EXAMPLE 122

4'-[(2-n-Butyl-5-and 6-cyano-benzimidazol-1-yl)-methyl]biphenyl-2-carboxylic acid Prepared in analogous manner to Example 9 from tert. butyl 4'-[(2-n-butyl-5-and 6-cyano-benzimidazol-1-yl)-methyl]biphenyl-2-carboxylate and trifluoroacetic acid in methylene chloride.

Yield: 70% of theoretical,
Melting point: 214°–215° C.
$C_{26}H_{23}N_3O_2$ (409.50)
Calculated: C 76.26 H 5.66 N 10.26
Found: C 76.06 H 5.44 N 10.11

EXAMPLE 123

4'-[(2-n-Butyl-5-(1H-tetrazol-5-yl)-benzimidazol-1-yl)-methyl]biphenyl-2-carboxylic acid Prepared in analogous manner to Example 9 from tert. butyl 4'-[(2-n-butyl-5-(1H-tetrazol-5-yl)-benzimidazol-1-yl)-methyl]biphenyl-2-carboxylate and trifluoroacetic acid in methylene chloride.

Yield: 66% of theoretical,
Melting point: 249°–250° C.
$C_{25}H_{24}N_6O_2$ (452.50)
Calculated: C 69.01 H 5.35 N 18.57
Found: C 69.92 H 5.48 N 18.78

EXAMPLE 124

4'-[(2-n-Butyl-5-and 6-(1H-tetrazol-5-yl)-benzimidazol-1-yl)-methyl]biphenyl-2-carboxylic acid Prepared in analogous manner to Example 9 from tert. butyl 4'-[(2-n-butyl-5-and 6-(1H-tetrazol-5-yl)-benzimidazol-1-yl)-methyl]biphenyl-2-carboxylate and trifluoroacetic acid in methylene chloride.

Yield: 55% of theoretical,
Melting point: 220° C. (decomposition)
$C_{26}H_{24}N_8O_2$ (452.50)
Calculated: C 69.01 H 5.35 N 18.57
Found: C 68.92 H 5.41 N 18.35

EXAMPLE 125

Tert.butyl 4'-[(2-n-butyl-5-dimethylaminosulphonyl-benzimidazol-1-yl)-methyl]biphenyl-2-carboxylic Prepared in analogous manner to Example 9 from tert. butyl 4'-[(2-n-butyl-5-dimethylaminosulphonyl-3-N-oxido-benzimidazol-1-yl)-methyl]biphenyl-2-carboxylate by catalytic hydrogenation in the presence of Raney nickel and subsequent reaction with trifluoroacetic acid in methylene chloride.

Yield: 92% of theoretical,
Melting point: 240°–242° C.
$C_{27}H_{28}N_3O_4S$ (491.60)
Calculated: C 65.97 H 5.95 N 8.55 S 6.52
Found: C 65.41 H 6.09 N 8.46 S 6.60

EXAMPLE 126

4'-[(2-n-Butyl-5-and 6-methoxycarbonylbenzimidazol-1-yl)-methyl]-2-(1H-tetrazol-5-yl)-biphenyl 0.71 g (1.0 mmol) of 4'-[(2-n-butyl-5-and 6-methoxycarbonyl-benzimidazol-1-yl)-methyl]-2-(1triphenylmethyl-tetrazol-5-yl)-biphenyl are heated with 25 ml of 5% strength methanolic ammonia at 125°–130° C. for 16 hours in a pressure vessel. After cooling, the solvent is distilled off, the residue is taken up in dilute acetic acid and extracted three times using ethyl acetate. The combined ethyl acetate phases are washed using sodium chloride solution, dried over sodium sulphate, evaporated and the residue is purified over a silica gel column using methylene chloride/ethanol=25:1 as eluting agent.

Yield: 0.34 g (73% of theoretical),
Melting point: 136°–138° C.
$C_{27}H_{25}N_6O_2$ (466.56)
Calculated: C 69.50 H 5.57 N 17.98
Found: C 69.42 H 5.33 N 17.44

EXAMPLE 127

4'-[(2-n-Butyl-5-and 6-n-butylaminocarbonyl-benzimidazol-1-yl)-methyl]-2-(1H-tetrazol-5-yl)-biphenyl 216 ng (1.05 mmol) of dicyclohexylcarbodiimide and 141 mg (1.05 mmol) of 1-hydroxybenzotriazole hydrate are dissolved in 30 ml of acetonitrile and 452 mg (1.00 mmol) of 4'-[(2-n-butyl-5-and 6-carboxy-benzimidazol-1-yl)-methyl]-2-(1H-tetrazol-5-yl)-biphenyl are added.

After stirring for 30 minutes at ambient temperature, 146 mg (2.00 mmol) of n-butylamine are added and the reaction mixture is stirred for 4 hours at ambient temperature. The dicyclohexylurea obtained is filtered off and the filtrate is evaporated. The residue obtained is taken up in methylene chloride and washed once using 5% strength sodium bicarbonate solution and once using sodium chloride solution. After evaporating once again, the final product is obtained by chromatography on a silica gel column (eluting agent: methylene chloride/ethanol=25:1).

Yield: 95 mg (19% of theoretical),
Melting point: 245°–247° C.
$C_{20}H_{23}N_7O$ (507.63)
Calculated: C 71.00 H 6.50 N 19.30
Found: C 70.77 H 6.66 N 19.36

EXAMPLE 128

4'-[(2-n-Butyl-5-and 6-aminocarbonyl-benzimidazol-1-yl)-methyl]-2-(1H-tetrazol-5-yl)-biphenyl Prepared in analogous manner to Example 127 from 4'-[(2-n-butyl-5-and 6-carboxy-benzimidazol-1-yl)-methyl]-2-(1H-tetrazol-5-yl)-biphenyl.

Yield: 17% of theoretical,
Melting point: 225°–227° C.

$C_{26}H_{25}N_7O$ (451.62)
Calculated: C 69.98 H 5.54 N 21.62
Found: C 69.85 H 5.30 N 21.48

EXAMPLE 129

4'-[(2-n-Butyl-5-and 6-hydroxymethyl-benzimidazol-1-yl)-methyl]-2-(1H-tetrazol-5-yl)-biphenyl 452 mg (1.00 mmol) of 4'-[(2-n-butyl-5-and 6-carboxy-benzimidazol-1-yl)-methyl]-2-(1H-tetrazol-5-yl)-biphenyl are dissolved in 20 ml of tetrahydrofuran and 67.0 mg (1.75 mmol) of lithium aluminium hydride are added. The suspension is stirred at 40° C. for 4 hours and then separated using 20 ml of water/ethanol (1:1). After filtering over kieselguhr, the product is evaporated and chromatographed on silica gel (eluting agent: methylene chloride/ethanol=9:1 with 1% ammonia added).

Yield: 90 mg (21% of theoretical),
Melting point: 173°–175° C.
$C_{26}H_{26}N_6O$ (438.54)
Calculated: C 71.50 H 5.96 N 19.20
Found: C 71.32 H 6.06 N 19.02

The following compound is obtained in analogous manner:

4'-[(2-n-butyl-5-and 6-(n-butylaminomethyl)-benzimidazol-1-yl)-methyl]-2-(1H-tetrazol-5-yl)-biphenyl
melting point: 146°–149° C.

EXAMPLE 130

4'-[(2-n-Butyl-5-and 6-carboxy-benzimidazol-1-yl)-methyl]-2-(1H-tetrazol-5-yl)-biphenyl 2.1 g (3.0 mmol) of 4'-[(2-n-butyl-5-and 6-methoxycarbonyl-benzimidazol-1-yl)-methyl]-2-(1-triphenylmethyl-tetrazol-5-yl)-biphenyl are dissolved in 100 ml of ethanol while heating, treated at 40° C. with 25 ml of 1N sodium hydroxide and stirred at ambient temperature of 60 hours. The reaction solution is evaporated, the residue obtained is dissolved in iced water and brought to pH 4–5 using 2N acetic acid. The crude product precipitated is filtered off under suction, washed until it is neutral using water and purified over a silica gel column (eluting agent: methylene chloride/ethanol=9:1 with 1% of glacial acetic acid added).

Yield: 0.65 g (48% of theoretical),
Melting point: 188°–190° C.
$C_{28}H_{24}N_6O_2$ (452.60)
Calculated: C 68.80 H 5.53 N 18.52
Found: C 68.63 H 5.34 N 18.65

EXAMPLE 131

4'-[(2-n-Butyl-7-cyano-benzimidazol-1-yl)-methyl]-biphenyl-2-carboxylic acid

Prepared in analogous manner to Example 9 from tert. butyl 4'-[(2-n-butyl-7-cyano-benzimidazol-1-yl)-methyl]biphenyl-2-carboxylate and trifluoroacetic acid in methylene chloride.

Yield: 68% of theoretical,
Melting point: 190°–192° C.
$C_{28}H_{23}N_3O_2$ (409.49)
Calculated: C 76.26 H 5.66 N 10.26
Found: C 75.99 H 5.46 N 10.25

EXAMPLE 132

4'-[(2-n-Butyl-5,7-difluoro-benzimidazol-1-yl)-methyl]biphenyl-2-carboxylic acid Prepared in analogous manner to Example 9 from tert. butyl 4'-[(2-n-butyl-5,7-difluoro-benzimidazol-1-yl)-methyl]biphenyl-2-carboxylate and trifluoroacetic acid in methylene chloride.

Yield: 49% of theoretical,
Melting point: from 155° C. (amorphous)
$C_{25}H_{22}F_2N_2O_2$ (420.40)
Calculated: C 71.41 H 5.27 N 6.66
Found: C 71.38 H 5.09 N 6.39

EXAMPLE 133

4'-[(2-n-Butyl-5-acetyl-benzimidazol-1-yl)-methyl] biphenyl-2-carboxylic acid

Prepared in analogous manner to Example 9 from tert. butyl 4'-[(2-n-butyl-5-acetyl-benzimidazol-1-yl)-methyl] biphenyl-2-carboxylate and trifluoroacetic acid in methylene chloride.

Yield: 59.5% of theoretical,
Melting point: 182°–184° C.
$C_{27}H_{28}N_2O_3$ (426.50)
Calculated: C 76.03 H 6.14 N 6.57
Found: C 75.89 H 6.35 N 6.33

EXAMPLE 134

4'-[(2-Cyclohexylmethyl-5,6-dihydroxy-benzimidazol-1-yl)-methyl]-biphenyl-2-carboxylic acid 0.29 ml (3 mmol) of boron tribromide is added dropwise to a suspension of 242 mg (0.5 mmol) of 4'-[(2-cyclohexylmethyl-5,6-dihydroxy-benzimidazol-1-yl)-methyl]biphenyl-2-carboxylic acid in 25 ml of dichloromethane at −5° C. When the addition is complete, the cooling bath is removed and the mixture is stirred at ambient temperature for 5 hours. 20 ml of methanol are then added while the mixture is cooled with ice, then the reaction mixture is evaporated to dryness and the residue is suspended in 10 ml of water while stirring.

The crude product precipitated is filtered off under suction, washed with a further 10 ml of water, dried and chromatographed over a silica gel column (eluting agent: dichloromethane/ethanol=9:1).

Yield: 51 mg (22% of theoretical),
Melting point: amorphous
$C_{28}H_{28}N_2O_4$ (456.50)
Calculated: C 73.66 H 6.18 N 6.14
Found: C 73.79 H 6.31 N 6.22

The following compounds are obtained in analogous manner:

4'-[(2-n-butyl-5-hydroxy-benzimidazol-1-yl)-methyl] biphenyl-2-carboxylic acid
melting point: 306°–307° C.

4'-[(2-n-butyl-4-hydroxy-benzimidazol-1-yl)-methyl] biphenyl-2-carboxylic acid
melting point: 292°–293° C.

4'-[(2-n-butyl-7-hydroxy-benzimidazol-1-yl)-methyl] biphenyl-2-carboxylic acid melting point: 295°–297° C.

EXAMPLE 135

4'-[(2-(3-Methylbutyl)-5-methoxy-6-hydroxy-benzimidazol-1-yl)-methyl]biphenyl-2-carboxylic acid and 4'-[(2-(3-methylbutyl)-5-hydroxy-6-methoxy-benzimidazol-1-yl)-methyl]biphenyl-2-carboxylic acid 3 g of aluminium trichloride are added to a suspension of 600 mg (1.3 mmol) of 4'-[(2-(3-methylbutyl)-5,6-dimethoxy-benzimidazol-1-yl)-methyl]biphenyl-2-carboxylic acid in 50 ml of dry dichloromethane and the mixture is heated under reflux for 15 minutes. The solvent is then distilled off, the residue is filtered off under suction, washed using 30 ml of water and dried. 360 mg (62% of theoretical) of a mixture of the isomeric products is obtained after chromatographing over silica gel (eluting agent: dichloromethane/ethanol=9:1).

To separate the isomers, 230 mg of the mixture are chromatographed again over silica gel (eluting agent: dichloromethane/ethanol=11:1). 80 mg of 4'-[(2-(3-methylbutyl)-5-methoxy-6-hydroxy-benzimidazol-1-yl)-methyl]biphenyl-2-carboxylic acid (melting point: 189°–192° C.)

$C_{27}H_{28}N_2O_4$ (444.50)

Calculated: C 72.95 H 6.35 N 6.30

Found: C 72.84 H 6.32 N 6.19 and 30 mg of 4'-[(2-(3-methylbutyl)-5-hydroxy-6-methoxy-benzimidazol-1-yl)-methyl]biphenyl-2-carboxylic acid (melting point: 188°–190° C.)

$C_{27}H_{28}N_2O_4$ (444.50)

Calculated: C 72.95 H 6.35 N 6.30

Found: C 73.13 H 6.39 N 6.41 are thus obtained.

EXAMPLE 136

Ethyl 4'-[(2-n-butyl-7-n-propylamino-benzimidazol-1-yl)-methyl]biphenyl-2-carboxylate 2.0 g (4.7 mmol) of ethyl 4'-[(7-amino-2-n-butyl-benzimidazol-1-yl)-methyl]biphenyl-2-carboxylate are dissolved in 50 ml of ethanol and 0.53 ml (7.5 mmol) of propionaldehyde and 0.05 g of 10% palladium on carbon are added and the mixture is hydrogenated for 2 hours at ambient temperature and 5 bar hydrogen pressure. The catalyst is then filtered off under suction and the solvent is removed in vacuum. The oily residue is purified over an aluminium oxide column (neutral, activity II-III), the column being eluted with cyclohexane/methylene chloride=3:1 and 1:1. The appropriate fractions are combined and rotary evaporated.

Yield: 2.0 g (90.9% of theoretical), oil, $R_f$ value: 0.050 (Silica gel: methylene chloride/ethanol)=19:1

The following compounds are obtained in analogous manner:

tert.butyl 4'-[(2-n-butyl-5-n-pentylamino-benzimid-azol-1-yl)-methyl]biphenyl-2-carboxylate $R_f$ value: 0.45 (Aluminium oxide, methylene chloride)

tert.butyl 4'-[(2-n-butyl-6-n-pentylamino-benzimid-azol-1-yl)-methyl]biphenyl-2-carboxylate oil, $R_f$ value: 0.40 (Silica gel: methylethylketone/xylene=1:1)

tert.butyl 4'-[(2-n-butyl-6-n-butylamino-benzimidazol-1-yl)-methyl]biphenyl-2-carboxylate oil, $R_f$ value: 0.50 (Silica gel: methylethylketone/xylene=1:1)

tert.butyl 4'-[(2-n-butyl-6-(2-cyclohexyl-ethylamino)-benzimidazol-1-yl)-methyl]biphenyl-2-carboxylate oil, $R_f$ value: 0.40 (Silica gel: ethyl acetate/petroleum ether=60:40)

tert.butyl 4'-[(2-n-butyl-6-(cis-and trans-decahydronaphth-2-yl-amino)-benzimidazol-1-yl)-methyl]biphenyl-2 -carboxylate oil, $R_f$ value: 0.65 (Aluminium oxide plate: petroleum ether/ethyl acetate=9:1)

EXAMPLE 137

4'-[(2-n-Butyl-7-n-propylamino-benzimidazol-1-yl)-methyl]biphenyl-2-carboxylic acid Prepared in analogous manner to Example 72 from ethyl 4'-[(2-n-butyl-7-n-propylamino-benzimidazol-1-yl)-methyl]biphenyl-2-carboxylate and 2N sodium hydroxide/ethanol.

Yield: 85.7% of theoretical,

Melting point: 262°–263° C.

$C_{28}H_{31}N_3O_2$ (441.57)

Calculated: C 76.16 H 7.08 N 9.52

Found: C 76.35 H 7.26 N 9.60

EXAMPLE 138

4'-[(2-n-Butyl-5-and 6-nitro-benzimidazol-1-yl)-methyl]biphenyl-2-carboxylic acid Prepared in analogous manner to Example 9 from tert. butyl 4'-[(2-n-butyl-5-and 6-nitro-benzimidazol-1-yl)-methyl]biphenyl-2-carboxylate and trifluoroacetic acid in methylene chloride.

Yield: 54.4% of theoretical,

Melting point: 223°–224° C.

$C_{23}H_{23}N_3O_4$ (429.48)

Calculated: C 69.92 H 5.60 N 9.78

Found: C 69.81 H 5.47 N 9.72

EXAMPLE 139

4'-[(2-n-Butyl-7-n-butylsulphonamino-benzimidazol-1-yl)-methyl]biphenyl-2-carboxylic acid Prepared in analogous manner to Example 72 from ethyl 4'-[(2-n-butyl-7-n-butylsulphonamino-benzimidazol-1-yl)-methyl]biphenyl-2-carboxylate and sodium hydroxide in ethanol.

Yield: 94.7% of theoretical,

Melting point: 225°–226° C.

$C_{28}H_{23}N_3O_4S$ (519.66)

Calculated: C 67.03 H 6.40 N 8.09 S 6.17

Found: C 66.92 H 6.63 N 8.09 S 5.91

EXAMPLE 140

4'-[(2-n-Butyl-5-n-pentylamino-benzimidazol-1-yl)-methyl]biphenyl-2-carboxylic acid hemi-trifluoroacetate Prepared in analogous manner to Example 9 from tert. butyl 4'-[(2-n-butyl-5-n-pentylamino-benzimidazol-1-yl)- methyl]biphenyl-2-carboxylate and trifluoroacetic acid in methylene chloride.

Yield: 92.3% of theoretical,
Melting point: 155°–157° C.
$C_{30}H_{25}N_3O_4 \times \frac{1}{2}\ CF_3COOH$ (526.64)
Calculated: C 70.70 H 6.79 N 7.98
Found: C 70.84 H 6.94 N 8.05

EXAMPLE 141

4'-[(2-n-Butyl-6-cyclohexylaminocarbonylamino-benzimidazol-1-yl)-methyl]-2-amino-biphenyl 2 g (3.2 mmol) of 4'-[(2-n-butyl-6-cyclohexylaminocarbonylamino-benzimidazol-1-yl)-methyl]-2-phthalimino-biphenyl are dissolved in 20 ml of methanol and 10 ml of dimethylformamide and, after adding 20 ml of 40% strength methylamino solution, are stirred for 2 hours at ambient temperature. The mixture is evaporated to dryness in vacuum. The remaining residue is suspended in ether and the insoluble N-methyl-phthalimide is filtered off. The filtrate is evaporated to dryness in vacuum and purified over silica gel (grain size: 0.063–0.2 mm, eluting agent: methylene chloride with 0.5–2% ethanol). The resulting product is suspended in ether, filtered under suction, washed using ether and dried in vacuum.

Yield: 1.37 g (85.6% of theoretical),
Melting point: 209°–211° C.
$C_{31}H_{27}N_5O$ (495.68)
Calculated: C 75.12 H 7.52 N 14.13
Found: C 75.33 H 7.57 N 14.01

The following compound is obtained in analogous manner:

4'-[(2-n-butyl-7-hydroxy-4-methyl-benzimidazol-1-yl)-methyl]-2-amino-biphenyl
melting point: 249°–250° C.

EXAMPLE 142

4'-[(2-n-Butyl-7-hydroxy-4-methyl-benzimidazol-1-yl)-methyl]-2-aminomethyl-biphenyl 3.3 g (7.1 mmol) of 4'-[(7-benzyloxy-2-n-butyl-4-methyl-benzimidazol-1-yl)-methyl]-2-cyano-biphenyl are dissolved in 100 ml of methanol and hydrogenated at ambient temperature in the presence of 0.5 g of palladium (10% on carbon) at 5 bar of hydrogen. After 3 hours the catalyst is filtered off. 20 ml of 20% strength ammonia in methanol is added to the filtrate and the mixture is hydrogenated again at 70° C. in the presence of 0.5 g of Raney nickel at 5 bar of hydrogen. After 4 hours of the catalyst is filtered off under suction and the filtrate is evaporated to dryness in vacuum. The crude crystalline product is suspended in ether, filtered under suction, washed using ether and dried in vacuum.

Yield: 2.6 g (92.8% of theoretical),
Melting point: 207°–212° C.
$C_{28}H_{29}N_3O$ (399.53)
Calculated: C 78.16 H 7.32 N 10.52
Found: C 77.97 H 7.34 N 10.51

EXAMPLE 143

4'-[(2-n-Butyl-6-cyclohexylaminocarbonylamino-benzimidazol-1-yl)-methyl)]-2-trifluoroacetamino-biphenyl 0.35 g (0.7 mmol) of 4'-[(2-n-butyl-6-cyclohexylaminocarbonylamino-benzimidazol-1-yl)-methyl)]-2-amino-biphenyl, dissolved in 15 ml of methylene chloride and 0.85 ml (6.1 mmol) of triethylamine, is cooled to −60° C. and 0.85 ml of trifluoroacetic anhydride in 2 ml of methylene chloride is added dropwise while stirring. The mixture is allowed to rise to ambient temperature overnight and is evaporated to dryness. The residue is purified over silica gel (eluting agent: methylene chloride with 0.5–2% ethanol. The eluates collected are evaporated, crystallised from ether/benzene 60°–80° C. and dried in vacuum.

Yield: 0.21 g (50% of theoretical),
Melting point: 231°–233° C.
$C_{33}H_{36}F_3N_5O_2$ (591.68)
Calculated: C 66.99 H 6.13 N 11.83
Found: C 66.83 H 5.96 N 11.71

The following compounds are obtained in analogous manner:

4'-[(7-benzyloxy-2-n-butyl-4-methyl-benzimidazol-1-yl)-methyl]-2-trifluoroacetamino-biphenyl
melting point: 147°–149° C.

4'-[(2-n-butyl-7-hydroxy-4-methyl-benzimidazol-1-yl)-methyl]-2-trifluoroacetaminomethyl-biphenyl
melting point: 247°–249° C.

4'-[(7-benzyloxy-2n-butyl-4-methyl-benzimidazol-1-yl)-methyl]-2-trifluoromethanesulphonamino-biphenyl
oil, $R_f$ value: 0.65 (Silica gel: petroleum ether/ethyl acetate= 1:1)

4'-[(2-n-butyl-7-trifluoromethanesulphonyloxy-4-methyl-benzimidazol-1-yl)-methyl]-2-trifluoromethanesulphonaminomethyl-biphenyl
melting point: 137°–139° C.

EXAMPLE 144

4'-[(2-n-Butyl-4-methoxy-benzimidazol-1-yl)-methyl]biphenyl-2-carboxylic acid

Prepared in analogous manner to Example 9 from tert. butyl 4'-[(2-n-butyl-4-methoxy-benzimidazol-1-yl)-methyl] biphenyl-2-carboxylate and trifluoroacetic acid.

Yield: 76.5% of theoretical,
Melting point: 179°–181° C.
$C_{26}H_{25}N_2O_3$ (414.51)
Calculated: C 75.34 H 6.32 N 6.76
Found: C 75.07 H 6.35 N 6.71

EXAMPLE 145

4'-[(2-n-Butyl-7-methoxy-benzimidazol-1-yl)-methyl]biphenyl-2-carboxylic acid

Prepared in analogous manner to Example 9 from tert. butyl 4'-[(2-n-butyl-7-methoxy-benzimidazol-1-yl)-methyl] biphenyl-2-carboxylate and trifluoroacetic acid.

Yield: 80% of theoretical,
Melting point: 260°–261° C.
$C_{20}H_{23}N_2O_3$ (414.51)
Calculated: C 75.34 H 6.32 N 6.76
Found: C 75.09 H 6.37 N 6.79

EXAMPLE 146

4'-[(5-Aminoacetamino-2-n-butyl-benzimidazol-1-yl)-methyl]biphenyl-2-carboxylic acid Prepared in analogous manner to Example 9 from tert. butyl 4'-[(5-aminoacetamino-2-n-butyl-benzimidazol-1-yl)-methyl]biphenyl-2-carboxylate and trifluoroacetic acid.

Yield: 40% of theoretical,
Melting point: 230°–232° C.
$C_{27}H_{28}N_4O_3$ (456.54)
Calculated: C 71.03 H 6.18 N 12.27
Found: C 70.83 H 6.36 N 11.98

EXAMPLE 147

4'-[(2-n-Butyl-5-n-pentylamino-benzimidazol-1-yl)-methyl]biphenyl-2-carboxylic acid hemi-trifluoroacetate Prepared in analogous manner to Example 9 from tert. butyl 4'-[(2-n-butyl-5-n-pentylamino-benzimidazol-1-yl)-methyl]biphenyl-2-carboxylate and trifluoroacetic acid.
Yield: 92.3% of theoretical,
Melting point: 155°–157° C. (decomposition)
$C_{30}H_{35}N_3O_2 \times \frac{1}{2}$ $CF_3COOH$ (526.64)
Calculated: C 70.70 H 6.79 N 7.98
Found: C 71.04 H 7.14 N 8.05

EXAMPLE 148

4'-[(2-n-Butyl-6-methylamino-benzimidazol-1-yl)-methyl]biphenyl-2-carboxylic acid hemi-trifluoroacetate Prepared in analogous manner to Example 9 from tert. butyl 4'-[(2-n-butyl-6-methylamino-benzimidazol-1-yl)-methyl]biphenyl-2-carboxylate and trifluoroacetic acid.
Yield: 77.3% of theoretical,
Melting point: 197°–199° C.
$C_{26}H_{27}N_3O_2 \times \frac{1}{2}$ $CF_3COOH$ (470.53)
Calculated: C 68.92 H 5.89 N 8.93
Found: C 68.82 H 5.80 N 8.62

EXAMPLE 149

4'-[(2-n-Butyl-6-(N-butanoyl-methylamino)-benzimidazol-1-yl)-methyl]biphenyl-2-carboxylic acid Prepared in analogous manner to Example 9 from tert. butyl 4'-[(2-n-butyl-6-(N-butanoyl-methylamino)-benzimidazol-1-yl)-methyl]biphenyl-2-carboxylate and trifluoroacetic acid.
Yield: 70.3% of theoretical,
Melting point: 165°–167° C.
$C_{30}H_{33}N_3O_3$ (483.62)
Calculated: C 74.51 H 6.87 N 8.68
Found: C 74.51 H 6.89 N 8.56

EXAMPLE 150

4'-[(6-Aminocarbonylamino-2-n-butyl-benzimidazol-1-yl)-methyl]biphenyl-2-carboxylic acid trifluoroacetate Prepared in analogous manner to Example 9 from tert. butyl 4'-[(6-aminocarbonylamino-2-n-butyl-benzimidazol-1-yl)-methyl]biphenyl-2-carboxylate and trifluoroacetic acid.
Yield: 93.8% of theoretical,
Melting point: 134°–136° C.
$C_{20}H_{30}N_4O_3 \times CF_3COOH$ (556.54)
Calculated: C 60.43 H 4.89 N 10.07
Found: C 60.22 H 4.87 N 9.80

EXAMPLE 151

4'-[(2-n-Butyl-6-(n-hexylaminocarbonylamino)-benzimidazol-1-yl)-methyl]biphenyl-2-carboxylic acid trifluoroacetate Prepared in analogous manner to Example 9 from tert. butyl 4'-[(2-n-butyl-6-(n-hexylaminocarbonylamino)-benzimidazol-1-yl)-methyl]biphenyl-2-carboxylate and trifluoroacetic acid.
Yield: 93.3% of theoretical,
Melting point: 138°–140° C.
$C_{32}H_{38}N_4O_3 \times CF_3COOH$ (640.70)
Calculated: C 63.74 H 6.14 N 8.74
Found: C 63.66 H 6.19 N 8.51

EXAMPLE 152

4'-[(2-n-Butyl-4-hydroxy-benzimidazol-1-yl)-methyl]biphenyl-2-carboxylic acid

Prepared in analogous manner to Example 9 from tert. butyl 4'-[(2-n-butyl-4-hydroxy-benzimidazol-1-yl)-methyl]biphenyl-2-carboxylate and trifluoroacetic acid.
Yield: 72.5% of theoretical,
Melting point: 292°–293° C.
$C_{23}H_{24}N_2O_3$ (400.48)
Calculated: C 74.98 H 6.04 N 7.00
Found: C 74.85 H 6.13 N 6.91

EXAMPLE 153

4'-[(2-n-Butyl-5-cyclohexylaminocarbonylamino-benzimidazol-1-yl)-methyl]biphenyl-2-carboxylic acid trifluoroacetate Prepared in analogous manner to Example 9 from tert. butyl 4'-[(2-n-butyl-5-cyclohexylaminocarbonylamino-benzimidazol-1-yl)-methyl]biphenyl-2-carboxylate and trifluoroacetic acid.
Yield: 81.1% of theoretical,
Melting point: 176°–177° C. (amorphous)
$C_{32}H_{36}N_4O_3 \times CF_3COOH$ (638.69)
Calculated: C 63.94 H 5.84 N 8.77
Found: C 64.04 H 6.00 N 9.05

EXAMPLE 154

4'-[(2-n-Butyl-7-isopropylaminomethyl-benzimidazol-1-yl)-methyl]biphenyl-2-carboxylic acid hydrate Prepared in analogous manner to Example 9 from tert. butyl 4'-[(2-n-butyl-7-isopropylaminomethyl-benzimidazol-1-yl)-methyl]biphenyl-2-carboxylate and trifluoroacetic acid.
Yield: 53% of theoretical,
Melting point: 156°–158° C.
$C_{28}H_{23}N_3O_3 \times H_2O$ (473.61)
Calculated: C 73.54 H 7.45 N 8.87
Found: C 73.69 H 7.37 N 8.91

EXAMPLE 155

4'-[(6-Aminothiocarbonylamino-2-n-butyl-benzimidazol-1-yl)-methyl]biphenyl-2-carboxylic acid hemi-hydrate Prepared in analogous manner to Example 9 from tert. butyl 4'-[(6-aminothiocarbonylamino-2-n-butylbenzimidazol-1-yl)-methyl]biphenyl-2-carboxylate and trifluoroacetic acid.

Yield: 80.4% of theoretical,
Melting point: 147°–149° C.
$C_{26}H_{28}N_4O_2S \times \frac{1}{2} H_2O$ (467.58)
Calculated: C 66.80 H 5.81 N 6.85
Found: C 66.92 H 5.91 N 6.66

EXAMPLE 156

4'-[(2-n-Butyl-6-cyclohexylaminothiocarbonylamino-benzimidazol-1-yl)-methyl]biphenyl-2-carboxylic acid Prepared in analogous manner to Example 9 from tert. butyl 4'-[(2-n-butyl-6-cyclohexylaminothiocarbonylamino-benzimidazol-1-yl)-methyl]biphenyl-2-carboxylate and trifluoroacetic acid.

Yield: 88.2% of theoretical,
Melting point: 223°–225° C. (decomposition)
$C_{22}H_{28}N_4O_2S$ (540.72)
Calculated: C 71.08 H 6.71 N 10.36 S 5.93
Found: C 70.95 H 6.77 N 10.53 S 6.23

EXAMPLE 157

4'-[(2-n-Butyl-6-hydroxy-benzimidazol-1-yl)-methyl]biphenyl-2-carboxylic acid

Prepared in analogous manner to Example 9 from tert. butyl 4'-[(2-n-butyl-6-hydroxy-benzimidazol-1-yl)-methyl]biphenyl-2-carboxylate and trifluoroacetic acid.

Yield: 76.5% of theoretical,
Melting point: 264°–266° C.
$C_{25}H_{24}N_2O_3$ (400.48)
Calculated: C 74.98 H 6.04 N 7.00
Found: C 75.06 H 5.95 N 6.98

EXAMPLE 158

4'-[(2-n-Butyl-7-(2-methoxy-ethoxy)-4-methyl-benzimidazol-1-yl)-methyl]biphenyl-2-carboxylic acid Prepared in analogous manner to Example 9 from tert. butyl 4'-[(2-n-butyl-7-(2-methoxy-ethoxy)-4-methyl-benzimidazol-1-yl)-methyl]biphenyl-2-carboxylate and trifluoroacetic acid.

Yield: 63.6% of theoretical,
Melting point: 205°–207° C.
$C_{20}H_{23}N_2O_4$ (472.58)
Calculated: C 73.71 H 6.82 N 5.93
Found: C 73.48 H 6.64 N 6.15

EXAMPLE 159

4'-[(2-n-Butyl-6-trifluoroacetylamino-benzimidazol-1-yl)-methyl]biphenyl-2-carboxylic acid Prepared in analogous manner to Example 9 from tert. butyl 4'-[(2-n-butyl-6-trifluoroacetylamino-benzimidazol-1-yl)-methyl]biphenyl-2-carboxylate and trifluoroacetic acid.

Yield: 69.6% of theoretical, Melting point: 84°–86° C.
$C_{27}H_{24}N_3O_3F_3$ (495.50) Calculated: C 65.45, H 4.88, N 8.48 Found: 65.20, 5.06, 8.64

EXAMPLE 160

4'-[(2-n-Butyl-4-cyclohexylaminocarbonylamino-benzimidazol-1-yl)-methyl]biphenyl-2-carboxylic acid Prepared in analogous manner to Example 9 from tert. butyl 4'-[(2-n-butyl-4-cyclohexylaminocarbonylamino-benzimidazol-1-yl)-methyl]biphenyl-2-carboxylate and trifluoroacetic acid.

Yield: 94.4% of theoretical, Melting point: 242°–244° C. (decomposition) $C_{22}H_{24}N_4O_3$ (524.66) Calculated: C 73.26, H 6.92, N 10.68 Found: 72.42, 6.93, 10.77

EXAMPLE 161

4'-[(6-Allylaminocarbonylamino-2-n-butyl-benzimidazol-1-yl)-methyl]biphenyl-2-carboxylic acid trifluoroacetate Prepared in analogous manner to Example 9 from tert. butyl 4'-[(6-allylaminocarbonylamino-2-n-butyl-benzimidazol-1-yl)-methyl]biphenyl-2carboxylate and trifluoroacetic acid Yield: 96% of theoretical, Melting point: 90°–92° C. $C_{20}H_{30}N_4O_3 \times CF_3COOH$ (596.61) Calculated: C 62.41, H 5.24, N 9.39 Found: 62.20, 5.17, 9.13

EXAMPLE 162

4'-[(6-Benzylaminocarbonylamino-2-n-butyl-benzimidazol-1-yl)-methyl]biphenyl-2-carboxylic acid Prepared in analogous manner to Example 9 from tert. butyl 4'-[(6-benzylaminocarbonylamino-2-n-butyl-benzimidazol-1-yl)-methyl]biphenyl-2-carboxylate and trifluoroacetic acid.

Yield: 79.4% of theoretical, Melting point: 244°–245° C. $C_{33}H_{23}N_4O_3$ (532.64) Calculated: C 74.41, H 6.06, N 10.52 Found: 74.32, 6.09, 10.31

EXAMPLE 163

4'-[(2-n-Butyl-6-(N-methylaminocarbonyl-n-pentylamino)-benzimidazol-1-yl)-methyl]biphenyl-2-carboxylic acid Prepared in analogous manner to Example 9 from tert. butyl 4'-[(2-n-butyl-6-(N-methylaminocarbonyl-n-pentylamino)-benzimidazol-1-yl)-methyl]biphenyl-2-carboxylate and trifluoroacetic acid.

Yield: 54% of theoretical, Melting point: 149°–152° C. $C_{23}H_{H33}N_4O_3$ (526.68) Calculated: C 72.98, H 7.27, N 10.64 Found: 72.95, 7.27, 10.73

EXAMPLE 164

4'-[(5-Aminothiocarbonylamino-2-n-butyl-benzimidazol-1-yl)-methyl]biphenyl-2-carboxylic acid hydrochloride Prepared in analogous manner to Example 9 from tert. butyl 4'-[(5-aminothiocarbonylamino-2-n-butyl-benzimidazol-1-yl)-methyl]biphenyl-2-carboxylate and trifluoroacetic acid.

Yield: 66.6% of theoretical, Melting point: 150°–152° C. $C_{26}H_{27}N_4O_2SCl$ (495.04) Calculated: C 63.08, H 5.49, N 11.31, S 6.46 Found: 62.83, 5.76, 11.15, 6.22

EXAMPLE 165

4'-[(2-n-Butyl-5-formylamino-benzimidazol-1-yl)-methyl]biphenyl-2-carboxylic acid Prepared in analogous manner to Example 9 from tert. butyl 4'-[(2-n-butyl-5-formylamino-benzimidazol-1-yl)-methyl]biphenyl-2-carboxylate and trifluoroacetic acid.

Yield: 64.6% of theoretical, Melting point: 229°–230° C. $C_{26}H_{25}N_3O_3$ (427.51) Calculated: C 73.05, H 5.89, N 9.83 Found: 73.31, 6.11, 9.58

EXAMPLE 166

4'-[(2-n-Butyl-5-(N-propanoyl-methylamino)-benzimidazol-1-yl)-methyl]biphenyl-2-carboxylic acid Prepared in analogous manner to Example 9 from tert. butyl 4'-[(2-n-butyl-5-(N-propanoyl-methylamino)-benzimidazol-1-yl)-methyl]biphenyl-2-carboxylate and trifluoroacetic acid.

Yield: 77.8% of theoretical, Melting point: 178°–180° C. $C_{29}H_{31}N_3O_2$ (469.59) Calculated: C 74.18, H 6.65, N 8.95 Found: 73.93, 6.70, 9.07

EXAMPLE 167

4'-[(2-n-Butyl-6-(N-methylaminocarbonyl-methylamino)-benzimidazol-1-yl)-methyl]biphenyl-2-carboxylic acid Prepared in analogous manner to Example 9 from tert. butyl 4'-[(2-n-butyl-6-(N-methylaminocarbonyl-methylamino)-benzimidazol-1-yl)-methyl]biphenyl-2-carboxylate and trifluoroacetic acid. Yield: 85.7% of theoretical, Melting point: 163°–165° C. $C_{29}H_{30}N_4O_3$ (470.58) Calculated: C 71.46, H 6.42, N 11.91 Found: 71.33, 6.64, 11.74

EXAMPLE 168

4'-[(2-n-Butyl-6-(N-(n-butylaminocarbonyl)-methylamino)-benzimidazol-1-yl)-methyl]biphenyl-2-carboxylic acid Prepared in analogous manner to Example 9 from tert. butyl 4'-[(2-n-butyl-6-(N-(n-butylaminocarbonyl)-methylamino)-benzimidazol-1-yl)-methyl]biphenyl-2-carboxylate and trifluoroacetic acid.

Yield: 90% of theoretical, Melting point: 145°–147° C. $C_{31}H_{30}N_4O_3$ (512.65) Calculated: C 72.64, H 7.08, N 10.93 Found: 72.90, 7.16, 10.69

EXAMPLE 169

4'-[(2-n-Butyl-5-(N-methylaminocarbonyl-n-pentylamino)-benzimidazol-1-yl)-methyl]biphenyl-2-carboxylic acid Prepared in analogous manner to Example 9 from tert. butyl 4'-[(2-n-butyl-5-(N-methylaminocarbonyl-n-pentylamino)-benzimidazol-1-yl)-methyl]biphenyl-2-carboxylate and trifluoroacetic acid.

Yield: 75% of theoretical, Melting point: 240°–242° C. $C_{32}H_{30}N_4O_3$ (526.69) Calculated: C 72.97, H 7.27, N 10.64 Found: 72.78, 7.23, 10.66

EXAMPLE 170

4'-[(2-n-Butyl-6-(N-propanoyl-methylamino)-benzimidazol-1-yl)-methyl]biphenyl-2-carboxylic acid Prepared in analogous manner to Example 9 from tert. butyl 4'-[(2-n-butyl-6-(N-propanoyl-methylamino)-benzimidazol-1-yl)-methyl]biphenyl-2-carboxylate and trifluoroacetic acid.

Yield: 53.7% of theoretical, Melting point: 152°–154° C. $C_{29}H_{31}N_3O_3$ (469.59) Calculated: C 74.16, H 6.65, N 8.95 Found: 73.96, 6.53, 8.97

EXAMPLE 171

4'-[(6-Acetamino-2-n-butyl-benzimidazol-1-yl)-methyl]-biphenyl-2-carboxylic acid Prepared in analogous manner to Example 9 from tert. butyl 4'-[(6-acetamino-2-n-butyl-benzimidazol-1-yl)-methyl]biphenyl-2-carboxylate and trifluoroacetic acid.

Yield: 87% of theoretical, Melting point: 252°–254° C. $C_{37}H_{27}N_3O_3$ (441.53) Calculated: C 73.45, H 6.16, N 9.52 Found: 73.28, 5.95, 9.39

EXAMPLE 172

4'-[(2-n-Butyl-6-propionylamino-benzimidazol-1-yl)-methyl]biphenyl-2-carboxylic acid Prepared in analogous manner to Example 9 from tert. butyl 4'-[(2-n-butyl-6-propionylamino-benzimidazol-1-yl)-methyl]biphenyl-2-carboxylate and trifluoroacetic acid.

Yield: 90% of theoretical, Melting point: 269°–271° C. $C_{26}H_{29}N_3O_3$ (455.56) Calculated: C 73.82, H 6.42, N 9.22 Found: 73.99, 6.42, 9.18

EXAMPLE 173

4'-[(6-n-Butanoylamino-2-n-butyl-benzimidazol-1-yl)-methyl]biphenyl-2-carboxylic acid Prepared in analogous manner to Example 9 from tert. butyl 4'-[(6-n-butanoyl-amino-2-n-butyl-benzimidazol-1-yl)-methyl]biphenyl-2-carboxylate and trifluoroacetic acid.

Yield: 79.1% of theoretical, Melting point: 253°–255° C. $C_{29}H_{31}N_3O_3$ (469.58) Calculated: C 74.18, H 6.6, N 8.96 Found: 73.99, 6.65, 8.87

EXAMPLE 174

4'-[(2-n-Butyl-6-(n-butylaminocarbonylamino)-benzimidazol-1-yl)-methyl]biphenyl-2-carboxylic acid Prepared in analogous manner to Example 9 from tert. butyl 4'-[(2-n-butyl-6-(n-butylaminocarbonylamino)-benzimidazol-1-yl)-methyl]biphenyl-2-carboxylate and trifluoroacetic acid.

Yield: 69.2% of theoretical, Melting point: 239°–242° C. $C_{30}H_{34}N_4O_3$ (498.62) Calculated: C 72.27, H 6.87, N 11.24 Found: 71.92, 6.86, 10.93

EXAMPLE 175

4'-[(2-n-Butyl-6-(N-cyclohexylaminocarbonylmethylamino)-benzimidazol-1-yl)-methyl]biphenyl-2-carboxylic acid Prepared in analogous manner to Example 9 from tert. butyl 4'-[(2-n-butyl-6-(N-cyclohexylaminocarbonylmethylamino)-benzimidazol-1-yl)-methyl]biphenyl-2-carboxylate and trifluoroacetic acid.

Yield: 80% of theoretical, Melting point: 215°–217° C. $C_{33}H_{33}N_4O_3$ (538.69) Calculated: C 73.58, H 7.11, N 10.40 Found: 73.52, 7.19, 10.54

EXAMPLE 176

4'-[(2-n-Butyl-6-(N-(dimethylaminocarbonyl)-methylamino)-benzimidazol-1-yl)-methyl]biphenyl-2-carboxylic acid Prepared in analogous manner to Example 9 from tert. butyl 4'-[(2-n-butyl-6-(N-(dimethylaminocarbonyl)- methylamino)-benzimidazol-1-yl)-methyl]biphenyl-2-carboxylate and trifluoroacetic acid.

Yield: 66% of theoretical, Melting point: 224°–226° C. $C_{29}H_{22}N_4O_3$ (484.60) Calculated: C 71.88, H 6.66, N 11.56 Found: 71.61, 6.92, 11.27

EXAMPLE 177

4'-[(2-n-Butyl-6-n-pentanoylamino-benzimidazol-1-yl)-methyl]biphenyl-2-carboxylic acid Prepared in analogous manner to Example 9 from tert. butyl 4'-[(2-n-butyl-6-n-pentanoylamino-benzimidazol-1-yl)-methyl]biphenyl-2-carboxylate and trifluoroacetic acid.

Yield: 74.5% of theoretical, Melting point: 253°–255° C. $C_{30}H_{33}N_3O_3$ (483.61) Calculated: C 74.57, H 6.88, N 8.70 Found: 74.23, 7.08, 8.63

EXAMPLE 178

4'-[(2n-Butyl-6-(N-(dimethylaminocarbonyl)-amino)-benzimidazol-1-yl)-methyl]biphenyl-2-carboxylic acid trifluoroacetate Prepared in analogous manner to Example 9 from tert. butyl 4'-[(2-n-butyl-6-(N-(dimethylaminocarbonyl)-amino)-benzimidazol-1-yl)-methyl]biphenyl-2-carboxylate and trifluoroacetic acid.

Yield: 83.1% of theoretical, Melting point: 198°–200° C. $C_{28}H_{30}N_4O_3$ x $CF_3COOH$ (584.60) Calculated: C 61.63, H 5.34, N 9.58 Found: 61.62, 5.50, 9.68

EXAMPLE 179

4'-[(2-n-Butyl-6-(N-(n-butylaminocarbonyl)-methylamino)-benzimidazol-1-yl)-methyl]biphenyl-2-carboxylicacid trifluoroacetate Prepared in analogous manner to Example 9 from tert. butyl 4'-[(2-n-butyl-6-(N-(n-butylaminocarbonyl)-methylamino)-benzimidazol-1-yl)-methyl]biphenyl-2-carboxylate and trifluoroacetic acid.

Yield: 70% of theoretical, Melting point: 152°–154° C. $C_{31}H_{30}N_4O_3$ x $CF_3COOH$ (626.68) Calculated: C 63.25, H 5.95, N 8.94 Found: 63.18, 6.07, 9.03

EXAMPLE 180

4'-[(2-n-Butyl-6-(N-cyclohexylaminocarbonyl-n-pentyl-amino)-benzimidazol-1-yl)-methyl]biphenyl-2-carboxylic acid Prepared in analogous manner to Example 9 from tert. butyl 4'-[(2-n-butyl-6-(N-cyclohexylaminocarbonyl-n-pentylamino)-benzimidazol-1-yl)-methyl]biphenyl-2-carboxylate and trifluoroacetic acid.

Yield: 46.7% of theoretical, Melting point: 134°–137° C. $C_{37}H_{46}N_4O_3$ (594.80) Calculated: C 74.72, H 7.79 N 9.62 Found: 74.52, 7.85, 9.34

EXAMPLE 181

Tert.butyl 4'-[(2-n-butyl-6-(N-acetyl-methylamino)-benzimidazol-1-yl)-methyl]biphenyl-2-carboxylate 4.5 g (9 mmol) of tert.butyl 4'-[(2-n-butyl-6-actylamino-benzimidazol-1-yl)-methyl]biphenyl-3-carboxylate are dissolved in 50 ml of dimethylformamide and 0.48 g (9 mmol+10%) of sodium hydride suspension in oil (50% strength) is added. The reaction mixture is stirred for 30 minutes at 80° C., cooled to ambient temperature and treated with 1.5 g of methyl iodide (9 mmol+20%). When the reaction is completed, the mixture is evaporated in vacuum, taken up in ethyl acetate and washed using water. The organic phase is dried over sodium sulphate and evaporated in vacuum, a oily residue being obtained. A yellowish oil is obtained after purifying over a silica gel column (grain size: 0.02–0.5 mm, eluting agent: methylene chloride/ethanol= 49:1, 24:1).

Yield: 3.7 g (80.4% of theoretical), oil, $R_f$ value: 0.75 (silica gel: methylene chloride/ethanol=19:1) $C_{23}N_{37}N_3O_3$ (511.66) Calculated: C 75.12, H 7.29, N 8.21 Found: 74.99, 7.32, 8.22

The following compounds are prepared in analogous manner:

tert.butyl 4'-[(2-n-butyl-5-(N-propionyl-methylamino)-benzimidazol-1-yl)-methyl]biphenyl-2-carboxylate oil, $R_f$ value: 0.80 (Silica gel: ethyl acetate/ethanol/ ammonia=90:10:1)

tert.butyl 4'-[(2-n-butyl-6-(N-propionyl-methylamino)-benzimidazol-1-yl)-methyl]biphenyl-2-carboxylate oil, $R_f$ value: 0.65 (Silica gel: methylene chloride/ethanol= 19:1)

EXAMPLE 182

4'-[(2-n-Butyl-6-(tetrahydropyran-2-yl-aminocarbonylamino)-benzimidazol-1-yl)-methyl]biphenyl-2-carboxylic acid Prepared in analogous manner to Example 7 from 4'-[(6-amino-2-n-butyl-benzimidazol-1-yl)-methyl]biphenyl-2-carboxylic acid and tetrahydropyran-2-yl-isocyanate.

Yield: 35.7% of theoretical, Melting point: 172°–174° C. $C_{31}H_{34}N_4O_4$ (562.64) Calculated: C 70.70, H 6.51, N 10.64 Found: 70.59, 6.77, 10.86

EXAMPLE 183

4'-[(2-n-Butyl-6-phenylacetamino-benzimidazol-1-yl)-methyl]biphenyl-2-carboxylic acid hemi-trifluoroacetate Prepared in analogous manner to Example 9 from tert. butyl 4'-[(2-n-butyl-6-phenylacetamino-benzimidazol-1-yl)-methyl]biphenyl-2-carboxylate and trifluoroacetic acid.

Yield: 29.2% of theoretical, Melting point: 273°–275° C. (decomposition) $C_{23}H_{31}N_3O_3$ x 0.5 $CF_3COOH$ (574.64) Calculated: C 71.07, H 5.53, N 7.31 Found: 71.01, 5.60, 7.11

EXAMPLE 184

4'-[(2-n-Butyl-6-(N-(n-hexylaminocarbonyl)-cyclohexylamino)-benzimidazol-1-yl)-methyl]biphenyl-2-carboxylic acid Prepared in analogous manner to Example 9 from tert. butyl 4'-[(2-n-butyl-6-(N-(n-hexylaminocarbonyl)-cyclohexylamino)-benzimidazol-1-yl)-methyl]biphenyl-2-carboxylate and trifluoroacetic acid.

Yield: 97.1% of theoretical, Melting point: 196°–197° C. $C_{16}H_{48}N_4O_3$ (608.82) Calculated: C 74.97, H 7.95, N 9.20 Found: 74.75, 7.92, 9.19

EXAMPLE 185

4'-[(2-n-Butyl-6-cyclohexylcarbonylamino-benzimidazol-1-yl)-methyl]biphenyl-2carboxylic acid Prepared in analogous manner to Example 9 from tert. butyl 4'-[(2-n-butyl-6-cyclohexylcarbonylaminobenzimidazol-1-yl)-methyl]biphenyl-2-carboxylate and trifluoroacetic acid.

Yield: 68.4% of theoretical, Melting point: 298°–300° C. (decomposition) $C_{22}H_{25}N_3O_4$ (509.65) Calculated: C 75.41, H 6.92, N 8.24 Found: 75.38, 6.78, 8.11

EXAMPLE 186

4'-[(6-Benzyloxycarbonylamino-2-n-butyl-benzimidazol-1-yl)-methyl]biphenyl-2-carboxylic acid Prepared in analogous manner to Example 9 from tert. butyl 4'-[(6-benzyloxycarbonylamino-2-n-butyl-benzimidazol-1-yl)-methyl]biphenyl-2-carboxylate and trifluoroacetic acid.

Yield: 64.9% of theoretical, Melting point: 238°–240° C. (decomposition) $C_{23}H_{31}N_2O_4$ (533.63) Calculated: C 74.28, H 5.86, N 7.87 Found: 74.14, 5.97, 7.72

EXAMPLE 187

4'-[(2-n-Butyl-6-(2-cyclohexyl-ethylamino)-benzimidazol-1-yl)-methyl]biphenyl-2-carboxylic acid Prepared in analogous manner to Example 9 from tert. butyl 4'-[(2-n-butyl-6-(2-cyclohexyl-ethylamino)-benzimidazol-1-yl)-methyl]biphenyl-2-carboxylate and trifluoroacetic acid.

Yield: 66.6% of theoretical, Melting point: 217°–219° C. $C_{23}H_{30}N_3O_2$ (509.69) Calculated: C 77.77, H 7.71, N 8.24 Found: 77.57, 7.56, 8.23

EXAMPLE 188

4'-[(2-n-Butyl-6-cyclohexylmethylaminocarbonyl-benzimidazol-1-yl)-methyl]biphenyl-2-carboxylic acid Prepared in analogous manner to Example 9 from tert. butyl 4'[(2-n-butyl-6-cyclohexylmethylaminocarbonyl-benzimidazol-1-yl)-methyl]biphenyl-2-carboxylate and trifluoroacetic acid.

Yield: 80.4% of theoretical, Melting point: 239°–241° C. $C_{33}H_{37}N_2O_2$ (523.67) Calculated: C 75.69, H 7.12, N 8.02 Found: 75.53, 6.94, 7.97

EXAMPLE 189

4'-[(2-n-Butyl-6-cyclohexylaminocarbonyl-benzimidazol-1-yl)-methyl]biphenyl-2-carboxylic acid Prepared in analogous manner to Example 9 from tert. butyl 4'-[(2-n-butyl-6-cyclohexylamino-carbonyl-benzimidazol-1-yl)-methyl]biphenyl-2-carboxylate and trifluoroacetic acid Yield: 89.2% of theoretical, Melting point: 305°–308° C. (decomposition) $C_{23}H_{33}N_2O_3$ (509.65) Calculated: C 75.42, H 6.92, N 8.24 Found: 75.31, 7.03, 8.11

EXAMPLE 190

4'-[(2-n-Butyl-6-(N-methyl-n-butylaminocarbonyl)-benzimidazol-1-yl)-methyl]biphenyl-2-carboxylic acid Prepared in analogous manner to Example 9 from tert. butyl 4'-[(2-n-butyl-6-(N-methyl-n-butylaminocarbonyl)-benzimidazol-1-yl)-methyl]biphenyl-2-carboxylate and trifluoroacetic acid Yield: 94.5% of theoretical, Melting point: 176°–178° C. $C_{31}H_{25}N_3O_3$ (497.64) Calculated: C 74.82, H 7.09, N 8.44 Found: 74.98, 7.21, 8.50

EXAMPLE 191

4'-[(2-n-Butyl-6-ethoxycarbonyl-benzimidazol-1-yl)-methyl]biphenyl-2-carboxylic acid Prepared in analogous manner to Example 9 from tert. butyl 4'-[(2-n-butyl-6-ethoxycarbonyl-benzimidazol-1-yl)-methyl]biphenyl-2-carboxylate and trifluoroacetic acid.

Yield: 59.7% of theoretical, Melting point: 219°–220° C. $C_{23}H_{26}N_3O_4$ (456.54) Calculated: C 73.66, H 6.18, N 6.14 Found: 73.49, 6.13, 5.94

EXAMPLE 192

4'-[(2-n-Butyl-5-n-butylaminocarbonyl-benzimidazol-1-yl)-methyl]biphenyl-2-carboxylic acid Prepared in analogous manner to Example 9 from tert. butyl 4'-[(2-n-butyl-5-n-butylaminocarbonyl-benzimidazol-1-yl)-methyl]biphenyl-2-carboxylate and trifluoroacetic acid Yield: 48.9% of theoretical Melting point: 209°–210° C. $C_{30}H_{23}N_3O_3$ (483.61) Calculated: C 74.51, H 6.88, N 8.69 Found: 74.54, 6.79, 8.79

EXAMPLE 193

4'-[(2-n-Butyl-6-(3-cyclohexyl-piperidino)-benzimidazol-1-yl)-methyl]biphenyl-2-carboxylic acid sesquitrifluoroacetate Prepared in analogous manner to Example 9 from tert. butyl 4'-[(2-n-butyl-6-(3-cyclohexyl-piperidino)-benzimidazol-1-yl)-methyl]biphenyl-2-carboxylate and trifluoroacetic acid.

Yield: 85.0% of theoretical Melting point: 155°–157° C. $C_{26}H_{43}N_3O_2$ x 1.5 $CF_3COOH$ (720.80) Calculated: C 64.99, H 6.22 N 5.83 Found: 64.88, 6.41, 5.95

EXAMPLE 194

4'-[(2-n-Butyl-6-(cis- and trans-decahydronaphth-2-ylamino)-benzimidazol-1-yl)-methyl]biphenyl-2-carboxylic acid dihydrochloride Prepared in analogous manner to Example 9 from tert. butyl 4'-[(2-n-butyl-6-(cis- and trans-decahydronaphth-2-ylamino)-benzimidazol-1-yl)-methyl]biphenyl-2-carboxylate and trifluoroacetic acid.

Yield: 24.0% of theoretical, Melting point: from 132° C. $C_{35}H_{41}H_3O_2$ x 2 HCl (608.65) Calculated: C 69.07, H 7.12, N 6.90 Found: 68.98, 7.23, 6.97

EXAMPLE 195

4'-[(2-n-Butyl-6-cyclohexylamino-benzimidazol-1-yl)-methyl]biphenyl-2-carboxylic acid sesquitrifluoroacetate Prepared in analogous manner to Example 9 from tert. butyl 4'-[(2-n-butyl-6-cyclohexylamino-benzimidazol-1-yl)-methyl]biphenyl-2-carboxylate and trifluoroacetic acid.

Yield: 99.0% of theoretical, Melting point: 64°–66° C. (amorphous) $C_{31}H_{64}H_3O_2$ x 1.5 $CF_3COOH$ (652.68) Calculated: C 62.57, H 5.64, N 6.44 Found: 62.68, 5.81, 6.25

EXAMPLE 196

4'-[(2-n-Butyl-6-(2-isopropyl-5-methyl-cyclohexyloxycarbonylamino)-benzimidazol-1-yl)-methyl]biphenyl-2-carboxylic acid semi-trifluoroacetate Prepared in analogous manner to Example 9 from tert. butyl 4'-[(2-n-butyl-6-(2-isopropyl-5-methyl-cyclohexyloxycarbonylamino)-benzimidazol-1-yl)-methyl]biphenyl-2-carboxylate and trifluoroacetic acid.

Yield: 94.1% of theoretical, Melting point: 149°–151° C. $C_{28}H_{42}N_3O_4$ x 0.5 $CF_3COOH$ (638.77) Calculated: C 69.57, H 6.86, N 6.58 Found: 69.39, 6.91, 6.56

EXAMPLE 197

4'-[(2-n-Butyl-6-cyclohexylacetamino-benzimidazol-1-yl)-methyl]biphenyl-2-carboxylic acid Prepared in analogous manner to Example 9 from tert. butyl 4'-[(2-n-butyl-6-cyclohexylacetamino-benzimidazol-1-yl)-methyl]biphenyl-2-carboxylate and trifluoroacetic acid.

EXAMPLE 198

4'-[(2-n-Butyl-benzimidazol-1-yl)-methyl]biphenyl-2-carboxylic acid-(N-benzenesulphonyl)-amide 960 mg (2.5 mmol) of 4'-[(2-n-butyl-benzimidazol-1-yl)-methyl]biphenyl-2-carboxylic acid are dissolved in 25 ml of methylene chloride, treated with 2 ml of thionyl chloride and heated under reflux for one hour. The solvent is then distilled off and evaporated 2 times after adding methylene chloride. 390 mg (2.5 mmol) of benzenesulphonamide are added to the residue and the mixture is heated for one hour at 140° C. After cooling, the oil obtained is taken up in ethyl acetate/sodium chloride solution and extracted 3 times using ethyl acetate. The combined ethyl acetate phases are dried over sodium sulphate, evaporated and the crude product obtained is purified over a silica gel column using methylene chloride/ethanol as eluting agent.

Yield: 0.15 g (11% of theoretical), Melting point: 131°–132° C. $C_{31}H_{29}N_3O_3S$ (523.65) Calculated: C 71.11, H 5.58, N 8.02 Found: 70.96, 5.49, 8.21

The following compounds are obtained in analogous manner:

4'-[(2-n-butyl-6-methoxy-benzimidazol-1-yl)-methyl]-biphenyl-2-carboxylic acid-(N-methanesulphonyl)-amide
4'-[(2-methoxymethyl-benzimidazol-1-yl)-methyl]biphenyl-2-carboxylic acid-(N-methanesulphonyl)-amide
4'-[(2-n-pentyl-benzimidazol-1-yl)-methyl]biphenyl-2-carboxylic acid-(N-methanesulphonyl)-amide
4'-[(2-n-butyl-4-methyl-7-methoxy-benzimidazol-1-yl)-methyl]biphenyl-2-carboxylic acid-(N-methanesulphonyl)-amide
4'-[(2-n-propyl-benzimidazol-1-yl)-methyl]biphenyl-2-carboxylic acid-(N-methanesulphonyl)-amide
4'-[(2-n-butyl-5-acetamino-benzimidazol-1-yl)-methyl]-biphenyl-2-carboxylic acid-(N-methanesulphonyl)-amide
4'-[(2-n-butyl-5-chloro-benzimidazol-1-yl)-methyl]biphenyl-2-carboxylic acid-(N-methanesulphonyl)-amide
4'-[(2-n-butyl-5-butylaminocarbonylamino-benzimidazol-1-yl)-methyl]biphenyl-2-carboxylic acid-(N-methanesulphonyl)-amide
4'-[(2-n-butyl-6-phenylaminocarbonylamino-benzimidazol-1-yl)-methyl]biphenyl-2-carboxylic acid-(N-methanesulphonyl)-amide
4'-[(2-n-butyl-6-cyclohexylaminocarbonylamino-benzimidazol-1-yl)-methyl]biphenyl-2-carboxylic acid-(N-methanesulphonyl)-amide
4'-[(2-n-butyl-5-butanoylamino-benzimidazol-1-yl)-methyl]biphenyl-2-carboxylic acid-(N-methanesulphonyl)-amide
4'-[(2-n-butyl-6-chloro-benzimidazol-1-yl)-methyl]-biphenyl-2-carboxylic acid-(N-methanesulphonyl)-amide
4'-[(2-n-butyl-5-methanesulphonamino-benzimidazol-1-yl)-methyl]biphenyl-2-carboxylic acid-(N-methanesulphonyl)-amide
4'-[(2-n-butyl-6-ethoxycarbonylamino-benzimidazol-1-yl)-methyl]biphenyl-2-carboxylic acid-(N-methanesulphonyl)-amide
4'-[(2-n-butyl-6-isopropylsulphonamino-benzimidazol-1-yl)-methyl]biphenyl-2-carboxylic acid-(N-methanesulphonyl)-amide
4'-[(2-n-butyl-4-butanoylamino-benzimidazol-1-yl)-methyl]biphenyl-2-carboxylic acid-(N-methanesulphonyl)-amide
4'-[(2-n-butyl-6-dimethylamino-benzimidazol-1-yl)-methyl]biphenyl-2-carboxylic acid-(N-methanesulphonyl)-amide
4'-[(2-n-butyl-5,6-dimethoxy-benzimidazol-1-yl)-methyl]-biphenyl-2-carboxylic acid-(N-methanesulphonyl)-amide
4'-[(2-(1-butyn-4-yl)-benzimidazol-1-yl)-methyl]biphenyl-2-carboxylic acid-(N-methanesulphonyl)-amide
4'-[(2-n-butyl-5-and 6-trifluoromethyl-benzimidazol-1-yl)-methyl]biphenyl-2-carboxylic acid-(N-methanesulphonyl)-amide
4'-[(2-n-butyl-5-and 6-n-butylaminocarbonyl-benzimidazol-1-yl)-methyl]biphenyl-2-carboxylic acid-(N-methanesulphonyl)-amide
4'-[(2-n-butyl-5-dimethylaminosulphonyl-benzimidazol-1-yl)-methyl]biphenyl-2-carboxylic acid-(N-methanesulphonyl)-amide
4'-[(2-n-butyl-7-cyano-benzimidazol-1-yl)-methyl]-biphenyl-2-carboxylic acid-(N-methanesulphonyl)-amide
4'-[(2-n-butyl-6-cyclohexylaminocarbonyl-benzimidazol-1-yl)-methyl]biphenyl-2-carboxylic acid-(N-methanesulphonyl)-amide
4'-[(2-n-butyl-6-(N-methyl-n-butylaminocarbonyl)-benzimidazol-1-yl)-methyl]biphenyl-2-carboxylic acid-(N-methanesulphonyl)-amide
4'-[(2-n-butyl-6-cyclohexylcarbonylamino-benzimidazol-1-yl)-methyl]biphenyl-2-carboxylic acid-(N-methanesulphonyl)-amide
4'-[(2-n-butyl-6-(N-cyclohexylaminocarbonyl-n-pentylamino)-benzimidazol-1-yl)-methyl]biphenyl-2-carboxylic acid-(N-methanesulphonyl)-amide
4'-[(6-butanoylamino-2-n-butyl-benzimidazol-1-yl)-methyl]biphenyl-2-carboxylic acid-(N-methanesulphonyl)-amide
4'-[(2-n-butyl-6-propionylamino-benzimidazol-1-yl)-methyl]biphenyl-2-carboxylic acid-(N-methanesulphonyl)-amide
4'-[(2-n-butyl-5-(N-methylaminocarbonyl-n-pentylamino)-benzimidazol-1-yl)-methyl]biphenyl-2-carboxylic acid-(N-methanesulphonyl)-amide
4'-[(2-n-butyl-6-(N-(n-butylaminocarbonyl)-methylamino)-benzimidazol-1-yl)-methyl]biphenyl-2-carboxylic acid-(N-methanesulphonyl)-amide
4'-[(2-n-butyl-5-(N-propanoyl-methylamino)-benzimidazol-1-yl)-methyl]biphenyl-2-carboxylic acid-(N-methanesulphonyl)-amide 4'-[(2-n-butyl-5-formylamino-benzimidazol-1-yl)-methyl]biphenyl-2-carboxylic acid-(N-methane-sulphonyl)-amide 4'-[(2-n-butyl-6-(N-methylaminocarbonyl-n-pentylamino)-benzimidazol-1-yl)-methyl]biphenyl-2-carboxylic acid-(N-methanesulphonyl)-amide 4'-[(6-aminothiocarbonylamino-2-n-butyl-benzimidazol-1-yl)-methyl]biphenyl-2-carboxylic acid-(N-methanesulphonyl)-amide 4'-[(2-n-butyl-7-methoxy-benzimidazol-1-yl)-methyl]biphenyl-2-carboxylic acid-(N-methanesulphonyl)-amide 4'-[(2-n-butyl-6-cyclohexylmethylaminocarbonyl-benzimidazol-1-yl)-methyl]biphenyl-2-carboxylic acid-(N-methanesulphonyl)-amide 4'-[(2-n-butyl-6-methoxy-benzimidazol-1-yl)-methyl]-biphenyl-2-carboxylic acid-(N-trifluoromethanesulphonyl)-amide 4'-[(2-methoxymethyl-benzimidazol-1-yl)-methyl]biphenyl-2-carboxylic acid-(N-trifluoromethanesulphonyl)-amide 4'-[(2-n-pentyl-benzimidazol-1-yl)-methyl]bi-phenyl-2-carboxylic acid-(N-trifluoromethane-sulphonyl)-amide 4'-[(2-n-butyl-4-methyl-7-methoxy-benzimidazol-1-yl)-methyl]biphenyl-2-carboxylic acid-(N-trifluoromethanesulphonyl)-amide 4'-[(2-n-propyl-benzimidazol-1-yl)-methyl]biphenyl-2-carboxylic acid-(N-trifluoromethanesulphonyl)-amide 4'-[(2-n-butyl-5-acetamino-benzimidazol-1-yl)-methyl]-biphenyl-2-carboxylic acid-(N-trifluoromethanesulphonyl)-amide 4'-[(2-n-butyl-5-chloro-benzimidazol-1-yl)-methyl]-biphenyl-2-carboxylic acid-(N-trifluoromethanesulphonyl)-amide 4'-[(2-n-butyl-5-butylaminocarbonylamino-benzimidazol-1-yl)-methyl]biphenyl-2-carboxylic acid-(N-trifluoromethanesulphonyl)-amide 4'-[(2-n-butyl-6-phenylaminocarbonylamino-benzimidazol-1-yl)-methyl]biphenyl-2-carboxylic acid-(N-trifluoromethanesulphonyl)-amide 4'-[(2-n-butyl-6-cyclohexylaminocarbonylamino-benzimidazol-1-yl)-methyl]biphenyl-2-carboxylic acid-(N-trifluoromethanesulphonyl)-amide 4'-[(2-n-butyl-5-butanoylamino-benzimidazol-1-yl)-methyl]biphenyl-2-carboxylic acid-(N-trifluoromethanesulphonyl)-amide 4'-[(2-n-butyl-6-chloro-benzimidazol-1-yl)-methyl]-biphenyl-2-carboxylic acid-(N-trifluoromethanesulphonyl)-amide 4'-[(2-n-butyl-5-methanesulphonamino-benzimidazol-1-yl)-methyl]biphenyl-2-carboxylic acid-(N-trifluoromethanesulphonyl)-amide 4'-[(2-n-butyl-6-ethoxycarbonylamino-benzimidazol-1-yl)-methyl]biphenyl-2-carboxylic acid-(N-trifluoromethanesulphonyl)-amide 4'-[(2-n-butyl-6-isopropylsulphonamino-benzimidazol-1-yl)-methyl]biphenyl-2-carboxylic acid-(N-trifluoromethanesulphonyl)-amide 4'-[(2-n-butyl-4-butanoylamino-benzimidazol-1-yl)-methyl]biphenyl-2-carboxylic acid-(N-trifluoromethanesulphonyl)-amide 4'-[(2-n-butyl-6-dimethylamino-benzimidazol-1-yl)-methyl]biphenyl-2-carboxylic acid-(N-trifluoromethanesulphonyl)-amide 4'-[(2-n-butyl-5,6-dimethoxy-benzimidazol-1-yl)-methyl]biphenyl-2-carboxylic acid-(N-trifluoromethanesulphonyl)-amide 4'-[(2-(1-butyn-4-yl)-benzimidazol-1-yl)-methyl]biphenyl-2-carboxylic acid-(N-trifluoromethanesulphonyl)-amide 4'-[(2-n-butyl-5-and 6-trifluoromethyl-benzimidazol-1-yl)-methyl]biphenyl-2-carboxylic acid-(N-trifluoromethanesulphonyl)-amide 4'-[(2-n-butyl-5-and 6-n-butylaminocarbonyl-benzimidazol-1-yl)-methyl]biphenyl-2-carboxylic acid-(N-trifluoromethanesulphonyl)-amide 4'-[(2-n-butyl-5-dimethylaminosulphonyl-benzimidazol-1-yl)-methyl]biphenyl-2-carboxylic acid-(N-trifluoromethanesulphonyl)-amide 4'-[(2-n-butyl-7-cyano-benzimidazol-1-yl)-methyl]-biphenyl-2-carboxylic acid-(N-trifluoromethanesulphonyl)-amide 4'-[(2-n-butyl-6-cyclohexylaminocarbonyl-benzimid-azol-1-yl)-methyl]biphenyl-2-carboxylic acid-(N-trifluoromethanesulphonyl)-amide 4'-[(2-n-butyl-6-(N-methyl-n-butylaminocarbonyl)-benzimidazol-1-yl)-methyl]biphenyl-2-carboxylic acid-(N-trifluoromethanesulphonyl)-amide 4'-[(2-n-butyl-6-cyclohexylcarbonylamino-benzimidazol-1-yl)-methyl]biphenyl-2-carboxylic acid-(N-trifluoromethanesulphonyl)-amide 4'-[(2-n-butyl-6-(N-cyclohexylaminocarbonyl-n-pentylamino)-benzimidazol-1-yl)-methyl]biphenyl-2-carboxylic acid-(N-trifluoromethanesulphonyl)-amide 4'-[(6-n-butanoylamino-2-n-butyl-benzimidazol-1-yl)-methyl]biphenyl-2carboxylic acid-(N-trifluoromethanesulphonyl)-amide 4'-[(2-n-butyl-6-propionylamino-benzimidazol-1-yl)-methyl]biphenyl-2-carboxylic acid-(N-trifluoromethanesulphonyl)-amide 4'-[(2-n-butyl-5-(N-methylaminocarbonyl-n-pentylamino)-benzimidazol-1-yl)-methyl]biphenyl-2-carboxylic acid-(N-trifluoromethanesulphonyl)-amide 4'-[(2-n-butyl-6-(N-(n-butylaminocarbonyl)-methylamino)-benzimidazol-1-yl)-methyl]biphenyl-2-carboxylic acid-(N-trifluoromethanesulphonyl)-amide 4'-[(2-n-butyl-5-(N-propanoyl-methylamino)-benzimidazol-1-yl)-methyl]biphenyl-2-carboxylic acid-(N-trifluoromethansulphonyl)-amide 4'-[(2-n-butyl-5-formylamino-benzimidazol-1-yl)-methyl]biphenyl-2-carboxylic acid-(N-trifluoromethanesulphonyl)-amide 4'-[(2-n-butyl-6-(N-methylaminocarbonyl-n-pentylamino)-benzimidazol-1-yl)-methyl]biphenyl-2-carboxylic acid-(N-trifluoromethanesulphonyl)-amide 4'-[(6-aminothiocarbonylamino-2-n-butyl-benzimidazol-1-yl)-methyl]biphenyl-2-carboxylic acid-(N-trifluoromethanesulphonyl)-amide 4'-[(2-n-butyl-7-methoxy-benzimidazol-1-yl)-methyl]-biphenyl-2-carboxylic acid-(N-trifluoromethanesulphonyl)-amide 4'-[(2-n-butyl-6-cyclohexylmethylaminocarbonyl-benzimidazol-1-yl)-methyl]biphenyl-2-carboxylic acid-(N-trifluoromethanesulphonyl)-amide 4'-[(2-n-butyl-6-methoxy-benzimidazol-1-yl)-methyl]-biphenyl-2-carboxylic acid-(N-benzenesulphonyl)-amide 4'-[(2-methoxymethyl-benzimidazol-1-yl)-methyl]biphenyl-2-carboxylic acid-(n-benzenesulphonyl)-amide 4'-[(2-n-pentyl-benzimidazol-1-yl)-methyl]biphenyl-2-carboxylic acid-(N-benzenesulphonyl)-amide 4'-[(2-n-butyl-4-methyl-7-methoxy-benzimidazol-1-yl)-methyl]biphenyl-2-carboxylic acid-(N-benzenesulphonyl)-amide 4'-[(2-n-propyl-benzimidazol-1-yl)-methyl]biphenyl-2-carboxylic acid-(N-benzenesulphonyl)-amide 4'-[(2-n-butyl-5-acetamino-benzimidazol-1-yl)-methyl]-biphenyl-2-carboxylic acid-(N-benzenesulphonyl)-amide 4'-[(2-n-butyl-5-chloro-benzimidazol-1-yl)-methyl]-biphenyl-2-carboxylic acid-(N-benzenesulphonyl)-amide 4'-[(2-n-butyl-5-butylaminocarbonylamino-benzimidazol-1-yl)-methyl]biphenyl-2-carboxylic acid-(N-benzenesulphonyl)-amide 4'-[(2-n-butyl-6-phenylaminocarbonylamino-benzimidazol-1-yl)-methyl]biphenyl-2-carboxylic acid-(N-benzenesulphonyl)-amide 4'-[(2-n-butyl-4-cyclohexylaminocarbonylamino-benzimidazol-1-yl)-methyl]biphenyl-2-carboxylic acid-(N-benzenesulphonyl)-amide 4'-[(2-n-butyl-5-butanoylamino-benzimidazol-1-yl)-methyl]biphenyl-2-carboxylic acid-(N-benzenesulphonyl)-amide 4'-[(2-n-butyl-6-chloro-benzimidazol-1-yl)-methyl]-biphenyl-2-carboxylic acid-(N-benzenesulphonyl)-amide 4'-[(2-n-butyl-5-methanesulphonamino-benzimidazol-1-yl)-methyl]biphenyl-2-carboxylic acid-(N-benzenesulphonyl)-amide 4'-[(2-n-butyl-6-ethoxycarbonylamino-benzimidazol-1-yl)-methyl]biphenyl-2-carboxylic acid-(N-benzenesulphonyl)-amide 4'-[(2-n-butyl-6-isopropylsulphonamino-benzimidazol-1-yl)-methyl]biphenyl-2-carboxylic acid-(N-benzenesulphonyl)-amide 4'-[(2-n-butyl-4-butanoylamino-benzimidazol-1-yl)-methyl]biphenyl-2-carboxylic acid-(N-benzenesulphonyl)-amide 4'-[(2-n-butyl-6-dimethylamino-benzimidazol-1-yl)-methyl]biphenyl-2-carboxylic acid-(N-benzenesulphonyl)-amide 4'-[(2-n-butyl-5,6-dimethoxy-benzimidazol-1-yl)-methyl]biphenyl-2-carboxylic acid-(N-benzene-sulphonyl)-amide 4'-[(2-(1-butyn-4-yl)-benzimidazol-1-yl)-methyl]biphenyl-2-carboxylic acid-(N-benzenesulphenyl)-amide.

4'-[(2-n-butyl-5-and 6-trifluoromethyl-benzimidazol-1-yl)-methyl]biphenyl-2-carboxylic acid-(N-benzenesulphonyl)-amide 4'-[(2-n-butyl-5-and 6-n-butylaminocarbonyl-benzimidazol-1-yl)-methyl]biphenyl-2-carboxylic acid-(N-benzenesulphonyl)-amide 4'-[(2-n-butyl-5-dimethylaminosulphonyl-benzimidazol-1-yl)-methyl]biphenyl-2-carboxylic acid-(N-benzenesulphonyl)-amide 4'-[(2-n-butyl-7-cyano-benzimidazol-1-yl)-methyl] biphenyl-2-carboxylic acid-(N-benzenesulphonyl)-amide 4'-[(2-n-butyl-6-cyclohexylaminocarbonyl-benzimid-azol-1-yl)-methyl]biphenyl-2-carboxylic acid-(N-benzenesulphenyl)-amide 4'-[(2-n-butyl-6-(N-methyl-n-butylaminocarbonyl)-benzimidazol-1-yl)-methyl]biphenyl-2-carboxylic acid-(N-benzenesulphonyl)-amide 4'-[(2-n-butyl-6-cyclohexylcarbonylamino-benzimid-azol-1-yl)-methyl]biphenyl-2-carboxylic acid-(N-benzenesulphonyl)-amide 4'-[(2-n-butyl-6-(N-cyclohexylaminocarbonyl-n-pentylamino)-benzimidazol-1-yl)-methyl]biphenyl-2-carboxylic acid-(N-benzenesulphonyl)-amide 4'-[(6-n-butanoylamino-2-n-butyl-benzimidazol-1-yl)-methyl]biphenyl-2-carboxylic acid-(N-benzene-sulphonyl)-amide 4'-[(2-n-butyl-6-propionylamino-benzimidazol-1-yl)-methyl]biphenyl-2-carboxylic acid-(N-benzenesulphonyl)-amide 4'-[(3-n-butyl-5-(N-methylaminocarbonyl-n-pentylamino)-benzimidazol-1-yl)-methyl]biphenyl-2-carboxylic acid-(N-benzenesulphenyl)-amide 4'-[(2-n-butyl-6-(N-butylaminocarbonyl)-methylamino)-benzimidazol-1-yl)-methyl]biphenyl-2-carboxylic acid-(N-benzenesulphonyl)-amide 4'-[(2-n-butyl-5-(N-propanoyl-methylamino)-benzimidazol-1-yl)-methyl]biphenyl-2-carboxylic acid-(N-benzenesulphonyl)-amide 4'-[(2-n-butyl-5-formylamino-benzimidazol-1-yl)-methyl] biphenyl-2-carboxylic acid-(N-benzenesulphonyl))-amide 4'-[(2-n-butyl-4-(N-methylaminocarbonyl-n-pentylamino)-benzimidazol-1-yl)-methyl]biphenyl-2-carboxylic acid-(N-benzenesulphonyl)-amide 4'-[(6-aminothiocarbonylamino-2-n-butyl-benzimidazol-1-yl)-methyl]biphenyl-2-carboxylic acid-(N-benzenesulphenyl)-amide 4'-[(2-n-butyl-7-methoxy-benzimidazol-1-yl)-methyl]-biphenyl-2-carboxylic acid-(N-benzenesulphonyl)-amide 4'-[(2-n-butyl-6-cyclohexylmethylaminocarbonyl-benzimidazol-1-yl)-methyl]biphenyl-2-carboxylic acid-(N-benzenesulphonyl)-amide

Example 199

4'-[(2-n-Butyl-6-formylamino-benzimidazol-1-yl)-methyl]biphenyl-2-carboxylic acid x 0.75 trifluoroacetic acid Prepared in analogous manner to Example 9 from tert. butyl 4'-[(2-n-butyl-6-formylamino-benzimidazol-1-yl)-methyl]biphenyl-2-carboxylic and trifluoroacetic acid.

Yield: 84.0% of theoretical, p Melting point: 110°–112° C. (amorphous) $C_{33}H_{37}N_2O_3$ x 0.75 $CF_3COOH$ (513.02)

Calculated: C 64.38 H 5.06 N 8.19 Found: 64.70 5.25 7.91

Example 200

4'-[(2-n-Butyl-6-(N-cyclohexylaminocarbonyl-cyclohexylamino)-benzimidazol-1-yl)-methyl] biphenyl-2-carboxylic acid semi-trifluoroacetate Prepared in analogous manner to Example 9 from tert. butyl 4'-[(2-n-butyl-6-(N-cyclohexylaminocarbonyl-cyclohexylamino)-benzimidazol-1-yl)-methyl]biphenyl-2-carboxylate and trifluoroacetic acid.

Yield: 91.9% of theoretical,

Melting point: 130°–132° C. (amorphous) $C_{38}H_{46}N_4O_3$ x 0.5 $CF_2COOH$ (663.82)

Calculated: C 70.57 H 7.06 N 8.44 Found: 70.48 7.13 8.60

Example 301

4'-[(2-n-Butyl-6-(N-(n-butylaminocarbonyl) cyclohexylamino)-benzimidazol-1-yl)-methyl] biphenyl-2-carboxylic acid Prepared in analogous manner to Example 9 from tert. butyl 4'-[(2-n-butyl-6-(N-(n-butylaminocarbonyl)-cyclohexylamino)-benzimidazol-1-yl)-methyl]biphenyl-2-carboxylate and trifluoroacetic acid.

Yield: 85.7% of theoretical,

Melting point: 227°–228° C. $C_{38}H_{44}H_4O_2$ (580.77)

Calculated: C 74.48 H 7.64 N 9.45 Found: 74.32 7.70 9.50

Example 202

4'-[(2-n-butyl-6-(N-methylaminocarbonyl-cyclohexyl-amino)-benzimidazol-1-yl)-methyl] biphenyl-2-carboxylic acid Prepared in analogous manner to Example 9 from tert. butyl 4'-[(2-n-butyl-6-(N-methylaminocarbonylcyclohexylamino)-benzimidazol-1-yl)-methyl]biphenyl-2-carboxylate and trifluoroacetic acid.

Yield: 88.3% of theoretical,

Melting point: 204°–206° C. $C_{32}H_{30}N_4O_3$ (536.69)

Calculated; C 73.58 N 7.11 N 10.40 Found: 73.65 6.99 10.49

Example 203

4'-[(2-n-Butyl-6-(N-ethoxycarbonyl-cyclohexylamino)-benzimidazol-1-yl)-methyl]biphenyl-2-carboxylic acid Prepared in analogous manner to Example 9 from tert. butyl 4'-[(2-n-butyl-6-(N-ethoxycarbonyl-cyclohexylamino)-benzimidazol-1-yl)-methyl]biphenyl-2-carboxylic and trifluoroacetic acid.

Yield: 89.0% of theoretical,

Melting point: 239°–240° C. $C_{34}H_{30}N_3O_4$ (553.70)

Calculated: C 73.75 H 7.10 N7.59 Found: 73.76 7.25 7.68

Example 204

4'-[(2-n-Butyl-6-cyclohexylacetamino-benzimidazol-1-yl)-methyl]biphenyl-2-carboxylic acid x 0.7 trifluoroacetic acid Prepared in analogous manner to Example 9 from tert. butyl 4'-[(2-n-butyl-6-cyclohexylacetamino-benzimidazol-1-yl)-methyl]biphenyl-2-carboxylate and trifluoroacetic acid.

Yield: 97.5% of theoretical,

Melting point: 117°–119° C. $C_{33}H_{37}N_3O_3$ x 0.7 $CF_3COOH$ (603.49)

Calculated: C 68.46 H 6.30 N 6.98 Found: 68.80 6.60 6.73

Example 205

4'-[(2-n-Butyl-6-phthalimino-benzimidazol-1-yl)-methyl]biphenyl-3-carboxylic acid semi-trifluoroacetate Prepared in analogous manner to Example 9 from tert. butyl 4'-[(2-n-butyl-6-phthalimino-benzimidazol-1-yl)-methyl]biphenyl-2-carboxylate and trifluoroacetic acid in methylene chloride.

Yield: 85.5% of theoretical,

Melting point: 181°–183° C. $C_{33}H_{25}N_2O_4$ x 0.5 $CF_3COOH$ (586.61)

Calculated: C 69.62 H 4.73 N 7.16 Found: 69.70 4.81 7.31

Example 206

4'-[(2-n-Butyl-benzimidazol-1-yl)-methyl]biphenyl-2-carboxylic acid-(N-methanesulphonyl)-amide Prepared in analogous manner to Example 198 from 4'-[(2-n-butyl-benzimidazol-1-yl)-methyl]biphenyl-2-carboxylic acid and thionyl chloride/methanesulphon-amide.

Yield: 32.4% of theoretical,

Melting point: 127°–129° C. $C_{20}H_{27}N_3O_3S$ (461.50)

Calculated: C 67.67 H 5.90 N 9.10 S 6.92 Found: 67.52 6.10 9.07 6.87

Example 207

4'-[(2-n-Butyl-6-((5-trifluoroacetoxy-n-pentyl)-aminocarbonylamino)-benzimidazol-1-yl)-methyl]biphenyl-2-carboxylic acid semi-trifluoroacetate semi-hydrate 1.92 g (3.3 mmol) of tert.butyl 4'-[(2-n-butyl-6-(tetrahydropyran-2-yl-aminocarbonylamino)-benzimidazol-1-yl)-methyl]biphenyl-2-carboxylate are dissolved in 100 ml of ethanol and 1.9 g of Raney nickel is added. The reaction solution is then hydrogenated for 4 hours at 120° C. and 100 bar hydrogen. Catalyst is then filtered off under suction and the solvent is distilled off in vacuum. The oil residue is purified over a column (silicon gel; grain size: 0.063–0.2 mm), the column being eluted using methylene chloride and increasing parts of 2–5% ethanol. After rotary evaporation of the appropriate fractions, the oil obtained is dissolved in a mixture of 10 ml of methylene chloride and 10 ml of trifluoroacetic acid, and the solution is left for 18 hours at ambient temperature. The solvent is removed by rotary evaporation, the residue is dissolved is about 50 ml of ethyl acetate and the organic phase is washed 3 times using about 50 ml of water. The organic solution is dried using about 20 g of magnesium sulphate, filtered off and rotary evaporated. The product thus obtained is dried at 50° C. is vacuum.

Yield: 1.5 g (66.0% of theoretical),

Melting point: 80°–82° C. (amorphous)

Calculated: C 59.13 H 5.33 N 8.11 Found: 59.22 5.52 7.95

Example 208

4'-[(2-n-Butyl-6-(N-ethoxycarbonyl-benzylamino)-benzimidazol-1-yl)-methyl]biphenyl-2-carboxylic acid Prepared in analogous manner to Example 9 from tert. butyl 4'-[(2-n-butyl-6-(N-ethoxycarbonyl-bensylamino)-benzimidazol-1-yl)-methyl]biphenyl-2-carboxylate and trifluoroacetic acid.

Yield: 86.4% of theoretical,

Melting point: 218°–220° C. $C_{25}H_{29}N_3O_4$ (561.68)

Calculated: C 74.84 H 6.28 N 7.48 Found: 74.57 6.14 7.59

Example 209

4'-[(2-n-Butyl-6-(N-methylaminocarbonyl-benzylamino)-benzimidazol-1-yl)-methyl]biphenyl-2-carboxylic acid Prepared in analogous manner to Example 9 from tert. butyl 4'-[(2-n-butyl-6-(N-methylaminocarbonyl-benzylamino)-benzimidazol-1-yl)-methyl]biphenyl-2-carboxylate and trifluoroacetic acid.

Yield: 83.3% of theoretical,

Melting point: 247°–249° C. $C_{34}H_{34}N_4O_3$ (546.67)

Calculated: C 74.70 H 6.27 N 10.25 Found: 74.95 6.37 10.12

Example 210

4'-[(2-n-Butyl-6-(n-hexyloxycarbonylamino)-benzimidazol-1-yl)-methyl]biphenyl-2-carboxylic acid Prepared in analogous manner to Example 9 from tert. butyl 4'-[(2-n-butyl-6-(n-hexyloxycarbonylamino)-benzimidazol-1-yl)-methyl]biphenyl-2-carboxylate and trifluoroacetic acid.

Yield: 89.5% of theoretical,

Melting point: 243°–244° C. $C_{23}H_{37}N_2O_4$ (527.66)

Calculated: C 72.84 H 7.07 N 7.96 Found: 72.65 7.15 7.98

Example 211

4'-[(2-n-Butyl-6-(N-hexylaminocarbonyl)-benzylamino)-benzimidazol-1-yl)-methyl]biphenyl-2-carboxylic acid Prepared in analogous manner to Example 6 from tert. butyl 4'-[(2-n-butyl-6-(N-(n-hexylaminocarbonyl)- benzylamino)-benzimidazol-1-yl)-methyl]biphenyl-2-carboxylate and trifluoroacetic acid.

Yield: 69.2% of theoretical,

Melting point: 186°–187° C. $C_{30}H_{44}N_4O_2$ (616.80)

Calculated: C 75.94 N 7.19 N 9.08 Found: 75.85 7.24 9.14

Example 212

4'-[(2-n-Butyl-6-(n-pentylamino)-benzimidazol-1-yl-methyl]biphenyl-2-carboxylic acid Prepared in analogous manner to Example 9 from tert. butyl 4'-[(2-n-butyl-6-(n-pentylamino)-benzimidazol-1-yl)-methyl]biphenyl-2-carboxylic and trifluoroacetic acid/methylene chloride.

Yield: 75% of theoretical,

Melting point: 108°–113° C. $C_{30}H_{35}N_3O_3$ (469.62)

Calculated: C 76.73 H 7.51 N 8.94 Found: 76.56 7.40 8.91

Example 213

4'-[(2-n-Butyl-6-(5,7-dioxo-1H,3H-imidazol[1,5-c]thiazol-4-yl)-benzimidazol-1-yl)-methyl]biphenyl-2-carboxylic acid Prepared in analogous manner to Example 9 from tert. butyl 4'-[(2-n-butyl-6-(5,7-dioxo-1H,3H-imidazo-[1,5-c]thiazol-6-yl)-benzimidazol-1-yl)-methyl]biphenyl-2-carboxylate and trifluoroacetic acid.

Yield: 95.1% of theoretical,

Melting point: 229°–239° C. $C_{30}H_{28}N_4O_4S$ (540.64)

Calculated: C 66.65 H 5.22 N 10.36 S 5.93 Found: 66.42 5.29 10.15 6.01

Example 214

4'-[(2-n-Butyl-6-((5-hydroxy-n-pentyl)-aminocarbonylamino)-benzimidazol-1-yl)-methyl]biphenyl-2-carboxylic acid monohydrate Prepared in analogous manner to Example 72 from ethyl 4'-[(2-n-butyl-6-((5-hydroxy-n-pentyl)-aminocarbonyl-amino)-benzimidazol-1-yl)methyl]biphenyl-2-carboxylate and 2N NaOH/ethanol.

Yield: 50.0% of theoretical,

Melting point: 158°–160° C. $C_{21}H_{29}N_4O_4$ x $H_2O$ (546.67)

Calculated: C 68.11 H 7.01 N 10.25 Found: 68.01 6.90 10.30

Example 215

Ethyl 4'-[(2-n-butyl-6-((5-hydroxy-n-pentyl)-aminocarbonyl-amino)-benzimidazol-1-yl)-methyl]biphenyl-2-carboxylate 7.5 g (13.5 mmol) of ethyl 4'-[(2-n-butyl-6-(tetrahydro-pyran-2-ylaminocarbonylamino)-benzimidazol-1-yl)-methyl]biphenyl-2-carboxylate are dissolved in 250 ml of ethanol and 7.5 g of Raney nickel are added. The solution is then hydrogenated in an autoclave for 2 hours at 120° C. and 100 bar of hydrogen. The catalyst is then filtered off under suction and the solvent is distilled off in vacuum. The oily product obtained is purified over a column (silica gel; grain size: 0.043–0.2 mm), the column being eluted using ethyl acetate/petroleum ether (9/1) and using ethyl acetate/ethanol (99/1). The appropriate fractions are evaporated in vacuum and dried at 50° C. in a vacuum drying oven.

Yield: 2.6 g (34.7% of theoretical), oil, $R_f$: 0.50 (silica gel: ethyl acetate/ethanol=9:1)

Example 216

4'-[(2-n-Butyl-6-(N-(n-butanoyl)-n-butylamino)-benzimidazol-1-yl)-methyl]biphenyl-2-carboxylic acid Prepared in analogous manner to Example 9 from tert. butyl 4'-[(2-n-butyl-6-(N-(n-butanoyl)-n-butylamino)-benzimidazol-1-yl)methyl]biphenyl-2-carboxylate and trifluoroacetic acid.

Yield: 90.6% of theoretical,

Melting point: 234°–235° C. $C_{33}H_{38}N_3O_3$ (525.69)

Calculated: C 75.40 H 7.48 N 7.99 Found: 75.55 7.49 8.02

Example 217

4'-[(2-n-Butyl-6-(N-(4-methyloxycarbonyl-thiazolidine-3-yl-carbonyl)-n-butylamino)-benzimidazol-1-yl)-methyl]biphenyl-2-carboxylic acid Prepared in analogous manner to Example 9 from tert. butyl 4'-[(2-n-butyl-6-(N-(4-methoxycarbonyl-thiazolidin-3-ylcarbonyl)-n-butylamino)-benzimidazol-1-yl)-methyl]biphenyl-2-carboxylate and trifluoroacetic acid.

Yield: 92.6% of theoretical,

Melting point: 86°–88° C. (amorphous) $C_{35}H_{40}N_4O_3S$ (628.79)

Calculated: C 66.86 H 6.41 N 8.91 S 5.10 Found: 66.68 6.40 8.50 5.41

Example 218

4'-[(2-n-Butyl-6-(N-cyclohexylaminocarbonyl-n-butyl-amino)-benzimidazol-1-yl)-methyl]biphenyl-2-carboxylic acid Prepared in analogous manner to Example 9 from tert. butyl 4'-[(2-n-butyl-6-(N-cyclohexylaminocarbonyl-n-butylamino)-benzimidazol-1-yl)-methyl]biphenyl-2-carboxylate and trifluoroacetic acid.

Yield: 96.8% of theoretical,

Melting point: 106°–108° C. (amorphous) $C_{38}H_{44}N_4O_3$ (580.77)

Calculated: C 74.45 H 7.64 N 9.65 Found: 74.54 7.65 9.50

Example 219

4'-[(2-n-Butyl-6-(N-cyclohexylaminocarbonyl-benzyl-amino)-benzimidazol-1-yl)-methyl]biphenyl-2-carboxylic acid Prepared in analogous manner to Example 9 from tert. butyl 4'-[(2-n-butyl-6-(N-cyclohexylaminocarbonyl-benzylamino)-benzimidazol-1-yl)-methyl]biphenyl-2-carboxylate.

Yield: 95.0% of theoretical,

Melting point: 203°–204° C. $C_{38}H_{42}N_4C_3$ (614.79)

Calculated: C 76.19 H 6.89 N 9.11 Found: 75.93 7.04 9.34

Example 220

4'-[(2-n-Butyl-6-(N-(2-trifluoromethylphenylamino-carbonyl)-methylamino)-benzimidazol-1-yl)-methyl]-biphenyl-2-carboxylic acid Prepared in analogous manner to Example 5 from tert. butyl 4'-[(2-n-butyl-6-(N-(2-trifluoromethylphenylaminocarbonyl)-methylamino)-benzimidazol-1-yl)-methyl]-biphenyl-2-carboxylate and trifluoroacetic acid/methylene chloride.

Yield: 72.2% of theoretical,

Melting point: 142°–144° C. $C_{34}H_{31}F_3N_4O_2$ x $CF_3COOH$ (714.67)

Calculated: C 60.52 H 4.51 N 7.84 Found: 60.3 4.48 8.03

Example 221

4'-[(2-n-Butyl-6-(N-cyclohexylaminocarbonyl-n-hexyl-amino)-benzimidazol-1-yl)-methyl]biphenyl-2-carboxylic acid Prepared in analogous manner to Example 9 from tert. butyl 4'-[(2-n-butyl-6-(N-cyclohexylamino-carbonyl-n-hexylamino)-benzimidazol-1-yl)-methyl]-biphenyl-2-carboxylate and trifluoroacetic acid.

Yield: 94.1% of theoretical,

Melting point: 177°–178° C. $C_{38}H_{40}N_4O_3$ (608.82)

Calculated: C 74.97 H 7.95 N 9.20 Found: 74.75 8.04 9.09

Example 222

4'-[(2-n-Butyl-6-(N-cyclohexylcarbonyl-n-hexylamino)-benzimidazol-1-yl)-methyl]biphenyl-2-carboxylic acid Prepared in analogous manner to Example 9 from tert. butyl 4'-[(2-n-butyl-6-(N-cyclohexylcarbonyl-n-hexylamino)-benzimidazol-1-yl)-methyl]biphenyl-2-carboxylate and trifluoroacetic acid.

Yield: 92.8% of theoretical,

Melting point: 195°–197° C. $C_{38}H_{47}H_3O_3$ (593.81)

Calculated: C 76.86 H 7.98 N 7.08 Found: 76.66 7.94 7.16

Example 223

4'-[(2-n-Butyl-6-(N-cyclohexylaminocarbonyl-n-propylamino)-benzimidazol-1-yl)-methyl]biphenyl-2-carboxylic acid Prepared in analogous manner in Example 9 from tert. butyl 4'-[(2-n-butyl-6-(N-cyclohexylaminocarbonyl-n-propylamino)-benzimidazol-1-yl)-methyl]biphenyl-2-carboxylate and trifluoroacetic acid.

Yield: 93.5% of theoretical,

Melting point: 180°–182° C. $C_{35}H_{42}N_4O_3$ (566.74)

Calculated: C 74.18 H 7.47 N 9.80 Found: 73.98 7.54 10.05

Example 224

4'-[(2-n-Butyl-6-(N-cyclohexylcarbonyl-methylamino)-benzimidazol-1-yl)-methyl]biphenyl-2-carboxylic acid semi-hydrate Prepared in analogous manner to Example 9 from tert. butyl 4'-[(2-n-butyl-6-(N-cyclohexylcarbonyl-methylamino)-benzimidazol-1-yl)-methyl]biphenyl-2-carboxylate and trifluoroacetic acid.

Yield: 93.8% of theoretical,

Melting point: 230°–231° C. $C_{32}H_{37}N_3O_3$ x 0.5 $H_2O$ (532.68)

Calculated: C 74.41 H 7.19 N 7.89 Found: 74.59 7.14 7.70

Example 225

4'-[(2-n-Butyl-6-(N-cyclohexylaminocarbonyl-ethyl-amino-benzimidazol-1-yl)-methyl]biphenyl-2-carboxylic acid Prepared in analogous manner to Example 9 from tert. butyl 4'-[(2-n-butyl-6-(N-cyclohexylaminocarbonyl-ethylamino)-benzimidazol-1-yl)-methyl]biphenyl-2-carboxylate and trifluoroacetic acid.

Yield: 95.5% of theoretical,

Melting point: 185°–186° C. $C_{34}H_{40}N_4O_3$ (552.72)

Calculated: C 73.89 H 7.29 N 10.14 Found: 73.79 7.13 10.11

Example 226

4'-[(2-n-Butyl-6-(N-(n-butanoyl)-n-pentylamino)-benzimidazol-1-yl)-methyl]biphenyl-2-carboxylic acid Prepared in analogous manner to Example 9 from tert. butyl 4'-[(2-n-butyl-6-(N-(n-butanoyl)-n-pentylamino)-benzimidazol-1-yl)-methyl]biphenyl-2-carboxylate and trifluoroacetic acid.

Yield: 77.8% of theoretical,

Melting point: 206°–208° C. $C_{34}H_{41}N_3O_3$ (539.72)

Calculated: C 75.66 H 7.66 N 7.79 Found: 75.54 7.47 7.67

Example 237

4'-[(2-n-Butyl-6-isopropylcarbonylamino-benzimidazol-1-yl)-methyl]biphenyl-2-carboxylic acid Prepared in analogous manner to Example 9 from tert. butyl 4'-[(2-n-butyl-6-isopropylcarbonylamino-benzimidazol-1-yl)-methyl]biphenyl-2-carboxylic and trifluoroacetic acid.

Yield: 73.3% of theoretical,

Melting point: 273°–275° C. $C_{28}H_{31}N_3O_2$ (469.58)

Calculated: C 74.18 H 6.65 H 8.95 Found: 73.93 6.66 8.84

Example 228

4'-[(2-n-Butyl-6-(N-ethoxycarbonyl-methylamino)-benzimidazol-1-yl)-methyl]biphenyl-2-carboxylic acid Prepared in analogous manner to Example 9 from tert. butyl 4'-[(2-n-butyl-6-(N-ethoxycarbonyl-methylamino)-benzimidazol-1-yl)-methyl]biphenyl-2-carboxylate and trifluoroacetic acid.

Yield: 91.8% of theoretical,

Melting point: 190°–192° C. $C_{28}H_{31}N_3O_4$ (485.58)

Calculated: C 71.73 H 6.43 N 8.65 Found: 71.60 6.40 8.69

Example 229

4'-[(2-n-Butyl-6-(N-ethoxycarbonyl-n-pentylamino)-benzimidazol-1-yl)-methyl]biphenyl-2-carboxylic acid Prepared in analogous manner to Example 9 from tert. butyl 4'-[(2-n-butyl-6-(N-ethoxycarbonyl-n-pentyl-amino)-benzimidazol-1-yl)-methyl]biphenyl-2-carboxylate and trifluoroacetic acid/methylene chloride.

Yield: 86.9% of theoretical,

Melting point: 201°–203° C. $C_{33}H_{38}N_3O_4$ (541.69)

Calculated: C 73.17 H 7.26 N 7.76 Found: 72.97 6.98 7.69

Example 230

4'-[(2-n-Butyl-6-(N-(dimethylaminocarbonyl)-benzylamino)-benzimidazol-1-yl)-methyl]biphenyl-2-carboxylic acid Prepared in analogous manner to Example 9 from tert. butyl 4'[(2-n-butyl-6-(N-(dimethylaminocarbonyl)- benzylamino)-benzimidazol-1-yl)-methyl]biphenyl-2-carboxylate and trifluoroacetic acid.

Yield: 75.3% of theoretical,
Melting point: 202°–203° C. $C_{25}H_{39}N_4O_3$(560.69)
Calculated: C 74.98 H 6.47 N 9.99 Found: 74.89 6.24 10.02

Example 231

4'-[(2,5-Di-n-butyl-benzimidazol-1-yl)-methyl] biphenyl-2-carboxylic acid

Prepared in analogous manner to Example 9 from tert. butyl 4'-[(2,5-di-n-butyl-benzimidazol-1-yl)-methyl] biphenyl-2-carboxylate and trifluoroacetic acid/methylene chloride.

Yield: 82.6% of theoretical,
Melting point: 199°–201° C. $C_{28}H_{32}N_2O_2$ (440.58)
Calculated: C 79.06 H 7.32 N 6.36 Found: 78.87 7.29 6.58

Example 232

4'-[(2-n-Butyl-6-(N-cyclohexylaminocarbonyl-N-(2-phenylethyl)-amino)-benzimidazol-1-yl)-methyl] biphenyl-2-carboxylic acid Prepared in analogous manner to Example 9 from tert. butyl 4'-[(2-n-butyl-6-(N-cyclohexylaminocarbonyl-N-(2-phenylethyl)-amino)-benzimidazol-1-yl)-methyl]biphenyl-2-carboxylate and trifluoroacetic acid.

Yield: 70.0% of theoretical,
Melting point: 168°–170° C. $C_{40}H_{44}N_4O_2$ (628.81)
Calculated: C 76.40 H 7.05 N 8.91 Found: 76.31 7.26 8.79

Example 233

4'-[(2-n-Butyl-6-diethylaminocarbonylamino-benzimidazol-1-yl)-methyl]biphenyl-2-carboxylic acid semi-trifluoroacetate Prepared in analogous manner to Example 9 from tert. butyl 4'-[(2-n-butyl-6-diethylaminocarbonylamino-benzimidazol-1-yl)-methyl]biphenyl-2-carboxylate and trifluoroacetic acid.

Yield: 79.4% of theoretical,
Melting point: 235°–237° C. $C_{30}H_{34}N_4O_3$ x 7.5 $CF_3COOH$ (555.64)
Calculated: C 67.01 H 6.26 N 10.05 Found: 66.99 6.02 10.12

Example 234

4'-[(2-n-Butyl-6-dimethylaminoacetamino-benzimidazol-1-yl)-methyl]biphenyl-2-carboxylic acid ditrifluoroacetate Prepared in analogous manner to Example 9 from tert. butyl 4'-[(2-n-butyl-6-(dimethylaminoacetamino)-benzimidazol-1-yl)-methyl]biphenyl-2-carboxylate and trifluoroacetic acid/methylene chloride.

Yield: 75.5% of theoretical,
Melting point: 218°–220° C. $C_{29}H_{32}N_4O_3$ x 2 $CF_3COOH$ (712.65)
Calculated: C 55.61 H 4.81 N 7.86 Found: 55.61 5.05 8.19

Example 235

4'-[(2-n-Butyl-6-(2,2-dimethyl-propionylamino)-benzimidazol-1-yl)-methyl]biphenyl-2-carboxylic acid Prepared in analogous manner to Example 9 from tert. butyl 4'-[(2-n-butyl-6-(2,2-dimethyl-propionylamino)-benzimidazol-1-yl)-methyl]biphenyl-2-carboxylate and trifluoroacetic acid.

Yield: 67.5% % of theoretical,
Melting point: 326°–327° C. $C_{30}H_{33}N_3O_3$ (483.61)
Calculated: C 74.51 H 6.88 N 8.69 Found: 74.32 7.06 8.58

Example 236

4'-[(2-n-Butyl-6-(N-(n-hexylaminocarbonyl)-N-(2-phenylethyl)-amino)-benzimidazol-1-yl)-methyl] biphenyl-2-carboxylic acid Prepared in analogous manner to Example 9 from tert. butyl 4'-[(2-n-butyl-6-(N-(n-hexylaminocarbonyl)-N-(2-phenylethyl)-amino)-benzimidazol-1-yl)-methyl]-biphenyl-2-carboxylate and trifluoroacetic acid.

Yield: 66.7% of theoretical,
Melting point: 176°–177° C. $C_{46}H_{48}N_4O_3$ (630.83)
Calculated: C 76.16 H 7.35 N 8.88 Found: 75.97 7.44 8.98

Example 237

4'-[(2,6-Di-n-butyl-benzimidazol-1-yl)-methyl] biphenyl-2-carboxylic acid

Prepared in analogous manner to Example 9 from tert. butyl 4'-[(2,6-di-n-butyl-benzimidazol-1-yl)-methyl] biphenyl-2-carboxylate and trifluoroacetic acid/methylene chloride.

Yield: 75.9% of theoretical,
Melting point: 188°–190° C. $C_{30}H_{32}N_2O_2$ (440.59)
Calculated: C 79.06 H 7.32 N 6.36 Found: 78.96 7.36 6.18

Example 238

4'-[(2-n-Butyl-6-cyclopentylcarbonylamino-benzimidazol-1-yl)-methyl]biphenyl-2-carboxylic acid semi-hydrate Prepared in analogous manner to Example 9 from tert. butyl 4'-[(2-n-butyl-6-cyclopentylcarbonylamino-benzimidazol-1-yl)-methyl]biphenyl-2-carboxylate and trifluoroacetic acid.

Yield: 72.2% of theoretical,
Melting point: 272°–274° C. $C_{31}H_{33}N_3O_3$ x 0.5 $H_2O$ (504.63)
Calculated: C 73.79 H 6.79 N 8.33 Found: 74.00 6.91 8.25

Example 239

4'-[(2-n-Butyl-6-cyclopropylcarbonylamino-benzimid-azol-1-yl)-methyl]biphenyl-2-carboxylic acid semi-hydrate Prepared in analogous manner to Example 9 from tert. butyl 4'-[(2-n-butyl-6-cyclopropylcarbonylamino-benzimidazol-1-yl)-methyl]biphenyl-2-carboxylate and trifluoroacetic acid.

Yield: 91.7% of theoretical,
Melting point: 275°–277° C. $C_{28}H_{29}H_3O_2$ x 0.5 $H_2O$ (476.57)
Calculated: C 73.09 H 6.34 N 8.82 Found: 72.97 6.50 8.52

Example 240

4'-[(2-n-Butyl-6-(1-oxo-isoindolin-2-yl)-benzimidazol-1-yl)-methyl]biphenyl-2-carboxylic acid trifluoroacetate 1.6 g (3 mmol) of 4'-[(2-n-butyl-6-phthalimino-benzimidazol-1-yl)-methyl]biphenyl-2-carboxylic acid trifluoroacetate are treated with 1.6 g of the zinc power in 30 ml of glacial acetic acid under reflux. After every hour, 1.6 g of zinc power are added and heated at reflux for one hour, this takes place 2 times. Excess zinc is filtered off under suction and the filtrate is rotary evaporated to dryness. The crude product is purified over a silica gel column (grain size: 0.063–0.2 mm) using ethyl acetate/ethanol/ammonia (90:10:0.1 to 80:20:01.) and crystallised from ether.

Yield: 0.45 g (64.1% of theoretical),

Melting point: 214°–216° C. $C_{23}H_{28}N_3O_3$ x $CF_3COOH$ (629.64) Calculated: C 66.76 H 4.80 N 6.67 Found: 66.62 5.08 6.69

Example 241

4'-[(2-(1-trans-Butenyl)-6-dimethylaminocarbonylamino-benzimidazol-1-yl)-methyl]biphenyl-2-carboxylic acid trifluoroacetate a) Tert.butyl 4'-[(2-(1-bromobutyl)-6-phthalimino-benzimidazol-1-yl)-methyl]biphenyl-2-carboxylate 10.3 g (17.6 mmol) of tert.butyl 4'-[(2-n-butyl-6-phthalimino-benzimidazol-1-yl)-methyl]biphenyl-2-carboxylate, 1 liter of carbon tetrachloride and 3.1 g (17.5 mmol) of N-bromosuccinimide are irradiated using a mercury immersion lamp for 3 hours while stirring. As a result of this, the internal temperature increases to 50° C. The greasy product obtained is then filtered off, the residue is dissolved in methylene chloride and extracted by shaking using water. The organic phase is dried over sodium sulphate and rotary evaporated. The crude product is purified over a silica gel column (grain size: 0.063–0.2 mm) ethyl acetate/petroleum ether (1:4).

Yield: 4.5 g (38.4% of theoretical), b) Tert.butyl 4'-[(2-(1-trans-butenyl)-6-phthalimino-benzimidazol-1-yl)-methyl]biphenyl-2-carboxylate 10.8 g (16.25 mmol) of tert.butyl 4'-[(2-(1-bromobutyl)-6-phthalimino-benzimidazol-1-yl)-methyl]biphenyl-2-carboxylate, 110 ml of dimethylformamide and 5.1 ml (5.2 g=34.1 mmol) of 1,8-diazabicyclo[5.4.0]undec-7-ene are stirred overnight at ambient temperature. The mixture is diluted using 200 ml of ether and extracted by shaking using 2N hydrochloric acid and water. The combined acid phase is extracted by shaking using ethyl acetate. The ethyl acetate phase is dried over sodium sulphate and, after rotary evaporation, is purified over a silica gel column (grain size: 0.063–0.2 mm) using ethyl acetate/petroleum ether (20:80 to 30:70). The product crystallises out on evaporation of the appropriate fractions. The product is filtered under suction and washed using ether.

Yield: 2.30 g (24.2% of theoretical),

Melting point: 232°–234° C. $C_{37}H_{33}N_2O_4$ (583.69)

Calculated: C 76.14 N 5.70 N 7.20 Found: 75.92 5.69 7.34 c) Tert.butyl 4'-[6-amino-(2-(1-trans-butenyl)-benzimidazol-1-yl)-methyl]biphenyl-2-carboxylate 2.3 g (3.94 mmol) of tert.butyl 4'-[(2-(1-trans-butenyl)-6-phthalimino-benzimidazol-1-yl)-methyl]biphenyl-2-carboxylate, 80 ml of ethanol and 25 ml of 40% strength aqueous methylamine are stirred for 3 hours at ambient temperature. The mixture is heated for ¼ hour on a steam bath, cooled and rotary evaporated. The residue is suspended in acetone, cooled and undissolved N-methyl-phthalimide is filtered off. The filtrate is evaporated to dryness.

Yield: 1.78 g (100% of theoretical),

Melting point: 174°–176° C.

d) Tert.butyl 4'-[(2-(1-trans-butenyl)-6-dimethylaminocarbonylamino-benzimidazol-1-yl)-methyl]biphenyl-2-carboxylate Prepared in analogous manner to Example 8 from tert.butyl 4'-[6-amino-(2-(1-trans-butenyl)-benzimidazol-1-yl)-methyl]biphenyl-2-carboxylate and dimethylcarbamoyl-chloride.

Yield: 82.8% of theoretical, oil, $R_f$ value: 0.35 (Silica gel; methylene chloride/ethanol=19:1)

e) 4'-[(2-(1-trans-Butenyl)-6-dimethylaminocarbonyl-amino-benzimidazol-1-yl)-methyl]biphenyl-2-carboxylic acid trifluoroacetate Prepared in analogous manner to Example 9 from tert.butyl 4'-[(2-(1-trans-butenyl)-6-dimethylamino-carbonylamino-benzimidazol-1-yl)-methyl]biphenyl-2-carboxylate and trifluoroacetic acid in methylene choride.

Yield: 66.6% of theoretical,

Melting point: 221°–223° C. $C_{20}H_{28}N_4O_3$ x $CF_3COOH$ x 0.5 $H_2O$ (591.59)

Calculated: C 60.90 H 5.11 N 9.47 Found: 60.83 4.96 9.53

The following compounds are prepared in analogous manner to Example 241c:

4'-[(6-amino-2-n-butyl-benzimidazol-1-yl)-methyl]-2-trifluoromethanesulphonamino-biphenyl oil, $R_f$ value: 0.30 (Silica gel: ethyl acetate/ethanol/ammonia=90:10:1)

4'-[(6-amino-2-n-butyl-benzimidazol-1-yl)-methyl]-biphenyl-2-carboxylic acid M.p.: 235°–237° C.

Example 242

4'-[(2-(1-trans-Butenyl)-6-cyclohexylaminocarbonyl-amino-benzimidazol-1-yl)-methyl]biphenyl-2-carboxylic acid trifluoroacetate Prepared in analogous manner to Example 241 from tert.butyl 4'-[(2-(1-trans-butenyl)-6-cyclohexylamino-carbonylamino-benzimidazol-1-yl)-methyl]biphenyl-2-carboxylate and trifluoroacetic acid in methylene chloride.

Yield: 93.7% of theoretical,

Melting point: 171°–173° C. $C_{32}H_{34}N_4O_2$ x $CF_3COOH$ (636.67)

Calculated: C 64.14 H 5.54 N 8.80 Found: 64.00 5.49 8.97

Example 243

Tert.butyl 4'-[(2-n-butyl-6-(cis-hexahydrophthalimino)-benzimidazol-1-yl)-methyl] biphenyl-2-carboxylate 1.8 g (4 mmol) of tert.butyl 4'-[(6-amino-2-n-butyl-benzimidazol-1-yl)-methyl]biphenyl-2-carboxylate, 30 ml of glacial acetic acid and 1.85 g (1.2 mmol) of cis-cyclohexane-1,2-dicarboxylic acid anhydride are heated at reflux for one hour with stirring. The reaction mixture is evaporated to dryness. The residue is dissolved in methylene chloride, washed until neutral using saturated sodium bicarbonate solution, dried over sodium sulphate and rotary evaporated. The crude product is purified over a silica gel column (grain size: 0.063–0.2 mm) using ethyl acetate/petroleum ether (10:90; 20:80 and 30;70).

Yield: 1.5 g (64.1% of theoretical), $C_{37}H_{41}N_3O_4$ (591.80)

Calculated: C 75.10 H 6.98 N 7.10 Found: 74.92 7.10 6.99

The following compounds are obtained in analogous manner:

tert.butyl 4'-[(2-n-butyl-6-(4,5-dimethyl-1,2,3,6-tetrahydrophthalimino)-benzimidazol-1-yl)-methyl]

biphenyl- 2-carboxylate oil, $R_f$ value: 0.30 (Silica gel; ethyl acetate/petroleum ether=1:1)

tert.butyl 4'-[(2-n-butyl-6-(3,4-dimethoxy-phthalimino)-benzimidazol-1-yl)-methyl]biphenyl-2-carboxylate Yield: 33.8% of theoretical, Melting point: 238°239° C.

tert.butyl 4'-[(2-n-butyl-6(cis-hexahydrophthalimino)-benzimidazol-1-yl)-methyl]biphenyl-2-carboxylate oil, $R_f$ value: 0.45 (Silica gel: ethyl acetate/petroleum ether=4:1)

4'-[(2-n-butyl-6-(cis-hexahydrophthalimino)-benzimidazol-1-yl)-methyl]-2-(1-triphenylmethyl-tetrazol-5-yl)-biphenyl oil, $R_f$ value: 0.55 (Silica gel: ethyl acetate/petroleum ether/ammonia=80:20:1)

tert.butyl 4'-[(2-n-butyl-6-(endo-bicyclo[2.2.2]oct-5-ene-2,3-dicarboxylic acid-imino)-benzimidazol-1-yl)-methyl]biphenyl-2-carboxylate M.p.: 180°–182.5° C.

tert.butyl 4'-[(2-n-butyl-6-(cis-hexahydrophthalimino)-benzimidazol-1-yl)-methyl]biphenyl-2-carboxylate oil, $R_f$ value: 0.43 (Silica gel: ethyl acetate/petroleum ether=2:1)

tert.butyl 4'-[(2-n-butyl-6-(methyl-5-norbornene-2,3-dicarboxylic acid-imino)-benzimidazol-1-yl)-methyl]-biphenyl-2-carboxylate tert.butyl 4'-[(2-n-butyl-6-(trans-hexahydrophthalimino)-benzimidazol-1-yl)-methyl]biphenyl-2-carboxylate M.p.: 168°–170° C.

tert.butyl 4'-[(2-n-butyl-6-(3,6-endoxo-1,2,3,6-tetrahydrophthalimino)-benzimidazol-1-yl)-methyl]biphenyl-2-carboxylate tert.butyl 4'-[(2-n-butyl-6-(cis-5-norbornene-endo-2,3-dicarboxylic acid-imino)-benzimidazol-1-yl)-methyl]biphenyl-2-carboxylate M.p.: 179°–180° C.

4'-[(2-n-Butyl-5-(N-cyclohexylaminocarbonyl-methylamine)-benzimidazol-1-yl)-methyl]-2-(1-triphenylmethyl-tetrazol-5-yl)-biphenyl oil, $R_f$ value: 0.45 (Silica gel: ethyl acetate/petroleum ether/ammonia=90:10:1)

4'-[(2-n-Butyl-5-(cis-hexahydrophthalimino)-benzimidazol-1-yl)-methyl]-2-(1-triphenylmethyl-tetrazol-5-yl)-biphenyl oil, $R_f$ value: 0,35 (Silica gel: ethyl acetate/petroleum ether=4:1)

Example 244

4'-[(2-n-Butyl-6-(cis-hexahydrophthalimino)-benzimidazol-1-yl)-methyl]biphenyl-2-carboxylic acid trifluoroacetate Prepared in analogous manner to Example 9 from tert. butyl 4'-[(2-n-butyl-6-(cis-hexahydrophthalimino)-benzimidazol-1-yl)-methyl]biphenyl-2-carboxylate and trifluoroacetic acid in methylene chloride.

Yield: 58.8% of theoretical,

Melting point: 270° C. (decomposition) $C_{23}H_{33}N_3O_4$ x $CF_3COOH$ (649.68)

Calculated: C 64.71 H 5.28 N 6.47 Found: 64.76 5.41 6.65

Example 245

4'-[(2-n-Butyl-6-(4,5-dimethyl-1,2,3,6-tetrahydrophthalimino)-benzimidazol-1-yl)-methyl]biphenyl-2-carboxylic acid hydrate Prepared in analogous manner to Example 9 from tert. butyl 4'-[(2-n-butyl-6-(4,5-dimethyl-1,2,3,6-tetrahydrophthalimino)-benzimidazol-1-yl)-methyl]biphenyl-2-carboxylate and trifluoroacetic acid in methylene chloride.

Yield: 30% of theoretical,

Melting point: 219°–221° C. $C_{35}H_{35}N_3O_4$ x $H_2O$ (579.69)

Calculated: C 72.52 H 6.43 N 7.23 Found: 72.66 6.49 7.43

EXAMPLE 246

4'-[(2-n-Butyl-6-(3,4-dimethoxy-phthalimino)-benzimidazol-1-yl)-methyl]biphenyl-2-carboxylic acid dihydrate Prepared in analogous manner to Example 9 from tert. butyl 4'-[(2-n-butyl-6-(3,4-dimethoxy-phthalimino)-benzimidazol-1-yl)-methyl]biphenyl-2-carboxylate and trifluoroacetic acid in methylene chloride.

Yield: 24.3% of theoretical,

Melting point: 206°–208° C. $C_{33}H_{31}N_3O_6$ x 2 $H_2O$ (625.68)

Calculated: C 67.19 H 5.64 N 6.72 Found: 67.22 5.84 6.97

Example 247

4'-[(2-n-Butyl-6-(N-(dimethylaminocarbonyl)-n-pentylamino)-benzimidazol-1-yl)-methyl]biphenyl-2-carboxylic acid trifluoroacetate Prepared in analogous manner to Example 9 from tert. butyl 4'-[(2-n-butyl-6-(N-(dimethylaminocarbonyl)-n-pentylamino)-1-yl)-methyl]biphenyl-2-carboxylate and trifluoroacetic acid in methylene chloride Yield: 81.8% of theoretical, Melting point: 174°–176° C. $C_{33}H_{40}N_4O_3$ x $CF_3COOH$ (654.73) Calculated: C 64.21 H 6.31 N 8.55 Found: 64.38 6.28 8.64

Example 248

4'-[(2-n-Butyl-6-(N-(4-phenylamino-n-butyl)-n-pentylamino)-benzimidazol-1-yl)-methyl]biphenyl-2-carboxylicacid Prepared in analogous manner to Example 9 from tert. butyl 4'-[(2-n-butyl-6-(N-(4-phenylamino-n-butyl)-n-pentylamino)-benzimidazol-1-yl)-methyl]biphenyl-2-carboxylate and trifluoroacetic acid in methylene chloride.

Example 249

4'-[(2-n-Butyl-6-cyclohexylaminocarbonylamino-benzimidazol-1-yl)-methyl]-2-(1N-tetrazol-5-yl)-biphenyl Prepared in analogous manner to Example 58b from 4'-[(6-amino-2-n-butyl-benzimidazol-1-yl)-methyl]-2-(1H-tetrazol-5-yl)-biphenyl and cyclohexyliscyanate in methylene chloride Melting point: 232°–234° C. $C_{32}H_{38}N_8O$ (548.69)

Calculated: C 70.05 H 6.61 N 20.42 Found: 69.86 6.66 20.25

Example 250

4'-[(2-n-Butyl-6-dimethylaminoaminocarbonylamino-benzimidazol-1-yl)-methyl]-2-(1H-tetrazol-5-yl)-biphenyl Prepared in analogous manner to Example 58b from 4'-[(2-n-butyl-4-dimethylaminoaminocarbonylamino-benzimidazol-1-yl)-methyl]-2-(1-triphenylmethyl-tetrazol- 5-yl)-biphenyl and hydrochloric acid in ether/methanol/ methylene chloride.

Yield: 69.8% of theoretical,

Melting point: 239°–241° C. $C_{26}H_{30}N_2O$ (494.60)

Calculated: C 67.99 H 6.11 N 22.65 Found: 67.85 6.08 22.55

Example 251

4'-[(2-n-Butyl-6-(N-cyclohexylaminoaminocarbonyl-methylamino)-benzimidazol-1-yl)-methyl]-2-(1H-tetrazol-5-yl)-biphenyl hydrate Prepared in analogous manner to Example 58 from 4'-[(2-n-butyl-6-methylamino-benzimidazol-1-yl)-methyl]-2-(1H-tetrazol-5-yl)-biphenyl and cyclohexylisocyanate.

Yield: 97.5% or theoretical

Melting point: 163°–165° C. $C_{33}H_{38}N_8O \times H_2O$ (580.75)

Calculated: C 68.25 H 6.94 N 19.30 Found: 68.43 6.90 19.15

Example 252

4'-[(2-n-Butyl-6-cyclohexylaminoaminocarbonylamino-benzimidazol-1-yl)-methyl]-2-trifluoromethanesulphonamino-biphenyl Prepared in analogous manner to Example 7 from 4'-[(6-amino-2-n-butyl-benzimidazol-1-yl)-methyl]-2-trifluoromethanesulphonamino-biphenyl and cyclohexylisocyanate.

Yield: 90.9% of theoretical,

Melting point: 163°–165° C. $C_{32}H_{38}N_2O_3S$ (627.73)

Calculated: C 61.23 H 5.78 N 11.15 Found: 61.12 5.67 11.29

Example 253

4'-[(2-n-Butyl-6-cyclohexylaminocarbonyloxy-benzimidazol-1-yl)-methyl]biphenyl-2-carboxylic acid Prepared in analogous manner to Example 9 from tert. butyl 4'-[(2-n-butyl-6-cyclohexylaminocarbonyloxy-benzimidazol-1-yl)-methyl]biphenyl-2-carboxylate and trifluoroacetic acid in methylene chloride.

Yield: 80.0% of theoretical,

Melting point: 218°–219° C. $C_{32}H_{35}N_2O_4$, (525.65)

Calculated: C 73.12 H 6.71 N 7.99 Found: 73.04 6.84 7.92

Example 254

4'-[(2-n-Butyl-6-cyclohexyloxycarbonylamino-benzimidazol-1-yl)-methyl]biphenyl-2-carboxylic acid Prepared in analogous manner to Example 9 from tert. butyl 4'-[(2-n-butyl-6-cyclohexyloxycarbonylamino-benzimidazol-1-yl)-methyl]biphenyl-2-carboxylate and trifluoroacetic acid in methylene chloride.

Yield: 90.9% of theoretical,

Melting point: 238°–240° C. $C_{32}H_{35}N_3O_4$ (525.65)

Calculated: C 73.12 H 6.71 N 7.99 Found: 73.18 6.74 8.11

Example 255

4'-[(2-n-Butyl-6-morpholinocarbonylamino-benzimidazol-1-yl)-methyl]biphenyl-2-carboxylic acid Prepared in analogous manner to Example 9 from tert. butyl 4'-[(2-n-butyl-6-morpholinocarbonylamino-benzimidazol-1-yl)-methyl]biphenyl-2-carboxylate and trifluoroacetic acid in methylene chloride.

Yield: 85.0% of theoretical,

Melting point: 278°–279° C. $C_{30}H_{32}N_4O_4$ (512.61)

Calculated: C 70.29 H 6.29 N 10.93 Found: 70.28 6.28 11.00

Example 256

4'-[(2-n-Butyl-6-pyrrolidinocarbonylamino-benzimidazol-1-yl)-methyl]biphenyl-2-carboxylic acid Prepared in analogous manner to Example 9 from tert. butyl 4'-[(2-n-butyl-6-pyrrolidinocarbonylamino-benzimidazol- 1-yl)-methyl]biphenyl-2-carboxylate and trifluoroacetic acid in methylene chloride.

Example 257

4'-[(2-n-Butyl-6-(N-methylaminocarbonyl-N-(3-cyclohexyl-n-propyl)-amino)-benzimidazol-1-yl)-methyl]biphenyl-2-carboxylic acid Prepared in analogous manner to Example 9 from tert. butyl 4'-[(2-n-butyl-6-(N-methylaminocarbonyl-N-(3-cyclohexyl-n-propyl)-amino)-benzimidazol-1-yl)-methyl]biphenyl-2-carboxylate and trifluoroacetic acid in methylene chloride.

Yield: 84.8% of theoretical,

Melting point: 215°–216° C. $C_{38}H_{44}N_4O_3$ (580.72)

Calculated: C 74.45 H 7.64 N 9.65 Found: 74.52 7.75 9.76

Example 258

4'-[(2-n-Butyl-benzimidazol-1-yl)-methyl]-2-phenyl-naphthalene-3-carboxylic acid Prepared in analogous manner to Example 9 from tert. butyl 4'-[(2-n-butyl-benzimidazol-1-yl)-methyl]-2-phenylnaphthalene-3-carboxylate and trifluoroacetic acid.

Yield: 57% of theoretical,

Melting point: fused from 100° C. $C_{28}H_{28}N_2O_2$ (434.54)

Calculated: C 80.34 H 5.81 N 6.46 Found: 80.63 5.89 6.28

Example 259

4'-[(2-n-Butyl-benzimidazol-1-yl)-methyl]-1-phenyl-naphthalene-2-carboxylic acid Prepared in analogous manner to Example 9 from tert. butyl 4'-[(2-n-butyl-benzimidazol-1-yl)-methyl]-1-phenyl-naphthalene-2-carboxylate and trifluoroacetic acid.

Yield: 42.5% of theoretical,

Melting point: 218°–220° C. $C_{28}H_{28}N_2O_2$ (434.54)

Calculated: C 80.34 H 5.81 N 6.46 Found: 80.18 6.01 6.85

Example 260

4'[(2-n-Butyl-6-(cis-hexahydrophthalimino-benzimidazol-1-yl)-methyl]-1-(1H-tetrazol-5-yl)-2-phenyl-naphthalene Prepared in analogous manner to Example 59 from 4'-[(2-n-butyl-(cis-hexahydrophthalimino-benzimidazol-1-yl)-methyl]-1-cyano-2-phenyl-naphthalene and ammonium chloride/sodium azide.

Example 261

4'-[(2-n-Propyl-6-(N-cyclohexylaminocarbonyl-methylamino)-benzimidazol-1-yl)-methyl]-1-(1H-tetrazol-5-yl)-2-phenyl-naphthalene Prepared in analogous manner to Example 55 from 4'-[(2-n-propyl-6-(N-cyclohexylaminocarbonyl-methyl-amino)

-benzimidazol-1-yl)-methyl]-1-cyano-2-phenyl-naphthalene and ammonium chloride/sodium azide.

Example 262

4'-[(2-n-Propyl-6-(N-cyclohexylaminocarbonyl-methyl-amino)-benzimidazol-1-yl)-methyl]-2-phenyl-naphthalene-1-carboxylic acid Prepared n analogous manner to Example 9 from tert. butyl 4'-[(2-n-propyl-6-(N-cyclohexylaminocarbonyl-methylamino)-benzimidazol-1-yl)-methyl]-2-phenyl-naphthalene-1-carboxylate and trifluoroacetic acid.

Yield: 73.0% of theoretical,

Melting point: 193°–195° C. $C_{30}H_{38}N_4O_3$ (574.70) Calculated: C 75.28 H 6.67 N 9.75 Found: 75.10 6.71 9.72

Example 263

4'-[(2-n-Butyl-benzimidazol-1-yl)-methyl]-2-phenyl-naphthalene-1-carboxylic acid Prepared in analogous manner to Example 9 from tert. butyl 4'-[(2-n-butyl-benzimidazol-1-yl)-methyl]-2-phenyl-naphthalene-1-carboxylate and trifluoroacetic acid.

Yield: 89.0% of theoretical,

Melting point: 228°–230° C. $C_{28}H_{28}N_2O_2$ (434.51) Calculated: C 80.16 H 6.03 N 6.45 Found: 80.11 6.00 6.30

Example 264

4'-[(2-n-Butyl-6-(cis-hexahydrophthalimino)-benzimidazol-1-yl)-methyl]-2-phenyl-naphthalene-1-carboxylic acid Prepared in analogous manner to Example 9 from tert. butyl 4'-[(2-n-butyl-6-(cis-hexahydrophthalimino)-benzimidazol-1-yl)-methyl]-2-phenyl-naphthalene-1-carboxylate and trifluoroacetic acid.

Prepared in analogous manner to Example 9 from tert. butyl 4'-[(2-n-butyl-6-(cis-hexahydrophthalimino)-benzimidazol-1-yl)-methyl]-2-phenyl-naphthalene-1-carboxylate and trifluoroacetic acid.

Yield: 37.0% of theoretical,

Melting point: 215°–218° C. $C_{28}H_{33}N_3O_4$ (571.65) Calculated: C 75.63 H 5.82 N 7.35 Found: 75.47 5.63 7.11

Example 265

4'-[(2-n-Butyl-6-(cis-hexahydrophthalimino)-benzimidazol-1-yl)-methyl]-4-bromo-biphenyl-2-carboxylic acid.

Prepared in analogous manner to Example 9 from tert. butyl 4'-[(2-n-Butyl-6-(cis-hexahydrophthalimino)-benzimidazol-1-yl)-methyl]-4-bromo-biphenyl-2-carboxylate and trifluoroacetic acid.

Yield: 63.0% of theoretical,

Melting point: 198°–200° C. $C_{23}H_{32}BrN_3O_4$ (614.56) Calculated: C 64.50 H 5.25 N 6.84 Br 13.00 Found: 64.38 5.22 6.73 13.05

Example 266

4'-[(2-n-Butyl-benzimidazol-1-yl)-methyl]-4-bromo-biphenyl-2-carboxylic acid

Prepared in analogous manner to Example 9 from tert. butyl 4'-[(2-n-butyl-benzimidazol-1-yl)-methyl]-4-bromo-biphenyl-2-carboxylate and trifluoroacetic acid.

Yield: 88% of theoretical,

Melting point: 209°–211° C. $C_{28}H_{32}BrH_2O_2$ (463.39) Calculated: C 64.80 H 5.00 N 6.05 Br 17.25 Found: 64.68 5.14 5.97 17.26

Example 267

4'-[(2-n-Butyl-benzimidazol-1-yl)-methyl]-5-chloro-biphenyl-2-carboxylic acid

Prepared in analogous manner to Example 9 from tert. butyl 4'-[(2-n-butyl-benzimidazol-1-yl)-methyl]-5-chloro-biphenyl-2-carboxylate and trifluoroacetic acid.

Yield: 74% of theoretical,

Melting point: 188°–190° C. $C_{23}H_{23}ClN_2O_2$(418.91) Calculated: C 71.67 N 5.53 N 6.69 Found: 71.49 5.52 6.66

Example 268

4'-[(2-n-Butyl-6-(cis-hexahydrophthalimino)-benzimidazol-1-yl)-methyl]-4-chloro-2-(1H-tetrazol-5-yl)-biphenyl Prepared in analogous manner to Example 59 from 4'-[(2-n-butyl-6-(cis-hexahydrophthalimino)-benzimidazol-1-yl)-methyl]-4-chloro-2-cyano-biphenyl and ammonium chloride/sodium azide.

Yield: 25.0% of theoretical,

Melting point: >125° C. $C_{23}H_{30}ClN_7O_2$ (594.11) Calculated: C 66.71 H 5.43 N 16.50 Cl 5.87 Found: 66.54 5.63 16.35 5.91

Example 269

4'-[(2-n-Butyl-6-(N-cyclohexylaminocarbonyl-methyl-amino)-benzimidazol-1-yl)-methyl]-4-chloro-2-(1H-tetrazol-5-yl)-biphenyl Prepared in analogous manner to Example 59 from 4'-[(2-n-butyl-6-(N-cyclohexylaminocarbonyl-methyl-amino)-benzimidazol-1-yl)-methyl]-4-chloro-2-cyano-biphenyl and ammonium chloride/sodium azide.

Example 270

4'-[(2-n-Butyl-6-(N-(n-dodecylaminocarbonyl)-methylamino)-benzimidazol-1-yl)-methyl]biphenyl-2-carboxylic acid trifluoroacetate Prepared in analogous manner to Example 9 from tert. butyl 4'-[(2-n-butyl-6-(N-(n-dodecylaminocarbonyl)-methylamino)-benzimidazol-1-yl)-methyl]biphenyl-2-carboxylate is trifluoroacetic acid/methylene chloride.

Yield: 85.7% of theoretical,

Melting point: 61°–62° C. $C_{32}H_{32}N_4O_3$ x $CF_3COOH$ (738.39) Calculated: C 66.65 H 7.23 N 7.58 Found: 66.68 7.47 7.83

Example 271

4'-[(2-n-Butyl-6-(N-(cyclohexylaminocarbonyl)-n-octylamino)-benzimidazol-1-yl)-methyl]biphenyl-2-carboxylic acid Prepared in analogous manner to Example 72 from ethyl 4'-[(2-n-butyl-6-(N-(cyclohexylamino-carbonyl)-n-octylamino)-benzimidazol-1-yl)-methyl)bi-phenyl-2-carboxylate in ethanol/2N sodium hydroxide solution.

Yield: 94.9% of theoretical.
Melting point: 151°–152° C. $C_{40}H_{32}N_4O_2$ (636.88)
Calculated: C 75.44 $H_{8.23}$ N 8.80 Found: 75.63 8.37 8.92

Example 272

4'(2-n-Butyl-6-(N-(n-octylaminocarbonyl)-methyl-amino)-benzimidazol-1-yl)-methyl]biphenyl-2-carboxylic acid Prepared in analogous manner to Example 9 from tert. butyl 4'-[(2-n-butyl-6-(N-(n-octylaminocarbonyl)-methylamino)-benzimidazol-1-yl)-methyl]biphenyl-2-carboxylate is trifluoroacetic acid/methylene chloride.
Yield: 87.5% of theoretical
Melting point: 169°–170° C. $C_{33}H_{44}N_4O_3$ (568.76)
Calculated: C 73.91 H 7.80 N 9.85 Found: 73.98 7.95 9.78

Example 273

4'-[(2-n-Butyl-6-(cis-hexahydrophthalimino)-benzimidazol-1-yl)-methyl]-2-(1H-tetrazol-5-yl)-biphenyl Prepared in analogous manner to Example 58 from 4'-[(2-n-butyl-6-(cis-hexahydrophthalimino)-benzimidazol-1-yl)-methyl]-2-(1-triphenylmethyl-tetrazol-5-yl)-biphenyl and hydrochloric acid in ether/methanol/methylene chloride.
Yield: 47.6% of theoretical,
Melting point: 147°–149° C. $C_{33}H_{33}N_7O_2$ (559.67)
Calculated: C 70.82 N 5.94 N 17.52 Found: 70.61 6.12 17.63

Example 274

4'-[(2-n-Butyl-6-(endo-bicyclo[2.2.2]oct-5-one-2,3-dicarboxylic acid-imino)-benzimidazol-1-yl)-methyl]-biphenyl-2-carboxylic acid trifluoroacetate Prepared in analogous manner to Example 9 from tert. butyl 4'-[(2-n-butyl-6-(endo-bicyclo[2.2.2]oct-5-ene-2,3-dicarboxylic acid-imino)-benzimidazol-1-yl)-methyl] biphenyl-2-carboxylate and trifluoroacetic acid in methylene chloride.
Yield: 88.6% of theoretical,
Melting point: 161°–163° C. $C_{25}H_{33}H_3O_4$ x $CF_3COOH$ (673.69) Calculated: C 65.96 N 5.08 N 6.23 Found: 75.72 4.99 6.11

Example 275

4'-[(2-n-Butyl-6-(methyl-5-norbornene-2,3-dicarboxylic acid-imino)-benzimidazol-1-yl)-methyl]biphenyl-2-carboxylic acid (isomer mixture)

Prepared in analogous manner to Example 9 from tert. butyl 4'-[(2-n-butyl-6-(methyl-5-norbornene-2,3-dicarboxylic acid-imino)-benzimidazol-1-yl)-methyl] biphenyl-2-carboxylate (isomer mixture) and trifluoroacetic acid in methylene chloride.
Yield: % of theoretical, Melting point: –°C. C H N O ( . )
Calculated: C . H . N . Found: . . .

Example 276

4-'[(2-n-Butyl-6-(trans-hexahydrophthalimino)-benzimidazol-1-yl)-methyl]biphenyl-2-carboxylic acid dihydrate Prepared in analogous manner to Example 9 from tert. butyl 4'-[(2-n-butyl-6-(trans-hexahydrophthalimino)-benzimidazol-1-yl)-methyl]biphenyl-2-carboxylate and trifluoroacetic acid in methylene chloride.
Yield: 60.7% of theoretical,
Melting point: 188°–190° C. $C_{33}H_{33}N_3O_4$ x 2 $H_2O$ (571.47)
Calculated: C 69.33 H 6.52 N 7.35 Found: 69.48 4.40 7.57

Example 277

4'-[(2-n-Butyl-6-(3,6-endoxo-1,2,3,6-tetrahydrophthalimino)-benzimidazol-1-yl)-methyl] biphenyl-2-carboxylic acid Prepared in analogous manner to Example 9 from tert. butyl 4'-[(2-n-butyl-6-(3,6-endoxo-1,2,3,6-tetrahydrophthalimino)-benzimidazol-1-yl)-methyl] biphenyl-2-carboxylate and trifluoroacetic acid in methylene chloride.
Yield: % of theoretical,
Melting point: –°C. C H N O ( . )
Calculated: C . H . N . Found: . . .

Example 278

4'-[(2-n-Butyl-6-(cis-5-norbornene-endo-2,3-dicarboxylic acid-imino)-benzimidazol-1-yl)methyl] biphenyl-2-carboxylic acid monohydrate Prepared in analogous manner to Example 9 from tert. butyl 4'-[(2-n-butyl-6-(cis-5-norbornene-endo-2,3-dicarboxylic acid-imino)-benzimidazol-1-yl)-methyl] biphenyl-2-carboxylate and trifluoroacetic acid in methylene chloride.
Yield: 22.1% of theoretical,
Melting point: 263°–265° C. $C_{34}H_{31}N_2O_4$ x $H_2O$ (563.65)
Calculated: C 72.44 H 5.90 N 7.45 Found: 72.28 5.81 7.46

Example 279

5'-[(2-n-Butyl-6-(2-carboxyl-cyclohexylcarbonylamino)-benzimidazol-1-yl)-methyl]biphenyl-2-carboxylic acid 0.6 g (1.5 mmol) of 4'-[(6-amino-2-n-butyl-benzimidazol-1-yl)-methyl]biphenyl-2-carboxylic acid are dissolved in 150 ml of methylene chloride with heating and cooled to ambient temperature. After the addition of 240 mg (1.55 mmol) of cis-cyclohexan-1,2-dicarboxylic acid anhydride the mixture is stirred for 5 hours at ambient temperature. The reaction product which crystallises out is suction filtered, washed with methylene chloride and dried in a vacuum drying chamber at 50° C.
Yield: 0.58 g (69.8% of theory),
Melting point: 186°–188° C.
Yield: 0.58 g (69.8% of theory),
Melting point: 186°–188° C. $C_{32}H_{39}N_3O_3$ (553.66)
Calculated: C 71.59 H 6.37 N 7.59 Fund: 71.42 4.56 7.56

Example 280

4'-[(2-n-Butyl-6-(2-carboxy-cyclohexylcarbonylamino)-benzimidazol-1-yl)-methyl]-4-bromo-biphenyl-2-carboxylic acid Prepared in analogous manner to Example 9 from tert. butyl 4'-[(2-n-butyl-6-(cis-hexahydrophthalimino)- benzimidazol-1-yl)-methyl]-4-bromo-biphenyl-2-carboxylate and trifluoroacetic acid in methylene chloride.

Yield: 88% of theory,

Melting point: from 145° C. (decomp.) $C_{33}H_{34}BrN_2O_3$ (632.58)

Calculated: C 62.66 H 8.42 Br 12.63 N 6.64 Found: 62.50 5.33 12.78 6.43

Example 281

4'-[(2-n-Butyl-6-(3-carboxy-cis-5-norbornene-endo-2-carbonylamino)-benzimidazol-1-yl)-methyl] biphenyl-3-carboxylic acid Prepared in analogous manner to Example 9 from tert. butyl 4'-[(2-n-butyl-6-(cis-5norbornene-endo-3,3-dicarboxylic acid imino)-benzimidazol-1-yl)-methyl] biphenyl-2-carboxylate and trifluoroacetic acid in methylene chloride.

Yield: 17.1% of theory,

Melting point: 199°–201° C. $C_{34}H_{39}N_2O_3$ (563.66)

Calculated: C 73.44 H 5.90 N 7.48 Found: 72.26 5.82 7.44

Example 282

4'[(2-n-Butyl-6-dimethylaminocarbonyloxy-benzimidazol-1-yl)-methyl]biphenyl-2-carboxylic acid Prepared in analogous manner to Example 9 from tert.-butyl 4'[(2-n-butyl-6-dimethylaminocarbonyloxy-benzimidazol-1-yl)-methyl]biphenyl-2-carboxylate and trifluoroacetic acid in methylene chloride.

Yield: 81.9% of theory.

Melting point: 241°–242° C. $C_{28}H_{29}N_2O_4$ (471.56)

Calculated: C 71.32 N 6.20 N 8.91 Found: 71.15 6.28 8.09

Example 283

4'-[(2-n-Butyl-6-(N-acetyl-n-octylamino)-benzimidazol-1-yl)-methyl]biphenyl-2-carboxylic acid Prepared in analogous manner to Example 9 from tert.-butyl 4'-[(2-n-butyl-6-(N-acetyl-n-octylamino)-benzimidazol-1-yl)-methyl]biphenyl-2-carboxylate Yield: 77.2% of theory, Melting point: 192°–193° C. $C_{39}H_{43}N_3O_3$ (583.74)

Calculated: C 75.92 H 7.83 N 7.59 Found: 75.75 8.03 7.45

Example 284

Tert.-butyl 4'-[(2-n-butyl-6-(2phenylethylamino-carbonyl)-benzimidazol-1-yl)-methyl]biphenyl-2-carboxylate 484 mg (1 mmol) of tert.-butyl 4'-[(2-n-butyl-6-carboxy-benzimidazol-1-yl)-methyl]biphenyl-2-carboxylate are dissolved in 10 ml of absolute tetrahydrofuran and cooled to −20° C. with stirring and cooling with dry ice/isopropanol. At this temperature 101 mg (1 mmol) of N-methylmorpholine are added. The resulting mixture is then cooled to −30° C. and a solution of 136 mg (1 mmol) of isobutylchloroformate dissolved in 5 ml of absolute tetrahydrofuran is slowly added dropwise. To complete the formation of the mixed anhydride the mixture is stirred for a further hour at −40° C. At −40° C. 134 mg (1.1 mmol) of 2-phenylethylamine dissolved in 2 ml of absolute tetrahydrofuran are slowly added dropwise. Then the mixture is allowed to rise slowly to ambient temperature and stirred for 16 hours at ambient temperature. The solvent is distilled off, the remaining viscous oil is taken up in saturated common salt solution/ethyl acetate and extracted 3 times in all with ethyl acetate. The ethyl acetate phases are dried over sodium sulphate and evaporated down. The viscous oil is dissolved in methylene chloride and purified over a silicon gel column (eluant: methylene chloride/ethanol 50:1 and 25:1).

Yield: 505 mg (86% of theory), oil, $R_f$ value: 0.5 (silica gel: ethanol/methylene chloride=1:19) $C_{38}H_{41}N_3O_2$ (587.80)

Calculated: C 77.65 H 7.03 N 7.15 Found: 77.58 7.24 7.34

The following compounds are obtained analogously:

tert.butyl 4'-[(2-n-butyl-6-(2-phenylamino-ethylaminocarbonyl)-benzimidazol-1-yl)-methyl]biphenyl-2-carboxylate oil, $R_f$ value: 0.45 (silica gel: ethanol/methylene chloride=1:19)

tert.butyl 4'-[(2-n-butyl-6-(5-carboxy-n-pentylaminocarbonyl)-benzimidazol-1-yl)-methyl] biphenyl-2-carboxylate Melting point: 166°–167° C.

Example 285

4'-[(2-n-butyl-6-(2-phenylethylaminocarbonyl)-benzimidazol-1-yl)-methyl]biphenyl-2-carboxylic acid Prepared in analogous manner to Example 9 from tert. butyl 4'-[(2-n-butyl-6-(2-phenylethylamino-carbonyl)-benzimidazol-1-yl)-methyl]biphenyl-2-carboxylate and trifluoroacetic acid in methylene chloride.

Yield: 19.7% of theory,

Melting point: 208°210° C. $C_{34}H_{33}W_2O_2$ (531.65)

Calculated: C 76.81 H 6.26 N 7.90 Found: 76.69 6.48 7.92

Example 286

4'-[(2-n-Butyl-6-(2-phenylaminoethylaminocarbonyl)-benzimidazol-1-yl)-methyl]biphenyl-2-carboxylic acid x 1.8 HCl Prepared analogously to Example 9 from tert.butyl 4'-[(2-n-butyl-6-(2-phenylaminoethylaminocarbonyl)-benzimidazol-1-yl)-methyl]biphenyl-2-carboxylate and trifluoroacetic acid in methylene chloride.

Yield: 30% of theory,

Melting point: 240°–242° C. $C_{36}H_{34}W_4O_3 \times 1.5$ HCl (601.36)

Calculated: C 67.91 H 5.95 N 9.32 Found: 67.88 5.93 9.15

Example 287

4'-[(2-n-Butyl-6-(5-carboxy-n-pentylaminocarbonyl)-benzimidazol-1-yl)-methyl]biphenyl-2-carboxylic acid Prepared in analogous manner to Example 9 from tert. butyl 4'-[(2-n-butyl-6-(5-carboxy-n-pentylamino-carbonyl)-benzimidazol-1-yl)methyl]biphenyl-2-carboxylate and trifluoroacetic acid in methylene chloride.

Yield: 37.4% of theory,

Melting point: from 114° C. (decomp.) $C_{37}H_{35}N_3O_3$ (541.70)

Calculated: C 70.96 H 6.51 N 7.76 Found: 70.84 6.42 7.85

Example 288

4'-[(2-n-Butyl-6-(2-carboxy-propionyl)-benzimidazol-1-yl)-methyl]biphenyl-2-carboxylic acid Prepared in analogous manner to Example 72 from methyl 4'-[(2-n-butyl-6-(2-carboxy-propionyl)-benzimidazol-1-yl)-methyl]biphenyl-2-carboxylate and sodium hydroxide solution/methanol.

Example 289

Tert.butyl 4'-[(2-n-butyl-6-homophthalimino-benzimidazol-1-yl)-methyl]-biphenyl-2-carboxylate 1.5 g (3.3 mmol) of tert.butyl 4'-[(6-amino-2-n-butyl-benzimidazol-1-yl)-methyl]biphenyl-2-carboxylate and 0.6 g (3.63 mmol) of homophthalic acid anhydride are refluxed for 20 hours in 20 ml of pyridine. Then the solvent is removed in vacuo and the residue is purified over a silica gel column (particle size 0.063–0.2 mm; eluant; methylene chloride/ethanol=100:2, 100:3 and 100.5).

Yield: 15.2% of theory,
Melting point: 109°112° C. $C_{38}H_{37}N_3O_4$ (599.73)
Calculated: C 76.10 H 6.22 N 7.01 Found: 75.90 6.28 6.90

The following compounds are obtained analogously:

tert.butyl 4'[(2-n-butyl-6-(3,3-tetramethylene-glutarimino)-benzimidazol-1-yl)-methyl]biphenyl-2-carboxylate tert.butyl 4'-[(2-n-butyl-6-(3,3-pentamethylene-glutarimino)-benzimidazol-1-yl)-methyl]biphenyl-2-carboxylate tert.butyl 4'-[(2-n-butyl-6-(7-methoxy-homophthalimino)-benzimidazol-1-yl)-methyl]biphenyl-2-carboxylate tert.butyl 4'-[(3-n-butyl-6-(4,4-dimethyl-7-methoxy-homophthalimino)-benzimidazol-1-yl)-methyl]biphenyl-2carboxylate tert.butyl 4'-[(2-n-butyl-6-(6,7-dimethoxy-homophthalimino)-benzimidazol-1-yl)-methyl]biphenyl-2-carboxylate tert.buytl 4'-[(2-n-butyl-6-(6,7-dimethoxy-4,4-dimethyl-homophthalimino)-benzimidazol-1-yl)-methyl]biphenyl-2-carboxylate tert.butyl 4'-[(2-n-butyl-6-glutarimino-benzimidazol-1-yl)-methyl]biphenyl-2-carboxylate tert.butyl 4'-[(2-n-butyl-6-(3-methyl-glutarimino)-benzimidazol-1-yl)-methyl]biphenyl-2-carboxylate tert.butyl 4'-[(2-n-butyl-6-(3,3-dimethyl-glutarimino)-benzimidazol-1-yl)-methyl]biphenyl-2-carboxylate tert.butyl 4'-[(2-n-butyl-6-(3-ethyl-3-methyl-glutarimino)-benzimidazol-1-yl)-methyl]biphenyl-2-carboxylate 4'-[(2-n-butyl-6-(cis-hexahydrophthalimino)-benzimidazol-1-yl)-methyl]-2-(1-triphenylmethyl-tetrazol-5-yl)-biphenyl tert.butyl 4'-[(2-n-butyl-6-(4,4-dimethyl-homophthalimino)-benzimidazol-1-yl)-methyl]biphenyl-2-carboxylate tert.butyl 4'-[(2-n-butyl-6-(5-methyl-hexahydrophthalimino)-benzimidazol-1-yl)-methyl]biphenyl-2-carboxylate oil, $R_f$ value: 0.75 (Silica gel: ethyl acetate/petroleum ether=4:1)

Example 290

4'-[(2-n-Butyl-6-homophthalimino-benzimidazol-1-yl)-methyl]biphenyl-2-carboxylic acid Prepared in analogous manner to Example 9 from tert. butyl 4'-[(2-n-butyl-6-homophthalimino-benzimidazol-1-yl)-methyl]biphenyl-2-carboxylate and trifluoroacetic acid in methylene chloride.

Yield: 79% of theory,
Melting point: 171°–173° C. $C_{34}H_{29}N_3O_4$ (543.62)
Calculated: C 75.12 H 5.38 N 7.73 Found: 74.95 5.18 7.64

Example 291

4'-[(2-n-Butyl-6-(4,4-dimethyl-homophthalimino)-benzimidazol-1-yl)-methyl]biphenyl-2-carboxylic acid hydrate Prepared in analogous manner to Example 9 from tert. butyl 4'-[(2-n-butyl-6-(4,4-dimethyl-homophthalimino)-benzimidazol-1-yl)-methyl]biphenyl-2-carboxylate and trifluoroacetic acid in methylene chloride.

Yield: 77.4% of theory,
Melting point: 299°301° C. $C_{36}H_{33}N_3O_4 \times H_2O$ (589,69)
Calculated: C 73.33 H 5.98 N 7.13 Found: 73.60 6.14 7.33

Example 292

4'-[(2-n-Butyl-6-(3,3-tetramethylene-glutarimino)-benzimidazol-1-yl)-methyl]biphenyl-2-carboxylic acid Prepared in analogous manner to Example 9 from tert. butyl 4'-[(2-n-butyl-6-(3,3-tetramethylene-glutarimino)-benzimidazol-1-yl)-methyl]biphenyl-2-carboxylate and trifluoroacetic acid in methylene chloride.

Yield: 40% of theory,
Melting point: 191°–194° C. $C_{34}H_{35}N_3O_4$ (549.64)
Calculated: C 72.29 H 6.42 N 7.65 Found: 74.08 6.31 7.52

Example 293

4'-[(2-n-Butyl-6-(3,3-pentamethylene-glutarimino)-benzimidazol-1-yl)-methyl]biphenyl-2-carboxylic acid Prepared in analogous manner to Example 9 from tert. butyl 4'-[(2--butyl-6-(3,3-antamethylene-glutarimino)-benzimidazol-1-yl)-methyl]biphenyl-2-carboxylate and trifluoroacetic acid in methylene chloride.

Yield: 31% of theory,
Melting point: 182°–185° C. $C_{35}H_{37}N_3O_4$(563.67)
Calculated: C 74.57 H 6.62 N 7.46 Found: 74.43 6.52 7.32

Example 294

4'-[(2-n-Butyl-6-(cis-hexahydro-phthalimino)-benzimidazol-1-yl)-methyl]-5-chloro-2-(1H-tetrazol-5-yl)-biphenyl Prepared in analogous manner to Example 59 from 4'-[(2-n-butyl-6-(cis-hexahydro-phthalimino)-benzimidazol-1-yl)-methyl]-5-chloro-2-cyano-biphenyl and sodium azide/ammonium chloride.

Yield: 22% of theory,
Melting point: from 135° C. (sintering) $C_{33}H_{32}ClN_2O_3$ (594.10)
Calculated: C 66.71 H 5.43 N 16.50 Cl 5.97 Found: 66.51 5.39 16.77 5.92

Example 295

4'-[(2-n-Butyl-6-(N-cyclohexylaminocarbonylamino)-benzimidazol-1-yl)-methyl]-5-chloro-2-(1H-tetrazol-5-yl)-biphenyl Prepared in analogous manner to Example 59 from 4'-[(3-n-butyl-6-(N-cyclohexylaminocarbonylamino)-

Example 296

4'-[(2-n-Butyl-6-(7-methoxy-homophthalimino)-benzimidazol-1-yl)-methyl]biphenyl-2-carboxylic acid Prepared in analogous manner to Example 9 from tert. butyl 4'-[(2-n-butyl-6-(7-methoxy-homophthalimino)-benzimidazol-1-yl)-methyl]biphenyl-2-carboxylate and trifluoroacetic acid.

Example 297

4'-[(2-n-Butyl-6-(4,4-dimethyl-7-methoxy-homophthalimino)-benzimidazol-2-yl)-methoxyl]biphenyl-2-carboxylic acid Prepared in analogous manner to Example 9 from tert. butyl 4'-[(2-n-butyl-6-(4,4-dimethyl-7-methoxy-homophthalimino)-benzimidazol-1-yl)-methyl]biphenyl-2-carboxylate and trifluoroacetic acid in methylene chloride.

Yield: 60,1% of theory,
Melting point: 104°–105° C. $C_{37}H_{35}N_3O_3$ (601.70)
Calculated: C 73.86 H 5.86 N 6.98 Found: 73.92 6.04 7.11

Example 298

4'-[(2-n-Butyl-6-(6,7-dimethoxy-homophthalimino)-benzimidazol-1-yl)-methyl]biphenyl-2-carboxylic acid Prepared in analogous manner to Example 9 from tert. butyl 4'-[(2-n-butyl-6-(6,7-dimethoxy-homophthalimino)-benzimidazol-1-yl)-methyl]biphenyl-2-carboxylate and trifluoroacetic acid in methylene chloride.

Example 299

4'-[(2-n-Butyl-6-(6,7-dimethoxy-4,4-dimethyl-homophthalimino)-benzimidazol-1-yl)-methyl]biphenyl-2-carboxylic acid Prepared in analogous manner to Example 9 from tert. butyl 4'-[(2-n-butyl-6-(6.7-dimethoxy-4,4-dimethyl-homophthalimino)-benzimidazol-1-yl)-methyl]biphenyl-2-carboxylate and trifluoroacetic acid in methylene chloride.

Example 300

4'-[(2-n-Butyl-6-(3,3-pentamethylene-glutarimino)-benzimidazol-1-yl)-methyl]-2-(1H-tetrazol-5-yl)-biphenyl Prepared in analogous manner to Example 59 from 4'-[(2-n-butyl-6-(3,3-pentamethylene-glutarimino)-benzimidazol-1-yl)-methyl]-2-cyano-biphenyl and sodium azide/ammonium chloride.

Yield: 29% of theory,
Melting point: from 140° C. (sintering) $C_{25}H_{27}N_2O_3$ (587.70)
Calculated C 71.52 H 6.25 N 16.68 Found: 71.37 6.20 16.71

Example 301

4'-[(2-n-Butyl-6-(3,3-tetramethylene-glutarimino)-benzimidazol-1-yl)-methyl]-2-(1N-tetrazol-5-yl)-biphenyl Prepared in analogous manner to Example 59 from 4'-[(2-n-butyl-6-(3,3-tetramethylene-glutarimino)-benzimidazol-1-yl)-methyl]-2-cyano-biphenyl and medium azide/ammonium chloride.

Yield: 31% of theory,
Melting point: from 166° C. (sintering) $C_{36}H_{29}N_7O_2$ (573.68)
Calculated: C 71.18 H 6.18 N 17.09 Found: 71.10 6.22 17.20

Example 302

4'-[(2-n-Butyl-6-(3,3-tetramethylene-glutarimino)-benzimidazol-1-yl)-methyl]-4-chloro-2-(1H-tetrazol-5-yl)-biphenyl Prepared in analogous manner to Example 59 from 4'-[(2-n-butyl-6-(3,3-tetramethylene-glutarimino)-benzimidazol-1-yl)-methyl]-4-chloro-cyano-biphenyl and sodium azide/ammonium chloride.

Example 303

4'-[(2-n-Butyl-6-glutarimino-benzimidazol-1-yl)-methyl]biphenyl-2-carboxylic acid Prepared in analogous manner to Example 9 from tert.-butyl 4'-[(2-n-butyl-6-glutarimino-benzimidazol-1-yl)-methyl]biphenyl-2-carboxylate and trifluoroacetic acid in methylene chloride.

Yield: 82% of theory,
Melting point: >220° C. $C_{30}H_{29}N_3O_4$ (495.56)
Calculated: C 72.71 H 5.90 N 8.45 Found: 72.56 5.79 8.22

Example 304

4'-[(2-n-Butyl-6-glutarimino-benzimidazol-1-yl)-methyl]-2-(1H-tetrazol-5-yl)-biphenyl Prepared in analogous manner to Example 59 from 4'-[(2-n-butyl-6-glutarimino-benzimidazol-1-yl)-methyl]-2-cyano-biphenyl and sodium azide/ammonium chloride.

Yield: 47% of theory,
Melting point; from 139° C. (sintering) $C_{30}H_{29}N_7O_2$ (519.59)
Calculated: C 69.34 H 5.62 N 18.87 Found: 69.30 5.52 18.69

Example 305

4'-[(2-n-Butyl-6-(3-methyl-glutarimino)-benzimidazol-1-yl)-methyl]biphenyl-2-carboxylic acid Prepared in analogous manner to Example 9 from tert. butyl 4'-[(2-n-butyl-6-(3-methyl-glutarimino)-benzimidazol-1-yl)-methyl]biphenyl-2-carboxylate and trifluoroacetic acid in methylene chloride.

Yield: 39% of theory,
Melting point: >220° C. $C_{31}H_{31}N_3O_4$ (509.58)
Calculated: C 73.06 H 6.13 N 8.25 Found: 72.91 5.88 8.02

Example 306

4'-[(2-n-Butyl-6-(3-methyl-glutarimino)-benzimidazol-1-yl)-methyl]-2-(1H-tetrazol-5-yl)-biphenyl Prepared in analogous manner to Example 59 from 4'-[(2-n-butyl-6-(3-methyl-glutarimino)-benzimidazol-1-yl)-methyl]-2-cyano-biphenyl and sodium azide/ammonium chloride.

Yield: 28% of theory.

Melting point: from 157° C. (sintering) $C_{31}H_{31}N_7O_3$ (533.61)

Calculated: C 69.77 H 5.86 N 18.38 Found: 69.69 5.81 18.16

Example 307

4'-[(2-n-Butyl-6-(3-methyl-glutarimino)-benzimidazol-1-yl)-methyl]-4-chloro-2-(1H-tetrazol-5-yl)-biphenyl Prepared in analogous manner to Example 59 from 4'-[(2-n-butyl-6-(3-methyl-glutarimino)-benzimidazol-1-yl)-methyl]-4-chloro-2-cyano-biphenyl and sodium azide/ammonium chloride.

Example 308

4'-[(2-n-Butyl-6-(3,3-dimethyl-glutarimino)-benzimidazol-1-yl)-methyl]biphenyl-2-carboxylic acid Prepared in analogous manner to Example 9 from tert. butyl 4'-[(2-n-butyl-6-(3,3-dimethyl-glutarimino)-benzimidazol-1-yl)-methyl]biphenyl-2-carboxylate and trifluoroacetic acid in methylene chloride.

Yield: 41% of theory,

Melting point: >220° C. $C_{32}H_{33}N_3O_4$ (523.61)

Calculated: C 73.40 H 6.35 N 8.03 Found: 73.29 6.21 7.91

Example 309

4'-[(2-n-Butyl-6-(3,3-dimethyl-glutarimino)-benzimidazol-1-yl)-methyl]-2-(1H-tetrazol-5-yl)-biphenyl Prepared in analogous manner to Example 59 from 4'-[(2-n-butyl-6-(3,3-dimethyl-glutarimino)-benzimidazol-1-yl)-methyl]-2-cyano-biphenyl and sodium azide/ammonium chloride.

Yield: 29% of theory,

Melting point: from 151° C. (sintering) $C_{32}H_{33}N_7O_2$ (547.64)

Calculated: C 70.18 H 6.07 N 17.91 Found: 69.91 5.98 17.85

Example 310

4'-[(2-n-Butyl-6-(3-ethyl-3-methyl-glutarimino)-benzimidazol-1-yl)-methyl]biphenyl-2-carboxylic acid Prepared in analogous manner to Example 9 from tert. butyl 4'-[(2-n-butyl-6-(3-ethyl-3-methyl-glutarimino)-benzimidazol-1-yl)-methyl]biphenyl-2-carboxylate and trifluoroacetic acid in methylene chloride.

Yield: 58% of theory,

Melting point: >220° C. $C_{32}H_{39}N_3O_4$ (537.63)

Calculated: C 73.72 H 6.56 N 7.82 Found: 73.55 6.41 7.76

Example 311

4'-[(2-n-Butyl-6-(3-ethyl-3-methyl-glutarimino)-benzimidazol-1-yl)-methyl]-2-(1H-tetrazol-5-yl)-biphenyl Prepared in analogous manner to Example 59 from 4'-[(2-n-butyl-6-(3-ethyl-3-methyl-glutarimino)-benzimidazol-1-yl)-methyl]-2-cyano-biphenyl and sodium azide/ammonium chloride.

Yield: 26% of theory,

Melting point: from 138° C. (sintering) $C_{33}H_{35}N_7O_2$ (561.67)

Calculated: C 70.56 H 6.28 N 17.46 Found: 70.47 6.02 17.33

Example 312

4'-[(2-n-Butyl-6-(3-methyl-glutarimino)-benzimidazol-1-yl)-methyl]-4-chloro-2-(1H-tetrazol-5-yl)-biphenyl Prepared in analogous manner to Example 59 from 4'-[(2-n-butyl-6-(3-ethyl-3-methyl-glutarimino)-benzimidazol-1-yl)-methyl]-4-chloro-2-cyano-biphenyl and sodium azide/ammonium chloride.

Example 313

4'-[(2-n-Butyl-5-(N-cyclohexylaminocarbonyl-methylamino)-benzimidazol-1-yl)-methyl]-2-(1H-tetrazol-5-yl)-biphenyl Prepared in analogous manner to Example 58b from 4'-[(2-n-butyl-5-(N-cyclohexylaminocarbonyl-methylamino)-benzimidazol-1-yl)-methyl]-2-(1-triphenylmethyl-tetrazol-5-yl)-biphenyl and hydrochloric acid in methylene chloride/ether/methanol.

Yield: 76.2% of theory,

Melting point: 150°–152° C. $C_{33}H_{38}H_8O$ (562.72)

Calculated: C 70.44 H 6.80 N 19.91 Found: 70.32 7.05 19.76

Example 314

4'-[(2-n-Butyl-6-(5-methyl-hexahydrophthalimino)-benzimidazol-1-yl)-methyl]biphenyl-2-carboxylic acid Prepared in analogous manner to Example 9 from tert. butyl 4'-[(2-n-butyl-6-(5-methyl-hexahydrophthalimino)-benzimidazol-1-yl)-methyl]biphenyl-2-carboxylate and trifluoroacetic acid in methylene chloride.

Yield: 37% of theory,

Melting point: 143°–144° C. $C_{34}H_{35}N_3O_4$ (549.67)

Calculated: C 74,29 H 6,42 N 7,62 Found: 74,47 6,67 7,55

Example 315

4'-[(2-n-Butyl-5-(cis-hexahydrophthalimino)-benzimidazol-1-yl)-methyl]-2-(1H-tetrazol-5-yl)-biphenyl Prepared in analogous manner to Example 58 from 4'-[(2-n-butyl-5-(cis-hexahydrophthalimino)-benzimidazol-1-yl)-methyl]-2-(1-triphenylmethyl-tetrazol-5-yl)-biphenyl and hydrochloric acid/ethanol.

Yield: 59.5% of theory,

Melting point: 230°–232° C. $C_{33}H_{33}H_7O_2$ (559,67)

Calculated: C 70,82 H 5,94 H 17,52 Found: 70.64 6.10 17.72

Example 316

4'-[(2-n-Butyl-5-(2-carboxymethyl-propionyl)-benzimidazol-1-yl)-methyl]biphenyl-2-carboxylic acid x 0.25 $H_2O$ Prepared is analogous manner to Example 72 from methyl 4'-[(2-n-butyl-5-(2-carboxymethyl-propionyl)- benzimidazol-1-yl(-methyl]biphenyl-2-carboxylate and aquous sodium hydroxide/ethanol.

Yield: 25% of theory

Melting point: 223°–225° C. $C_{30}H_{30}N_2O_5$ x $H_2O$ (503, 08)

Calculated: C 71,62 H 6,11 N 5,56 Found: 71,56 6,14 5,58

Each suitable compound of the formula I, for example the compounds of the above examples, may be used as active substance in the following pharmaceutical application examples:

Example I

Ampoules containing 50 mg of active ingredient per 5 ml

| Active ingredient | 50 mg |
|---|---|
| $KH_2PO_4$ | 2 mg |
| $Na_2HPO_4$ x $2H_2O$ | 50 mg |
| NaCl | 12 mg |
| Water for injections ad | 5 ml |

Preparation

The buffer substances and the isotonic agent are dissolved in part of the water. The active ingredient is added and after it is completely dissolved, the solution is made up to the nominal volume with water.

Example II

Ampoule containing 100 mg of action ingredient per 5 ml

| Active ingredient | 100 mg |
|---|---|
| Methylglucamine | 35 mg |
| Glycofurol | 1,000 mg |
| Polyethylene glycol-polypropylene glycol block polymer | 250 mg |
| Water for injections ad | 5 ml |

Preparation

Methylglucamine is dissolved in part of the water and the active ingredient is dissolved with stirring and heating. After adding the solvent, the solution is made up to the nominal volume with water.

Example III

Tablets containing 50 mg of active ingredient

| Active ingredient | 50.0 mg |
|---|---|
| Calcium phosphate | 70.0 mg |
| Lactose | 40.0 mg |
| Corn starch | 35.0 mg |
| Polyvinylpyrrolidone | 3.5 mg |
| Magnesium stearate | 1.5 mg |
| | 200.0 mg |

Preparation

The active ingredient, $CaHPO_4$, lactose and corn starch are moistened evenly with an aqueous PVP solution. The mixture is passed through a 2 sieve, dried at 50° C. is an oven with circulating air and sieved again.

After admixing the lubricant, the granules are pressed on a tableting machine.

Example IV

Coated tablets containing 50 mg of active ingredient

| Active ingredient | 50.0 mg |
|---|---|
| Lysine | 25.0 mg |
| Lactose | 60.0 mg |
| Corn starch | 34.0 mg |
| Gelatine | 10.0 mg |
| Magnesium stearate | 1.0 mg |
| | 180.0 mg |

Preparation

The active ingredient is mixed with the auxiliaries and moistened with an aqueous gelatine solution. After sieving and drying, the granules are mixed with magnesium stearate and pressed to form cores.

The cores thus prepared are coated with a shell in accordance with known processes. Dyestuff may be added to the coating suspension or solution.

Example V

Coated tablets containing 100 mg of active ingredient

| Active ingredient | 100.0 mg |
|---|---|
| Lysine | 50.0 mg |
| Lactose | 86.0 mg |
| Corn starch | 50.0 mg |
| Polyvinylpyrrolidone | 2.8 mg |
| Microcrystalline celluse | 60.0 mg |
| Magnesium stearate | 1.2 mg |
| | 350.0 mg |

Preparation

The active ingredient is mixed with the auxiliaries and moistened with an aqueous PVP solution. The moist mixture is passed through a 1.5 mm sieve and dried at 45° C. After drying, the mixture is sieved again and the magnesium stearate is admixed. This mixture is pressed to form cores.

The cores thus prepared are coated with a shell in accordance with known processes. Dyestuffs may be added to the coating suspension or solution.

Example VI

Capsules containing 250 mg of active ingredient

| Active ingredient | 250.0 mg |
|---|---|
| Corn starch | 68.5 mg |
| Magnesium stearate | 1.5 mg |
| | 320.0 mg |

Preparation

Active ingredient and corn starch are mixed and moistened with water. The moist mixture is sieved and dried. The dry granules are sieved and mixed with magnesium stearate. The final mixture is placed in size 1 hard gelatine capsules.

Example VII

Oral suspension containing 50 mg of active ingredient per 5 ml

| | |
|---|---|
| Active ingredient | 50.0 mg |
| Hydroxyethylcellulose | 50.0 mg |
| Sorbic acid | 5.0 mg |
| Sorbitol 70% strength | 600.0 mg |
| Glycerol | 200.0 mg |
| Flavor | 15.0 mg |
| Water ad | 5.0 ml |

Preparation

Distilled water is heated to 70° C. Hydroxyethylcellulose is dissolved in the water with stirring. The solution is cooled to ambient temperature by adding sorbitol solution and glycerol. Sorbic acid, flavour and active ingredient are added at ambient temperature. Air is removed from the suspension by evacuating while stirring. 5.0 ml contains one dose=50 mg.

Example VIII

Suppositories containing 100 mg of active ingredient

| | |
|---|---|
| Active ingredient | 100.0 mg |
| Solid lard | 1,600.0 mg |
| | 1,700.0 mg |

Preparation

The hard fat is melted. The ground active substance is dispersed homogeneously in the melt at 40° C. The mixture is cooled to 38° C. and poured into slightly pre-cooled suppository moulds.

We claim:

1. A compound of the formula I

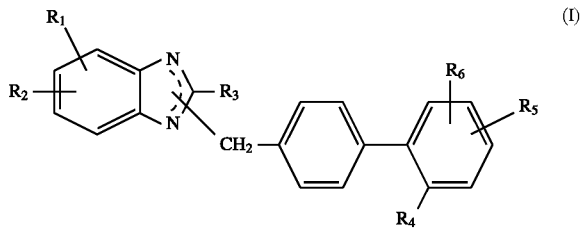

wherein $R_1$ represent a carboxy or $C_{1-3}$-alkoxycarbonyl group, $R_2$ represents a hydrogen atom or a methyl group, $R_3$ represents a n-$C_{3-5}$alkyl group wherein one methylene group may be replaced by an oxygen or sulphur atom, $R_4$ represents a carboxy or 1H-tetrazolyl group, $R_5$ and $R_6$ each represents a hydrogen atom, or a pharmaceutically acceptable salt thereof.

2. A compound of the formula I according to claim 1, wherein $R_1$ represent a carboxy, methoxycarbonyl, ethoxycarbonyl or n-propoxycarbonyl group, $R_2$ represents a hydrogen atom or a methyl group, $R_3$ represents an $C_{2-4}$-alkoxy or $C_{2-4}$-alkylthio group, $R_4$ represents a carboxy or 1H-tetrazolyl group, $R_5$ and $R_6$ each represents a hydrogen atom, or a pharmaceutically acceptable salt thereof.

3. 4'-[(2-Ethylthio-benzimidazolyl-1-yl)-methyl]-biphenyl-2-carboxylic acid or a pharmaceutically acceptable salt thereof.

* * * * *